US012467065B2

(12) United States Patent
Pekrun et al.

(10) Patent No.: US 12,467,065 B2
(45) Date of Patent: Nov. 11, 2025

(54) RECOMBINANT ADENO-ASSOCIATED VIRUS CAPSIDS WITH ENHANCED HUMAN PANCREATIC TROPISM

(71) Applicant: The Board of Trustees of the Leland Stanford Junior University, Stanford, CA (US)

(72) Inventors: Katja Pekrun, Palo Alto, CA (US); Mark A. Kay, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 148 days.

(21) Appl. No.: 18/062,333

(22) Filed: Dec. 6, 2022

(65) Prior Publication Data

US 2023/0304039 A1 Sep. 28, 2023

Related U.S. Application Data

(62) Division of application No. 16/370,735, filed on Mar. 29, 2019, now Pat. No. 11,608,510.

(60) Provisional application No. 62/651,010, filed on Mar. 30, 2018, provisional application No. 62/745,226, filed on Oct. 12, 2018.

(51) Int. Cl.

| | |
|---|---|
| ***C12N 15/86*** | (2006.01) |
| ***A61K 47/69*** | (2017.01) |
| ***C07K 14/00*** | (2006.01) |
| ***C07K 14/005*** | (2006.01) |
| ***C07K 14/015*** | (2006.01) |
| ***C07K 14/075*** | (2006.01) |
| ***C12N 15/10*** | (2006.01) |
| *C12N 7/00* | (2006.01) |
| *C12N 15/90* | (2006.01) |

(52) U.S. Cl.

CPC .......... *C12N 15/86* (2013.01); *A61K 47/6901* (2017.08); *C07K 14/015* (2013.01); *C07K 14/075* (2013.01); *C12N 15/102* (2013.01); *C12N 7/00* (2013.01); *C12N 15/902* (2013.01); *C12N 2710/10041* (2013.01); *C12N 2710/10071* (2013.01); *C12N 2710/10134* (2013.01); *C12N 2710/10141* (2013.01); *C12N 2750/14123* (2013.01)

(58) Field of Classification Search

CPC ................ C12N 15/86; C12N 15/8645; C12N 710/10041; C12N 710/10071; C12N 2750/14111; C12N 2750/14122; C07K 14/00; C07K 14/005; C07K 14/015

See application file for complete search history.

(56) References Cited

U.S. PATENT DOCUMENTS

| | | | | |
|---|---|---|---|---|
| 5,139,941 | A | 8/1992 | Muzyczka et al. | |
| 5,173,414 | A | 12/1992 | Lebkowski et al. | |
| 6,200,560 | B1 | 3/2001 | Couto et al. | |
| 6,221,349 | B1 | 4/2001 | Couto et al. | |
| 6,491,907 | B1 | 12/2002 | Rabinowitz et al. | |
| 6,951,758 | B2 | 10/2005 | Ferrari et al. | |
| 7,271,002 | B2 | 9/2007 | Kotin et al. | |
| 7,439,065 | B2 | 10/2008 | Ferrari et al. | |
| 9,169,299 | B2 * | 10/2015 | Lisowski | C12N 15/1058 |
| 10,414,803 | B2 * | 9/2019 | Nathwani | C07K 14/005 |
| 11,015,189 | B2 | 5/2021 | Lisowski et al. | |
| 11,083,800 | B2 * | 8/2021 | Arbetman | C12N 7/00 |
| 11,608,510 | B2 * | 3/2023 | Pekrun | C07K 14/075 |
| 2005/0053922 | A1 | 3/2005 | Schaffer et al. | |
| 2005/0075492 | A1 | 4/2005 | Chen et al. | |
| 2005/0142581 | A1 | 6/2005 | Griffey et al. | |
| 2005/0266552 | A1 | 12/2005 | Doench et al. | |
| 2005/0272923 | A1 | 12/2005 | Zhang et al. | |
| 2009/0202490 | A1 | 8/2009 | Schaffer et al. | |
| 2009/0203071 | A1 | 8/2009 | Chen | |
| 2012/0164106 | A1 | 6/2012 | Schaffer et al. | |
| 2014/0242031 | A1 | 8/2014 | Schaffer et al. | |
| 2014/0348794 | A1 | 11/2014 | Chiorini et al. | |
| 2015/0023924 | A1 | 1/2015 | High et al. | |
| 2015/0176027 | A1 | 6/2015 | Gao et al. | |
| 2016/0017295 | A1 * | 1/2016 | Schaffer | A61K 48/0008 435/235.1 |

FOREIGN PATENT DOCUMENTS

| | | | |
|---|---|---|---|
| WO | WO 1992/001070 | A1 | 1/1992 |
| WO | WO 1993/003769 | A1 | 3/1993 |
| WO | WO 1998/010088 | A1 | 3/1998 |
| WO | WO 2013/029030 | A1 | 2/2013 |
| WO | WO 2016/054557 | A1 | 4/2016 |
| WO | WO 2017/143100 | A1 | 8/2017 |

OTHER PUBLICATIONS

Lochrie et al, J. Virology 80(2): 821-834, 2006.*
Adachi et al, Nature Communications 5: 3075, 14 pages, doi: 10.1038/ncomms4075; 2014.*
Zhong et al, Molecular Therapy 22 (Suppl 1): Abstract 290, May 2014.*
Yan et al, Human Gene Therapy 26: 38-49, 2015.*
Perrin, Make mouse studies work, Nature (507): 423-425, 2014.*
Greenberg, Gene Therapy for heart failure, Trends in Cardiovascular Medicine 27: 216-222, 2017.*
Maguire et al, Viral vectors for gene delivery to the inner ear, Hearing Research 394: e107927, 13 pages, doi.org/10.1016/j.heares.2020.107927, 2020.*

(Continued)

*Primary Examiner* — Kevin K Hill
(74) *Attorney, Agent, or Firm* — Sara E. Sims; Christina A. MacDougall; Morgan, Lewis & Bockius, LLP

(57) ABSTRACT

The present invention relates to variant AAV capsid polypeptides, wherein the variant AAV capsid polypeptides exhibit increased transduction and/or tropism in human pancreatic tissue or human islets as compared non-variant parent capsid polypeptides.

2 Claims, 70 Drawing Sheets

Specification includes a Sequence Listing.

(56) References Cited

OTHER PUBLICATIONS

Adachi, Kei et al. "Drawing a high-resolution functional map of adeno-associated virus capsid by massively parallel sequencing." Nature communications vol. 5 (2014): 3075. doi:10.1038/ncomms4075.
Adachi, Kei, and Hiroyuki Nakai. "A New Recombinant Adeno-Associated Virus (AAV)-Based Random Peptide Display Library System: Infection-Defective AAV1.9-3 as a Novel Detargeted Platform for Vector Evolution." Gene therapy and regulation vol. 5,1 (2010): 31-55. doi:10.1142/S1568558610000197.
Aiello, L et al. "Adenovirus 5 DNA sequences present and RNA sequences transcribed in transformed human embryo kidney cells (HEK-Ad-5 or 293)." Virology vol. 94,2 (1979): 460-9. doi:10.1016/0042-6822(79)90476-8.
Andersen, J K et al. "Herpesvirus-mediated gene delivery into the rat brain: specificity and efficiency of the neuron-specific enolase promoter." Cellular and molecular neurobiology vol. 13,5 (1993): 503-15. doi:10.1007/BF00711459.
Apt, Doris et al. "Tetravalent neutralizing antibody response against four dengue serotypes by a single chimeric dengue envelope antigen." Vaccine vol. 24,3 (2006): 335-44. doi:10.1016/j.vaccine.2005.07.100.
Arbuthnot, P B et al. "In vitro and in vivo hepatoma cell-specific expression of a gene transferred with an adenoviral vector." Human gene therapy vol. 7,13 (1996): 1503-14. doi:10.1089/hum.1996.7.13-1503.
Asuri, Prashanth et al. "Directed evolution of adeno-associated virus for enhanced gene delivery and gene targeting in human pluripotent stem cells." Molecular therapy : the journal of the American Society of Gene Therapy vol. 20,2 (2012): 329-38. doi:10.1038/mt.2011.255.
Balazs, Alejandro B et al. "Antibody-based protection against HIV infection by vectored immunoprophylaxis." Nature vol. 481,7379 81-4. Nov. 30, 2011, doi:10.1038/nature10660.
Balazs, Alejandro B et al. "Broad protection against influenza infection by vectored immunoprophylaxis in mice." Nature biotechnology vol. 31,7 (2013): 647-52. doi:10.1038/nbt.2618.
Balazs, Alejandro B et al. "Vectored immunoprophylaxis protects humanized mice from mucosal HIV transmission." Nature medicine vol. 20,3 (2014): 296-300. doi:10.1038/nm.3471.
Bowles, Dawn E et al. "Phase 1 gene therapy for Duchenne muscular dystrophy using a translational optimized AAV vector." Molecular therapy : the journal of the American Society of Gene Therapy vol. 20,2 (2012): 443-55. doi:10.1038/mt.2011.237.
Brantly, Mark L et al. "Sustained transgene expression despite T lymphocyte responses in a clinical trial of rAAV1-AAT gene therapy." Proceedings of the National Academy of Sciences of the United States of America vol. 106,38 (2009): 16363-8. doi:10.1073/pnas.0904514106.
Bruni, Anthony et al. "Islet cell transplantation for the treatment of type 1 diabetes: recent advances and future challenges." Diabetes, metabolic syndrome and obesity : targets and therapy vol. 7 211-23. Jun. 23, 2014, doi:10.2147/DMSO.S50789.
Capecchi, M R. "High efficiency transformation by direct microinjection of DNA into cultured mammalian cells." Cell vol. 22,2 Pt 2 (1980): 479-88. doi:10.1016/0092-8674(80)90358-x.
Carter, B J. "Adeno-associated virus vectors." Current opinion in biotechnology vol. 3,5 (1992): 533-9. doi:10.1016/0958-1669(92)90082-t.
Chakravarthy, Harini et al. "Converting Adult Pancreatic Islet α Cells into β Cells by Targeting Both Dnmt1 and Arx." Cell metabolism vol. 25,3 (2017): 622-634. doi:10.1016/j.cmet.2017.01.009.
Chakravarti, Dhrubajyoti, and Paula C Mailander. "Formation of template-switching artifacts by linear amplification." Journal of biomolecular techniques : JBT vol. 19,3 (2008): 184-8.
Chang, C C et al. "Evolution of a cytokine using DNA family shuffling." Nature biotechnology vol. 17,8 (1999): 793-7. doi:10.1038/11737.
Charville, Gregory W et al. "Ex Vivo Expansion and In Vivo Self-Renewal of Human Muscle Stem Cells." Stem cell reports vol. 5,4 (2015): 621-32. doi:10.1016/j.stemcr.2015.08.004.
Chen, Haifeng. "Intron splicing-mediated expression of AAV Rep and Cap genes and production of AAV vectors in insect cells." Molecular therapy : the journal of the American Society of Gene Therapy vol. 16,5 (2008): 924-30. doi:10.1038/mt.2008.35.
Chen, J et al. "Expression of rat bone sialoprotein promoter in transgenic mice." Journal of bone and mineral research : the official journal of the American Society for Bone and Mineral Research vol. 11,5 (1996): 654-64. doi:10.1002/jbmr.5650110513.
Chen, Min et al. "Efficient Gene Delivery and Expression in Pancreas and Pancreatic Tumors by Capsid-Optimized AAV8 Vectors." Human gene therapy methods vol. 28,1 (2017): 49-59. doi:10.1089/hgtb.2016.089.
Choudhury, Sourav R et al. "In Vivo Selection Yields AAV-B1 Capsid for Central Nervous System and Muscle Gene Therapy." Molecular therapy : the journal of the American Society of Gene Therapy vol. 24,7 (2016): 1247-57. doi:10.1038/mt.2016.84.
Christians, F C et al. "Directed evolution of thymidine kinase for AZT phosphorylation using DNA family shuffling." Nature biotechnology vol. 17,3 (1999): 259-64. doi:10.1038/7003.
Chu, G, and P A Sharp. "SV40 DNA transfection of cells in suspension: analysis of efficiency of transcription and translation of T-antigen." Gene vol. 13,2 (1981): 197-202. doi:10.1016/0378-1119(81)90008-1.
Coco, W M et al. "DNA shuffling method for generating highly recombined genes and evolved enzymes." Nature biotechnology vol. 19,4 (2001): 354-9. doi:10.1038/86744.
Colella, Pasqualina et al. "Emerging Issues in AAV-Mediated In Vivo Gene Therapy." Molecular therapy. Methods & clinical development vol. 8 87-104. Dec. 1, 2017, doi:10.1016/j.omtm.2017.11.007.
Collombat, Patrick et al. "The ectopic expression of Pax4 in the mouse pancreas converts progenitor cells into alpha and subsequently beta cells." Cell vol. 138,3 (2009): 449-62. doi:10.1016/j.cell.2009.05.035.
Courtney, Monica et al. "The inactivation of Arx in pancreatic a-cells triggers their neogenesis and conversion into functional β-like cells." PLoS genetics vol. 9,10 (2013): e1003934. doi:10.1371/journal.pgen.1003934.
Craig, Anthony T et al. "Transduction of rat pancreatic islets with pseudotyped adeno-associated virus vectors." Virology journal vol. 6 61. May 18, 2009, doi:10.1186/1743-422X-6-61.
Crameri, A et al. "DNA shuffling of a family of genes from diverse species accelerates directed evolution." Nature vol. 391,6664 (1998): 288-91. doi:10.1038/34663.
Crameri, A et al. "Molecular evolution of an arsenate detoxification pathway by DNA shuffling." Nature biotechnology vol. 15,5 (1997): 436-8. doi:10.1038/nbt0597-436.
Dalkara, Deniz et al. "In vivo-directed evolution of a new adeno-associated virus for therapeutic outer retinal gene delivery from the vitreous." Science translational medicine vol. 5,189 (2013): 189ra76. doi:10.1126/scitranslmed.3005708.
Dorrell, Craig et al. "Isolation of major pancreatic cell types and long-term culture-initiating cells using novel human surface markers." Stem cell research vol. 1,3 (2008): 183-94. doi:10.1016/j.scr.2008.04.001.
Doshi, Bhavya S, and Valder R Arruda. "Gene therapy for hemophilia: what does the future hold ?." Therapeutic advances in hematology vol. 9,9 273-293. Aug. 27, 2018, doi:10.1177/2040620718791933.
Eisenberg, D et al. "Analysis of membrane and surface protein sequences with the hydrophobic moment plot." Journal of molecular biology vol. 179, 1 (1984): 125-42. doi:10.1016/0022-2836(84)90309-7.
Felgner, P L et al. "Lipofection: a highly efficient, lipid-mediated DNA-transfection procedure." Proceedings of the National Academy of Sciences of the United States of America vol. 84,21 (1987): 7413-7. doi:10.1073/pnas.84.21.7413.

(56) References Cited

OTHER PUBLICATIONS

Flores, R R et al. "Expression of IL-2 in β cells by AAV8 gene transfer in pre-diabetic NOD mice prevents diabetes through activation of FoxP3-positive regulatory T cells." Gene therapy vol. 21,8 (2014): 715-22. doi:10.1038/gt.2014.45.
Flotte, T et al. "Efficient ex vivo transduction of pancreatic islet cells with recombinant adeno-associated virus vectors." Diabetes vol. 50,3 (2001): 515-20. doi:10.2337/diabetes.50.3.515.
Flotte, Terence R et al. "Phase 2 clinical trial of a recombinant adeno-associated viral vector expressing α1-antitrypsin: interim results." Human gene therapy vol. 22, 10 (2011): 1239-47. doi:10.1089/hum.2011.053.
Flotte, Terence R et al. "Phase I trial of intramuscular injection of a recombinant adeno-associated virus alpha 1-antitrypsin (rAAV2-CB-hAAT) gene vector to AAT-deficient adults." Human gene therapy vol. 15,1 (2004): 93-128. doi:10.1089/10430340460732490.
Furuyama, Kenichiro et al. "Diabetes relief in mice by glucose-sensing insulin-secreting human α-cells." Nature vol. 567,7746 (2019): 43-48. doi:10.1038/s41586-019-0942-8.
Gao, Guangping et al. "Adeno-associated viruses undergo substantial evolution in primates during natural infections." Proceedings of the National Academy of Sciences of the United States of America vol. 100,10 (2003): 6081-6. doi:10.1073/pnas.0937739100.
George, L, et al. (2017). Spk-8011: preliminary results from a phase 1/2 dose escalation trial of an investigational AAV-mediated gene therapy for hemophilia A. Blood 130.
Gillam E.M.J., C, J.N., Ackerley, D.F. (2014). Directed Evolution Library Creation, Methods and Protocols, Humana Press.
Gossen, M et al. "Transcriptional activation by tetracyclines in mammalian cells." Science (New York, N.Y.) vol. 268,5218 (1995): 1766-9. doi:10.1126/science.7792603.
Gossen, M, and H Bujard. "Tight control of gene expression in mammalian cells by tetracycline-responsive promoters." Proceedings of the National Academy of Sciences of the United States of America vol. 89,12 (1992): 5547-51. doi:10.1073/pnas.89.12.5547.
Graham, F L et al. "Characteristics of a human cell line transformed by DNA from human adenovirus type 5." The Journal of general virology vol. 36,1 (1977): 59-74. doi:10.1099/0022-1317-36-1-59.
Graham, F L, and A J van der Eb. "A new technique for the assay of infectivity of human adenovirus 5 DNA." Virology vol. 52,2 (1973): 456-67. doi:10.1016/0042-6822(73)90341-3.
Gray, Steven J et al. "Production of recombinant adeno-associated viral vectors and use in in vitro and in vivo administration." Current protocols in neuroscience vol. Chapter 4 (2011): Unit 4.17. doi:10.1002/0471142301.ns0417s57.
Grimm, D, and M A Kay. "From virus evolution to vector revolution: use of naturally occurring serotypes of adeno-associated virus (AAV) as novel vectors for human gene therapy." Current gene therapy vol. 3,4 (2003): 281-304. doi:10.2174/1566523034578285.
Grimm, Dirk et al. "In vitro and in vivo gene therapy vector evolution via multispecies interbreeding and retargeting of adeno-associated viruses." Journal of virology vol. 82,12 (2008): 5887-911. doi:10.1128/JVI.00254-08.
Grimm, Dirk, and Sergei Zolotukhin. "E Pluribus Unum: 50 Years of Research, Millions of Viruses, and One Goal—Tailored Acceleration of AAV Evolution." Molecular therapy : the journal of the American Society of Gene Therapy vol. 23,12 (2015): 1819-31. doi:10.1038/mt.2015.173.
Grosse, Stefanie et al. "Relevance of Assembly-Activating Protein for Adeno-associated Virus Vector Production and Capsid Protein Stability in Mammalian and Insect Cells." Journal of virology vol. 91,20 e01198-17. Sep. 27, 2017, doi:10.1128/JVI.01198-17.
Hansal, S A et al. "Induction of antigen-specific hyporesponsiveness by transplantation of hemopoietic cells containing an MHC class I transgene regulated by a lymphocyte-specific promoter." Journal of immunology (Baltimore, Md. : 1950) vol. 161,3 (1998): 1063-8.
Harvey, D M, and C T Caskey. "Inducible control of gene expression: prospects for gene therapy." Current opinion in chemical biology vol. 2,4 (1998): 512-8. doi:10.1016/s1367-5931(98)80128-2.
Herrmann, Anne-Kathrin et al. "A Robust and All-Inclusive Pipeline for Shuffling of Adeno-Associated Viruses." ACS synthetic biology vol. 8,1 (2019): 194-206. doi:10.1021/acssynbio.8b00373.
Herrmann, Anne-Kathrin et al. "Impact of the Assembly-Activating Protein on Molecular Evolution of Synthetic Adeno-Associated Virus Capsids." Human gene therapy vol. 30,1 (2019): 21-35. doi:10.1089/hum.2018.085.
Hildinger, Markus, and Alberto Auricchio. "Advances in AAV-mediated gene transfer for the treatment of inherited disorders." European journal of human genetics : EJHG vol. 12,4 (2004): 263-71. doi:10.1038/sj.ejhg.5201153.
Huang, Weiliang et al. "ReX: A suite of computational tools for the design, visualization, and analysis of chimeric protein libraries." BioTechniques vol. 60,2 91-4. Feb. 1, 2016, doi:10.2144/000114381.
International Search Report and Written Opinion for International Patent Application No. PCT/US2019/025026 dated Jul. 22, 2019, 18 pages.
Jimenez, V et al. "In vivo genetic engineering of murine pancreatic beta cells mediated by single-stranded adeno-associated viral vectors of serotypes 6, 8 and 9." Diabetologia vol. 54,5 (2011): 1075-86. doi:10.1007/s00125-011-2070-3.
Johnson, Philip R et al. "Vector-mediated gene transfer engenders long-lived neutralizing activity and protection against SIV infection in monkeys." Nature medicine vol. 15,8 (2009): 901-6. doi:10.1038/nm.1967.
Kapturczak, M H et al. "Adeno-associated virus (AAV) as a vehicle for therapeutic gene delivery: improvements in vector design and viral production enhance potential to prolong graft survival in pancreatic islet cell transplantation for the reversal of type 1 diabetes." Current molecular medicine vol. 1,2 (2001): 245-58. doi:10.2174/1566524013363979.
Kay, Mark A. "Selecting the Best AAV Capsid for Human Studies." Molecular therapy : the journal of the American Society of Gene Therapy vol. 23,12 (2015): 1800-1. doi:10.1038/mt.2015.206.
Keiser, Nicholas W et al. "Unique characteristics of AAV1, 2, and 5 viral entry, intracellular trafficking, and nuclear import define transduction efficiency in Hela cells." Human gene therapy vol. 22,11 (2011): 1433-44. doi:10.1089/hum.2011.044.
Kienle, Eike et al. "Engineering and evolution of synthetic adeno-associated virus (AAV) gene therapy vectors via DNA family shuffling." Journal of visualized experiments : JoVE,62 3819. Apr. 2, 2012, doi:10.3791/3819.
Kienle, Eike. "Secrets to finding the ideal mate:New insights into parameters that govern successful Adeno-associated virus (AAV) vector evolution." (2014).
Kikuchi, M et al. "Novel family shuffling methods for the in vitro evolution of enzymes." Gene vol. 236,1 (1999): 159-67. doi:10.1016/s0378-1119(99)00240-1.
Klein, T. et al. High-velocity microprojectiles for delivering nucleic acids into living cells. Nature 327, 70-73 (1987). https://doi.org/10.1038/327070a0.
Koerber, James T et al. "DNA shuffling of adeno-associated virus yields functionally diverse viral progeny." Molecular therapy : the journal of the American Society of Gene Therapy vol. 16,10 (2008): 1703-9. doi:10.1038/mt.2008.167.
Koerber, James T et al. "Molecular evolution of adeno-associated virus for enhanced glial gene delivery." Molecular therapy : the journal of the American Society of Gene Therapy vol. 17,12 (2009): 2088-95. doi:10.1038/mt.2009.184.
Kotin, R M. "Prospects for the use of adeno-associated virus as a vector for human gene therapy." Human gene therapy vol. 5,7 (1994): 793-801. doi:10.1089/hum.1994.5.7-793.
Kuck, Dirk et al. "Intranasal vaccination with recombinant adeno-associated virus type 5 against human papillomavirus type 16 L1." Journal of virology vol. 80,6 (2006): 2621-30. doi:10.1128/JVI.80.6.2621-2630.2006.
Lagos-Quintana, M et al. "Identification of novel genes coding for small expressed RNAs." Science (New York, N.Y.) vol. 294,5543 (2001): 853-8. doi:10.1126/science.1064921.
Lagos-Quintana, Mariana et al. "Identification of tissue-specific microRNAs from mouse." Current biology : CB vol. 12,9 (2002): 735-9. doi:10.1016/s0960-9822(02)00809-6.

(56) References Cited

OTHER PUBLICATIONS

Lagos-Quintana, Mariana et al. "New microRNAs from mouse and human." RNA (New York, N.Y.) vol. 9,2 (2003): 175-9. doi:10.1261/rna.2146903.
Lau, N C et al. "An abundant class of tiny RNAs with probable regulatory roles in Caenorhabditis elegans." Science (New York, N.Y.) vol. 294,5543 (2001): 858-62. doi:10.1126/science.1065062.
Lebkowski, J S et al. "Adeno-associated virus: a vector system for efficient introduction and integration of DNA into a variety of mammalian cell types." Molecular and cellular biology vol. 8,10 (1988): 3988-96. doi:10.1128/mcb.8.10.3988-3996.1988.
Lee, R C, and V Ambros. "An extensive class of small RNAs in Caenorhabditis elegans." Science (New York, N.Y.) vol. 294,5543 (2001): 862-4. doi:10.1126/science.1065329.
Leong, Steven R et al. "Optimized expression and specific activity of IL-12 by directed molecular evolution." Proceedings of the National Academy of Sciences of the United States of America vol. 100,3 (2003): 1163-8. doi:10.1073/pnas.0237327100.
Lerch, Thomas F, and Michael S Chapman. "Identification of the heparin binding site on adeno-associated virus serotype 3B (AAV-3B)." Virology vol. 423,1 (2012): 6-13. doi:10.1016/j.virol.2011.10.007.
Li, Chengwen et al. "Adeno-associated virus vectors: potential applications for cancer gene therapy." Cancer gene therapy vol. 12,12 (2005): 913-25. doi:10.1038/sj.cgt.7700876.
Li, Wuping et al. "Engineering and selection of shuffled AAV genomes: a new strategy for producing targeted biological nanoparticles." Molecular therapy : the journal of the American Society of Gene Therapy vol. 16,7 (2008): 1252-60. doi:10.1038/mt.2008.100.
Li, X et al. "Synthetic muscle promoters: activities exceeding naturally occurring regulatory sequences." Nature biotechnology vol. 17,3 (1999): 241-5. doi:10.1038/6981.
Lim, Lee P et al. "The microRNAs of Caenorhabditis elegans." Genes & development vol. 17,8 (2003): 991-1008. doi:10.1101/gad.1074403.
Lim, Lee P et al. "Vertebrate microRNA genes." Science (New York, N.Y.) vol. 299,5612 (2003): 1540. doi:10.1126/science.1080372.
Lima, Maria J et al. "Generation of Functional Beta-Like Cells from Human Exocrine Pancreas." PloS one vol. 11,5 e0156204. May 31, 2016, doi:10.1371/journal.pone.0156204.
Limberis, Maria P et al. "Intranasal antibody gene transfer in mice and ferrets elicits broad protection against pandemic influenza." Science translational medicine vol. 5,187 (2013): 187ra72. doi:10.1126/scitranslmed.3006299.
Limberis, Maria P et al. "Vectored expression of the broadly neutralizing antibody FI6 in mouse airway provides partial protection against a new avian influenza A virus, H7N9." Clinical and vaccine immunology : CVI vol. 20, 12 (2013): 1836-7. doi:10.1128/CVI.00545-13.
Lin, Jianping et al. "A new genetic vaccine platform based on an adeno-associated virus isolated from a rhesus macaque." Journal of virology vol. 83,24 (2009): 12738-50. doi:10.1128/JVI.01441-09.
Lisowski, Leszek et al. "Selection and evaluation of clinically relevant AAV variants in a xenograft liver model." Nature vol. 506,7488 (2014): 382-6. doi:10.1038/nature12875.
Lochrie, Michael A et al. "Mutations on the external surfaces of adeno-associated virus type 2 capsids that affect transduction and neutralization." Journal of virology vol. 80,2 (2006): 821-34. doi:10.1128/JVI.80.2.821-834.2006.
Loiler, S A et al. "Targeting recombinant adeno-associated virus vectors to enhance gene transfer to pancreatic islets and liver." Gene therapy vol. 10,18 (2003): 1551-8. doi:10.1038/sj.gt.3302046.
Magari, S R et al. "Pharmacologic control of a humanized gene therapy system implanted into nude mice." The Journal of clinical investigation vol. 100, 11 (1997): 2865-72. doi:10.1172/JCI119835.
Maheshri, Narendra et al. "Directed evolution of adeno-associated virus yields enhanced gene delivery vectors." Nature biotechnology vol. 24,2 (2006): 198-204. doi:10.1038/nbt1182.
Mallol, Cristina et al. "AAV-mediated pancreatic overexpression of Igf1 counteracts progression to autoimmune diabetes in mice." Molecular metabolism vol. 6,7 664-680. May 17, 2017, doi:10.1016/j.molmet.2017.05.007.
Mannino, R J, and S Gould-Fogerite. "Liposome mediated gene transfer." BioTechniques vol. 6,7 (1988): 682-90.
Martini, Sabrina V et al. "Tyrosine Mutation in AAV9 Capsid Improves Gene Transfer to the Mouse Lung." Cellular physiology and biochemistry : international journal of experimental cellular physiology, biochemistry, and pharmacology vol. 39,2 (2016): 544-53. doi:10.1159/000445646.
Matsuoka, Taka-Aki et al. "Mafa Enables Pdx1 to Effectively Convert Pancreatic Islet Progenitors and Committed Islet α-Cells Into β-Cells In Vivo." Diabetes vol. 66,5 (2017): 1293-1300. doi:10.2337/db16-0887.
Mays, Lauren E et al. "Mapping the structural determinants responsible for enhanced T cell activation to the immunogenic adeno-associated virus capsid from isolate rhesus 32.33." Journal of virology vol. 87,17 (2013): 9473-85. doi:10.1128/JVI.00596-13.
Meliani, Amine et al. "Determination of anti-adeno-associated virus vector neutralizing antibody titer with an in vitro reporter system." Human gene therapy methods vol. 26,2 (2015): 45-53. doi:10.1089/hgtb.2015.037.
Miyatake, S et al. "Transcriptional targeting of herpes simplex virus for cell-specific replication." Journal of virology vol. 71,7 (1997): 5124-32. doi:10.1128/JVI.71.7.5124-5132.1997.
Mowat, F M et al. "Tyrosine capsid-mutant AAV vectors for gene delivery to the canine retina from a subretinal or intravitreal approach." Gene therapy vol. 21,1 (2014): 96-105. doi:10.1038/gt.2013.64.
Mueller, Christian et al. "Human Treg responses allow sustained recombinant adeno-associated virus-mediated transgene expression." The Journal of clinical investigation vol. 123,12 (2013): 5310-8. doi:10.1172/JCI70314.
Münch, Robert C et al. "Displaying high-affinity ligands on adeno-associated viral vectors enables tumor cell-specific and safe gene transfer." Molecular therapy : the journal of the American Society of Gene Therapy vol. 21,1 (2013): 109-18. doi:10.1038/mt.2012.186.
Muzyczka, N. "Use of adeno-associated virus as a general transduction vector for mammalian cells." Current topics in microbiology and immunology vol. 158 (1992): 97-129. doi:10.1007/978-3-642-75608-5_5.
Nair, Gopika G et al. "Recapitulating endocrine cell clustering in culture promotes maturation of human stem-cell-derived β cells." Nature cell biology vol. 21,2 (2019): 263-274. doi:10.1038/s41556-018-0271-4.
Naumer, Matthias et al. "Properties of the adeno-associated virus assembly-activating protein." Journal of virology vol. 86,23 (2012): 13038-48. doi:10.1128/JVI.01675-12.
Ness, J E et al. "DNA shuffling of subgenomic sequences of subtilisin." Nature biotechnology vol. 17,9 (1999): 893-6. doi:10.1038/12884.
Nieto, Karen et al. "Combined prophylactic and therapeutic intranasal vaccination against human papillomavirus type-16 using different adeno-associated virus serotype vectors." Antiviral therapy vol. 14,8 (2009): 1125-37. doi:10.3851/IMP1469.
Nieto, Karen et al. "Intranasal vaccination with AAV5 and 9 vectors against human papillomavirus type 16 in rhesus macaques." Human gene therapy vol. 23,7 (2012): 733-41. doi:10.1089/hum.2011.202.
No, D et al. "Ecdysone-inducible gene expression in mammalian cells and transgenic mice." Proceedings of the National Academy of Sciences of the United States of America vol. 93,8 (1996): 3346-51. doi:10.1073/pnas.93.8.3346.
Nonnenmacher, Mathieu et al. "High capsid-genome correlation facilitates creation of AAV libraries for directed evolution." Molecular therapy : the journal of the American Society of Gene Therapy vol. 23,4 (2015): 675-82. doi:10.1038/mt.2015.3.
Odelberg, S J et al. "Template-switching during DNA synthesis by Thermus aquaticus DNA polymerase I." Nucleic acids research vol. 23,11 (1995): 2049-57. doi:10.1093/nar/23.11.2049.

(56) References Cited

OTHER PUBLICATIONS

Pääbo, S et al. "DNA damage promotes jumping between templates during enzymatic amplification." The Journal of biological chemistry vol. 265,8 (1990): 4718-21.
Paulk, Nicole K et al. "Bioengineered AAV Capsids with Combined High Human Liver Transduction In Vivo and Unique Humoral Seroreactivity." Molecular therapy : the journal of the American Society of Gene Therapy vol. 26, 1 (2018): 289-303. doi:10.1016/j.ymthe.2017.09.021.
Paulk, Nicole K et al. "Bioengineered Viral Platform for Intramuscular Passive Vaccine Delivery to Human Skeletal Muscle." Molecular therapy. Methods & clinical development vol. 10 144-155. Jul. 24, 2018, doi:10.1016/j.omtm.2018.06.001.
Pekrun, K. et al. "Screening of Barcoded Capsid Shuffled AAV Libraries Results in the Selection of Capsids with Enhanced Transduction Efficiency for Human Islets", Molecular Therapy,vol. 26, No. 5S1, May 1, 2018 (May 1, 2018), p. 41.
Pekrun, Katja et al. "Evolution of a human immunodeficiency virus type 1 variant with enhanced replication in pig-tailed macaque cells by DNA shuffling." Journal of virology vol. 76,6 (2002): 2924-35. doi:10.1128/jvi.76.6.2924-2935.2002.
Pekrun, Katja et al. "Using a barcoded AAV capsid library to select for clinically relevant gene therapy vectors." JCI insight vol. 4,22 e131610. Nov. 14, 2019, doi:10.1172/jci.insight.131610.
Piccioli, P et al. "Neuroantibodies: ectopic expression of a recombinant anti-substance P antibody in the central nervous system of transgenic mice." Neuron vol. 15,2 (1995): 373-84. doi:10.1016/0896-6273(95)90041-1.
Piccioli, P et al. "Neuroantibodies: molecular cloning of a monoclonal antibody against substance P for expression in the central nervous system." Proceedings of the National Academy of Sciences of the United States of America vol. 88, 13 (1991): 5611-5. doi:10.1073/pnas.88.13.5611.
Pillay, Sirika, and Jan E Carette. "Host determinants of adeno-associated viral vector entry." Current opinion in virology vol. 24 (2017): 124-131. doi:10.1016/j.coviro.2017.06.003.
Ploquin, Aurélie et al. "Protection against henipavirus infection by use of recombinant adeno-associated virus-vector vaccines." The Journal of infectious diseases vol. 207,3 (2013): 469-78. doi:10.1093/infdis/jis699.
Powell, S K et al. "Breeding of retroviruses by DNA shuffling for improved stability and processing yields." Nature biotechnology vol. 18,12 (2000): 1279-82. doi:10.1038/82391.
Quirin, Kayla A et al. "Safety and Efficacy of AAV Retrograde Pancreatic Ductal Gene Delivery in Normal and Pancreatic Cancer Mice." Molecular therapy. Methods & clinical development vol. 8 8-20. Sep. 30, 2017, doi:10.1016/j.omtm.2017.09.006.
Raillard, S et al. "Novel enzyme activities and functional plasticity revealed by recombining highly homologous enzymes." Chemistry & biology vol. 8,9 (2001): 891-8. doi:10.1016/s1074-5521(01)00061-8.
Russ, Holger A et al. "Controlled induction of human pancreatic progenitors produces functional beta-like cells in vitro." The EMBO journal vol. 34,13 (2015): 1759-72. doi:10.15252/embj.201591058.
Sakata, Naoaki et al. "Pleckstrin homology-like domain family A, member 3 (PHLDA3) deficiency improves islets engraftment through the suppression of hypoxic damage." PloS one vol. 12,11 e0187927. Nov. 9, 2017, doi:10.1371/journal.pone.0187927.
Sandig, V et al. "HBV-derived promoters direct liver-specific expression of an adenovirally transduced LDL receptor gene." Gene therapy vol. 3,11 (1996): 1002-9.
Shelling, A N, and M G Smith. "Targeted integration of transfected and infected adeno-associated virus vectors containing the neomycin resistance gene." Gene therapy vol. 1,3 (1994): 165-9.
Shigekawa, K, and W J Dower. "Electroporation of eukaryotes and prokaryotes: a general approach to the introduction of macromolecules into cells." BioTechniques vol. 6,8 (1988): 742-51.
Sipo, Isaac et al. "Vaccine protection against lethal homologous and heterologous challenge using recombinant AAV vectors expressing codon-optimized genes from pandemic swine origin influenza virus (SOIV)." Vaccine vol. 29,8 (2011): 1690-9. doi:10.1016/j.vaccine.2010.12.037.
Song, Liujiang et al. "High-efficiency transduction of primary human hematopoietic stem cells and erythroid lineage-restricted expression by optimized AAV6 serotype vectors in vitro and in a murine xenograft model in vivo." PloS one vol. 8,3 (2013): e58757. doi:10.1371/journal.pone.0058757.
Song, Liujiang et al. "Optimizing the transduction efficiency of capsid-modified AAV6 serotype vectors in primary human hematopoietic stem cells in vitro and in a xenograft mouse model in vivo." Cytotherapy vol. 15,8 (2013): 986-98. doi:10.1016/j.jcyt.2013.04.003.
Song, Z, Galivo, FH, Adachi, K, Grompe, M, Nakai, H (2017). Strong Alpha Cell Preference of the AAV Strains That Best Transduce Human Pancreatic Islets In Vitro. Molecular Therapy 25: 47.
Sonntag, F et al. "The assembly-activating protein promotes capsid assembly of different adeno-associated virus serotypes." Journal of virology vol. 85,23 (2011): 12686-97. doi:10.1128/JVI.05359-11.
Sonntag, Florian et al. "A viral assembly factor promotes AAV2 capsid formation in the nucleolus." Proceedings of the National Academy of Sciences of the United States of America vol. 107,22 (2010): 10220-5. doi:10.1073/pnas.1001673107.
Soong, N W et al. "Molecular breeding of viruses." Nature genetics vol. 25,4 (2000): 436-9. doi:10.1038/78132.
Stamatakis, A et al. "RAxML-III: a fast program for maximum likelihood-based inference of large phylogenetic trees." Bioinformatics (Oxford, England) vol. 21,4 (2005): 456-63. doi:10.1093/bioinformatics/bti191.
Stamatakis, Alexandros. "Using RAxML to Infer Phylogenies." Current protocols in bioinformatics vol. 51 6.14.1-6.14.14. Sep. 3, 2015, doi:10.1002/0471250953.bi0614s51.
Stein, G S et al. "The osteocalcin gene: a model for multiple parameters of skeletal-specific transcriptional control." Molecular biology reports vol. 24,3 (1997): 185-96. doi:10.1023/a:1006803615430.
Stemmer, W P. "DNA shuffling by random fragmentation and reassembly: in vitro recombination for molecular evolution." Proceedings of the National Academy of Sciences of the United States of America vol. 91,22 (1994): 10747-51. doi:10.1073/pnas.91.22.10747.
Stemmer, W P. "Rapid evolution of a protein in vitro by DNA shuffling." Nature vol. 370,6488 (1994): 389-91. doi:10.1038/370389a0.
Stutzman-Engwall, Kim et al. "Semi-synthetic DNA shuffling of aveC leads to improved industrial scale production of doramectin by *Streptomyces avermitilis*." Metabolic engineering vol. 7,1 (2005): 27-37. doi:10.1016/j.ymben.2004.07.003.
Tervo, D Gowanlock R et al. "A Designer AAV Variant Permits Efficient Retrograde Access to Projection Neurons." Neuron vol. 92,2 (2016): 372-382. doi:10.1016/j.neuron.2016.09.021.
Thomas, Clare E et al. "Rapid uncoating of vector genomes is the key to efficient liver transduction with pseudotyped adeno-associated virus vectors." Journal of virology vol. 78,6 (2004): 3110-22. doi:10.1128/jvi.78.6.3110-3122.2004.
Toole, J J et al. "Molecular cloning of a cDNA encoding human antihaemophilic factor." Nature vol. 312,5992 (1984): 342-7. doi:10.1038/312342a0.
Vasileva, Ana, and Rolf Jessberger. "Precise hit: adeno-associated virus in gene targeting." Nature reviews. Microbiology vol. 3,11 (2005): 837-47. doi:10.1038/nrmicro1266.
Vehar, G A et al. "Structure of human factor VIII." Nature vol. 312,5992 (1984): 337-42. doi:10.1038/312337a0.
Vieira, A et al. "β-Cell replacement as a treatment for type 1 diabetes: an overview of possible cell sources and current axes of research." Diabetes, obesity & metabolism vol. 18 Suppl 1 (2016): 137-43. doi:10.1111/dom.12721.
Wang, Xiaojie et al. "Improving islet engraftment by gene therapy." Journal of transplantation vol. 2011 (2011): 594851. doi:10.1155/2011/594851.
Wang, Y et al. "Ligand-inducible and liver-specific target gene expression in transgenic mice." Nature biotechnology vol. 15,3 (1997): 239-43. doi:10.1038/nbt0397-239.

(56) References Cited

OTHER PUBLICATIONS

Wang, Y et al. "Positive and negative regulation of gene expression in eukaryotic cells with an inducible transcriptional regulator." Gene therapy vol. 4,5 (1997): 432-41. doi:10.1038/sj.gt.3300402.
Wang, Yuhan et al. "Long-Term Correction of Diabetes in Mice by In Vivo Reprogramming of Pancreatic Ducts." Molecular therapy : the journal of the American Society of Gene Therapy vol. 26,5 (2018): 1327-1342. doi:10.1016/j.ymthe.2018.02.014.
Wang, Zhong et al. "Widespread and stable pancreatic gene transfer by adeno-associated virus vectors via different routes." Diabetes vol. 55,4 (2006): 875-84. doi:10.2337/diabetes.55.04.06.db05-0927.
Ward, Peter, and Christopher E Walsh. "Chimeric AAV Cap sequences alter gene transduction." Virology vol. 386,2 (2009): 237-48. doi:10.1016/j.virol.2009.01.012.
Wood, W I et al. "Expression of active human factor VIII from recombinant DNA clones." Nature vol. 312,5992 (1984): 330-7. doi:10.1038/312330a0.
Wright, Anne et al. "Diverse plasmid DNA vectors by directed molecular evolution of cytomegalovirus promoters." Human gene therapy vol. 16,7 (2005): 881-92. doi:10.1089/hum.2005.16.881.
Wu, Jianqing et al. "Self-complementary recombinant adeno-associated viral vectors: packaging capacity and the role of rep proteins in vector purity." Human gene therapy vol. 18,2 (2007): 171-82. doi:10.1089/hum.2006.088.
Xiao, Xiangwei et al. "Endogenous Reprogramming of Alpha Cells into Beta Cells, Induced by Viral Gene Therapy, Reverses Autoimmune Diabetes." Cell stem cell vol. 22,1 (2018): 78-90.e4. doi:10.1016/j.stem.2017.11.020.
Xie, Qing et al. "Structure-function analysis of receptor-binding in adeno-associated virus serotype 6 (AAV-6)." Virology vol. 420,1 (2011): 10-9. doi:10.1016/j.virol.2011.08.011.
Yan, Ziying et al. "Ferret and pig models of cystic fibrosis: prospects and promise for gene therapy." Human gene therapy. Clinical development vol. 26,1 (2015): 38-49. doi:10.1089/humc.2014.154.
Yang, Lin et al. "A myocardium tropic adeno-associated virus (AAV) evolved by DNA shuffling and in vivo selection." Proceedings of the National Academy of Sciences of the United States of America vol. 106,10 (2009): 3946-51. doi:10.1073/pnas.0813207106.
Zhang, J H et al. "Directed evolution of a fucosidase from a galactosidase by DNA shuffling and screening." Proceedings of the National Academy of Sciences of the United States of America vol. 94,9 (1997): 4504-9. doi:10.1073/pnas.94.9.4504.
Zhang, Yanqing et al. "PAX4 Gene Transfer Induces α-to-β Cell Phenotypic Conversion and Confers Therapeutic Benefits for Diabetes Treatment." Molecular therapy : the journal of the American Society of Gene Therapy vol. 24,2 (2016): 251-260. doi:10.1038/mt.2015.181.
Zhao, Chunxia et al. "Overcoming Insulin Insufficiency by Forced Follistatin Expression in β-cells of db/db Mice." Molecular therapy : the journal of the American Society of Gene Therapy vol. 23,5 (2015): 866-874. doi:10.1038/mt.2015.29.
Zhao, H et al. "Molecular evolution by staggered extension process (StEP) in vitro recombination." Nature biotechnology vol. 16,3 (1998): 258-61. doi: 10.1038/nbt0398-258.
Zhong, Li et al. "Next generation of adeno-associated virus 2 vectors: point mutations in tyrosines lead to high-efficiency transduction at lower doses." Proceedings of the National Academy of Sciences of the United States of America vol. 105,22 (2008): 7827-32. doi:10.1073/pnas.0802866105.
Zhou, Liqiao et al. "Long-term protection against human papillomavirus e7-positive tumor by a single vaccination of adeno-associated virus vectors encoding a fusion protein of inactivated e7 of human papillomavirus 16/18 and heat shock protein 70." Human gene therapy vol. 21,1 (2010): 109-19. doi:10.1089/hum.2009.139.
Zhou, S Z et al. "Adeno-associated virus 2-mediated high efficiency gene transfer into immature and mature subsets of hematopoietic progenitor cells in human umbilical cord blood." The Journal of experimental medicine vol. 179,6 (1994): 1867-75. doi:10.1084/jem.179.6.1867.
Zinn, Eric et al. "In Silico Reconstruction of the Viral Evolutionary Lineage Yields a Potent Gene Therapy Vector." Cell reports vol. 12,6 (2015): 1056-68. doi:10.1016/j.celrep.2015.07.019.
Zhong et al., "A Rationally Engineered Novel Capsid Variant of AAV9 for Peripheral Tissue-Detargeted and CNS-Directed Systemic Gene Delivery." Molecular Therapy. vol. 22, Supplement 1, May 2014, p. S112. doi: 10.1016/S1525-0016(16)35303-5.

* cited by examiner

REPLACEMENT SHEET
41/70

Ventral

Dorsal

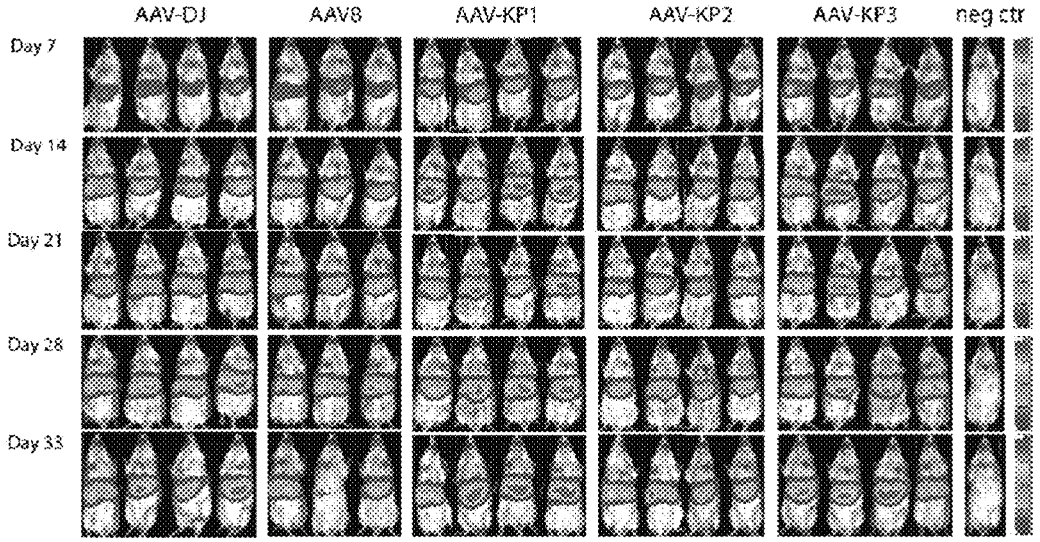
FIGURE 64B
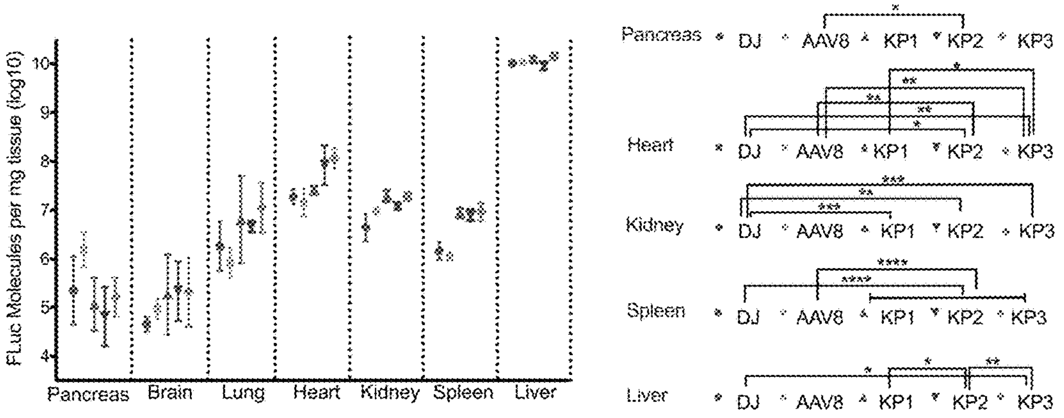
FIGURE 64C
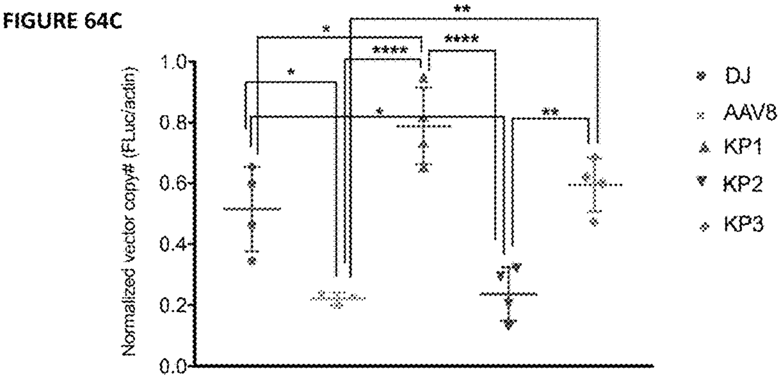

SEQUENCE LISTING

```
Sequence total quantity: 128
SEQ ID NO: 1           moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 1
MAADGYLPDW LEDTLSEGIR QWWKLKPGPP PPKPAERHKD DSRGLVLPGY KYLGPGNGLD  60
KGEPVNAADA AALEHDKAYD QQLKAGDNPY LRYNHADAEF QERLQEDTSF GGNLGRAVFQ  120
AKKRVLEPLG LVEEPVKTAP GKKRPVEHSP VEPDSSSGTG KAGQQPARKR LNFGQTGDTD  180
SAADPQPLGE PPAAPSGLGT GTMAAGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTQNEGT KTIANNLTST VQVFTDSEYQ LPYVLGSAHQ  360
GCLPPFPADV FMIPQYGYLT LNNGSQAMGR SSFYCLEYFP SQMLRTGNNF QFTYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQILI KNTPVPADPP  660
TAFNKDKLNS FITQYSTGQV SVEIEWELQK ENSKRWNPEI QYTSNYYKST SVDFAVNTEG  720
VYSEPRPIGT RYLTRNL                                                 737

SEQ ID NO: 2           moltype = AA  length = 738
FEATURE                Location/Qualifiers
REGION                 1..738
                       note = source = /note="Description of Artificial Sequence:
                        Syntheticpolypeptide"
source                 1..738
                       mol_type = protein
                       organism = synthetic construct
SEQUENCE: 2
MAADGYLPDW LEDTLSEGIR QWWKLKPGPP PPKPAERHKD DSRGLVLPGY KYLGPFNGLD  60
KGEPVNEADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGNASGNWH CDSTWLGDRV  240
ITTSTRTWAL PTYNNHLYKQ ISSASTGASN DNHYFGYSTP WGYFDFNRFH CHFSPRDWQR  300
LINNNWGFRP KRLNFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFSYTFEDV  420
PFHSSYAHSQ SLDRLMNPLI DQYLYYLNRT QGTTSGTTNQ SRLLFSQAGP QSMSLQARNW  480
LPGPCYRQQR LSKTANDNNN SNFPWTAASK YHLNGRDSLV NPGPAMASHK DDEEKFFPMH  540
GNLIFGKEGT TASNAELDNV MITDEEEIRT TNPVATEQYG TVANNLQSSN TAPTTRTVND  600
QGALPGMVWQ DRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738

SEQ ID NO: 3           moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 3
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRLLEPLG LVEEAAKTAP GKKRPVEQSP QEPDSSSGIG KTGQQPAKKR LNFGQTGDTE  180
SVPDPQPLGE PPAAPTSLGS NTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK KLSFKLFNIQ VKEVTQNDGT TTIANNLTST IQVFTDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRPL                                                 737

SEQ ID NO: 4           moltype = AA  length = 737
```

```
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 4
MAADGYLPDW LEDNLSEGIR EWWDLKPGAP KPKANQQKQD DARGLVLPGY KYLGPGNGLD  60
KGEPVNAADA AALEHDKAYD QQLQAGDNPY LRYNHADAEF QERLQEDTSF GGNLGRAVFQ  120
AKKRVLEPLG LVEEAAKTAP GKKRPVEQSP QEPDSSSGIG KTGQQPAKKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQILI KNTPVPANPP  660
AEFSATKFAS FITQYSTGQV SVEIEWELQK ENSKRWNPEI QYTSNYNKSV NVDFTVDTNG  720
VYSEPRPIGT RYLTRPL                                                737

SEQ ID NO: 5           moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 5
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEHSP VEPDSSSGIG KTGQQPAKKR LNFGQTGDAD  180
SVPDPQPLGQ PPAAPSGLGT NTMATGSGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTQNEGT TTIANNLTST VQVFTDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRPL                                                737

SEQ ID NO: 6           moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 6
MAADGYLPDW LEDNLSEGIR QWWKLKPGPP PPKPAERHKD DSRGLVLPGY KYLGPFNGLD  60
KGEPVNAADA AALEHDKAYD QQLKAGDNPY LRYNHADAEF QERLKEDTSF GGNLGRAVFQ  120
AKKRVLEPLG LVEEGAKTAP GKKRPVEHSP VEPDSSSGIG KTGQQPAKKR LNFGQTGDSE  180
SVPDPQPLGE PPAAPSGLGT NTMASGGGAP MADNNEGADG VGNSSGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFTDSEYQ LPYVLGSAHQ  360
GCLPPFPADV FMVPQYGYLT LNNGSQAVGR SSFYCLEYFP SQMLRTGNNF QFTYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRPL                                                737

SEQ ID NO: 7           moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 7
MAADGYLPDW LEDTLSEGIR QWWKLKPGPP PPKPAERHKD DSRGLVLPGY KYLGPFNGLD  60
KGEPVNAADA AALEHDKAYD QQLKAGDNPY LRYNHADAEF QERLQEDTSF GGNLGRAVFQ  120
```

```
AKKRLLEPLG LVEEAAKTAP GKKRPVEHSP VEPDSSSGTG KAGQQPAKKR LNFGQTGDSE  180
SVPDPQPLGE PPAAPSGVGP NTMAAGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLSFKLFNIQ VKEVTTNDGV TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRPL                                                737

SEQ ID NO: 8           moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 8
MAADGYLPDW LEDNLSEGIR EWWALQPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPIGE PPAGPSGLGT GTMASGSGAP MADNNEGADG VGNSSGNWHC DSQWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST IQVFTDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRPL                                                737

SEQ ID NO: 9           moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 9
MAADGYLPDW LEDTLSEGIR QWWKLKPGPP PPKPAERHKD DSRGLVLPGY KYLGPFNGLD  60
KGEPVNAADA AALEHDKAYD QQLKAGDNPY LRYNHADAEF QERLKEDTSF GGNLGRAVFQ  120
AKKRVLEPFG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK KLSFKLFNIQ VKEVTQNEGT KTIANNLTST IQVFTDSEYQ LPYVLGSAHQ  360
GCLPPFPADV FMIPQYGYLT LNNGSQAVGR SSFYCLEYFP SQMLRTGNNF QFTYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG MKHPPPQILI KNTPVPADPP  660
TAFNKDKLNS FITQYSTGQV SVEIEWELQK ENSKRWNPEI QYTSNYYKST SVDFAVNTEG  720
VYSEPRPIGT RYLTRNL                                                737

SEQ ID NO: 10          moltype = AA  length = 736
FEATURE                Location/Qualifiers
REGION                 1..736
                       note = source = /note="Description of Artificial Sequence:
                        Syntheticpolypeptide"
source                 1..736
                       mol_type = protein
                       organism = synthetic construct
SEQUENCE: 10
MAADGYLPDW LEDTLSEGIR QWWKLKPGPP PPKPAERHKD DSRGLVLPGY KYLGPFNGLD  60
KGEPVNEADA AALEHDKAYD QQLKAGDNPY LKYNHADAEF QERLKEDTSF GGNLGRAVFQ  120
AKKRVLEPLG LVEEAAKTAP GKKRPVEHSP VEPDSSSGTG KAGQQPARKR LNFGQTGDAD  180
SVPDPQPLGE PPAAPTSLGS NTMASGGGAP MADNNEGADG VGSSSGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTQNEGT KTIANNLTST IQVFTDSEYQ LPYVLGSAHQ  360
GCLPPFPADV FMIPQYGYLT LNNGSQAMGR SSFYCLEYFP SQMLRTGNNF TFSYTFEDVP  420
FHSSYAHSQS LDRLMNPLID QYLYYLSRTQ STGGTAGTQQ LLFSQAGPNN MSAQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTRTVNDQG  600
ALPGMVWQDR DVYLQGPIWA KIPHTDGHFH PSPLMGGFGL KHPPPQILIK NTPVPADPPT  660
TFNQSKLNSF ITQYSTGQVS VEIEWELQKE NSKRWNPEIQ YTSNYNKSVN VDFTVDTNGV  720
```

```
YSEPRPIGTR YLTRNL                                                 736

SEQ ID NO: 11          moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 11
MAADGYLPDW LEDTLSEGIR QWWKLKPGPP PPKPAERHKD DSRGLVLPGY KYLGPFNGLD  60
KGEPVNAADA AALEHDKAYD QQLKAGDNPY LRYNHADAEF QERLQEDTSF GGNLGRAVFQ  120
AKKRLLEPLG LVEEAAKTAP GKKRPVEHSP VEPDSSSGTG KAGQQPARKR LNFGQTGDAD  180
SVPDPQPLGE PPAAPTSLGS NTMATGSGAP MADNNEGADG VGNSSGNWHC DSQWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQILI KNTPVPANPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 12          moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 12
MAADGYLPDW LEDTLSEGIR QWWKLKPGPP PPKPAERHKD DSRGLVLPGY KYLGPFNGLD  60
KGEPVNAADA AALEHDKAYD QQLKAGDNPY LRYNHADAEF QERLQEDTSF GGNLGRAVFQ  120
AKKRVLEPFG LVEEGAKTAP GKKRPVEHSP VEPDSSSGTG KAGQQPARKR LNFGQTGDSE  180
SVPDPQPLGE PPAAPSGVGP NTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYYKST SVDFAVNTEG  720
VYSEPRPIGT RYLTRNL                                                737

SEQ ID NO: 13          moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 13
MAADGYLPDW LEDNLSEGIR EWWDLKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRLLEPLG LVEEAAKTAP GKKRPVEHSP VEPDSSSGTG KAGQQPARKR LNFGQTGDAD  180
SVPDPQPIGE PPAAPSGVGS LTMAAGGGAP MADNNEGADG VGNSSGNWHC DSTWMGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRPL                                                737

SEQ ID NO: 14          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
```

```
SEQUENCE: 14
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tccgggttac aaatacctcg gacccggcaa cggactcgac  180
aagggggagc ccgtcaacgc ggcggacgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aacctgttaa gacggctccg  420
ggaaaaaaga ggccggtaga gcactctcct gtggagccag actcctcctc gggaaccgga  480
aaggcgggcc agcagcctgc gaggaagcga ctcaactttg gtcagactgg agacaccgac  540
tccgccgctg acccccagcc tctcggagaa ccaccagcag ccccctctgg tctgggaact  600
ggtacaatgg ctgcaggcgg tggcgctcca atggcagaca ataacgaagg cgccgacgga  660
gtgggtaatg cctcgggaaa ttggcattgc gattccacat ggctgggcga cagagtcatc  720
accaccagca cccgcacctg ggccttgccc acctacaata accacctcta caagcaaatc  780
tccagtgctt caacgggggc cagcaacgac aaccactact tcggctacag cacccccctgg  840
gggtactttg acttcaaccg cttccactgc cacttctcac cacgtgactg gcaaagactc  900
atcaacaaca actggggatt ccggcccaag agactcaact tcaagctctt caacatccag  960
gtcaaggagg tcacgcagaa tgaaggcacc aagaccatcg ccaataacct taccagcacg  1020
gttcaggtgt ttactgactc ggagtaccag ctgccgtacg ttctcggctc tgcccaccag  1080
ggctgcctgc ctccgttccc ggcggacgtg ttcatgattc cgcagtacgg ctacctaacg  1140
ctcaacaatg gcagccaggc gatgggtcgc tcgtccttct actgcctgga gtactttccg  1200
tcgcagatgc tgagaaccgg caacaacttc cagtttactt acaccttcga ggacgtgcct  1260
ttccacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aatttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg cggctttggc  1920
ctgaaacatc ctccgcctca gatcctgatc aagaacacgc ctgtacctgc ggatcctcca  1980
acggccttca acaaggacaa gctgaactct ttcatcaccc agtattctac tggccaagtc  2040
agcgtggaga tcgagtggga gctgcagaag gaaaacagca agcgctggaa ccccgagatc  2100
cagtacacct ccaactacta caaatctaca agtgtggact ttgctgttaa tacagaaggc  2160
gtgtactctg aaccccgccc cattggcacc cgttacctca cccgtaatct gtaa        2214

SEQ ID NO: 15           moltype = DNA  length = 2217
FEATURE                 Location/Qualifiers
misc_feature            1..2217
                        note = source = /note="Description of Artificial Sequence:
                         Syntheticpolynucleotide"
source                  1..2217
                        mol_type = other DNA
                        organism = synthetic construct
SEQUENCE: 15
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aaaggagagc cggtcaacga ggcggatgca gcggccctcg agcacgacaa ggcctacgac  240
cagcagctca aagcgggtga caatccgtac cttcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccaacagcc cgccagaaaa agactcaatt ttggtcagac tggcgactca  540
gagtcagttc cagaccctca acctctcgga gaacctccag cagcgccctc tggtgtggga  600
cctaatacaa tggctgcagg cggtggcgca ccaatggcag acaataacga aggcgccgac  660
ggagtgggta atgcctcagg aaattggcat tgcgattcca catggctggg cgacagagtc  720
atcaccacca gcacccgcac ctgggccttg cccacctaca ataaccacct ctacaagcaa  780
atctccagtg cttcaacggg ggccagcaac gacaaccact acttcggcta cagcacccct  840
tgggggtatt ttgacttcaa cagattccac tgccactttt caccacgtga ctggcaaaga  900
ctcatcaaca acaactgggg attccgaccc aagagactca acttcaagct ctttaacatt  960
caagtcaaag aggtcacgca gaatgaaggc accaagacca tcgccaataa cctcaccagc  1020
accatccagg tgtttacgga ctcggagtac cagctgccgt acgttctcgg ctctgcccac  1080
cagggctgcc tgcctccgtt cccggcggac gtgttcatga ttccccagta cggctaccta  1140
acactcaaca acggtagtca ggccgtggga cgctcctcct tttactgcct ggagtacttc  1200
ccttcgcaga tgctaaggac tggaaataac ttccaattca gctatacctt cgaggatgta  1260
ccttttcaca gcagctacgc tcacagccag agtttggatc gcttgatgaa tcctcttatt  1320
gatcagtatc tgtactacct gaacagaacg caaggaacaa cctctggaac aaccaaccaa  1380
tcacggctgc tttttagcca ggctgggcct cagtctatgt ctttgcaggc cagaaattgg  1440
ctacctgggc cctgctaccg gcaacagaga ctttcaaaga ctgctaacga caacaacaac  1500
agtaactttc cttggacagc ggccagcaaa tatcatctca atggccgcga ctcgctggtg  1560
aatccaggac cagctatggc cagtcacaag gacgatgaag aaaaattttt ccctatgcac  1620
ggcaatctaa tatttggcaa agaagggaca acggcaagta acgcagaatt agataatgta  1680
atgattacgg atgaagaaga gattcgtacc accaatcctg tggcaacaga gcagtatgga  1740
actgtggcaa ataacttgca gagctcaaat acagctccca cgactagaac tgtcaatgat  1800
cagggggcct tacctggcat ggtgtggcaa gatagagacg tgtacctgca gggtcctatc  1860
```

```
tgggccaaga ttcctcacac ggacggaaac tttcatccct cgccgctgat gggaggcttt  1920
ggactgaaac acccgcctcc tcagatcctg atcaagaaca cgcctgtacc tgcggatcct  1980
ccgaccacct tcaaccagtc aaagctgaac tctttcatca cgcaatacag caccggacag  2040
gtcagcgtgg aaattgaatg ggagctgcag aaggaaaaca gcaagcgctg gaaccccgag  2100
atccagtaca cctccaacta ctacaaatct acaagtgtgg actttgctgt taatacagaa  2160
ggcgtgtact ctgaaccccg ccccattggc acccgttacc tcacccgtaa tctgtaa     2217

SEQ ID NO: 16          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 16
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaaaaaga ggcttcttga acctcttggt ctggttgagg aagcggctaa gacggctcct  420
ggaaagaaac gtccggtaga gcagtcgcca caagagccag actcctcctc gggcatcggc  480
aagacaggcc agcagcccgc taaaaagaga ctcaatttcg gtcagactgg cgacacagag  540
tcagtcccag accctcaacc tctcggagaa ccaccagcag cccccacaag tttgggatct  600
aatacaatgg cttcaggcgg tggcgcacca atggcagaca ataacgaagg cgccgacgga  660
gtgggtaatg cctcaggaaa ttggcattgc gattccacat ggctgggcga cagagtcatc  720
accaccagca cccgcacctg ggccttgccc acctacaata accacctcta caagcaaatc  780
tccagtgctt caacgggggc cagcaacgac aaccactact tcggctacag caccccctgg  840
gggtattttg atttcaacag attccactgc catttctcac cacgtgactg gcagcgactc  900
atcaacaaca attggggatt ccggcccaag aaactcagct tcaagctctt caacatccaa  960
gttaaagagg tcacgcagaa cgatggcacg acgactattg ccaataacct taccagcacg  1020
attcaggtct ttacggactc ggagtaccag ctgccgtacg ttctcggctc tgcccaccag  1080
ggctgcctcc ctccgttccc ggcggacgtg ttcatgattc cgcagtacgg ctacctaacg  1140
ctcaacaatg gcagccaagc cgtgggacgt tcatcctttt actgcctgga gtactttcct  1200
tctcaaatgc tgagaacggg caacaacttt accttcagct acacctttga ggaagtgcct  1260
ttccacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aatttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gccaagattc ctcacacgga tggacacttt catccttctc ctctgatggg aggctttgga  1920
ctgaaacatc cgcctcctca aatcatgatc aaaaatactc cggtaccggc aaatcctccg  1980
acgactttca gcccggccaa gtttgcttca tttatcacgc agtacagcac cggacaggtc  2040
agcgtggaaa ttgaatggga gctgcagaaa gaaaacagca aacgttggaa tccagagatt  2100
cagtacactt ccaactacaa caagtctgtt aatgtggact ttactgtaga cactaatggt  2160
gtttatagtg aacctcgccc cattggcacc cgttacctta cccgtcccct gtaa        2214

SEQ ID NO: 17          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 17
atggctgccg atggttatct tccagattgg ctcgaggaca acctttctga aggcattcgc  60
gagtggtggg acttgaaacc tggagccccg aaacccaaag ccaaccagca aaagcaggac  120
gacgctcggg gtcttgtgct tccgggttac aaataccttg gacccggcaa cggactcgac  180
aagggggagc ccgtcaacgc ggcggacgca gcggccctcg agcacgacaa agcctacgac  240
cagcagctgc aggcgggtga caatccgtac ctgcggtaca accacgccga cgcggagttt  300
caggagcgtc tgcaagaaga tacgtctttt gggggcaacc tcgggcgagc agtcttccag  360
gccaagaaga gggttctcga acctctcggt ctggttgagg aagcggctaa gacggctcct  420
ggaaagaaac gtccggtaga gcagtcgcca caagagccag actcctcctc gggcatcggc  480
aagacaggcc agcagcccgc taaaaagaga ctcaattttg gtcagactgg cgactcagag  540
tcagtcccag accctcaacc tctcggagaa ccaccagcag cccccacaag tttgggatct  600
aatacaatgg cttcaggcgg tggcgcacca atggcagaca ataacgaggg tgccgacgga  660
gtgggtaatt cctcgggaaa ttggcattgc gattcccaat ggctgggcga ccgagtcatc  720
accaccagca cccgcacctg ggccttgccc acctacaata accacctcta caagcaaatc  780
tccagtgctt caacgggggc cagcaacgac aaccactact tcggctacag caccccctgg  840
gggtattttg atttcaacag attccactgc cacttttcac cacgtgactg gcaaagactc  900
atcaacaaca actggggatt ccgacccaag agactcaact tcaaactctt caacatccaa  960
```

```
gtcaaggagg tcacgacgaa tgatggcgtc acgaccatcg ccaataacct taccagcacg  1020
gttcaagtgt ttacggactc ggagtatcag ctcccgtacg tgctcgggtc ggcgcaccaa  1080
ggctgtctcc cgccgtttcc agcggacgtc ttcatggtcc ctcagtatgg atacctcacc  1140
ctgaacaacg gaagtcaagc ggtgggacgc tcatcctttt actgcctgga gtacttccct  1200
tcgcagatgc taaggactgg aaataacttc caattcagct ataccttcga ggatgtacct  1260
tttcacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aatttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt cacccgtctc ctctcatggg cggctttgga  1920
cttaagcacc cgcctcctca gatcctcatc aaaaacacgc ctgttcctgc gaatcctccg  1980
gcagagtttt cggctacaaa gtttgcttca ttcatcaccc agtattccac aggacaagtg  2040
agcgtggaaa ttgaatggga gctgcagaaa gaaaacagca aacgctggaa tccagagatt  2100
cagtacactt ccaactacaa caagtctgtt aatgtggact ttactgtaga cactaatggt  2160
gtttatagtg aacctcgccc cattggcacc cgttacctca cccgtcccct gtaa        2214
```

```
SEQ ID NO: 18          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 18
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctca aagcgggtga caatccgtac cttcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggtgctaa gacggctcct  420
ggaaagaaac gtccggtaga gcactctcct gtggagccag actcctcctc gggcatcggc  480
aagacaggcc agcagcccgc taaaaagaga ctcaattttg gtcagactgg cgacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatg cctcaggaaa ttggcattgc gattccacat ggctgggcga cagagtcatc  720
accaccagca cccgaacatg ggccttgccc acctataaca accacctcta caagcaaatc  780
tccagtgctt caacgggggc cagcaacgac aaccactact tcggctacag caccccctgg  840
gggtactttg acttcaaccg cttccactgc cacttctccc cgcgagactg gcagcggctc  900
atcaacaaca actgggggtt ccggcccaag cgactcaact tcaagctctt caacatccag  960
gtcaaggagg tcacgcagaa tgaaggcacg acgactattg ccaataacct taccagcacg  1020
gttcaagtgt ttacggactc ggagtatcag ctcccgtacg tgctcggctc tgcccaccag  1080
ggctgcctgc ctccgttccc ggcggacgtg ttcatgattc cccagtacgg ctacctaaca  1140
ctcaacaacg gtagtcaggc cgtgggacgc tcctccttct actgcctgga atactttcct  1200
tctcagatgc tgcgtaccgg aaacaacttt accttcagct acacttttga ggacgttcct  1260
ttccacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aatttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg aggctttgga  1920
ctgaaacatc cgcctcctca aatcatgatc aaaaatactc cggtaccggc aaatcctccg  1980
acgactttca gcccggccaa gtttgcttca tttatcactc agtactccac tggacaggtc  2040
agcgtggaaa ttgagtggga gctacagaaa gaaaacagca aacgttggaa tccagagatt  2100
cagtacactt ccaactacaa caagtctgtt aatgtggact ttactgtaga cactaatggt  2160
gtttatagtg agcctcgccc cattggcacc cgttacctca cccgtcccct gtaa        2214
```

```
SEQ ID NO: 19          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 19
atggctgccg atggttatct tccagattgg ctcgaggaca acctctctga aggaataaga  60
```

-continued

```
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtaca accacgccga cgccgagttc  300
caggagcggc tcaaagaaga tacgtctttt gggggcaacc tcgggcgagc agtcttccag  360
gccaagaagc gggttctcga acctctcggt ctggttgagg aaggcgctaa gacggctcct  420
ggaaagaaga ggcctgtaga gcactctcct gtggagccag actcctcctc gggcatcggc  480
aagacaggcc agcagcccgc taaaaagaga ctcaattttg gtcagactgg cgactcagag  540
tcagtccccg acccacaacc tctcggagaa ccaccagcag ccccctctgg tctgggaact  600
aatacgatgg cttcaggcgg tggcgcacca atggcagaca ataacgaggg tgccgatgga  660
gtgggtaatt cctcaggaaa ttggcattgc gattccacat ggctgggcga cagagtcatc  720
accaccagca cccgaacctg ggccctgccc acctacaaca atcacctcta caagcaaatc  780
tccagtgctt caacgggggc cagcaacgac aaccactact tcggctacag caccccctgg  840
gggtattttg atttcaacag attccactgc cacttttcac cacgtgactg gcagcgactc  900
atcaacaaca attggggatt ccggcccaag agactcaact tcaagctctt caacatccaa  960
gtcaaggagg tcacgacgaa tgatggcgtc acgaccatcg ccaataacct taccagcacg  1020
gttcaagtgt ttacggactc ggagtaccag ctcccgtacg tcctcggctc ggcgcatcaa  1080
ggatgcctcc cgccgttccc agcagacgtc ttcatggtgc cgcagtacgg gtacctgact  1140
ctgaacaatg gtagtcaggc cgtgggacgc tcctccttct actgcctgga atactttcct  1200
tcgcagatgc tgagaaccgg caacaacttc cagtttactt acaccttcga ggacgtgcct  1260
ttccacagca gctacgccca cagccagagc ttggaccggc tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aattttcccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg aggctttgga  1920
ctgaaacatc cgcctcctca aatcatgatc aaaaatactc cggtaccggc aaatcctccg  1980
acgactttca gcccggccaa gtttgcttca tttatcactc agtactccac gggacaggtc  2040
agcgtggaaa ttgagtggga gctacagaaa gaaaacagca aacgctggaa tcccgaaatt  2100
cagtacactt ccaactacaa caagtctgtt aatgtggact ttactgtgga cactaatggt  2160
gtttatagtg aacctcgccc cattggcacc cgttacctca cccgtcccct gtaa        2214
```

```
SEQ ID NO: 20          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 20
atggctgctg acggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaaaaaga ggcttcttga acctcttggt ctggttgagg aagcggctaa gacggctccg  420
ggaaaaaaga ggccggtaga gcactctcct gtggagccag actcctcctc gggaaccgga  480
aaggcgggcc agcagcccgc taaaaagaga ctcaattttg gtcagactgg cgactcagag  540
tcagttccag accctcaacc tctcggagaa cctccagcag cgccctctgg tgtgggacct  600
aatacaatgg ctgcaggcgg tggcgcacca atggcagaca ataacgaagg cgccgacgga  660
gtgggtaatg cctcaggaaa ttggcattgc gattccacat ggctgggcga cagagtcatc  720
accaccagca cccgaacctg ggccctgccc acctacaaca accacctcta caagcaaatc  780
tccagtgctt caacgggggc cagcaacgac aaccactact ttggctacag caccccttgg  840
gggtattttg actttaacag attccactgc cacttctcac cacgtgactg gcagcgactc  900
attaacaaca actggggatt ccggcccaag agactcagct tcaagctctt caacatccaa  960
gtcaaggagg tcacgacgaa tgatggcgtc acgaccatcg ccaataacct taccagcacg  1020
gttcaagtgt ttacggactc ggagtatcag ctcccgtacg tcctcggatc agcgcaccaa  1080
ggctgtctcc cgccgtttcc agcggacgtc ttcatggtcc ctcagtatgg atacctcacc  1140
ctgaacaacg ggagtcaggc agtaggacgc tcttcatttt actgcctgga gtacttccct  1200
tcgcagatgc taaggactgg aaataacttc caattcagct ataccttcga ggatgtacct  1260
tttcacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aattttcccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg aggctttgga  1920
ctgaaacatc cgcctcctca aatcatgatc aaaaatactc cggtaccggc aaatcctccg  1980
```

```
acgactttca gcccggccaa gtttgcttca tttatcactc agtactccac tggacaggtc  2040
agcgtggaaa ttgagtggga gctacagaaa gaaaacagca aacgttggaa tccagagatt  2100
cagtacactt ccaactacaa caagtctgtt aatgtggact ttactgtgga cactaatggc  2160
gtgtattcag agcctcgccc cattggcacc cgttacctca cccgtcccct gtaa        2214

SEQ ID NO: 21          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 21
atggctgctg acggttatct tccagattgg ctcgaggaca acctttctga aggcattcga  60
gagtggtggg cgctgcaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc ttcaagaaga tacgtctttt gggggcaacc tcgggcgagc agtcttccag  360
gccaagaagc gggttctcga acctctcggt ctggttgagg aaggcgctaa gacggctcct  420
ggaaagaaac gtccggtaga gcagtcgcca caagagccag actcctcctc gggcatcggc  480
aagacaggcc agcagcccgc gaaaaagaga ctcaactttg ggcagactgg cgactcagag  540
tcagtgcccg accctcaacc aatcggagaa ccccccgcag gcccctctgg tctgggaact  600
ggtacgatgg cttcaggcag tggcgcacca atggcagaca ataacgaagg cgccgatgga  660
gtgggtaatt cctcaggaaa ttggcattgc gattcccaat ggctgggcga cagagtcatc  720
accaccagca ccagaacctg ggccttgccc acctacaata accacctcta caagcaaatc  780
tccagtgctt caacgggggc cagcaacgac aaccactact tcggctacag caccccctgg  840
gggtattttg actttaacag attccactgc cacttctcac cacgtgactg gcagcgactc  900
attaacaaca actggggatt ccggcccaag agactcaact tcaagctctt caacatccaa  960
gtcaaggagg tcacgacgaa tgatggcgtc acgaccattg ccaataacct caccagcacc  1020
atccaggtgt ttacggactc ggagtaccag ttgccgtacg tcctcggctc tgcgcaccag  1080
ggctgcctcc ctccgttccc ggcggacgtg ttcatgattc cgcaatacgg ctacctgacg  1140
ctcaacaatg gcagccaggc agtgggacgg tcatcctttt actgcctgga atatttccca  1200
tcgcagatgc tgagaacggg caataacttt accttcagct acaccttcga ggacgtgcct  1260
ttccacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aattttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg aggctttgga  1920
ctgaaacatc cgcctcctca aatcatgatc aaaaatactc cggtaccggc aaatcctccg  1980
acgactttca gcccggccaa gtttgcttca tttatcactc agtactccac tggacaggtc  2040
agcgtggaaa ttgagtggga gctacagaaa gaaaacagca aacgttggaa tccagagatt  2100
cagtacactt ccaactacaa caagtctgtt aatgtggact ttactgtaga cactaatggt  2160
gtttatagtg aacctcgccc cattggcacc cgttacctta cccgtcccct gtaa        2214

SEQ ID NO: 22          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 22
atggctgctg acggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgcggagttt  300
caggagcgcc ttaaagaaga tacgtctttt gggggcaacc tcggacgagc agtcttccag  360
gccaagaaga gggttctcga accttttggt ctggttgagg aagcggctaa gacggctcct  420
ggaaagaaga ggcctgtaga tcagtctcct caggaaccgg actcatcatc tggtgttggc  480
aaatcgggca aacagcctgc cagaaaaaga ctaaatttcg gtcagactgg cgactcagag  540
tcagtcccag accctcaacc tctcggagaa ccaccagcag cccccacaag tttgggatct  600
aatacaatgg cttcaggcgg tggcgcacca atggcagaca ataacgaggg tgccgacgga  660
gtgggtaatg cctcaggaaa ttggcattgc gattccacat ggctgggcga ccgagtcatc  720
accaccagca cccgcacctg ggccctgccc acctacaaca accatctcta caagcaaatc  780
tccagtgctt caacgggggc cagcaacgac aaccactact tcggctacag caccccctgg  840
gggtattttg actttaacag attccactgc cacttttcac cacgtgactg gcagcgactc  900
atcaacaaca actggggatt ccggcccaag aaactcagct tcaagctctt caacatccag  960
gtcaaggagg tcacgcagaa tgaaggcacc aagaccatcg ccaataacct caccagcacc  1020
atccaggtgt ttacggactc ggagtaccag ctgccgtacg ttctcggctc tgcgcaccag  1080
```

```
ggctgcctcc ctccgttccc ggcggacgtg ttcatgattc cgcaatacgg ctacctgacg  1140
ctcaacaatg gcagccaagc cgtgggacgt tcatcctttt actgcctgga atatttccca  1200
tcgcagatgc tgagaaccgg caacaacttc cagtttactt acaccttcga ggatgtacct  1260
tttcacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aattttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg agggtttgga  1920
atgaaacacc cgcctcctca gatcctcatc aaaaacacac ctgtacctgc ggatcctcca  1980
acggccttca acaaggacaa gctgaactct ttcatcaccc agtattctac tggccaagtc  2040
agcgtggaaa ttgaatggga gctgcagaag gaaaacagca agcgctggaa ccccgagatc  2100
cagtacacct ccaactacta caaatctaca agtgtggact ttgctgttaa tacagaaggc  2160
gtgtactctg aaccccgccc cattggcacc cgttacctca cccgtaatct gtaa        2214
```

```
SEQ ID NO: 23           moltype = DNA  length = 2211
FEATURE                 Location/Qualifiers
misc_feature            1..2211
                        note = source = /note="Description of Artificial Sequence:
                         Syntheticpolynucleotide"
source                  1..2211
                        mol_type = other DNA
                        organism = synthetic construct
SEQUENCE: 23
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa ggcctacgac  240
cagcagctca aagcgggtga caatccgtac ctcaagtaca accacgccga cgccgagttc  300
caggagcggc tcaaagaaga tacgtctttt gggggcaacc tcgggcgagc agtcttccag  360
gcgaaaaaga gggttcttga acctctgggc ctggttgagg aagcggctaa gacggctcct  420
ggaaagaaga ggcctgtaga gcactctcct gtggagccag actcctcctc gggaaccgga  480
aaggcgggcc agcagcctgc aagaaaaaga ttgaattttg gtcagactgg agacgcagac  540
tcagtcccag accctcaacc tctcggagaa ccaccagcag cccccacaag tttgggatct  600
aatacaatgg cttcaggcgg tggcgcacca atggcagaca ataacgaagg cgccgacgga  660
gtgggtagtt cctcaggaaa ttggcattgc gattccacat ggctgggcga cagagtcatc  720
accaccagca cccgcacctg ggccctgccc acttacaaca accatctcta caagcaaatc  780
tccagtgctt caacgggggc cagcaacgac aaccactact tcggctacag cacccccctgg  840
gggtattttg atttcaacag attccactgc catttctcac cacgtgactg gcagcgactc  900
atcaacaaca actggggatt ccggcccaag cgactcaact tcaagctctt caacatccag  960
gtcaaggagg tcacgcagaa tgaaggcacc aagaccatcg ccaataacct taccagcacg  1020
attcaggtct ttacggactc ggaataccag ctcccgtacg tcctcggctc tgcccaccag  1080
ggctgcctgc ctccgttccc ggcggacgtg ttcatgattc cccagtacgg ctacctaaca  1140
ctcaacaacg gtagtcaggc gatgggtcgc tcgtccttct actgcctgga gtactttccg  1200
tcgcagatgc tgcggacggg gaacaacttc acgttcagct acaccttcga ggacgtgccc  1260
ttccacagca gctacgcgca cagccagagt ctggaccggc tgatgaatcc tctgattgac  1320
cagtacctgt actacttgtc tcggactcag tccacgggag gtaccgcagg aactcagcag  1380
ttgctatttt ctcaggccgg gcctaataac atgtcggctc aggccagaaa ttggctacct  1440
gggccctgct accggcaaca gagactttca aagactgcta acgacaacaa caacagtaac  1500
tttccttgga cagcggccag caaatatcat ctcaatggcc gcgactcgct ggtgaatcca  1560
ggaccagcta tggccagtca caaggacgat gaagaaaaat tttccctat gcacggcaat  1620
ctaatatttg gcaaagaagg gacaacggca agtaacgcag aattagataa tgtaatgatt  1680
acggatgaag aagagattcg taccaccaat cctgtggcaa cagagcagta tggaactgtg  1740
gcaaataact tgcagagctc aaatacagct cccacgacta gaactgtcaa tgatcagggg  1800
gccttacctg gcatggtgtg gcaagatcgt gacgtgtacc ttcaaggacc tatctgggca  1860
aagattcctc acacggatgg acactttcat ccctcgccgc tgatgggagg ctttggactg  1920
aaacacccgc ctcctcagat cctcatcaaa aacacacctg tacctgcgga tcctccgacc  1980
accttcaacc agtcaaagct gaactctttc atcacccagt actccactgg acaggtcagc  2040
gtggagatcg agtgggagct gcagaaggaa aacagcaaac gctggaatcc cgaaattcag  2100
tacacttcca actacaacaa gtctgttaat gtggacttta ctgtggacac taatggcgtg  2160
tattcagagc ctcgccccat tggcacccgt tacctcaccc gtaatctgta a           2211
```

```
SEQ ID NO: 24           moltype = DNA  length = 2214
FEATURE                 Location/Qualifiers
misc_feature            1..2214
                        note = source = /note="Description of Artificial Sequence:
                         Syntheticpolynucleotide"
source                  1..2214
                        mol_type = other DNA
                        organism = synthetic construct
SEQUENCE: 24
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctggctac aagtacctcg gacccttcaa cggactcgac  180
```

```
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcactctcct gtggagccag actcctcctc gggaaccgga  480
aaggcgggcc agcagcctgc aagaaaaaga ttgaattttg gtcagactgg agacgcagac  540
tcagtcccag accctcaacc tctcggagaa ccaccagcag cccccacaag tttgggatct  600
aatacaatgg ctacaggcag tggcgcacca atggcagaca ataacgaggg tgccgatgga  660
gtgggtaatt cctcaggaaa ttggcattgc gattcccaat ggctgggcga cagagtcatc  720
accaccagca cccgaacatg ggccttgccc acctataaca accacctcta caagcaaatc  780
tccagtgctt caacgggggc cagcaacgac aaccactact tcggctacag cacccccctgg  840
gggtactttg acttcaaccg cttccactgc cacttctccc cgcgagactg gcagcggctc  900
atcaacaaca actggggggtt ccggcccaag cgactcaact tcaagctctt caacatccaa  960
gtcaaggagg tcacgacgaa tgatggcgtc acgaccatcg ctaataacct taccagcacg  1020
gttcaagtgt ttacggactc ggagtatcag ctcccgtacg tcctcggctc tgcgcaccag  1080
ggctgcctcc ctccgttccc ggcggacgtc ttcatggtcc ctcagtatgg atacctcacc  1140
ctgaacaacg gaagtcaagc ggtgggacgc tcatcctttt actgcctgga gtacttccct  1200
tcgcagatgc taaggactgg aaataacttc caattcagct ataccttcga ggatgtacct  1260
tttcacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aatttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg aggctttgga  1920
ctgaaacacc ctcctccaca gattctcatc aagaacaccc cggtacctgc gaatcctccg  1980
accaccttca accagtcaaa gctgaactct ttcatcaccc agtattctac tggccaagtc  2040
agcgtggaga tcgagtggga gctgcagaag gaaaacagca agcgctggaa ccccgagatc  2100
cagtacacct ccaactacta caaatctaca agtgtggact ttgctgttaa tacagaaggc  2160
gtgtactctg aaccccgccc cattggcacc cgttacctca cccgtaatct gtaa        2214
```

```
SEQ ID NO: 25           moltype = DNA  length = 2214
FEATURE                 Location/Qualifiers
misc_feature            1..2214
                        note = source = /note="Description of Artificial Sequence:
                         Syntheticpolynucleotide"
source                  1..2214
                        mol_type = other DNA
                        organism = synthetic construct
SEQUENCE: 25
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaaga gggttctcga accttttggt ctggttgagg aaggtgctaa gacggctcct  420
ggaaagaaac gtccggtaga gcactctcct gtggagccag actcctcctc gggaaccgga  480
aaggcgggcc agcagcctgc aagaaaaaga ttgaattttg gtcagactgg cgactcagag  540
tcagttccag accctcaacc tctcggagaa cctccagcag cgccctctgg tgtgggacct  600
aatacaatgg cttcaggcgg tggcgcacca atggcagaca ataacgaagg cgccgacgga  660
gtgggtaatg cctcaggaaa ttggcattgc gattccacat ggctgggcga cagagtcatc  720
accaccagca cccgcacctg ggccttgccc acctacaata accacctcta caagcaaatc  780
tccagtgctt caacgggggc cagcaacgac aaccactact tcggctacag cacccccctgg  840
gggtattttg acttcaacag attccactgc catttctcac cacgtgactg gcagcgactc  900
atcaacaaca attggggatt ccggcccaag agactcaact tcaagctctt caacatccaa  960
gtcaaggagg tcacgcagaa tgacggtacg acgacgattg ccaataacct taccagcacg  1020
gttcaagtgt ttacggactc ggagtatcag ctcccgtacg tgctcgggtc ggcgcaccaa  1080
ggctgtctcc cgccgtttcc agcggacgtc ttcatggtcc cgcagtacgg gtatttgacg  1140
ctgaacaacg gaagtcaagc ggtgggacgc tcatcctttt actgcctgga gtacttccct  1200
tcgcagatgc taaggactgg aaataacttc caattcagct ataccttcga ggatgtacct  1260
tttcacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aatttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg cggctttgga  1920
ctgaaacatc cgcctcctca aatcatgatc aaaaatactc cggtaccggc aaatcctccg  1980
acgactttca gcccggccaa gtttgcttca tttatcactc agtactccac gggacaggtc  2040
agcgtggaga tcgagtggga gctgcagaag gaaaacagca agcgctggaa ccccgagatc  2100
```

```
cagtacacct ccaactacta caaatctaca agtgtggact ttgctgttaa tacagaaggc  2160
gtgtactctg aaccccgccc cattggcacc cgttacctca cccgtaatct gtaa        2214

SEQ ID NO: 26          moltype = DNA  length = 2214
FEATURE                Location/Qualifiers
misc_feature           1..2214
                       note = source = /note="Description of Artificial Sequence:
                        Syntheticpolynucleotide"
source                 1..2214
                       mol_type = other DNA
                       organism = synthetic construct
SEQUENCE: 26
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctgc aggcgggtga caatccgtac ctgcggtata accacgccga cgccgagttt  300
caggagcgtc tgcaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcactctcct gtggagccag actcctcctc gggaaccgga  480
aaggcgggcc agcagcctgc aagaaaaaga ttgaattttg gtcagactgg agacgcagac  540
tcagtcccag accctcaacc aatcggagaa cctcccgcag ccccctcagg tgtgggatct  600
cttacaatgg ctgcaggcgg tggcgcacca atggcagaca ataacgaggg tgccgacgga  660
gtgggtaatt cctcgggaaa ttggcattgc gattccacat ggatgggcga cagagtcatc  720
accaccagca cccgaacctg ggccctgccc acctataaca accacctcta caagcaaatc  780
tccagtgctt caacgggggc cagcaacgac aaccactact tcggctacag caccccctgg  840
gggtattttg atttcaaccg cttccactgc cacttctcac cacgtgactg gcagcgactc  900
atcaacaaca actggggatt ccggcccaag agactcaact tcaaactctt caacatccaa  960
gtcaaggagg tcacgacgaa tgatggcgtc acgaccatcg ctaataacct taccagcacg  1020
gttcaagtct tctcggactc ggagtaccag ttgccgtacg tcctcggctc tgcgcaccag  1080
ggctgcctcc ctccgttccc ggcggacgtg ttcatgattc cgcagtacgg ctacctaaca  1140
ctcaacaacg gtagtcaggc cgtgggacgc tcctccttct actgcctgga atatttccca  1200
tcgcagatgc tgagaacggg caataacttt accttcagct acaccttcga ggacgtgcct  1260
ttccacagca gctacgcgca cagccagagc ctggaccggc tgatgaaccc cctcatcgac  1320
cagtacctgt actacctgaa cagaacgcaa ggaacaacct ctggaacaac caaccaatca  1380
cggctgcttt ttagccaggc tgggcctcag tctatgtctt tgcaggccag aaattggcta  1440
cctgggccct gctaccggca acagagactt tcaaagactg ctaacgacaa caacaacagt  1500
aactttcctt ggacagcggc cagcaaatat catctcaatg gccgcgactc gctggtgaat  1560
ccaggaccag ctatggccag tcacaaggac gatgaagaaa aattttttccc tatgcacggc  1620
aatctaatat ttggcaaaga agggacaacg gcaagtaacg cagaattaga taatgtaatg  1680
attacggatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctggcatggt gtggcaagat cgtgacgtgt accttcaagg acctatctgg  1860
gcaaagattc ctcacacgga tggacacttt catccttctc ctctgatggg aggctttgga  1920
ctgaaacatc cgcctcctca aatcatgatc aaaaatactc cggtaccggc aaatcctccg  1980
acgactttca gcccggccaa gtttgcttca tttatcactc agtactccac tggacaggtc  2040
agcgtggaaa ttgagtggga gctacagaaa gaaaacagca aacgttggaa tccagagatt  2100
cagtacactt ccaactacaa caagtctgtt aatgtggact ttactgtaga cactaatggt  2160
gtttatagtg aacctcgccc cattggcacc cgttacctta cccgtcccct gtaa        2214

SEQ ID NO: 27          moltype = AA  length = 743
FEATURE                Location/Qualifiers
REGION                 1..743
                       note = source = /note="Description of Unknown:Parent AAV
                        Capsid sequence"
source                 1..743
                       mol_type = protein
                       organism = synthetic construct
SEQUENCE: 27
MSLISDAIPD WLERLVKKGV NAAADFYHLE SGPPRPKANQ QTQESLEKDD SRGLVFPGYN  60
YLGPFNGLDK GEPVNEADAA ALEHDKAYDL EIKDGHNPYF EYNEADRRFQ ERLKDDTSFG  120
GNLGKAIFQA KKRVLEPFGL VEDSKTAPTG DKRKGEDEPR LPDTPPQTPK KNKKPRKERP  180
SGGAEDPGEG TSSNAGAAAP ASSVGSSIMA EGGGGPVGDA GQGADGVGNS SGNWHCDSQW  240
LENGVVTRTT RTWVLPSYNN HLYKRIQGPS GGDNNNKFFG FSTPWGYFDY NRFHCHFSPR  300
DWQRLINNNW GIRPKAMRFR LFNIQVKEVT VQDSNTTIAN NLTSTVQVFA DKDYQLPYVL  360
GSATEGTFPP FPADIYTIPQ YGYCTLNYNN EAVDRSAFYC LDYFPSDMLR TGNNFEFTYT  420
FEDVPFHSMF AHNQTLDRLM NPLVDQYLWA FSSVSQAGSS GRALHYSRAT KTNMAAQYRN  480
WLPGPFFRDQ QIFTGASNIT KNNVFSVWEK GKQWELDNRT NLMQPGPAAA TTFSGEPDRQ  540
AMQNTLAFSR TVYDQTTATT DRNQILITNE DEIRPTNSVG IDAWGAVPTN NQSIVTPGTR  600
AAVNNQGALP GMVWQNRDIY LQGPIWAKIP DTDNHFHPSP LIGGFGCKHP PPQIFIKNTP  660
VPANPSETFQ TAKVASFINQ YSTGQCTVEI FWELKKETSK RWNPEIQFTS NFGNAADIQF  720
AVSDTGSYSE PRPIGTRYLT KPL                                          743

SEQ ID NO: 28          moltype = AA  length = 716
FEATURE                Location/Qualifiers
REGION                 1..716
                       note = source = /note="Description of Unknown:Parent AAV
                        Capsid sequence"
source                 1..716
```

```
                         mol_type = protein
                         organism = synthetic construct
SEQUENCE: 28
MSFVDHPPDW LEEIGEGLKE FLGLEPGPPK PKPNQQKQDD ARGLVLPGYN YLGPGNGLDR  60
GEPVNRADEV AREHDISYNE QLQAGDNPYL KYNHADAEFQ EKLADDTSFG GNLGKAVFQA  120
KKRVLEPFGL VEEPVKTAAK GERIDDHYPK KKKARIEETE AGTSGAQQLQ IPAQPASSLG  180
ADTMSAGGGS PLGDNNQGAD GVGNASGDWH CDSTWMGDRV ITKSTRTWVL PSYNNHQYLE  240
IHSGSVDGSN ANAYFGYSTP WGYFDFNRFH SHWSPRDWQR LVNNYWGFRP RSLKVKIFNI  300
QVKEVTTQDG TTTIANNLTS TVQVFTDNDY QLPYVIGNGT EGCLPAFPPQ VFTLPQYGYA  360
TLNRNNTDDP TERSSFFCLE YFPSKMLRTG NNFEFTYSFE EVPFHCSFAP SQNLFKLANP  420
LVDQYLYRFV STDTSGNLQF QKNLKARYAN TYKNWFPGPM CRTQGWYTSA GTYNNKGVAN  480
FDTSNKMELE GASYQVNPQP NGMTNTLQDS NKYALENTMI FNAQNAPPGT TSLYQENNLL  540
ITSESETQPV NRLAYNTGGQ VSNNNQNSNT HPTVGVYNHQ EVLPGSVWMD RDVYLQGPIW  600
AKIPETGAHF HPSPAMGGFG LKHPPPMMLI KNTPVPSNVA AFSDVPVKSF ITQYSTGQVT  660
VEIEWELKKE NSKRWNPEIQ YTNNYNNPTF VDFAPDTSGE YRTTRAIGTR YLTRPL      716

SEQ ID NO: 29            moltype = AA  length = 724
FEATURE                  Location/Qualifiers
REGION                   1..724
                         note = source = /note="Description of Unknown:Parent AAV
                          Capsid sequence"
source                   1..724
                         mol_type = protein
                         organism = synthetic construct
SEQUENCE: 29
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST VQVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLEGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                                 724

SEQ ID NO: 30            moltype = AA  length = 726
FEATURE                  Location/Qualifiers
REGION                   1..726
                         note = source = /note="Description of Unknown:Parent AAV
                          Capsid sequence"
source                   1..726
                         mol_type = protein
                         organism = synthetic construct
SEQUENCE: 30
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST VQVFTDDDYQ LPYVVGNGTE GCLPAFPPQV  360
FTLPQYGYAT LNRDNGDNPT ERSSFFCLEY FPSKMLRTGN NFEFTYSFEE VPFHCSFAPS  420
QNLFKLANPL VDQYLYRFVS TSATGAIQFQ KNLAGRYANT YKNWFPGPMG RTQGWNTSSG  480
SSTNRVSVNN FSVSNRMNLE GASYQVNPQP NGMTNTLQGS NRYALENTMI FNAQNATPGT  540
TSVYPEDNLL LTSESETQPV NRVAYNTGGQ MATNAQNATT APTVGTYNLQ EVLPGSVWME  600
RDVYLQGPIW AKIPETGAHF HPSPAMGGFG LKHPPPMMLI KNTPVPGNIT SFSDVPVSSF  660
ITQYSTGQVT VEMEWELKKE NSKRWNPEIQ YTNNYNDPQF VDFAPDGSGE YRTTRAIGTR  720
YLTRPL                                                               726

SEQ ID NO: 31            moltype = AA  length = 713
FEATURE                  Location/Qualifiers
REGION                   1..713
                         note = source = /note="Description of Unknown:Parent AAV
                          Capsid sequence"
source                   1..713
                         mol_type = protein
                         organism = synthetic construct
SEQUENCE: 31
MSFFDWLGKQ YAQGAAEFWD LKSGPPAPKK ARKDGSAGFN FPGHKYLGPG NSLDRGDPVD  60
ADDAAAQKHD QSYQEQLEAG DNPYLKYNHA DREFQEALKD DTSFEGNLAR GLFEAKKLVA  120
EPLGLVEPEL APPSGRKRPV QSSQESGYSS SQDKRPNLDV DEEDREFAAA AAETETGSAP  180
PTGNLGPGTM AGGGSAPIDD GSYGADGVGN ASGDWHCDST WLDNCVITRT TRTWNLPTYN  240
NHIYKRLNGT TSGDQSYFGF STPWGYFDFN RFHCHFSPRD WQRLINNNWG LRPKSLRFKI  300
FNIQVKEVTT QDSTKIISNN LTSTVQVFAD TEYQLPYVIG SAHEGCLPPF PADVFMLPQY  360
GYCTRQDGNS NNPTPRSAFY CLEYFPSKML RTGNSFEFTY NFEKVPFHSM WAHNQSLDRL  420
MNPLIDQYLY YLDVTSSTGF TYQKGVHTNL PEQERNWLPG PGIRNQAWFN SATGNNPLTG  480
```

```
TWQYSNKYVL ENRASKIAPG PAMGIESTKF DGNGIIFSKE YITNVNTANP NQVNITRETE  540
INSTNPLAGG SLGAHANNSQ NTTTAPTLDH TNVMGVFPGS VWQDRDIYLQ GQIWAKIPHT  600
DGHFHPSPLM GGFGLKNPPP QILIKNTPVP ADPPTEFNAN KISSFITQYS TGQVTVEMEW  660
ELQKETSKRW NPEIQYSDDS SSTSGSILHF APDDVGNYKE FRSIGTRYLT RPL         713

SEQ ID NO: 32           moltype = AA  length = 726
FEATURE                 Location/Qualifiers
REGION                  1..726
                        note = source = /note="Description of Unknown:Parent AAV
                         Capsid sequence"
source                  1..726
                        mol_type = protein
                        organism = synthetic construct
SEQUENCE: 32
MSFVDHPPDW LEEVGEGLHE FLELEAGPPK PKPNQQKQDN ARGLVLPGYN YLGPFNGLDK  60
GEPVNRADAV AREHDISYNE QLQAGDNPYL KYNHADAEFQ EKLKDDTSFG GNLGKAIFQA  120
KKRVLEPFGL VEAPVKTAPA KKRPIEKSPA EPSSSKGIGK AGQQPARKRL NFGQTGDTDS  180
AADPQPLGEP PAAPSGLGTG TMASGSGAPM ADNNEGADGV GNASGNWHCD STWLGDRVIT  240
TSTRTWALPT YNNHLYKQIS SQSGANNDNH YFGYSTPWGY FDFNRFHCHF SPRDWQRLIN  300
NNWGFRPKRL NFKLFNIQVK EVTQTDGTKT IANNLTSTVQ VFADSEYQLP YVLGSAHQGC  360
FPPFPADVFM VPQYGYLTLN NGSQAMGRSS FYCLEYFPSQ MLRTGNNFTF SYTFEDVPFH  420
SSYAHSQSLD RLMNPLIDQY LYYLSKTNGG LGFSQAGPNS MRDQSRNWLP GPCFRQQRIS  480
TVPTQNNNGD FSWTGATKYH LNGRNSAMNP GPAMASHKDD EHRFFPQNGV LIFGKQGADK  540
TNAILEKVIV TDEEEIRTTN PVATEEYGFV ATNLQSSAET AETERVNAQG ILPGMVWQDR  600
DVYLQGPIWA KIPHTDGHFR PSPLMGGFGL KHPPPQILIK NTPVPSNPPE TFNPEKLNSF  660
ITQYSTGQVS VEIEWELQKE NSKRWNPEVQ YTSNYNKSVN VEFTVDNNGV YSEPRTIGTR  720
YLTRNL                                                             726

SEQ ID NO: 33           moltype = AA  length = 736
FEATURE                 Location/Qualifiers
REGION                  1..736
                        note = source = /note="Description of Unknown:Parent AAV
                         Capsid sequence"
source                  1..736
                        mol_type = protein
                        organism = synthetic construct
SEQUENCE: 33
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 34           moltype = AA  length = 736
FEATURE                 Location/Qualifiers
REGION                  1..736
                        note = source = /note="Description of Unknown:Parent AAV
                         Capsid sequence"
source                  1..736
                        mol_type = protein
                        organism = synthetic construct
SEQUENCE: 34
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                  736

SEQ ID NO: 35           moltype = AA  length = 736
FEATURE                 Location/Qualifiers
REGION                  1..736
                        note = source = /note="Description of Unknown:Parent AAV
                         Capsid sequence"
```

```
source                  1..736
                        mol_type = protein
                        organism = synthetic construct
SEQUENCE: 35
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPFG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD KDKFFPMSGV  540
MIFGKESAGA SNTALDNVMI TDEEEIKATN PVATERFGTV AVNLQSSSTD PATGDVHVMG  600
ALPGMVWQDR DVYLQGPIWA KIPHTDGHFH PSPLMGGFGL KHPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                736

SEQ ID NO: 36           moltype = AA  length = 736
FEATURE                 Location/Qualifiers
REGION                  1..736
                        note = source = /note="Description of Unknown:Parent AAV
                         Capsid sequence"
source                  1..736
                        mol_type = protein
                        organism = synthetic construct
SEQUENCE: 36
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTRTVNDQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                736

SEQ ID NO: 37           moltype = AA  length = 736
FEATURE                 Location/Qualifiers
REGION                  1..736
                        note = source = /note="Description of Unknown:Parent AAV
                         Capsid sequence"
source                  1..736
                        mol_type = protein
                        organism = synthetic construct
SEQUENCE: 37
MAADGYLPDW LEDNLSEGIR EWWALQPGAP KPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTRTVNDQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRPL                                                736

SEQ ID NO: 38           moltype = AA  length = 738
FEATURE                 Location/Qualifiers
REGION                  1..738
                        note = source = /note="Description of Unknown:Parent AAV
                         Capsid sequence"
source                  1..738
                        mol_type = protein
                        organism = synthetic construct
SEQUENCE: 38
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
```

```
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 39          moltype = AA  length = 738
FEATURE                Location/Qualifiers
REGION                 1..738
                       note = source = /note="Description of Unknown:Parent AAV
                        Capsid sequence"
source                 1..738
                       mol_type = protein
                       organism = synthetic construct
SEQUENCE: 39
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYQFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTD  720
GTYSEPRPIG TRYLTRNL                                               738

SEQ ID NO: 40          moltype = AA  length = 735
FEATURE                Location/Qualifiers
REGION                 1..735
                       note = source = /note="Description of Unknown:Parent AAV
                        Capsid sequence"
source                 1..735
                       mol_type = protein
                       organism = synthetic construct
SEQUENCE: 40
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 41          moltype = AA  length = 737
FEATURE                Location/Qualifiers
REGION                 1..737
                       note = source = /note="Description of Unknown:Parent AAV
                        Capsid sequence"
source                 1..737
                       mol_type = protein
                       organism = synthetic construct
SEQUENCE: 41
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRLLEPLG LVEEAAKTAP GKKRPVEHSP VEPDSSSGTG KAGQQPARKR LNFGQTGDAD  180
SVPDPQPIGE PPAAPSGVGS LTMAAGGGAP MADNNEGADG VGNSSGNWHC DSTWMGDRVI  240
TTSTRTWALP TYNNHLYKQI SNSTSGGSSN DNAYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTTNTQ TLGFSQGGPN TMANQAKNWL  480
PGPCYRQQRV SKTSADNNNS EYSWTGATKY HLNGRDSLVN PGPAMASHKD DEEKFFPQSG  540
VLIFGKQGSE KTNVDIEKVM ITDEEEIRTT NPVATEQYGS VSTNLQRGNR QAATADVNTQ  600
GVLPGMVWQD RDVYLQGPIW AKIPHTDGHF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 42          moltype = AA  length = 736
FEATURE                Location/Qualifiers
```

```
REGION                  1..736
                        note = source = /note="Description of Unknown:Parent AAV
                         Capsid sequence"
source                  1..736
                        mol_type = protein
                        organism = synthetic construct
SEQUENCE: 42
MSFVDHPPDW LESIGDGFRE FLGLEAGPPK PKANQQKQDN ARGLVLPGYK YLGPGNGLDK  60
GDPVNFADEV AREHDLSYQK QLEAGDNPYL KYNHADAEFQ EKLASDTSFG GNLGKAVFQA  120
KKRILEPLGL VETPDKTAPA AKKRPLEQSP QEPDSSSGVG KKGKQPARKR LNFDDEPGAG  180
DGPPPEGPSS GAMSTETEMR AAAGGNGGDA GQGAEGVGNA SGDWHCDSTW SESHVTTTST  240
RTWVLPTYNN HLYLRLGSSN ASDTFNGFST PWGYFDFNRF HCHFSPRDWQ RLINNHWGLR  300
PKSMQVRIFN IQVKEVTTSN GETTVSNNLT STVQIFADST YELPYVMDAG QEGSLPPFPN  360
DVFMVPQYGY CGLVTGGSSQ NQTDRNAFYC LEYFPSQMLR TGNNFEMVYK FENVPFHSMY  420
AHSQSLDRLM NPLLDQYLWE LQSTTSGGTL NQGNSATNFA KLTKTNFSGY RKNWLPGPMM  480
KQQRFSKTAS QNYKIPQGRN NSLLHYETRT TLDGRWSNFA PGTAMATAAN DATDFSQAQL  540
IFAGPNITGN TTTDANNLMF TSEDELRATN PRDTDLFGHL ATNQQNATTV PTVDDVDGVG  600
VYPGMVWQDR DIYYQGPIWA KIPHTDGHFH PSPLIGGFGL KSPPPQIFIK NTPVPANPAT  660
TFSPARINSF ITQYSTGQVA VKIEWEIQKE RSKRWNPEVQ FTSNYGAQDS LLWAPDNAGA  720
YKEPRAIGSR YLTNHL                                                 736

SEQ ID NO: 43           moltype = AA  length = 734
FEATURE                 Location/Qualifiers
REGION                  1..734
                        note = source = /note="Description of Unknown:Parent AAV
                         Capsid sequence"
source                  1..734
                        mol_type = protein
                        organism = synthetic construct
SEQUENCE: 43
MTDGYLPDWL EDNLSEGVRE WWALQPGAPK PKANQQHQDN ARGLVLPGYK YLGPGNGLDK  60
GEPVNAADAA ALEHDKAYDQ QLKAGDNPYL KYNHADAEFQ QRLQGDTSFG GNLGRAVFQA  120
KKRVLEPLGL VEQAGETAPG KKRPLIESPQ QPDSSTGIGK KGKQPAKKKL VFEDETGAGD  180
GPPEGSTSGA MSDDSEMRAA AGGAAVEGGQ GADGVGNASG DWHCDSTWSE GHVTTTSTRT  240
WVLPTYNNHL YKRLGESLQS NTYNGFSTPW GYFDFNRFHC HFSPRDWQRL INNNWGMRPK  300
AMRVKIFNIQ VKEVTTSNGE TTVANNLTST VQIFADSSYE LPYVMDAGQE GSLPPFPNDV  360
FMVPQYGYCG LVTGNTSQQQ TDRNAFYCLE YFPSQMLRTG NNFEITYSFE KVPFHSMYAH  420
SQSLDRLMNP LIDQYLWGLQ STTTGTTLNA GTATTNFTKL RPTNFSNFKK NWLPGPSIKQ  480
QGFSKTANQN YKIPATGSDS LIKYETHSTL DGRWSALTPG PPMATAGPAD SKFSNSQLIF  540
AGPEQNGNTA TVPGTLIFTS EEELAATNAT DTDMWGNLPG GDQSNSNLPT VDRLTALGAV  600
PGMVWQNRDI YYQGPIWAKI PHTDGHFHPS PLIGGFGLKH PPPQIFIKNT PVPANPATTF  660
SSTPVNSFIT QYSTGQVSVQ IDWEIQKERS KRWNPEVQFT SNYGQQNSLL WAPDAAGKYT  720
EPRAIGTRYL THHL                                                   734

SEQ ID NO: 44           moltype = AA  length = 742
FEATURE                 Location/Qualifiers
REGION                  1..742
                        note = source = /note="Description of Unknown:Parent AAV
                         Capsid sequence"
source                  1..742
                        mol_type = protein
                        organism = synthetic construct
SEQUENCE: 44
MAADGYLPDW LEDNLSEGIR EWWALKPGAP QPKANQQHQD NGRGLVLPGY KYLGPFNGLD  60
KGEPVNEADA AALEHDKAYD KQLEQGDNPY LKYNHGDAEF QQRLATDTSF GGNLGRAVFQ  120
AKKRILEPLG LVEEGVKTAP GKKRPLEKTP NRPTNPDSGK APAKKKQKDG EPADSARRTL  180
DFEDSGAGDG PPEGSSSGEM SHDAEMRAAP GGNAVEAGQG ADGVGNASGD WHCDSTWSEG  240
RVTTTSTRTW VLPTYNNHLY LRIGTTANSN TYNGFSTPWG YFDFNRFHCH FSPRDWQRLI  300
NNNWGLRPKS MRVKIFNIQV KEVTTSNGET TVANNLTSTV QIFADSTYEL PYVMDAGQEG  360
SFPPFPNDVF MVPQYGYCGV VTGKNQNQTD RNAFYCLEYF PSQMLRTGNN FEVSYQFEKV  420
PFHSMYAHSQ SLDRMMNPLL DQYLWHLQST TTGNSLNQGT ATTTYGKITT GDFAYYRKNW  480
LPGACIKQQK FSKNANQNYK IPASGGDALL KYDTHTTLNG RWSNMAPGPP MATAGAGDSD  540
FSNSQLIFAG PNPSGNTTTS SNNLLFTSEE EIATTNPRDT DMFGQIADNN QNATTAPHIA  600
NLDAMGIVPG MVWQNRDIYY QGPIWAKVPH TDGHFHPSPL MGGFGLKHPP PQIFIKNTPV  660
PANPNTTFSA ARINSFLTQY STGQVAVQID WEIQKEHSKR WNPEVQFTSN YGTQNSMLWA  720
PDNAGNYHEL RAIGSRFLTH HL                                          742

SEQ ID NO: 45           moltype = DNA  length = 2232
FEATURE                 Location/Qualifiers
misc_feature            1..2232
                        note = source = /note="Description of Unknown:Parent AAV
                         Capsid sequence"
source                  1..2232
                        mol_type = other DNA
                        organism = synthetic construct
SEQUENCE: 45
atgtctctca tttctgatgc gattccagat tggttggagc ggttggtcaa aaagggagtg  60
aatgctgcag ctgatttcta ccatttggaa agcggtcctc ctcgtcctaa ggcaaatcag  120
caaactcaag aatctcttga aaaggacgat tcgagaggtc tcgtgttccc aggctacaat  180
```

```
tatctaggcc ctttcaacgg tctagataaa ggagaacccg tcaacgaggc agacgctgcc  240
gccttagaac acgacaaggc ttacgacctc gaaatcaagg acgggcacaa cccgtacttt  300
gagtacaacg aggccgacag acgtttccag gaacgtctca aagacgatac ctcctttgga  360
ggcaatttag gtaaagccat cttccaggcc aaaaagaggg ttctcgaacc ctttggtctg  420
gtggaagact caaagacggc tccgaccgga gacaagcgga aaggcgaaga cgaacctcgt  480
ctgcccgaca ctcctccaca gactcccaag aaaaacaaga agcctcgcaa ggaaagacct  540
tccggcgggg cagaagatcc gggcgaaggc acctcttcca acgctggagc agcagcaccc  600
gcctctagtg tgggatcatc tatcatggct gaaggaggtg gcggcccagt gggcgatgca  660
ggccagggtg ccgatggagt gggcaattcc tcgggaaatt ggcattgcga ttcccaatgg  720
ctggaaaacg gagtcgtcac tcgaaccacc cgaacctggg tcttgcccag ctacaacaac  780
cacctgtaca aacgaatcca aggacccagc ggaggcgaca acaacaacaa attctttgga  840
ttcagcaccc cctggggata ctttgactac aatcgattcc actgccactt ttccccgcga  900
gactggcaac gactcatcaa caacaactgg ggcatccgtc ccaaagcgat gcgctttaga  960
ctctttaaca tccaggttaa agaggtcacg gtccaagact ccaacaccac catcgccaac  1020
aacctcacca gtacggtcca ggtctttgcg gacaaggact accaactgcc gtacgtcctc  1080
ggatcggcta ccgaaggcac cttcccgccg ttcccagcgg atatctacac gatcccgcag  1140
tacgggtact gcacgctaaa ctacaacaac gaggcggtgg atcgttcggc cttctactgt  1200
ctggactact ttccctcaga catgctgcgg acaggaaata actttgagtt tacttacacc  1260
ttcgaggacg ttcctttcca tagcatgttt gcccacaacc agacgctaga ccggctgatg  1320
aatcccctcg tggatcagta cctctgggct ttcagctccg tcagccaagc aggctcatct  1380
ggacgagctc ttcattactc gcgggcgact aaaaccaaca tggcggctca atataggaac  1440
tggttacctg ggcctttctt ccgtgatcag caaatcttta cgggcgctag caacatcact  1500
aaaaataacg tctttagcgt ttgggaaaaa ggcaagcaat gggaactcga caatcggacc  1560
aacctaatgc agcccggtcc tgcggcagcg accaccttta gcggagaacc tgaccgtcaa  1620
gccatgcaaa acacgctggc ttttagcagg accgtctacg atcaaacgac cgccacgacc  1680
gatcgtaacc agatactcat caccaacgaa gacgaaatca gacccaccaa ctcggtcggt  1740
atcgacgcgt ggggagcagt tcccaccaac aaccagtcga tcgtgacccc cggcactcgc  1800
gcggccgtca acaatcaagg ggcgcttccc gggatggtgt ggcaaaacag agacatttac  1860
ctacagggac ccatttgggc caaaattccc gacactgaca atcacttcca tccgtccccg  1920
cttattggcg ggtttggctg caagcatccc cctccccaga ttttcattaa aaacacaccc  1980
gtccctgcca acccttcgga aacgttccag acggccaaag tggcctcctt catcaaccag  2040
tactcgaccg gacagtgcac cgtcgaaatc ttttgggaac tcaagaagga aacctccaag  2100
cgctggaacc ccgaaatcca gttcacctcc aactttggca acgcggccga catccagttt  2160
gccgtctccg acacgggatc ctattccgaa cctcgtccca tcggtacccg ttaccttacc  2220
aaacctctgt aa                                                    2232
```

```
SEQ ID NO: 46           moltype = DNA  length = 2151
FEATURE                 Location/Qualifiers
misc_feature            1..2151
                        note = source = /note="Description of Unknown:Parent AAV
                         Capsid sequence"
source                  1..2151
                        mol_type = other DNA
                        organism = synthetic construct
SEQUENCE: 46
atgtcgtttg ttgatcaccc tccagattgg cttgaggaga ttggtgaggg tctaaaggag  60
tttttgggac tcgaacctgg cccacccaaa ccgaagccca accagcagaa gcaagacgac  120
gcccgtggtc ttgtactgcc tggatataat tacctgggac ccggaaacgg tctcgaccgc  180
ggagaacctg tcaaccgggc tgacgaggtc gcgcgagagc acgacatctc gtacaacgag  240
cagctccagg cgggagacaa cccctacctc aagtacaacc acgcggacgc cgagtttcag  300
gagaagctcg cggacgacac ctccttcggg ggcaacctcg gcaaggcagt ctttcaggcc  360
aaaaaaaggg ttctcgaacc ttttggcctg gttgaggagc ctgttaagac ggctgctaaa  420
ggcgagcgga tagacgacca ctatcccaaa aagaagaagg ctcggatcga agagaccgaa  480
gctggaacca gcggagccca gcagctgcag atcccagccc aaccagcctc aagtttggga  540
gctgatacaa tgtctgcggg aggtggcagc ccactgggcg acaataacca aggcgccgat  600
ggagtgggca atgcctcggg agattggcat tgcgattcca cgtggatggg ggaccgagtc  660
atcaccaagt ccacccgaac ctgggtgctg cccagctaca acaaccatca gtaccttgag  720
atccacagcg gttccgtcga cggaagcaac gctaacgctt attttggata cagcaccccc  780
tgggggtact ttgacttcaa ccgcttccac agccactgga gcccccgaga ctggcagcga  840
ctcgtcaaca actactgggg attcagaccc cggtccctca aggtcaagat ctttaacatc  900
caagtcaagg aagtcacgac gcaggacggc accaccacca tcgccaacaa cctcacctcc  960
accgtccaag tgtttacgga caacgactac cagctaccgt acgtcatcgg caacggaacg  1020
gaggggtgcc tgccggcctt ccctccgcag gtctttacgc tgccgcagta cggctacgcg  1080
acactgaacc gtaacaacac cgacgatccc accgagcgga gcagtttctt ctgcctggaa  1140
tactttccca gcaagatgct gcggacgggc aacaactttg aattcaccta cagcttcgag  1200
gaggtgccct tccactgcag cttcgctccc agccagaacc tcttcaagct ggccaatccg  1260
ctggtggacc agtacctgta ccgctttgtg agcaccgaca cttccggtaa cctacagttc  1320
caaaagaact tgaaggccag atatgccaac acttacaaga attggtttcc ggggcccatg  1380
tgccggaccc agggctggta cacaagcgcg ggcacatata acaacaaagg cgttgccaac  1440
tttgatactt caaacaagat ggaactggag gggctagtt accaagtaaa ccctcaacca  1500
aatggaatga caaacacgct tcaggatagt aacaaatacg cgcttgaaaa caccatgatc  1560
ttcaacgcac agaacgcccc tccgggaacg acctctctgt accaggagaa caatcttttg  1620
ataaccagcg agagcgagac gcagcctgtg aaccgattgg cctacaacac cggtggtcag  1680
gtatcaaaca acaaccagaa ttcaaataca catcctacgg tcggagtata caatcaccag  1740
gaagtgttgc ctggtagcgt gtggatggac agagacgtat accttcaggg ccccatctgg  1800
gccaaaatcc cggagacagg ggcacacttt catccttctc cggctatggg cggattcgga  1860
ctcaaacacc caccgcccat gatgctcatc aagaacacac cggtacctag caacgtcgct  1920
gccttctctg acgtgcccgt taaaagcttc atcacccagt acagcaccgg acaggtcacg  1980
gtggagattg aatgggagct caagaaagaa aactccaaga ggtggaatcc cgagatacag  2040
```

```
tacaccaaca actacaacaa ccctacattc gtggactttg ctccagacac ctccggcgag  2100
tacaggacta cgagggctat tggaacccgt taccttaccc gacccctgta a           2151

SEQ ID NO: 47          moltype = DNA  length = 2175
FEATURE                Location/Qualifiers
misc_feature           1..2175
                       note = source = /note="Description of Unknown:Parent AAV
                        Capsid sequence"
source                 1..2175
                       mol_type = other DNA
                       organism = synthetic construct
SEQUENCE: 47
atgtcttttg ttgatcaccc tccagattgg ttggaagaag ttggtgaagg tcttcgcgag  60
tttttgggcc ttgaagcggg cccaccgaaa ccaaaaccca atcagcagca tcaagatcaa  120
gcccgtggtc ttgtgctgcc tggttataac tatctcggac ccggaaacgg tctcgatcga  180
ggagagcctg tcaacagggc agacgaggtc gcgcgagagc acgacatctc gtacaacgag  240
cagcttgagg cgggagacaa cccctacctc aagtacaacc acgcggacgc cgagtttcag  300
gagaagctcg ccgacgacac atccttcggg ggaaacctcg gaaaggcagt ctttcaggcc  360
aagaaaaggg ttctcgaacc ttttggcctg gttgaagagg gtgctaagac ggcccctacc  420
ggaaagcgga tagacgacca ctttccaaaa agaaagaagg ctcggaccga agaggactcc  480
aagccttcca cctcgtcaga cgccgaagct ggacccagcg gatcccagca gctgcaaatc  540
ccagcccaac cagcctcaag tttgggagct gatacaatgt ctgcgggagg tggcggccca  600
ttgggcgaca ataaccaagg tgccgatgga gtgggcaatg cctcgggaga ttggcattgc  660
gattccacgt ggatgggggga cagagtcgtc accaagtcca cccgaacctg ggtgctgccc  720
agctacaaca accaccagta ccgagagatc aaaagcggct ccgtcgacgg aagcaacgcc  780
aacgcctact ttggatacag cacccccctgg gggtactttg actttaaccg cttccacagc  840
cactggagcc cccgagactg gcaaagactc atcaacaact actggggctt cagaccccgg  900
tccctcagag tcaaaatctt caacattcaa gtcaaagagg tcacggtgca ggactccacc  960
accaccatcg ccaacaacct cacctccacc gtccaagtgt ttacggacga cgactaccag  1020
ctgccctacg tcgtcggcaa cgggaccgag ggatgcctgc cggccttccc tccgcaggtc  1080
tttacgctgc cgcagtacgg ttacgcgacg ctgaaccgcg acaacacaga aaatcccacc  1140
gagaggagca gcttcttctg cctagagtac tttcccagca agatgctgag aacgggcaac  1200
aactttgagt ttacctacaa ctttgaggag gtgcccttcc actccagctt cgctcccagt  1260
cagaacctct tcaagctggc caacccgctg gtggaccagt acttgtaccg cttcgtgagc  1320
acaaataaca ctggcggagt ccagttcaac aagaacctgg ccgggagata cgccaacacc  1380
tacaaaaact ggttcccggg gcccatgggc cgaacccagg gctggaacct gggctccggg  1440
gtcaaccgcg ccagtgtcag cgccttcgcc acgaccaata ggatggagct cgagggcgcg  1500
agttaccagg tgcccccgca gccgaacggc atgaccaaca acctccaggg cagcaacacc  1560
tatgccctgg agaacactat gatcttcaac agccagccgg cgaacccggg caccaccgcc  1620
acgtacctcg agggcaacat gctcatcacc agcgagagcg agacgcagcc ggtgaaccgc  1680
gtggcgtaca acgtcggcgg gcagatggcc accaacaacc agagctccac cactgccccc  1740
gcgaccggca cgtacaacct ccaggaaatc gtgcccggca gcgtgtggat ggagagggac  1800
gtgtacctcc aaggacccat ctgggccaag atcccagaga cgggggcgca ctttcacccc  1860
tctccggcca tgggcggatt cggactcaaa cacccaccgc ccatgatgct catcaagaac  1920
acgcctgtgc ccggaaatat caccagcttc tcggacgtgc ccgtcagcag cttcatcacc  1980
cagtacagca ccgggcaggt caccgtggag atggagtggg agctcaagaa ggaaaactcc  2040
aagaggtgga acccagagat ccagtacaca aacaactaca acgaccccca gtttgtggac  2100
tttgccccgg acagcaccgg ggaatacaga accaccagac ctatcggaac ccgatacctt  2160
acccgacccc tttaa                                                   2175

SEQ ID NO: 48          moltype = DNA  length = 2181
FEATURE                Location/Qualifiers
misc_feature           1..2181
                       note = source = /note="Description of Unknown:Parent AAV
                        Capsid sequence"
source                 1..2181
                       mol_type = other DNA
                       organism = synthetic construct
SEQUENCE: 48
atgtcttttg ttgatcaccc tccagattgg ttggaagaag ttggtgaagg tcttcgcgag  60
tttttgggcc ttgaagcggg cccaccgaaa ccgaaaccca accagcagca tcaagatcaa  120
gcccgtggtc ttgtgctgcc tggttataac tatctcggac ccggaaacgg tctcgatcga  180
ggagagcctg tcaacagggc agacgaggtc gcgcgagagc acgacatctc gtacaacgag  240
cagcttgagg cgggagacaa cccctacctc aagtacaacc acgcggacgc cgagttccag  300
gagaagctcg ccgacgacac atccttcggg ggaaacctcg gaaaggcagt ctttcaggcc  360
aagaaaaggg ttctcgaacc ttttggcctg gttgaagagg gtgctaagac ggcccctacc  420
ggaaagcgga tagacgacca ctttccaaaa agaaagaagg ctcggaccga agaggactcc  480
aagccttcca cctcgtcaga cgccgaagct ggacccagcg gatcccagca gctgcaaatc  540
ccagcacaac cagcctcaag tttgggagct gatacaatgt ctgcgggagg tggcggccca  600
ttgggcgaca ataaccaagg tgccgatgga gtgggcaatg cctcgggaga ttggcattgc  660
gattccacgt ggatgggggga cagagtcgtc accaagtcca cccgcacctg ggtgctgccc  720
agctacaaca accaccagta ccgagagatc aaaagcggct ccgtcgacgg aagcaacgcc  780
aacgcctact ttggatacag cacccccctgg gggtactttg actttaaccg cttccacagc  840
cactggagcc cccgagactg gcaaagactc atcaacaact attggggctt cagaccccgg  900
tctctcagag tcaaaatctt caacatccaa gtcaaagagg tcacggtgca ggactccacc  960
accaccatcg ccaacaacct cacctccacc gtccaagtgt ttacggacga cgactaccaa  1020
ctcccgtacg tcgtcggcaa cgggaccgag ggatgcctgc cggccttccc cccgcaggtc  1080
tttacgctgc cgcagtacgg ctacgcgacg ctgaaccgag acaacggaga caacccgaca  1140
gagcggagca gcttcttttg cctagagtac tttcccagca agatgctgag gacgggcaac  1200
```

```
aactttgagt ttacctacag ctttgaagag gtgcccttcc actgcagctt cgccccgagc  1260
cagaacctct ttaagctggc caacccgctg gtggaccagt acctgtaccg cttcgtgagc  1320
acctcggcca cgggcgccat ccagttccaa aagaacctgg cgggcagata cgccaacacc  1380
tacaaaaact ggttcccggg gcccatgggc cgaacccagg gctggaacac gagctctggc  1440
agcagcacca acagagtcag cgtcaacaac ttttccgtct caaaccggat gaacctggag  1500
ggggccagct accaagtgaa cccccagccc aacgggatga caaacacgct ccaaggcagc  1560
aaccgctacg cgctggaaaa caccatgatc ttcaacgctc aaaacgccac gccgggaact  1620
acctcggtgt acccagagga caatctactg ctgaccagcg agagcgagac tcagcccgtc  1680
aaccgggtgg cttacaacac gggcggtcag atggccacca acgcccagaa cgccaccacg  1740
gctcccacgg tcgggaccta caacctccag gaagtgcttc ctggcagcgt atggatggag  1800
agggacgtgt acctccaagg acccatctgg gccaagatcc cagagacggg ggcgcacttt  1860
cacccctctc cggccatggg cggattcgga ctcaaacacc cgccgcccat gatgctcatc  1920
aaaaacacgc cggtgcccgg caacatcacc agcttctcgg acgtgcccgt cagcagcttc  1980
atcacccagt acagcaccgg gcaggtcacc gtggagatgg aatgggagct caaaaaggaa  2040
aactccaaga ggtggaaccc agagatccag tacaccaaca actacaacga cccccagttt  2100
gtggactttg ctccagacgg ctccggcgaa tacagaacca ccagagccat cggaacccga  2160
tacctcaccc gaccccttta a                                             2181
```

```
SEQ ID NO: 49          moltype = DNA  length = 2142
FEATURE                Location/Qualifiers
misc_feature           1..2142
                       note = source = /note="Description of Unknown:Parent AAV
                        Capsid sequence"
source                 1..2142
                       mol_type = other DNA
                       organism = synthetic construct
SEQUENCE: 49
atgtctttct ttgattggtt aggtaaacag tacgctcaag gagctgctga attctgggat  60
ttgaagtccg gtcctcctgc accaaaaaag gcgcgaaagg acggatcagc cggattcaat  120
ttccctgggc acaaatacct gggtcctggc aattcattgg atcgcggaga tcccgtggac  180
gctgacgacg ccgctgctca aaagcacgac cagtcgtacc aagagcagct tgaggcggga  240
gacaatccct acctcaagta caaccacgcc gaccgcgagt tccaggaggc gttgaaggac  300
gacacctcct ttgaaggaaa tctcgcgaga ggactctttg aggccaagaa gctcgtggca  360
gagcctcttg gtctcgtgga accagaactg gcgccaccca gtggccgtaa acgaccggtg  420
caatcgagtc aagagtctgg ttactcgagt agccaagaca agcggcccaa cctcgacgta  480
gacgaggagg accgtgagtt cgctgccgct gcagcggaga ccgaaactgg aagcgctccc  540
cccaccggca atttgggacc tggtacgatg gctggaggcg gtagcgcgcc aatcgacgac  600
ggctcgtatg gtgccgatgg agtgggcaat gcctcgggag attggcattg cgattccaca  660
tggctggaca actgtgtcat cacccgaacc actcggacct ggaatctgcc aacctacaac  720
aaccacatct acaaacgact caacggaacg acctccggag accaaagcta cttcggattc  780
agcacccccct ggggatactt tgacttcaac cgcttccact gtcatttctc ccctcgagac  840
tggcaaagac tcatcaacaa taactgggga ctccgaccaa agagcctacg gttcaaaatc  900
tttaacattc aagttaaaga agtcacgacg caagactcaa cgaagatcat ctccaataac  960
cttaccagca cggttcaggt atttgcggac acggagtacc agctcccgta cgtgattgga  1020
tcggctcacg aaggatgtct gcctcctttc ccggctgacg tgttcatgct gccgcagtat  1080
ggatactgta ctcgacaaga cggaaacagc aacaatccga ccccgagaag cgccttctat  1140
tgtttggagt actttcccag caagatgcta agaactggga acagttttga atttacatat  1200
aactttgaga aggtgccgtt ccacagcatg tgggctcaca accagagtct ggatcgattg  1260
atgaatccat tgattgatca gtacctgtac taccttgatg tcacttcgag taccgggttt  1320
acctatcaaa aggagttca cacgaacttg cccgaacaag agcgcaactg gctgccggga  1380
ccaggaattc gaaatcaagc ttggtttaat tctgcaactg gaaacaaccc actaactggt  1440
acctggcaat attccaacaa atacgtacta gaaaaccgtg cttcgaagat tgctcctgga  1500
cctgccatgg gaattgaatc aacaaaattc gacgggaacg gaatcatctt ttctaaagaa  1560
tacatcacca atgtaaatac agccaatccg aatcaagtaa acatcacacg cgagaccgaa  1620
ataaactcaa cgaacccctt ggctggagga tctctcggag cccacgctaa taattcacaa  1680
aacacaacaa cggcaccgac gctagaccac accaacgtca tgggtgtgtt tccgggtagt  1740
gtctggcaag acagagacat ttaccttcaa ggacaaatct gggccaagat tccccacaca  1800
gacggacatt tccacccttc tcctctcatg ggaggatttg gactgaagaa cccgcctcct  1860
caaattctga tcaaaaacac acctgttccg gctgacccac caactgaatt caatgcgaac  1920
aaaatctctt ctttcatcac tcaatactca accggacaag ttacagtgga aatggaatgg  1980
gaacttcaga aagaaacctc caaaagatgg aatccagaaa tccagtacag cgacgactcg  2040
tcttcgacgt ctggctccat tctgcacttt gctccggatg atgttggaaa ctacaaagag  2100
ttccgctcta tcggaactcg ttaccttacc cgtcctctgt aa                      2142
```

```
SEQ ID NO: 50          moltype = DNA  length = 2181
FEATURE                Location/Qualifiers
misc_feature           1..2181
                       note = source = /note="Description of Unknown:Parent AAV
                        Capsid sequence"
source                 1..2181
                       mol_type = other DNA
                       organism = synthetic construct
SEQUENCE: 50
atgtcgtttg ttgatcaccc tccagattgg ttagaagaag ttggtgaagg ccttcacgag  60
tttttggagc tcgaagctgg cccacccaaa ccgaagccca accagcagaa gcaggacaac  120
gcccgtggtc ttgtactgcc tggatataat tatctgggac ccttcaacgg actcgacaag  180
ggagagcccg tcaaccgagc ggacgctgtt gcgcgagagc acgacatctc gtacaacgag  240
cagctccagg cgggagacaa cccctacctc aagtacaacc acgcggacgc cgagtttcag  300
gagaagctca aggacgacac ctcctttggg ggcaacctcg gaaaggcaat ctttcaggcc  360
```

```
aagaaaaggg ttctcgaacc ttttggcctg gttgaggcac ctgttaagac ggctccagcc  420
aagaagcggc cgatagagaa gtctccggcg gaaccgagct cttcgaaggg catcggcaag  480
gcgggccagc agcctgcgag gaagcgactc aactttggtc agactggaga caccgactcc  540
gccgctgacc cccagcctct cggagaacca ccagcagccc cctctggtct gggaactggt  600
acgatggctt caggcagtgg cgcaccaatg gcagacaata acgaaggcgc cgacggagtg  660
ggtaatgcct cgggaaattg gcattgcgat tccacatggc tgggcgaccg agtcatcacc  720
accagcaccc gcacctgggc cctgcccacc tacaacaacc atctctacaa gcaaatctcc  780
agccagtctg gagccaacaa cgacaaccac tactttggct acagcacccc ctgggggtac  840
tttgacttca accgcttcca ctgccacttc tccccgcgag actggcagcg gctcatcaac  900
aacaactggg ggttccggcc caagcgactc aacttcaagc tcttcaacat ccaagtcaag  960
gaggtcactc agacggacgg cacgaagacc atcgccaata accttaccag cacggttcag  1020
gtctttgcgg actcggagta ccagctcccg tacgtcctcg gatcagcgca ccagggctgc  1080
ttcccgccgt tcccggcgga cgtcttcatg gtcccgcagt acgggtattt gacgctgaac  1140
aacggcagcc aggcgatggg tcgctcgtcc ttctactgcc tggagtactt tccgtcgcag  1200
atgctgcgga cggggaacaa cttcacgttc agctacacct tcgaggacgt gcccttccac  1260
agcagctacg cgcacagcca gagtctggac cggctcatga acccactcat cgaccagtac  1320
ctgtactacc taagcaagac aaatggcggt ctaggatttt cccaagcggg acccaacagc  1380
atgcgcgacc agtccaggaa ttggctgccg ggaccctgct tcagacaaca acggatttca  1440
actgtaccta cacaaaataa caacggagac ttttcgtgga cgggagccac aaagtatcat  1500
ctcaatggaa gaaactcagc aatgaatccc ggcccggcca tggccagcca caaagacgac  1560
gaacacagat tcttccctca gaacggtgtg ctcatctttg gaaaacaggg cgcagacaag  1620
acaaatgcga tactagaaaa agtgatcgtt acagacgaag aggagattag gacaacaaat  1680
cctgtagcca cggaggagta tgggtttgtc gccactaatc tacaaagctc ggcagaaaca  1740
gccgagaccg aaagagtcaa cgcgcaaggc atcctccctg gcatggtgtg gcaagaccga  1800
gatgtgtatc tgcaggggcc catctgggcc aagatccccc acaccgacgg acacttccgc  1860
ccctcaccac tcatgggagg attcggcctc aagcacccgc ctccgcagat cctcatcaag  1920
aacacgcctg tgccttcgaa tcctccagag acgttcaacc cggaaaagct caattctttc  1980
ataactcaat attctacggg ccaggtcagc gtggagatcg agtgggagct gcagaaggag  2040
aacagcaagc gctggaaccc cgaggtccag tacacgtcca actacaacaa gtccgtcaac  2100
gtggaattta cagtggacaa caacggcgtg tattcggaac cgcgcaccat cggcacccgc  2160
taccttactc gtaatctgta a                                            2181

SEQ ID NO: 51          moltype = DNA  length = 2211
FEATURE                Location/Qualifiers
misc_feature           1..2211
                       note = source = /note="Description of Unknown:Parent AAV
                        Capsid sequence"
source                 1..2211
                       mol_type = other DNA
                       organism = synthetic construct
SEQUENCE: 51
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aaacacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211
```

```
SEQ ID NO: 52          moltype = DNA  length = 2211
FEATURE                Location/Qualifiers
misc_feature           1..2211
                       note = source = /note="Description of Unknown:Parent AAV
                        Capsid sequence"
source                 1..2211
                       mol_type = other DNA
                       organism = synthetic construct
SEQUENCE: 52
atggctgccg atggttatct tccagattgg ctcgaggaca acctctctga gggcattcgc  60
gagtggtggg acttgaaacc tggagccccg aagcccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac cttcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaac gtccggtaga gcagtcgcca caagagccag actcctcctc gggcatcggc  480
aagacaggcc agcagcccgc taaaaagaga ctcaattttg gtcagactgg cgactcagag  540
tcagtccccg acccacaacc tctcggagaa cctccagcaa cccccgctgc tgtgggacct  600
actacaatgg cttcaggcgg tggcgcacca atggcagaca ataacgaagg cgccgacgga  660
gtgggtaatg cctcaggaaa ttggcattgc gattccacat ggctgggcga cagagtcatc  720
accaccagca cccgcacctg ggccttgccc acctacaata accacctcta caagcaaatc  780
tccagtgctt caacgggggc cagcaacgac aaccactact tcggctacag cacccccctgg  840
gggtattttg atttcaacag attccactgc cacttttcac cacgtgactg gcagcgactc  900
atcaacaaca attggggatt ccggcccaag agactcaact tcaaactctt caacatccaa  960
gtcaaggagg tcacgacgaa tgatggcgtc acaaccatcg ctaataacct taccagcacg  1020
gttcaagtct tctcggactc ggagtaccag cttccgtacg tcctcggctc tgcgcaccag  1080
ggctgcctcc ctccgttccc ggcggacgtg ttcatgattc cgcaatacgg ctacctgacg  1140
ctcaacaatg gcagccaagc cgtgggacgt tcatcctttt actgcctgga atatttccct  1200
tctcagatgc tgagaacggg caacaacttt accttcagct acacctttga ggaagtgcct  1260
ttccacagca gctacgcgca cagccagagc ctggaccggc tgatgaatcc tctcatcgac  1320
caatacctgt attacctgaa cagaactcaa aatcagtccg gaagtgccca aaacaaggac  1380
ttgctgttta gccgtgggtc tccagctggc atgtctgttc agcccaaaaa ctggctacct  1440
ggaccctgtt atcggcagca gcgcgtttct aaaacaaaaa cagacaacaa caacagcaat  1500
tttacctgga ctggtgcttc aaaatataac ctcaatgggc gtgaatccat catcaaccct  1560
ggcactgcta tggcctcaca caaagacgac gaagacaagt tctttcccat gagcggtgtc  1620
atgatttttg gaaaagagag cgccggagct tcaaacactg cattggacaa tgtcatgatt  1680
acagacgaag aggaaattaa agccactaac cctgtggcca ccgaaagatt tgggaccgtg  1740
gcagtcaatt tccagagcag cagcacagac cctgcgaccg gagatgtgca tgctatggga  1800
gcattacctg gcatggtgtg gcaagataga gacgtgtacc tgcagggtcc catttgggcc  1860
aaaattcctc acacagatgg acactttcac ccgtctcctc ttatgggcgg ctttggactc  1920
aagaacccgc ctcctcagat cctcatcaaa aacacgcctg ttcctgcgaa tcctccggcg  1980
gagttttcag ctacaaagtt tgcttcattc atcacccaat actccacagg acaagtgagt  2040
gtggaaattg aatgggagct gcagaaagaa aacagcaagc gctggaatcc cgaagtgcag  2100
tacacatcca attatgcaaa atctgccaac gttgatttta ctgtggacaa caatggactt  2160
tatactgagc ctcgccccat tggcacccgt tacctcaccc gtcccctgta a           2211

SEQ ID NO: 53          moltype = DNA  length = 2211
FEATURE                Location/Qualifiers
misc_feature           1..2211
                       note = source = /note="Description of Unknown:Parent AAV
                        Capsid sequence"
source                 1..2211
                       mol_type = other DNA
                       organism = synthetic construct
SEQUENCE: 53
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaaga gggttctcga accttttggt ctggttgagg aaggtgctaa gacggctcct  420
ggaaagaaac gtccggtaga gcagtcgcca caagagccag actcctcctc gggcattggc  480
aagacaggcc agcagcccgc taaaaagaga ctcaattttg gtcagactgg cgactcagag  540
tcagtccccg acccacaacc tctcggagaa cctccagcaa cccccgctgc tgtgggacct  600
actacaatgg cttcaggcgg tggcgcacca atggcagaca ataacgaagg cgccgacgga  660
gtgggtaatg cctcaggaaa ttggcattgc gattccacat ggctgggcga cagagtcatc  720
accaccagca cccgaacatg ggccttgccc acctataaca accacctcta caagcaaatc  780
tccagtgctt caacgggggc cagcaacgac aaccactact tcggctacag cacccccctgg  840
gggtattttg atttcaacag attccactgc catttctcac cacgtgactg gcagcgactc  900
atcaacaaca attggggatt ccggcccaag agactcaact tcaagctctt caacatccaa  960
gtcaaggagg tcacgacgaa tgatggcgtc acgaccatcg ctaataacct taccagcacg  1020
gttcaagtct tctcggactc ggagtaccag ttgccgtacg tcctcggctc tgcgcaccag  1080
ggctgcctcc ctccgttccc ggcggacgtg ttcatgattc cgcagtacgg ctacctaacg  1140
ctcaacaatg gcagccaggc agtgggacgg tcatcctttt actgcctgga atatttccca  1200
tcgcagatgc tgagaacggg caataacttt accttcagct acaccttcga ggacgtgcct  1260
ttccacagca gctacgcgca cagccagagc ctggaccggc tgatgaatcc tctcatcgac  1320
cagtacctgt attacctgaa cagaactcag aatcagtccg gaagtgccca aaacaaggac  1380
```

```
ttgctgttta gccgggggtc tccagctggc atgtctgttc agcccaaaaa ctggctacct  1440
ggaccctgtt accggcagca gcgcgtttct aaaacaaaaa cagacaacaa caacagcaac  1500
tttacctgga ctggtgcttc aaaatataac cttaatgggc gtgaatctat aatcaaccct  1560
ggcactgcta tggcctcaca caaagacgac aaagacaagt tctttcccat gagcggtgtc  1620
atgatttttg gaaaggagag cgccggagct tcaaacactg cattggacaa tgtcatgatc  1680
acagacgaag aggaaatcaa agccactaac cccgtggcca ccgaaagatt tgggactgtg  1740
gcagtcaatc tccagagcag cagcacagac cctgcgaccg gagatgtgca tgttatggga  1800
gccttacctg gaatggtgtg gcaagacaga gacgtatacc tgcagggtcc tatttgggcc  1860
aaaattcctc acacggatgg acactttcac ccgtctcctc tcatgggcgg ctttggactt  1920
aagcacccgc ctcctcagat cctcatcaaa aacacgcctg ttcctgcgaa tcctccggca  1980
gagttttcgg ctacaaagtt tgcttcattc atcacccagt attccacagg acaagtgagc  2040
gtggagattg aatgggagct gcagaaagaa aacagcaaac gctggaatcc cgaagtgcag  2100
tatacatcta actatgcaaa atctgccaac gttgatttca ctgtggacaa caatggactt  2160
tatactgagc ctcgccccat tggcacccgt tacctcaccc gtcccctgta a           2211
```

```
SEQ ID NO: 54          moltype = DNA  length = 2211
FEATURE                Location/Qualifiers
misc_feature           1..2211
                       note = source = /note="Description of Unknown:Parent AAV
                        Capsid sequence"
source                 1..2211
                       mol_type = other DNA
                       organism = synthetic construct
SEQUENCE: 54
atggctgctg acggttatct tccagattgg ctcgaggaca acctttctga aggcattcgt  60
gagtggtggg ctctgaaacc tggagtccct caacccaaag cgaaccaaca acaccaggac  120
aaccgtcggg gtcttgtgct tccgggttac aaatacctcg gacccggtaa cggactcgac  180
aaaggagagc cggtcaacga ggcggacgcg gcagccctcg aacacgacaa agcctacgac  240
cagcagctca aggccggtga caacccgtac ctcaagtaca accacgccga cgccgagttt  300
caggagcgtc ttcaagaaga tacgtctttt gggggcaacc ttggcagagc agtcttccag  360
gccaaaaaga ggatccttga gcctcttggt ctggttgagg aagcagctaa aacggctcct  420
ggaaagaaga ggcctgtaga tcagtctcct caggaaccgg actcatcatc tggtgttggc  480
aaatcgggca aacagcctgc cagaaaaaga ctaaatttcg gtcagactgg cgactcagag  540
tcagtcccag accctcaacc tctcggagaa ccaccagcag cccccacaag tttgggatct  600
aatacaatgg cttcaggcgg tggcgcacca atggcagaca ataacgaggg tgccgatgga  660
gtgggtaatt cctcaggaaa ttggcattgc gattcccaat ggctgggcga cagagtcatc  720
accaccagca ccagaacctg ggccctgccc acttacaaca accatctcta caagcaaatc  780
tccagccaat caggagcttc aaacgacaac cactactttg gctacagcac cccttggggg  840
tattttgact ttaacagatt ccactgccac ttctcaccac gtgactggca gcgactcatt  900
aacaacaact ggggattccg gcccaagaaa ctcagcttca agctcttcaa catccaagtt  960
aaagaggtca cgcagaacga tggcacgacg actattgcca ataaccttac cagcacggtt  1020
caagtgttta cggactcgga gtatcagctc ccgtacgtgc tcgggtcggc gcaccaaggc  1080
tgtctcccgc cgtttccagc ggacgtcttc atggtccctc agtatggata cctcaccctg  1140
aacaacggaa gtcaagcggt gggacgctca tccttttact gcctggagta cttcccttcg  1200
cagatgctaa ggactggaaa taacttccaa ttcagctata ccttcgagga tgtacctttt  1260
cacagcagct acgctcacag ccagagtttg gatcgcttga tgaatcctct tattgatcag  1320
tatctgtact acctgaacag aacgcaagga acaacctctg gaacaaccaa ccaatcacgg  1380
ctgcttttta gccaggctgg gcctcagtct atgtctttgc aggccagaaa ttggctacct  1440
gggccctgct accggcaaca gagactttca aagactgcta acgacaacaa caacagtaac  1500
tttccttgga cagcggccag caaatatcat ctcaatggcc gcgactcgct ggtgaatcca  1560
ggaccagcta tggccagtca caaggacgat gaagaaaaat tttttcccat gcacggcaat  1620
ctaatatttg gcaaagaagg gacaacggca agtaacgcag aattagataa tgtaatgatt  1680
acggatgaag aagagattcg taccaccaat cctgtggcaa cagagcagta tggaactgtg  1740
gcaaataact tgcagagctc aaatacagct cccacgacta gaactgtcaa tgatcagggg  1800
gccttacctg gcatggtgtg gcaagatcgt gacgtgtacc ttcaaggacc tatctgggca  1860
aagattcctc acacggatgg acactttcat ccttctcctc tgatgggagg ctttggactg  1920
aaacatccgc ctcctcaaat catgatcaaa aatactccgg taccggcaaa tcctccgacg  1980
actttcagcc cggccaagtt tgcttcattt atcactcagt actccactgg acaggtcagc  2040
gtggaaattg agtgggagct acagaaagaa aacagcaaac gttggaatcc agagattcag  2100
tacacttcca actacaacaa gtctgttaat gtggacttta ctgtagacac taatggtgtt  2160
tatagtgaac ctcgccctat tggaacccgg tatctcacac gaaacttgta a           2211
```

```
SEQ ID NO: 55          moltype = DNA  length = 2211
FEATURE                Location/Qualifiers
misc_feature           1..2211
                       note = source = /note="Description of Unknown:Parent AAV
                        Capsid sequence"
source                 1..2211
                       mol_type = other DNA
                       organism = synthetic construct
SEQUENCE: 55
atggctgctg acggttatct tccagattgg ctcgaggaca acctttctga aggcattcga  60
gagtggtggg cgctgcaacc tggagcccct aaacccaagg caaatcaaca acatcaggac  120
aacgctcggg gtcttgtgct tccgggttac aaatacctcg gacccggcaa cggactcgac  180
aagggggaac ccgtcaacgc agcggacgcg gcagccctcg agcacgacaa ggcctacgac  240
cagcagctca aggccggtga caacccctac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga tcagtctcct caggaaccgg actcatcatc tggtgttggc  480
```

```
aaatcgggca aacagcctgc cagaaaaaga ctaaatttcg gtcagactgg cgactcagag  540
tcagtcccag accctcaacc tctcggagaa ccaccagcag cccccacaag tttgggatct  600
aatacaatgg cttcaggcgg tggcgcacca atggcagaca ataacgaggg tgccgatgga  660
gtgggtaatt cctcaggaaa ttggcattgc gattcccaat ggctgggcga cagagtcatc  720
accaccagca ccagaacctg ggccctgccc acttacaaca accatctcta caagcaaatc  780
tccagccaat caggagcttc aaacgacaac cactactttg gctacagcac cccttggggg  840
tattttgact ttaacagatt ccactgccac ttctcaccac gtgactggca gcgactcatt  900
aacaacaact ggggattccg gcccaagaaa ctcagcttca agctcttcaa catccaagtt  960
aaagaggtca cgcagaacga tggcacgacg actattgcca ataaccttac cagcacggtt  1020
caagtgttta cggactcgga gtatcagctc ccgtacgtgc tcgggtcggc gcaccaaggc  1080
tgtctcccgc cgtttccagc ggacgtcttc atggtccctc agtatggata cctcaccctg  1140
aacaacggaa gtcaagcggt gggacgctca tccttttact gcctggagta cttcccttcg  1200
cagatgctaa ggactggaaa taacttccaa ttcagctata ccttcgagga tgtacctttt  1260
cacagcagct acgctcacag ccagagtttg gatcgcttga tgaatcctct tattgatcag  1320
tatctgtact acctgaacag aacgcaagga acaacctctg gaacaaccaa ccaatcacgg  1380
ctgcttttta gccaggctgg gcctcagtct atgtctttgc aggccagaaa ttggctacct  1440
gggccctgct accggcaaca gagactttca aagactgcta acgacaacaa caacagtaac  1500
tttccttgga cagcggccag caaatatcat ctcaatggcc gcgactcgct ggtgaatcca  1560
ggaccagcta tggccagtca caaggacgat gaagaaaaat tttccctat gcacggcaat  1620
ctaatatttg gcaaagaagg gacaacggca agtaacgcag aattagataa tgtaatgatt  1680
acggatgaag aagagattcg taccaccaat cctgtggcaa cagagcagta tggaactgtg  1740
gcaaataact tgcagagctc aaatacagct cccacgacta gaactgtcaa tgatcagggg  1800
gccttacctg gcatggtgtg gcaagatcgt gacgtgtacc ttcaaggacc tatctgggca  1860
aagattcctc acacggatgg acactttcat ccttctcctc tgatgggagg ctttggactg  1920
aaacatccgc ctcctcaaat catgatcaaa aatactccgg taccggcaaa tcctccgacg  1980
actttcagcc cggccaagtt tgcttcattt atcactcagt actccactgg acaggtcagc  2040
gtggaaattg agtgggagct acagaaagaa aacagcaaac gttggaatcc agagattcag  2100
tacacttcca actacaacaa gtctgttaat gtggacttta ctgtagacac taatggtgtt  2160
tatagtgaac ctcgccccat tggcacccgt taccttaccc gtcccctgta a           2211

SEQ ID NO: 56          moltype = DNA  length = 2217
FEATURE                Location/Qualifiers
misc_feature           1..2217
                       note = source = /note="Description of Unknown:Parent AAV
                        Capsid sequence"
source                 1..2217
                       mol_type = other DNA
                       organism = synthetic construct
SEQUENCE: 56
atggctgccg atggttatct tccagattgg ctcgaggaca acctctctga gggcattcgc  60
gagtggtggg cgctgaaacc tggagccccg aagcccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctgc aggcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccaacagcc cgccagaaaa agactcaatt ttggtcagac tggcgactca  540
gagtcagttc cagaccctca acctctcgga gaacctccag cagcgccctc tggtgtggga  600
cctaatacaa tggctgcagg cggtggcgca ccaatggcag acaataacga aggcgccgac  660
ggagtgggta gttcctcggg aaattggcat tgcgattcca catggctggg cgacagagtc  720
atcaccacca gcacccgaac ctgggccctg cccacctaca acaaccacct ctacaagcaa  780
atctccaacg ggacatcggg aggagccacc aacgacaaca cctacttcgg ctacagcacc  840
ccctgggggt attttgactt taacagattc cactgccact tttcaccacg tgactggcag  900
cgactcatca acaacaactg gggattccgg cccaagagac tcagcttcaa gctcttcaac  960
atccaggtca aggaggtcac gcagaatgaa ggcaccaaga ccatcgccaa taacctcacc  1020
agcaccatcc aggtgtttac ggactcggag taccagctgc cgtacgttct cggctctgcc  1080
caccagggct gcctgcctcc gttcccggcg gacgtgttca tgattcccca gtacggctac  1140
ctaacactca acaacggtag tcaggccgtg ggacgctcct ccttctactg cctggaatac  1200
tttccttcgc agatgctgag aaccggcaac aacttccagt ttacttacac cttcgaggac  1260
gtgcctttcc acagcagcta cgcccacagc cagagcttgg accggctgat gaatcctctg  1320
attgaccagt acctgtacta cttgtctcgg actcaaacaa caggaggcac ggcaaatacg  1380
cagactctgg gcttcagcca aggtgggcct aatacaatgg ccaatcaggc aaagaactgg  1440
ctgccaggac cctgttaccg ccaacaacgc gtctcaacga caaccgggca aaacaacaat  1500
agcaactttg cctggactgc tggaccaaa taccatctga atggaagaaa ttcattggct  1560
aatcctggca tcgctatggc aacacacaaa gacgacgagg agcgtttttt tcccagtaac  1620
gggatcctga tttttggcaa acaaaatgct gccagagaca atgcggatta cagcgatgtc  1680
atgctcacca gcgaggaaga aatcaaaacc actaaccctg tggctacaga ggaatacggt  1740
atcgtggcag ataacttgca gcagcaaaac acggctcctc aaattggaac tgtcaacagc  1800
cagggggcct tacccggtat ggtctggcag aaccgggacg tgtacctgca gggtcccatc  1860
tgggccaaga ttcctcacac ggacggcaac ttccacccgt ctccgctgat gggcggcttt  1920
ggcctgaaac atcctccgcc tcagatcctg atcaagaaca cgcctgtacc tgcggatcct  1980
ccgaccacct tcaaccagtc aaagctgaac tctttcatca cgcaatacag caccggacag  2040
gtcagcgtgg aaattgaatg ggagctgcag aaggaaaaca gcaagcgctg gaaccccgag  2100
atccagtaca cctccaacta ctacaaatct acaagtgtgg actttgctgt taatacagaa  2160
ggcgtgtact ctgaaccccg ccccattggc acccgttacc tcacccgtaa tctgtaa     2217

SEQ ID NO: 57          moltype = DNA  length = 2217
FEATURE                Location/Qualifiers
```

```
misc_feature           1..2217
                       note = source = /note="Description of Unknown:Parent AAV
                        Capsid sequence"
source                 1..2217
                       mol_type = other DNA
                       organism = synthetic construct
SEQUENCE: 57
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccagcagcc cgcgaaaaag agactcaact ttgggcagac tggcgactca  540
gagtcagtgc ccgaccctca accaatcgga gaacccccg caggcccctc tggtctggga  600
tctggtacaa tggctgcagg cggtggcgct ccaatggcag acaataacga aggcgccgac  660
ggagtgggta gttcctcagg aaattggcat tgcgattcca catggctggg cgacagagtc  720
atcaccacca gcacccgaac ctgggccctc cccacctaca acaaccacct ctacaagcaa  780
atctccaacg ggacttcggg aggaagcacc aacgacaaca cctacttcgg ctacagcacc  840
ccctgggggt attttgactt taacagattc cactgccact tctcaccacg tgactggcag  900
cgactcatca acaacaactg gggattccgg cccaagagac tcaacttcaa gctcttcaac  960
atccaggtca aggaggtcac gcagaatgaa ggcaccaaga ccatcgccaa taaccttacc  1020
agcacgattc aggtctttac ggactcggaa taccagctcc cgtacgtcct cggctctgcg  1080
caccagggct gcctgcctcc gttcccggcg gacgtcttca tgattcctca gtacgggtac  1140
ctgactctga acaatggcag tcaggccgtg ggccgttcct ccttctactg cctggagtac  1200
tttccttctc aaatgctgag aacgggcaac aactttgagt tcagctacca gtttgaggac  1260
gtgccttttc acagcagcta cgcgcacagc caaagcctgg accggctgat gaacccccctc  1320
atcgaccagt acctgtacta cctgtctcgg actcagtcca cgggaggtac cgcaggaact  1380
cagcagttgc tattttctca ggccgggcct aataacatgt cggctcaggc caaaaactgg  1440
ctacccgggc cctgctaccg gcagcaacgc gtctccacga cactgtcgca aaataacaac  1500
agcaactttg cctggaccgg tgccaccaag tatcatctga atggcagaga ctctctggta  1560
aatcccggtg tcgctatggc aacccacaag gacgacgaag agcgattttt tccgtccagc  1620
ggagtcttaa tgtttgggaa acagggagct ggaaaagaca acgtggacta tagcagcgtt  1680
atgctaacca gtgaggaaga aattaaaacc accaacccag tggccacaga acagtacggc  1740
gtggtggccg ataacctgca acagcaaaac gccgctccta ttgtaggggc cgtcaacagt  1800
caaggagcct tacctggcat ggtctggcag aaccgggacg tgtacctgca gggtcctatc  1860
tgggccaaga ttcctcacac ggacggaaac tttcatccct cgccgctgat gggaggcttt  1920
ggactgaaac acccgcctcc tcagatcctg attaagaata cacctgttcc cgcggatcct  1980
ccaactacct tcagtcaagc taagctggcg tcgttcatca cgcagtacag caccggacag  2040
gtcagcgtgg aaattgaatg ggagctgcag aaagaaaaca gcaaacgctg gaacccagag  2100
attcaataca cttccaacta ctacaaatct acaaatgtgg actttgctgt taacacagat  2160
ggcacttatt ctgagcctcg ccccatcggc acccgttacc tcacccgtaa tctgtaa     2217

SEQ ID NO: 58          moltype = DNA  length = 2208
FEATURE                Location/Qualifiers
misc_feature           1..2208
                       note = source = /note="Description of Unknown:Parent AAV
                        Capsid sequence"
source                 1..2208
                       mol_type = other DNA
                       organism = synthetic construct
SEQUENCE: 58
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
```

```
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cagacaagca gctaccgcag atgtcaacac acaaggcgtt  1800
cttccaggca tggtctggca ggacagagat gtgtaccttc aggggcccat ctgggcaaag  1860
attccacaca cggacggaca ttttcacccc tctcccctca tgggtggatt cggacttaaa  1920
caccctcctc cacagattct catcaagaac accccggtac ctgcgaatcc ttcgaccacc  1980
ttcagtgcgg caaagtttgc ttccttcatc acacagtact ccacgggaca ggtcagcgtg  2040
gagatcgagt gggagctgca gaaggaaaac agcaaacgct ggaatcccga aattcagtac  2100
acttccaact acaacaagtc tgttaatgtg gactttactg tggacactaa tggcgtgtat  2160
tcagagcctc gccccattgg caccagatac ctgactcgta atctgtaa              2208

SEQ ID NO: 59          moltype = DNA  length = 2214
FEATURE                Location/Qualifiers
misc_feature           1..2214
                       note = source = /note="Description of Unknown:Parent AAV
                        Capsid sequence"
source                 1..2214
                       mol_type = other DNA
                       organism = synthetic construct
SEQUENCE: 59
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcactctcct gtggagccag actcctcctc gggaaccgga  480
aaggcgggcc agcagcctgc aagaaaaaga ttgaattttg gtcagactgg agacgcagac  540
tcagtcccag accctcaacc aatcggagaa cctcccgcag ccccctcagg tgtgggatct  600
cttacaatgg ctgcaggcgg tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caagcaaatc  780
tccaacagca catctggagg atcttcaaat gacaacgcct acttcggcta cagcaccccc  840
tgggggtatt ttgactttaa cagattccac tgccactttt caccacgtga ctggcagcga  900
ctcatcaaca acaactgggg attccggccc aagagactca gcttcaagct cttcaacatc  960
caggtcaagg aggtcacgca gaatgaaggc accaagacca tcgccaataa cctcaccagc  1020
accatccagg tgtttacgga ctcggagtac cagctgccgt acgttctcgg ctctgcccac  1080
cagggctgcc tgcctccgtt cccggcggac gtgttcatga ttccccagta cggctaccta  1140
acactcaaca acggtagtca ggccgtggga cgctcctcct tctactgcct ggaatacttt  1200
ccttcgcaga tgctgagaac cggcaacaac ttccagttta cttacacctt cgaggacgtg  1260
cctttccaca gcagctacgc ccacagccag agcttggacc ggctgatgaa tcctctgatt  1320
gaccagtacc tgtactactt gtctcggact caaacaacag gaggcacgac aaatacgcag  1380
actctgggct tcagccaagg tggggcctaat acaatggcca atcaggcaaa gaactggctg  1440
ccaggaccct gttaccgcca gcagcgagta tcaaagacat ctgcggataa caacaacagt  1500
gaatactcgt ggactggagc taccaagtac cacctcaatg gcagagactc tctggtgaat  1560
ccgggcccgg ccatggcaag ccacaaggac gatgaagaaa agttttttcc tcagagcggg  1620
gttctcatct ttgggaagca aggctcagag aaaacaaatg tggacattga aaaggtcatg  1680
attacagacg aagaggaaat caggacaacc aatcccgtgg ctacggagca gtatggttct  1740
gtatctacca acctccagag aggcaacaga caagcagcta ccgcagatgt caacacacaa  1800
ggcgttcttc caggcatggt ctggcaggac agagatgtgt accttcaggg gcccatctgg  1860
gcaaagattc cacacacgga cggacatttt cacccctctc ccctcatggg tggattcgga  1920
cttaaacacc ctccgcctca gatcctgatc aagaacacgc ctgtacctgc ggatcctccg  1980
accaccttca accagtcaaa gctgaactct ttcatcaccc agtattctac tggccaagtc  2040
agcgtggaga tcgagtggga gctgcagaag gaaaacagca agcgctggaa ccccgagatc  2100
cagtacacct ccaactacta caaatctaca agtgtggact ttgctgttaa tacagaaggc  2160
gtgtactctg aaccccgccc cattggcacc cgttacctca cccgtaatct gtaa        2214

SEQ ID NO: 60          moltype = DNA  length = 2211
FEATURE                Location/Qualifiers
misc_feature           1..2211
                       note = source = /note="Description of Unknown:Parent AAV
                        Capsid sequence"
source                 1..2211
                       mol_type = other DNA
                       organism = synthetic construct
SEQUENCE: 60
atgtcttttg ttgaccaccc tccagattgg ttggaatcga tcggcgacgg ctttcgtgaa  60
tttctcggcc ttgaggcggg tcccccgaaa cccaaggcca atcaacagaa gcaagataac  120
gctcgaggtc ttgtgcttcc tgggtacaag tatcttggtc ctgggaacgg ccttgataag  180
ggcgatcctg tcaattttgc tgacgaggtt gcccgagagc acgacctctc ctaccagaaa  240
cagcttgagg cgggcgataa cccttacctc aagtacaacc acgcggacgc agagtttcag  300
gagaaactcg cttctgacac ttcttttggg ggaaaccttg ggaaggctgt tttccaggct  360
aaaaagagga ttctcgaacc tcttggcctg gttgagacgc cggataaaac ggcgcctgcg  420
gcaaaaaaga ggcctctaga gcagagtcct caagagccag actcctcgag cggagttggc  480
aagaaaggca aacagcctgc cagaaagaga ctcaactttg acgacgaacc tggagccgga  540
gacgggcctc cccagaagg accatcttcc ggagctatgt ctactgagac tgaaatgcgt  600
```

```
gcagcagctg gcggaaatgg tggcgatgcg ggacaaggtg ccgagggagt gggtaatgcc  660
tccggtgatt ggcattgcga ttccacttgg tcagagagcc acgtcaccac cacctcaacc  720
cgcacctggg tcctgccgac ctacaacaac cacctgtacc tgcggctcgg ctcgagcaac  780
gccagcgaca ccttcaacgg attctccacc ccctggggat actttgactt taaccgcttc  840
cactgccact tctcgccaag agactggcaa aggctcatca acaaccactg ggactgcgc   900
cccaaaagca tgcaagtccg catcttcaac atccaagtta aggaggtcac gacgtctaac  960
ggggagacga ccgtatccaa caacctcacc agcacggtcc agatctttgc ggacagcacg  1020
tacgagctcc cgtacgtgat ggatgcaggt caggagggca gcttgcctcc tttccccaac  1080
gacgtgttca tggtgcctca gtacgggtac tgcggactgg taaccggagg cagctctcaa  1140
aaccagacag acagaaatgc cttctactgt ctggagtact ttcccagcca gatgctgaga  1200
accggaaaca actttgagat ggtgtacaag tttgaaaacg tgcccttcca ctccatgtac  1260
gctcacagcc agagcctgga taggctgatg aacccgctgc tggaccagta cctgtgggag  1320
ctccagtcta ccacctctgg aggaactctc aaccagggca attcagccac caactttgcc  1380
aagctgacca aaacaaactt ttctggctac cgcaaaaact ggctcccggg gcccatgatg  1440
aagcagcaga gattctccaa gactgccagt caaaactaca agattcccca gggaagaaac  1500
aacagtctgc tccattatga gaccagaact accctcgacg gaagatggag caattttgcc  1560
ccgggaacgg ccatggcaac cgcagccaac gacgccaccg acttctctca ggcccagctc  1620
atctttgcgg ggcccaacat caccggcaac accaccacag atgccaataa cctgatgttc  1680
acttcagaag atgaacttag ggccaccaac ccccgggaca ctgacctgtt tggccacctg  1740
gcaaccaacc agcaaaacgc caccaccgtt cctaccgtag acgacgtgga cggagtcggc  1800
gtgtacccgg gaatggtgtg gcaggacaga gacatttact accaagggcc catttgggcc  1860
aaaattccac acacggatgg acactttcac ccgtctcctc tcattggcgg atttggactg  1920
aaaagcccgc ctccacaaat attcatcaaa aacactcctg tacccgccaa tcccgcaacg  1980
accttctctc cggccagaat caacagcttc atcacccagt acagcaccgg acaggtggct  2040
gtcaaaatag aatgggaaat ccagaaggag cggtccaaga gatggaaccc agaggtccag  2100
ttcacgtcca actacggagc acaggactcg cttctctggg ctcccgacaa cgccggagcc  2160
tacaaagagc ccagggccat tggatcccga tacctcacca accacctcta a           2211
```

```
SEQ ID NO: 61          moltype = DNA  length = 2205
FEATURE                Location/Qualifiers
misc_feature           1..2205
                       note = source = /note="Description of Unknown:Parent AAV
                        Capsid sequence"
source                 1..2205
                       mol_type = other DNA
                       organism = synthetic construct
SEQUENCE: 61
atgactgacg gttaccttcc agattggcta gaggacaacc tctctgaagg cgttcgagag  60
tggtgggcgc tgcaacctgg agcccctaaa cccaaggcaa atcaacaaca tcaggacaac  120
gctcggggtc ttgtgcttcc gggttacaaa tacctcggac ccggcaacgg actcgacaag  180
ggggaacccg tcaacgcagc ggacgcggca gccctcgagc acgacaaggc ctacgaccag  240
cagctcaagg ccggtgacaa cccctacctc aagtacaacc acgccgacgc ggagttccag  300
cagcggcttc agggcgacac atcgtttggg ggcaacctcg gcagagcagt cttccaggcc  360
aaaaagaggg ttcttgaacc tcttggtctg gttgagcaag cgggtgagac ggctcctgga  420
aagaagagac cgttgattga atccccccag cagcccgact cctccacggg tatcggcaaa  480
aaaggcaagc agccggctaa aaagaagctc gttttcgaag acgaaactgg agcaggcgac  540
ggacccccctg agggatcaac ttccggagcc atgtctgatg acagtgagat gcgtgcagca  600
gctggcggag ctgcagtcga gggcggacaa ggtgccgatg gagtgggtaa tgcctcgggt  660
gattggcatt gcgattccac ctggtctgag ggccacgtca cgaccaccag caccagaacc  720
tgggtcttgc ccacctacaa caaccacctc tacaagcgac tcggagagag cctgcagtcc  780
aacacctaca acggattctc cacccccctgg ggatactttg acttcaaccg cttccactgc  840
cacttctcac cacgtgactg gcagcgactc atcaacaaca actggggcat gcgacccaaa  900
gccatgcggg tcaaaatctt caacatccag gtcaaggagg tcacgacgtc gaacggcgag  960
acaacggtgg ctaataacct taccagcacg gttcagatct ttgcggactc gtcgtacgaa  1020
ctgccgtacg tgatggatgc gggtcaagag ggcagcctgc ctccgtttcc caacgacgtc  1080
tttatggtgc cccagtacgg ctactgtgga ctggtgaccg gcaacacttc gcagcagcag  1140
actgacagaa atgccttcta ctgcctggag tactttcctt cgcagatgct gcggactggc  1200
aacaactttg aaattacgta cagttttgag aaggtgcctt tccactcgat gtacgcgcac  1260
agccagagcc tggaccggct gatgaaccct ctcatcgacc agtacctgtg ggactgcaa   1320
tcgaccacca ccggaaccac cctgaatgcc gggactgcca ccaccaactt taccaagctg  1380
cggcctacca acttttccaa ctttaaaaag aactggctgc ccgggccttc aatcaagcag  1440
cagggcttct caaagactgc caatcaaaac tacaagatcc ctgccaccgg gtcagacagt  1500
ctcatcaaat acgagacgca cagcactctg gacggaagat ggagtgccct gaccccccgga  1560
cctccaatgg ccacggctgg acctgcggac agcaagttca gcaacagcca gctcatcttt  1620
gcggggcctg aacagaacgg caacacggcc accgtacccg ggactctgat cttcacctct  1680
gaggaggagc tggcagccac caacgccacc gatacggaca tgtggggcaa cctacctggc  1740
ggtgaccaga gcaacagcaa cctgccgacc gtggacagac tgacagcctt gggagccgtg  1800
cctggaatgg tctggcaaaa cagagacatt tactaccagg gtcccatttg ggccaagatt  1860
cctcataccg atggacactt tcacccctca ccgctgattg gtgggtttgg gctgaaacac  1920
ccgcctcctc aaatttttat caagaacacc ccggtacctg cgaatcctgc aacgaccttc  1980
agctctactc cggtaaactc cttcattact cagtacagca ctggccaggt gtcggtgcag  2040
attgactggg agatccagaa ggagcggtcc aaacgctgga accccgaggt ccagtttacc  2100
tccaactacg gacagcaaaa ctctctgttg tgggctcccg atgcggctgg gaaatacact  2160
gagcctaggg ctatcggtac ccgctacctc acccaccacc tgtaa                  2205
```

```
SEQ ID NO: 62          moltype = DNA  length = 2229
FEATURE                Location/Qualifiers
misc_feature           1..2229
                       note = source = /note="Description of Unknown:Parent AAV
```

```
                         Capsid sequence"
source                  1..2229
                        mol_type = other DNA
                        organism = synthetic construct
SEQUENCE: 62
atggctgctg acggttatct tccagattgg ctcgaggaca acctctctga aggcattcgc  60
gagtggtggg cgctgaaacc tggagctcca caacccaagg ccaaccaaca gcatcaggac  120
aacggcaggg gtcttgtgct tcctgggtac aagtacctcg gacccttcaa cggactcgac  180
aagggagagc cggtcaacga ggcagacgcc gcggccctcg agcacgacaa ggcctacgac  240
aagcagctcg agcaggggga caacccgtat ctcaagtaca accacggcga cgccgagttc  300
cagcagcgct tggcgaccga cacctctttt gggggcaacc tcgggcgagc agtcttccag  360
gccaaaaaga ggattctcga gcctctgggt ctggttgaag agggcgttaa aacggctcct  420
ggaaagaaac gcccattaga aaagactcca aatcggccga ccaacccgga ctctgggaag  480
gccccggcca agaaaaagca aaaagacggc gaaccagccg actctgctag aaggacactc  540
gactttgaag actctggagc aggagacgga ccccctgagg gatcatcttc cggagaaatg  600
tctcatgatg ctgagatgcg tgcggcgcca ggcggaaatg ctgtcgaggc gggacaaggt  660
gccgatggag tgggtaatgc ctccggtgat tggcattgcg attccacctg gtcagagggc  720
cgagtcacca ccaccagcac ccgaacctgg gtcctaccca cgtacaacaa ccacctgtac  780
ctgcgaatcg gaacaacggc caacagcaac acctacaacg gattctccac cccctgggga  840
tactttgact ttaaccgctt ccactgccac ttttccccac gcgactggca gcgactcatc  900
aacaacaact ggggactcag gccgaaatcg atgcgtgtta aaatcttcaa catacaggtc  960
aaggaggtca cgacgtcaaa cggcgagact acggtcgcta ataaccttac cagcacggtt  1020
cagatctttg cggattcgac gtatgaactc ccatacgtga tggacgccgg tcaggagggg  1080
agctttcctc cgtttcccaa cgacgtcttt atggttcccc aatacggata ctgcggagtt  1140
gtcactggaa aaaaccagaa ccagacagac agaaatgcct tttactgcct ggaatacttt  1200
ccatcccaaa tgctaagaac tggcaacaat tttgaagtca gttaccaatt tgaaaaagtt  1260
cctttccatt caatgtacgc gcacagccag agcctggaca gaatgatgaa tcctttactg  1320
gatcagtacc tgtggcatct gcaatcgacc actaccggaa attcccttaa tcaaggaaca  1380
gctaccacca cgtacgggaa aattaccact ggagactttg cctactacag gaaaaactgg  1440
ttgcctggag cctgcattaa acaacaaaaa ttttcaaaga atgccaatca aaactacaag  1500
attcccgcca gcgggggaga cgccctttta aagtatgaca cgcataccac tctaaatggg  1560
cgatggagta acatggctcc tggacctcca atggcaaccg caggtgccgg ggactcggat  1620
tttagcaaca gccagctgat ctttgccgga cccaatccga gcggtaacac gaccacatct  1680
tcaaacaatt tgttgtttac ctcagaagag gagattgcca caacaaaccc acgagacacg  1740
gacatgtttg gacagattgc agataataat caaaatgcca ccaccgcccc tcacatcgct  1800
aacctggacg ctatgggaat tgttcccgga atggtctggc aaaacagaga catctactac  1860
cagggcccta tttgggccaa ggtccctcac acggacggac actttcaccc ttcgccgctg  1920
atgggaggat ttggactgaa acacccgcct ccacagattt tcatcaaaaa cacccccgta  1980
cccgccaatc ccaatactac ctttagcgct gcaaggatta attcttttct gacgcagtac  2040
agcaccggac aagttgccgt tcagatcgac tgggaaattc agaaggagca ttccaaacgc  2100
tggaatcccg aagttcaatt tacttcaaac tacggcactc aaaattctat gctgtgggct  2160
cccgacaatg ctggcaacta ccacgaactc cgggctattg ggtcccgttt cctcacccac  2220
cacttgtaa                                                         2229

SEQ ID NO: 63           moltype = DNA  length = 42
FEATURE                 Location/Qualifiers
misc_feature            1..42
                        note = source = /note="Description of Artificial Sequence:
                         Syntheticoligonucleotide"
source                  1..42
                        mol_type = other DNA
                        organism = synthetic construct
SEQUENCE: 63
ctaaaccggt nnnnnnnnnn nnacggaaat acgatgtcgg ga                     42

SEQ ID NO: 64           moltype = DNA  length = 42
FEATURE                 Location/Qualifiers
misc_feature            1..42
                        note = source = /note="Description of Artificial Sequence:
                         Syntheticoligonucleotide"
source                  1..42
                        mol_type = other DNA
                        organism = synthetic construct
SEQUENCE: 64
ttctcggccg nnnnnnnnnn nntcccgaca tcgtatttcc gt                     42

SEQ ID NO: 65           moltype = DNA  length = 19
FEATURE                 Location/Qualifiers
misc_feature            1..19
                        note = source = /note="Description of Artificial Sequence:
                         Syntheticprimer"
source                  1..19
                        mol_type = other DNA
                        organism = synthetic construct
SEQUENCE: 65
cgcgccacta gtaataaac                                               19

SEQ ID NO: 66           moltype = DNA  length = 18
FEATURE                 Location/Qualifiers
```

```
misc_feature           1..18
                       note = source = /note="Description of Artificial Sequence:
                        Syntheticprimer"
source                 1..18
                       mol_type = other DNA
                       organism = synthetic construct
SEQUENCE: 66
tagagcaact agagttcg                                                  18

SEQ ID NO: 67          moltype = DNA  length = 19
FEATURE                Location/Qualifiers
misc_feature           1..19
                       note = source = /note="Description of Artificial Sequence:
                        Syntheticprimer"
source                 1..19
                       mol_type = other DNA
                       organism = synthetic construct
SEQUENCE: 67
aattaaccct cactaaagg                                                 19

SEQ ID NO: 68          moltype = DNA  length = 22
FEATURE                Location/Qualifiers
misc_feature           1..22
                       note = source = /note="Description of Artificial Sequence:
                        Syntheticprimer"
source                 1..22
                       mol_type = other DNA
                       organism = synthetic construct
SEQUENCE: 68
gtaatacgac tcactatagg gc                                             22

SEQ ID NO: 69          moltype = DNA  length = 20
FEATURE                Location/Qualifiers
misc_feature           1..20
                       note = source = /note="Description of Artificial Sequence:
                        Syntheticprimer"
source                 1..20
                       mol_type = other DNA
                       organism = synthetic construct
SEQUENCE: 69
gtctgagtga ctagcattcg                                                20

SEQ ID NO: 70          moltype = DNA  length = 20
FEATURE                Location/Qualifiers
misc_feature           1..20
                       note = source = /note="Description of Artificial Sequence:
                        Syntheticprimer"
source                 1..20
                       mol_type = other DNA
                       organism = synthetic construct
SEQUENCE: 70
gtctactgaa gctcactgag                                                20

SEQ ID NO: 71          moltype = DNA  length = 20
FEATURE                Location/Qualifiers
misc_feature           1..20
                       note = source = /note="Description of Artificial Sequence:
                        Syntheticprimer"
source                 1..20
                       mol_type = other DNA
                       organism = synthetic construct
SEQUENCE: 71
tggatgactg catctttgaa                                                20

SEQ ID NO: 72          moltype = DNA  length = 17
FEATURE                Location/Qualifiers
misc_feature           1..17
                       note = source = /note="Description of Artificial Sequence:
                        Syntheticprimer"
source                 1..17
                       mol_type = other DNA
                       organism = synthetic construct
SEQUENCE: 72
attggcattg cgattcc                                                   17

SEQ ID NO: 73          moltype = DNA  length = 18
FEATURE                Location/Qualifiers
misc_feature           1..18
                       note = source = /note="Description of Artificial Sequence:
```

```
                         Syntheticprimer"
source                  1..18
                        mol_type = other DNA
                        organism = synthetic construct
SEQUENCE: 73
tagagcaact agagttcg                                              18

SEQ ID NO: 74           moltype = DNA  length = 21
FEATURE                 Location/Qualifiers
misc_feature            1..21
                        note = source = /note="Description of Artificial Sequence:
                         Syntheticprimer"
source                  1..21
                        mol_type = other DNA
                        organism = synthetic construct
SEQUENCE: 74
ttcgatcaac tacgcagaca g                                          21

SEQ ID NO: 75           moltype = DNA  length = 22
FEATURE                 Location/Qualifiers
misc_feature            1..22
                        note = source = /note="Description of Artificial Sequence:
                         Syntheticprimer"
source                  1..22
                        mol_type = other DNA
                        organism = synthetic construct
SEQUENCE: 75
gtccgtgagt gaagcagata tt                                         22

SEQ ID NO: 76           moltype = DNA  length = 24
FEATURE                 Location/Qualifiers
misc_feature            1..24
                        note = source = /note="Description of Artificial Sequence:
                         Syntheticprobe"
source                  1..24
                        mol_type = other DNA
                        organism = synthetic construct
SEQUENCE: 76
tctgatgctg tttccctgca gaca                                       24

SEQ ID NO: 77           moltype = DNA  length = 58
FEATURE                 Location/Qualifiers
misc_feature            1..58
                        note = source = /note="Description of Artificial Sequence:
                         Syntheticprimer"
source                  1..58
                        mol_type = other DNA
                        organism = synthetic construct
SEQUENCE: 77
aatgatacgg cgaccaccga gatctacact ctttccctac acgacgctct tccgatct    58

SEQ ID NO: 78           moltype = DNA  length = 19
FEATURE                 Location/Qualifiers
misc_feature            1..19
                        note = source = /note="Description of Artificial Sequence:
                         Syntheticprimer"
source                  1..19
                        mol_type = other DNA
                        organism = synthetic construct
SEQUENCE: 78
cgcgccacta gtaataaac                                             19

SEQ ID NO: 79           moltype = DNA  length = 61
FEATURE                 Location/Qualifiers
misc_feature            1..61
                        note = source = /note="Description of Artificial Sequence:
                         Syntheticprimer"
source                  1..61
                        mol_type = other DNA
                        organism = synthetic construct
SEQUENCE: 79
caagcagaag acggcatacg agatcggtct cggcattcct gctgaaccgc tcttccgatc  60
t                                                                  61

SEQ ID NO: 80           moltype = DNA  length = 18
FEATURE                 Location/Qualifiers
misc_feature            1..18
                        note = source = /note="Description of Artificial Sequence:
                         Syntheticprimer"
```

```
source                  1..18
                        mol_type = other DNA
                        organism = synthetic construct
SEQUENCE: 80
tagagcaact agagttcg                                            18

SEQ ID NO: 81           moltype = DNA  length = 22
FEATURE                 Location/Qualifiers
misc_feature            1..22
                        note = source = /note="Description of Artificial Sequence:
                         Syntheticprimer"
source                  1..22
                        mol_type = other DNA
                        organism = synthetic construct
SEQUENCE: 81
cacatatcga ggtggacatt ac                                       22

SEQ ID NO: 82           moltype = DNA  length = 20
FEATURE                 Location/Qualifiers
misc_feature            1..20
                        note = source = /note="Description of Artificial Sequence:
                         Syntheticprimer"
source                  1..20
                        mol_type = other DNA
                        organism = synthetic construct
SEQUENCE: 82
tgtttgtatt cagcccatag                                          20

SEQ ID NO: 83           moltype = DNA  length = 20
FEATURE                 Location/Qualifiers
misc_feature            1..20
                        note = source = /note="Description of Artificial Sequence:
                         Syntheticprimer"
source                  1..20
                        mol_type = other DNA
                        organism = synthetic construct
SEQUENCE: 83
cctgtatgcc tctggtcgta                                          20

SEQ ID NO: 84           moltype = DNA  length = 19
FEATURE                 Location/Qualifiers
misc_feature            1..19
                        note = source = /note="Description of Artificial Sequence:
                         Syntheticprimer"
source                  1..19
                        mol_type = other DNA
                        organism = synthetic construct
SEQUENCE: 84
cctcgtagat gggcacagt                                           19

SEQ ID NO: 85           moltype = DNA  length = 42
FEATURE                 Location/Qualifiers
misc_feature            1..42
                        note = source = /note="Description of Artificial Sequence:
                         Syntheticoligonucleotide"
source                  1..42
                        mol_type = other DNA
                        organism = synthetic construct
SEQUENCE: 85
ctaaaccggt nnnnnnnnnn nnacggaaat acgatgtcgg ga                 42

SEQ ID NO: 86           moltype = DNA  length = 42
FEATURE                 Location/Qualifiers
misc_feature            1..42
                        note = source = /note="Description of Artificial Sequence:
                         Syntheticoligonucleotide"
source                  1..42
                        mol_type = other DNA
                        organism = synthetic construct
SEQUENCE: 86
ttctcggccg nnnnnnnnnn nntcccgaca tcgtatttcc gt                 42

SEQ ID NO: 87           moltype = DNA  length = 62
FEATURE                 Location/Qualifiers
misc_feature            1..62
                        note = source = /note="Description of Unknown:Parent AAV
                         sequence"
source                  1..62
                        mol_type = other DNA
```

```
                       organism = synthetic construct
SEQUENCE: 87
gtaataaacc ggttgtacgg cagacacgga aatacgatgt cgggaagtac ctcccagcgg  60
cc                                                                 62

SEQ ID NO: 88          moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 88
gtaataaacc ggttgaaact accccacgga aatacgatgt cgggaaccta caagagacgg  60
cc                                                                 62

SEQ ID NO: 89          moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 89
gtaataaacc ggtaggggaa agcggacgga aatacgatgt cgggaaaaaa taaacatcgg  60
cc                                                                 62

SEQ ID NO: 90          moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 90
gtaataaacc ggttggcgga tgcagacgga aatacgatgt cgggaaggaa agatcttcgg  60
cc                                                                 62

SEQ ID NO: 91          moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 91
gtaataaacc ggtactaagt atcaaacgga aatacgatgt cgggatccac ttcaagacgg  60
cc                                                                 62

SEQ ID NO: 92          moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 92
gtaataaacc ggtttttcgc tggaaacgga aatacgatgt cgggacctgc cccgcctcgg  60
cc                                                                 62

SEQ ID NO: 93          moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 93
gtaataaacc ggttcgaaag tatgtacgga aatacgatgt cgggactaaa aattacccgg  60
cc                                                                 62

SEQ ID NO: 94          moltype = DNA  length = 62
FEATURE                Location/Qualifiers
```

```
misc_feature          1..62
                      note = source = /note="Description of Unknown:Parent AAV
                       sequence"
source                1..62
                      mol_type = other DNA
                      organism = synthetic construct
SEQUENCE: 94
gtaataaacc ggtccaacaa aatttacgga aatacgatgt cgggatcggt caaaggacgg  60
cc                                                                 62

SEQ ID NO: 95         moltype = DNA  length = 62
FEATURE               Location/Qualifiers
misc_feature          1..62
                      note = source = /note="Description of Unknown:Parent AAV
                       sequence"
source                1..62
                      mol_type = other DNA
                      organism = synthetic construct
SEQUENCE: 95
gtaataaacc ggtgtcgtat gtgtgacgga aatacgatgt cgggattatg tcagtcacgg  60
cc                                                                 62

SEQ ID NO: 96         moltype = DNA  length = 62
FEATURE               Location/Qualifiers
misc_feature          1..62
                      note = source = /note="Description of Unknown:Parent AAV
                       sequence"
source                1..62
                      mol_type = other DNA
                      organism = synthetic construct
SEQUENCE: 96
gtaataaacc ggtaacgagg tcacgacgga aatacgatgt cgggacgtaa cctagaacgg  60
cc                                                                 62

SEQ ID NO: 97         moltype = DNA  length = 62
FEATURE               Location/Qualifiers
misc_feature          1..62
                      note = source = /note="Description of Unknown:Parent AAV
                       sequence"
source                1..62
                      mol_type = other DNA
                      organism = synthetic construct
SEQUENCE: 97
gtaataaacc ggtcaataat gaagaacgga aatacgatgt cgggacgagt tcatattcgg  60
cc                                                                 62

SEQ ID NO: 98         moltype = DNA  length = 62
FEATURE               Location/Qualifiers
misc_feature          1..62
                      note = source = /note="Description of Unknown:Parent AAV
                       sequence"
source                1..62
                      mol_type = other DNA
                      organism = synthetic construct
SEQUENCE: 98
gtaataaacc ggtgggagtg cagacacgga aatacgatgt cgggaaaccc ttaccaacgg  60
cc                                                                 62

SEQ ID NO: 99         moltype = DNA  length = 62
FEATURE               Location/Qualifiers
misc_feature          1..62
                      note = source = /note="Description of Unknown:Parent AAV
                       sequence"
source                1..62
                      mol_type = other DNA
                      organism = synthetic construct
SEQUENCE: 99
gtaataaacc ggtccatcct attcgacgga aatacgatgt cgggaactgc ctcggtacgg  60
cc                                                                 62

SEQ ID NO: 100        moltype = DNA  length = 62
FEATURE               Location/Qualifiers
misc_feature          1..62
                      note = source = /note="Description of Unknown:Parent AAV
                       sequence"
source                1..62
                      mol_type = other DNA
                      organism = synthetic construct
SEQUENCE: 100
```

```
gtaataaacc ggtaagagtt acgccacgga aatacgatgt cgggaccgat aaccacccgg  60
cc                                                                 62

SEQ ID NO: 101         moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 101
gtaataaacc ggtcgaacgg agataacgga aatacgatgt cgggacccag agtaccacgg  60
cc                                                                 62

SEQ ID NO: 102         moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 102
gtaataaacc ggtggggccg ctcggacgga aatacgatgt cgggaggtcc gaccctacgg  60
cc                                                                 62

SEQ ID NO: 103         moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 103
gtaataaacc ggtattacta catctacgga aatacgatgt cgggaaccat gacttgccgg  60
cc                                                                 62

SEQ ID NO: 104         moltype = DNA  length = 62
FEATURE                Location/Qualifiers
misc_feature           1..62
                       note = source = /note="Description of Unknown:Parent AAV
                        sequence"
source                 1..62
                       mol_type = other DNA
                       organism = synthetic construct
SEQUENCE: 104
gtaataaacc ggtcaatgtt gccatacgga aatacgatgt cgggattacc ttcaattcgg  60
cc                                                                 62

SEQ ID NO: 105         moltype = AA  length = 736
FEATURE                Location/Qualifiers
VARIANT                162
                       note = /replace="Ala" or "Ser" or "Lys"
VARIANT                200
                       note = /replace="Thr" or "Ser"
VARIANT                328
                       note = /replace="Glu" or "Asn"
VARIANT                411
                       note = /replace="Gln" or "Glu"
VARIANT                494
                       note = /replace="Ala" or "Asn" or "Gly" or "Ser"
VARIANT                548
                       note = /replace="Ser" or "Thr"
VARIANT                549
                       note = /replace="Glu" or "Thr" or "Ala" or "Asp"
VARIANT                554
                       note = /replace="Asp" or "Glu" or "Ile"
VARIANT                664
                       note = /replace="Pro" or "Gln" or "Lys"
VARIANT                709
                       note = /replace="Val" or "Thr" or "Asn"
SITE                   1..736
                       note = /note="Variant residues given in the sequence have
                        nopreference with respect to those in the annotationsfor
                        variant positions"
REGION                 1..736
                       note = source = /note="Description of Artificial Sequence:
```

```
                         Syntheticpolypeptide"
source                   1..736
                         mol_type = protein
                         organism = synthetic construct
SEQUENCE: 105
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPARKR LNFGQTGDSE  180
SVPDPQPLGE PPAAPSGLGP NTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTQNDGT KTIANNLTST VQVFTDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ GTSGTTNQSR LLFSQAGPQS MSIQARNWLP  480
GPCYRQQRVS KTATDNNNSN FPWTGASKYH LNGRDSLVNP GPAMASHKDD EEKFFPMSGV  540
LIFGKEGAGA SNAALDNVMI TDEEEIRTTN PVATEQYGTV ANNLQSSNTA PTTGTVNDQG  600
ALPGMVWQDR DVYLQGPIWA KIPHTDGHFH PSPLMGGFGL KHPPPQILIK NTPVPANPPT  660
TFSAAKLASF ITQYSTGQVS VEIEWELQKE NSKRWNPEIQ YTSNYYKSAN VDFTVDTNGV  720
YSEPRPIGTR YLTRNL                                                 736

SEQ ID NO: 106           moltype = AA  length = 736
FEATURE                  Location/Qualifiers
REGION                   1..736
                         note = source = /note="Description of Unknown:Parent AAV
                          Capsid sequence"
source                   1..736
                         mol_type = protein
                         organism = synthetic construct
SEQUENCE: 106
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 107           moltype = AA  length = 735
FEATURE                  Location/Qualifiers
REGION                   1..735
                         note = source = /note="Description of Unknown:Parent AAV
                          Capsid sequence"
source                   1..735
                         mol_type = protein
                         organism = synthetic construct
SEQUENCE: 107
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 108           moltype = AA  length = 736
FEATURE                  Location/Qualifiers
REGION                   1..736
                         note = source = /note="Description of Unknown:Parent AAV
                          Capsid sequence"
source                   1..736
                         mol_type = protein
                         organism = synthetic construct
SEQUENCE: 108
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
```

```
NNNWGFRPKK LSFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSIQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTRTVNDQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                 736

SEQ ID NO: 109         moltype = AA  length = 736
FEATURE                Location/Qualifiers
REGION                 1..736
                       note = source = /note="Description of Unknown:Parent AAV
                        Capsid sequence"
source                 1..736
                       mol_type = protein
                       organism = synthetic construct
SEQUENCE: 109
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPFG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD KDKFFPMSGV  540
MIFGKESAGA SNTALDNVMI TDEEEIKATN PVATERFGTV AVNLQSSSTD PATGDVHVMG  600
ALPGMVWQDR DVYLQGPIWA KIPHTDGHFH PSPLMGGFGL KHPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 110         moltype = AA  length = 738
FEATURE                Location/Qualifiers
REGION                 1..738
                       note = source = /note="Description of Unknown:Parent AAV
                        Capsid sequence"
source                 1..738
                       mol_type = protein
                       organism = synthetic construct
SEQUENCE: 110
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 111         moltype = AA  length = 736
FEATURE                Location/Qualifiers
REGION                 1..736
                       note = source = /note="Description of Unknown:Parent AAV
                        Capsid sequence"
source                 1..736
                       mol_type = protein
                       organism = synthetic construct
SEQUENCE: 111
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 112         moltype = AA  length = 738
```

```
FEATURE                Location/Qualifiers
REGION                 1..738
                       note = source = /note="Description of Unknown:Parent AAV
                        Capsid sequence"
source                 1..738
                       mol_type = protein
                       organism = synthetic construct
SEQUENCE: 112
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYQFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTD  720
GTYSEPRPIG TRYLTRNL                                              738

SEQ ID NO: 113         moltype = AA  length = 726
FEATURE                Location/Qualifiers
REGION                 1..726
                       note = source = /note="Description of Unknown:Parent AAV
                        Capsid sequence"
source                 1..726
                       mol_type = protein
                       organism = synthetic construct
SEQUENCE: 113
MSFVDHPPDW LEEVGEGLHE FLELEAGPPK PKPNQQKQDN ARGLVLPGNK YLGPFNGLDK  60
GEPVNRADAV AREHDISYNE QLQAGDNPYL KYNHADAEFQ EKLKDDTSFG GNLKRIVFQA  120
KKRVLEPFGL VEAPVKTAPA KKRPIEKSPA EPDSSKGIGK AGQQPARKRL NFGQTGDTDS  180
AADPQPLGEP PAAPSGLGTG TMASGSGAPM ADNNEGADGV GNASGNWHCD STWLGDRVIT  240
TSTRTWALPT YNNHLYKQIS SQSGANNDNH YFGYSTPWGY FDFNRFHCHF SPRDWQRLIN  300
NNWGFRPKRL NFKLFNIQVK EVTQTDGTKT IANNLTSTVQ VFADSEYQLP YVLGSAHQGC  360
FPPFPADVFM IPVYGYLTLN NGSQAVGMSS FYCLEYFPSQ MLRTGNNFTF SYTFEDVPFH  420
SSYAHSQSLD RLMNPLIDQY LYYLSKTNGG LGFSQAGPNS MRDQSRNWLP GPCFRQQRIS  480
TVPTQNNNGD FSWTGATKYH LNGRNSAMNP GPAMASHKDD EHRFFPQNGV LIFGKQGADK  540
TNAILEKVIV TDEEEIRTTN PVATEEYGFV ATNLQSSAET AETERVNAQG ILPGMVWQDR  600
DVYLQGPIWA KIPHTDGHFR PSPLMGGFGL KHPPPQILIK NTPVPSNPPE TFNPEKLNSF  660
ITQYSTGQVS VEIEWELQKE NSKRWNPEVQ YTSNYNKSVN VEFTVDNNGV YSEPRTIGTR  720
YLTRNL                                                           726

SEQ ID NO: 114         moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 114
MAADGYLPDW LEDTLSEGIR QWWKLKPGPP PPKPAERHKD DSRGLVLPGY KYLGPGNGLD  60
KGEPVNAADA AALEHDKAYD QQLKAGDNPY LRYNHADAEF QERLQEDTSF GGNLGRAVFQ  120
AKKRVLEPLG LVEEPVKTAP GKKRPVEHSP VEPDSSSGTG KAGQQPARKR LNFGQTGDTD  180
SAADPQPLGE PPAAPSGLGT GTMAAGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTQNEGT KTIANNLTST VQVFTDSEYQ LPYVLGSAHQ  360
GCLPPFPADV FMIPQYGYLT LNNGSQAMGR SSFYCLEYFP SQMLRTGNNF QFTYTFEDVP  420
FHSSYAHSQS LDRLMNPLID QYLYYLNRTQ GTTSGTTNQS RLLFSQAGPQ SMSIQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQILI KNTPVPADPP  660
TAFNKDKLNS FITQYSTGQV SVEIEWELQK ENSKRWNPEI QYTSNYYKST SVDFAVNTEG  720
VYSEPRPIGT RYLTRNL                                               737

SEQ ID NO: 115         moltype = AA  length = 737
FEATURE                Location/Qualifiers
REGION                 1..737
                       note = source = /note="Description of Artificial Sequence:
                        Syntheticpolypeptide"
source                 1..737
                       mol_type = protein
                       organism = synthetic construct
SEQUENCE: 115
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
```

```
AKKRVLEPLG LVEEGAKTAP GKKRPVEHSP VEPDSSSGIG KTGQQPAKKR LNFGQTGDAD  180
SVPDPQPLGQ PPAAPSGLGT NTMATGSGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTQNEGT TTIANNLTST VQVFTDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ GTTSGTTNQS RLLFSQAGPQ SMSIQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRPL                                                737

SEQ ID NO: 116         moltype = AA  length = 738
FEATURE                Location/Qualifiers
REGION                 1..738
                       note = source = /note="Description of Artificial Sequence:
                        Syntheticpolypeptide"
source                 1..738
                       mol_type = protein
                       organism = synthetic construct
SEQUENCE: 116
MAADGYLPDW LEDTLSEGIR QWWKLKPGPP PPKPAERHKD DSRGLVLPGY KYLGPFNGLD  60
KGEPVNEADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGNASGNWH CDSTWLGDRV  240
ITTSTRTWAL PTYNNHLYKQ ISSASTGASN DNHYFGYSTP WGYFDFNRFH CHFSPRDWQR  300
LINNNWGFRP KRLNFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFSYTFEDV  420
PFHSSYAHSQ SLDRLMNPLI DQYLYYLNRT QGTTSGTTNQ SRLLFSQAGP QSMSIQARNW  480
LPGPCYRQQR LSKTANDNNN SNFPWTAASK YHLNGRDSLV NPGPAMASHK DDEEKFFPMH  540
GNLIFGKEGT TASNAELDNV MITDEEEIRT TNPVATEQYG TVANNLQSSN TAPTTRTVND  600
QGALPGMVWQ DRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 117         moltype = AA  length = 196
FEATURE                Location/Qualifiers
VARIANT                8
                       note = /replace="Leu" or "Gln"
VARIANT                16
                       note = /replace="His" or "Pro"
VARIANT                91
                       note = /replace="Glu" or "Asp"
VARIANT                155
                       note = /replace="Arg" or "Pro"
SITE                   1..196
                       note = /note="Variant residues given in the sequence have
                        nopreference with respect to those in the annotationsfor
                        variant positions"
REGION                 1..196
                       note = source = /note="Description of Artificial Sequence:
                        Syntheticpolypeptide"
source                 1..196
                       mol_type = protein
                       organism = synthetic construct
SEQUENCE: 117
LATQSQSPTI NLSENLQQPP LVWDLIQWLQ AVAHQWQTIT KAPTEWVMPQ EIGIAIPHGW  60
ATESSPPAPE PGPCPPTTTT STSKSPVIQR GPATTTTTSA TAPPGGILTS TDSTATSHHV  120
TGSDSSTTTG DSGPRDSTSS SSTSKSRRSR RMKASRPSPI TLPARFRCLR TRSTSSRTSS  180
ALRTRAASLR SRRTCS                                                 196

SEQ ID NO: 118         moltype = AA  length = 196
FEATURE                Location/Qualifiers
REGION                 1..196
                       note = source = /note="Description of Unknown:Parent AAV
                        Capsid sequence"
source                 1..196
                       mol_type = protein
                       organism = synthetic construct
SEQUENCE: 118
LATQSQSPTH NLSENLQQPP LLWDLLQWLQ AVAHQWQTIT KAPTEWVMPQ EIGIAIPHGW  60
ATESSPPAPA PGPCPPTITT STSKSPVIQR GPATTTTTSA TAPPGGILIS TDSTATFHHV  120
TGSDSSTTIG DSGPRDSTSN SSTSKSRRSR RMMASQPSLI TLPARFKSSR TRSTSFRTSS  180
ALRTRAASLR SRRTCS                                                 196

SEQ ID NO: 119         moltype = AA  length = 204
FEATURE                Location/Qualifiers
REGION                 1..204
                       note = source = /note="Description of Unknown:Parent AAV
```

```
                         Capsid sequence"
source                  1..204
                        mol_type = protein
                        organism = synthetic construct
SEQUENCE: 119
LETQTQYLTP SLSDSHQQPP LVWELIRWLQ AVAHQWQTIT RAPTEWVIPR EIGIAIPHGW  60
ATESSPPAPE PGPCPPTTTT STNKFPANQE PRTTITTLAT APLGGILTST DSTATFHHVT  120
GKDSSTTTGD SDPRDSTSSS LTFKSKRSRR MTVRRRLPIT LPARFRCLLT RSTSSRTSSA  180
RRIKDASRRS QQTSSWCHSM DTSP                                         204

SEQ ID NO: 120          moltype = AA  length = 204
FEATURE                 Location/Qualifiers
REGION                  1..204
                        note = source = /note="Description of Unknown:Parent AAV
                         Capsid sequence"
source                  1..204
                        mol_type = protein
                        organism = synthetic construct
SEQUENCE: 120
LATQSQSQTI NLSENHQQPP QVWDLIQWLQ AVAHQWQTIT RVPMEWVIPQ EIGIAIPNGW  60
ATESSPPAPE PGPCPLTTTI STSKSPANQE LQTTTTTLAT APLGGILTLT DSTATSHHVT  120
GSDSLTTTGD SGPRNSASSS STSKLKRSRR TMARRLLPIT LPARFKCLRT RSISSRTCSG  180
RRTKAVSRRF QRTSSWSLSM DTSP                                         204

SEQ ID NO: 121          moltype = AA  length = 196
FEATURE                 Location/Qualifiers
REGION                  1..196
                        note = source = /note="Description of Unknown:Parent AAV
                         Capsid sequence"
source                  1..196
                        mol_type = protein
                        organism = synthetic construct
SEQUENCE: 121
LATQSQSPTH NLSENLQQPP LLWDLLQWLQ AVAHQWQTIT KAPTEWVMPQ EIGIAIPHGW  60
ATESSPPAPE HGPCPPITTT STSKSPVIQR GPATTTTTSA TAPPGGILIS TDSTAISHHV  120
TGSDSSTTIG DSGPRDSTSS SSTSKSRRSR RMMASRPSLI TLPARFKSSR TRSTSCRTSS  180
ALRTRAASLR SRRTCS                                                  196

SEQ ID NO: 122          moltype = AA  length = 197
FEATURE                 Location/Qualifiers
REGION                  1..197
                        note = source = /note="Description of Unknown:Parent AAV
                         Capsid sequence"
source                  1..197
                        mol_type = protein
                        organism = synthetic construct
SEQUENCE: 122
LATQSQFQTI NLSENLQQRP LVWDLIQWLQ AVAHQWQTIT KAPTEWVVPR EIGIAIPHGW  60
ATESSPPAPE PGPCPPTTTT STSKSPTGHR EEPPTTTPTS ATAPPGGILT LTDSTATFHH  120
VTGSDSSTTT GDSGPRDSAS SSSTSRSRRS RRMKAPRPSP ITSPAPSRCL RTRSTSCRTF  180
SALPTRAACL RSRRTCS                                                 197

SEQ ID NO: 123          moltype = AA  length = 197
FEATURE                 Location/Qualifiers
REGION                  1..197
                        note = source = /note="Description of Unknown:Parent AAV
                         Capsid sequence"
source                  1..197
                        mol_type = protein
                        organism = synthetic construct
SEQUENCE: 123
LATQSQSQTI NQSENLPQPP QVWDLLQWLQ VVAHQWQTIT KVPMEWVVPR EIGIAIPNGW  60
GTESSPPAPE PGPCPPTTIT STSKSPTAHL EDLQMTTPTS ATAPPGGILT STDSTATSHH  120
VTGSDSSTTT GDSGLSDSTS SSSTFRSKRL RTTMESRPSP ITLPARSRSS RTQTISSRTC  180
SGRLTRAASR RSQRTFS                                                 197

SEQ ID NO: 124          moltype = AA  length = 197
FEATURE                 Location/Qualifiers
REGION                  1..197
                        note = source = /note="Description of Unknown:Parent AAV
                         Capsid sequence"
source                  1..197
                        mol_type = protein
                        organism = synthetic construct
SEQUENCE: 124
LATQSQCPTI NQSENPPQAP LVWDLVQWLQ AVALQWQTIT KAPTEWVVPQ EIGIAIPHGW  60
ATESSPPAPE PGPSPPTTTT STSKSPTGLR EEAPTTTPTS ATAPPGGILT LTDSTATSHH  120
VTGSDSSTTT GDSGPRDSTS SSSTSRSRRS RRMKAPRPSP ITLPARFRSL RTRNTSSRTS  180
SALRTRAACL RSRRTSS                                                 197
```

```
SEQ ID NO: 125          moltype = AA  length = 202
FEATURE                 Location/Qualifiers
REGION                  1..202
                        note = source = /note="Description of Unknown:Parent AAV
                         Capsid sequence"
source                  1..202
                        mol_type = protein
                        organism = synthetic construct
SEQUENCE: 125
LETPTPPLTP SLSENHQQPP LVWELVRWLQ AVAHQWQTIT KAPTEWVMPR EIGIAIPHGW  60
ATESSPPAPA PGPCPPTTTI STSKSPASLE PTTTTTLAT APPGGTLTST ASTATSPRET  120
GSGSSTTTGG SGPSDSTSSS STSKSRRSLR RTARRPSPIT LPARFRSLRT RSTSSRTSSD  180
QRTRAASRRS RRTSSWSRST GI                                         202

SEQ ID NO: 126          moltype = AA  length = 196
FEATURE                 Location/Qualifiers
REGION                  1..196
                        note = source = /note="Description of Artificial Sequence:
                         Syntheticpolypeptide"
source                  1..196
                        mol_type = protein
                        organism = synthetic construct
SEQUENCE: 126
LETPTPPLTP SLSENHQQPP LVWELVQWLQ AVALQWQTIT KAPTEWVMPR EIGIAIPHGW  60
ATESSPPAPA PGPCPPTITT STSKSPVIQR GPATTTTTSA TAPPGGTLTS TASTATSHHV  120
TGKDSSTTTG DSGPRDSTSS SSTSRSRRSR RMKAPRPSPI TLPARFRCLL TRSTSCRTFS  180
ALPTRAACLR SRRTCS                                                196

SEQ ID NO: 127          moltype = AA  length = 196
FEATURE                 Location/Qualifiers
REGION                  1..196
                        note = source = /note="Description of Artificial Sequence:
                         Syntheticpolypeptide"
source                  1..196
                        mol_type = protein
                        organism = synthetic construct
SEQUENCE: 127
LATQTQYLTP SLSDSHQQPP LVWELIRWLQ AVAHQWQTIT RAPTEWVMPQ EIGIAIPHGW  60
ATESSPPAPE HGPCPPTITT STSKSPVIQR GPATTTTTSA TAPPGGTLTS TASTATSPRE  120
TGSGSSTTTG GSGPSDSTSS SSTSRSRRSR RMKARRLLPI TLPARFKCLR TRSISSRTCS  180
ALPTRAACLR SRRTCS                                                196

SEQ ID NO: 128          moltype = AA  length = 196
FEATURE                 Location/Qualifiers
REGION                  1..196
                        note = source = /note="Description of Artificial Sequence:
                         Syntheticpolypeptide"
source                  1..196
                        mol_type = protein
                        organism = synthetic construct
SEQUENCE: 128
LATQSQFQTI NLSENLQQRP LVWDLIQWLQ AVAHQWQTIT KAPTEWVMPQ EIGIAIPHGW  60
ATESSPPAPA PGPCPPTITT STSKSPVIQR GPATTTTTSA TAPLGGILTS TDSTATFHHV  120
TGKDSSTTTG DSDPRDSTSS SLTFKSKRSR RMKAPRPSPI TSPAPSRCLR TRSTSCRTFS  180
ALPTRAACLR SRRTCS                                                196
```

RECOMBINANT ADENO-ASSOCIATED VIRUS CAPSIDS WITH ENHANCED HUMAN PANCREATIC TROPISM

CROSS REFERENCE TO RELATED APPLICATION

This application is a divisional of U.S. application Ser. No. 16/370,735, filed Mar. 29, 2019, which claims priority to U.S. Provisional Application No. 62/651,010, filed Mar. 30, 2018, and U.S. Provisional Application No. 62/745,226, filed Oct. 12, 2018, all of which are hereby incorporated by reference in their entireties.

STATEMENT AS TO RIGHTS TO INVENTIONS MADE UNDER FEDERALLY SPONSORED RESEARCH OR DEVELOPMENT

This invention was made with U.S. Government support under contracts DK089569 and DK104143 awarded by the National Institutes of Health. The Government has certain rights in the invention.

FIELD OF THE INVENTION

The present invention relates to variant AAV capsid polypeptides, wherein the variant AAV capsid polypeptides exhibit increased transduction and/or tropism in human pancreatic tissue or human islets as compared to non-variant parent capsid polypeptides.

REFERENCE TO A "SEQUENCE LISTING," A TABLE, OR A COMPUTER PROGRAM, LISTING APPENDIX SUBMITTED ON A COMPACT DISK

The instant application contains a Sequence Listing which has been submitted electronically in XML file format and is hereby incorporated by reference in its entirety. Said XML file, created on Dec. 6, 2022, is named 068597-5036-US01_Sequence_Listing.xml and is 279,743 bytes in size.

BACKGROUND OF THE INVENTION

Genetic disorders caused by absence of or a defect in a desirable gene (loss of function) or expression of an undesirable or defective gene (gain of function) lead to a variety of diseases. At present, adeno-associated virus (AAV) vectors are recognized as the gene transfer vectors of choice for therapeutic applications since they have the best safety (replication deficient, low integration rate and minimum immune response) and efficacy profile for the delivery of genes in vivo. AAV vectors small, non-enveloped, non-pathogenic, helper virus dependent ssDNA virus, and they have numerous serotypes with varying tissue tropisms and transduction efficiencies. Of the AAV serotypes isolated so far, AAV2 and AAV8 have been used to target the liver of humans affected by severe hemophilia B. Both vectors worked efficiently and, in the case of AAV8, long-term expression of the therapeutic transgene was documented. Recent data from humans showed that targeting the liver with an AAV vector achieves long-term expression of the FIX transgene at therapeutic levels. Additionally, several Phase 1 and Phase 2 clinical trials using AAV serotypes 1, 2 and/or chimeric 2.5 have been reported for the treatment of cystic fibrosis, hemophilia, Canavan's disease, Duchenne muscular dystrophy (DMD) and alpha-1 antitrypsin deficiency (M. Hildinger and A. Auricchio. *Eur J Hum Genet,* 12, 263-271 (2004); C. Li, D. E. Bowles, T. V. Dyke and R. J. Samulski, *Cancer Gene Ther.,* 12(12): 913-926 (2005); D. E. Bowles, S. W J McPhee, C. Li, S. J. Gray, J. J. Samulski, A. S. Camp, J. Li, B. Wang, P. E. Monahan, J. E. Rabinowitz, J. C. Grieger, La. Govindasamy, M. Agbandje-McKenna, X. Xiao and R. J. Samulski, *Molecular Therapy,* 20, 443-455 (2012); M. L. Brantly, J. D. Chulay, L. Wang, C. Mueller, M. Humphries, L. T. Spencer, F. Rouhani, T. J. Conlon, R. Calcedo, M. R. Betts, C. Spencer, B. J. Byrne, J. M. Wilson, T. R. Flotte, Sustained transgene expression despite T lymphocyte responses in a clinical trial of rAAV1-AAT gene therapy. *Proceedings of the National Academy of Sciences of the United States of America* 106, 16363-16368 (2009); T. R. Flotte, M. L. Brantly, L. T. Spencer, B. J. Byrne, C. T. Spencer, D. J. Baker, M. Humphries, Phase I trial of intramuscular injection of a recombinant adeno-associated virus alpha 1-antitrypsin (rAAV2-CB-hAAT) gene vector to AAT-deficient adults. *Human gene therapy* 15, 93-128 (2004); T. R. Flotte, B. C. Trapnell, M. Humphries, B. Carey, R. Calcedo, F. Rouhani, M. Campbell-Thompson, A. T. Yachnis, R. A. Sandhaus, N. G. McElvaney, C. Mueller, L. M. Messina, J. M. Wilson, M. Brantly, D. R. Knop, G. J. Ye, J. D. Chulay, Phase 2 clinical trial of a recombinant adeno-associated viral vector expressing alphal-antitrypsin: interim results. *Human gene therapy* 22, 1239-1247 (2011); C. Mueller, J. D. Chulay, B. C. Trapnell, M. Humphries, B. Carey, R. A. Sandhaus, N. G. McElvaney, L. Messina, Q. Tang, F. N. Rouhani, M. Campbell-Thompson, A. D. Fu, A. Yachnis, D. R. Knop, G. J. Ye, M. Brantly, R. Calcedo, S. Somanathan, L. P. Richman, R. H. Vonderheide, M. A. Hulme, T. M. Brusko, J. M. Wilson, T. R. Flotte, Human Treg responses allow sustained recombinant adeno-associated virus-mediated transgene expression. *The Journal of clinical investigation* 123, 5310-5318 (2013)).

Adeno-associated virus (AAV), a member of the Parvovirus family, is a small nonenveloped, icosahedral virus with single-stranded linear DNA genomes of 4.7 kilobases (kb). AAV is assigned to the genus, Dependovirus, because the virus was discovered as a contaminant in purified adenovirus stocks (D. M. Knipe, P. M Howley, *Field's Virology.* , Lippincott Williams & Wilkins, Philadelphia, ed. Sixth, 2013). In its wild-type state, AAV depends on a helper virus—typically adenovirus—to provide necessary protein factors for replication, as AAV is naturally replication-defective. The 4.7-kb genome of AAV is flanked by two inverted terminal repeats (ITRs) that fold into a hairpin shape important for replication. Being naturally replication-defective and capable of transducing nearly every cell type in the human body, AAV represents an ideal vector for therapeutic use in gene therapy or vaccine delivery. In it's wild-type state, AAV's life cycle includes a latent phase during which AAV genomes, after infection, are site-specifically integrated into host chromosomes and an infectious phase during which, following either adenovirus or herpes simplex virus infection, the integrated genomes are subsequently rescued, replicated, and packaged into infectious viruses. When vectorized, the viral Rep and Cap genes of AAV are removed and provided in trans during virus production, making the ITRs the only viral DNA that remains (A. Vasileva, R. Jessberger, *Nature reviews. Microbiology,* 3, 837-847 (2005)). Rep and Cap are then replaced with an array of possible transfer vector configurations to perform gene addition or gene targeting. These vectorized recombinant AAVs (rAAV) transduce both dividing and non-dividing cells, and show robust stable expression in quiescent tissues like pancreatic tissue. The number of rAAV gene therapy clinical trials that have been completed or are ongoing to treat various inherited or acquired diseases is increasing dramatically as rAAV-based therapies increase in popularity. Similarly, in the clinical vaccine space, there have been numerous recent preclinical studies and one ongoing clinical trial using rAAV as a vector to deliver antibody expression cassettes in passive vaccine approaches for human/simian immunodeficiency virus (HIV/SIV), influenza virus, henipavirus, and human papilloma virus (HPV). (See, P. R. Johnson, B. C. Schnepp, J. Zhang, M. J. Connell, S. M. Greene, E. Yuste, R. C. Desrosiers, K. R. Clark, *Nature medicine* 15, 901-906 (2009); A. B. Balazs, J. Chen, C. M. Hong, D. S. Rao, L. Yang, D. Baltimore, *Nature* 481, 81-84 (2012); A. B. Balazs, Y. Ouyang, C. M. Hong, J. Chen, S. M. Nguyen, D. S. Rao, D. S. An, D. Baltimore, *Nature medicine* 20, 296-300 (2014); A. B. Balazs, J. D. Bloom, C. M. Hong, D. S. Rao, D. Baltimore, *Nature biotechnology* 31, 647-652 (2013); M. P. Limberis, V. S. Adam, G. Wong, J. Gren, D. Kobasa, T. M. Ross, G. P. Kobinger, A. Tretiakova, J. M., *Science translational medicine* 5, 187ra172 (2013); M. P. Limberis, T. Racine, D. Kobasa, Y. Li, G. F. Gao, G. Kobinger, J. M. Wilson, Vectored expression of the broadly neutralizing antibody FI6 in mouse airway provides partial protection against a new avian influenza A virus, H7N9. *Clinical and vaccine immunology: CVI*20, 1836-1837 (2013); J. Lin, R. Calcedo, L. H. Vandenberghe, P. Bell, S. Somanathan, J. M. Wilson, *Journal of virology* 83, 12738-12750 (2009); I. Sipo, M. Knauf, H. Fechner, W. Poller, O. Planz, R. Kurth, S. Norley, *Vaccine* 29, 1690-1699 (2011); A. Ploquin, J. Szecsi, C. Mathieu, V. Guillaume, V. Barateau, K. C. Ong, K. T. Wong, F. L. Cosset, B. Horvat, A. Salvetti, *The Journal of infectious diseases* 207, 469-478 (2013); D. Kuck, T. Lau, B. Leuchs, A. Kern, M. Muller, L. Gissmann, J. A. Kleinschmidt, *Journal of virology* 80, 2621-2630 (2006); K. Nieto, A. Kern, B. Leuchs, L. Gissmann, M. Muller, J. A. Kleinschmidt, *Antiviral therapy* 14, 1125-1137 (2009); K. Nieto, C. Stahl-Hennig, B. Leuchs, M. Muller, L. Gissmann, J. A. Kleinschmidt, *Human gene therapy* 23, 733-741 (2012); and L. Zhou, T. Zhu, X. Ye, L. Yang, B. Wang, X. Liang, L. Lu, Y. P. Tsao, S. L. Chen, J. Li, X. Xiao, *Human gene therapy* 21, 109-119 (2010).) The properties of non-pathogenicity, broad host range of infectivity, including non-dividing cells, and potential site-specific chromosomal integration make AAV an attractive tool for gene transfer.

The first rAAV-based gene therapy to be approved in the Western world (Glybera® for lipoprotein lipase deficiency, approved for use in 2012 in the European Union) has stimulated the gene therapy community, investors and regulators to the real possibility of moving rAAV therapies into the clinic globally. Yet, despite the impressive abilities of rAAV to transduce a variety of tissue and cell types, several drawbacks have limited its use for clinical applications, such as its promiscuity, limited transgene packaging size, and the high prevalence of pre-existing neutralizing antibodies in the general population. For gene therapy purposes, transduction needs to be both efficient and highly cell type specific. Pancreatic tissue has been historically one of the most challenging tissues to transduce at high levels sufficient to provide therapeutic levels of expression of delivered transgene products.

The recent excitement surrounding the possible use of rAAV as a vector for delivery of vaccines providing passive immunoprotection against pathogenic viruses like HIV and influenza virus in particular, has renewed the urgency for rAAV capsids capable of highly efficient pancreas delivery for this unique vaccination approach in humans. Given the limitations with efficient human pancreas transduction with existing rAAV serotypes, bioengineering of a clinical rAAV vector candidate that can efficiently transduce human pancreatic tissue or human islets at a level sufficient to express therapeutic levels of broad-spectrum antibodies for vaccine strategies or genes essential for pancreatic disorder treatment was pursued.

A variety of published US applications describe AAV vectors and virions, including U.S. Publication Nos. 2015/0176027, 2015/0023924, 2014/0348794, 2014/0242031, and 2012/0164106; all of which are incorporated by reference herein in their entireties.

However, high levels of transduction are needed for pancreatic gene therapy trials as there are physical limitations to how much AAV can be delivered in a single intraperitoneal injection which is further complicated by the fact that injections need to ensure that the injected vector targets the diseased pancreatic tissue or islet cells specifically and efficiently.

If an AAV had superior human pancreas transduction, a lower dose and fewer injections would be needed to achieve therapeutic relevance. Similarly, for use as a vaccine delivery tool, high efficiency transduction and stability is needed to achieve robust secretion of antibodies encoded within the AAV to reach therapeutic levels of circulating antibodies in the blood.

There remains, therefore, a need in the art for AAV vectors with improved human pancreatic tissue transduction. The present invention meets this need by providing variant AAV capsid polypeptides that demonstrate significantly improved human pancreatic tissue transduction over non-variant parent capsid polypeptides with regard to transducing human pancreatic tissue and/or islet cells. The present invention utilizes directed evolution by DNA gene shuffling and re-programming strategies to characterize and screen for such variant AAV capsid polypeptides that have high transduction efficiency for human islet cells than the best parent (i.e. LK03—mainly α-cell specific), and high cell-type specific transduction (e.g. α- or β-cell specific).

BRIEF SUMMARY OF THE INVENTION

The present invention provides variant adeno-associated virus (AAV) capsid polypeptides. The variant AAV capsid polypeptides exhibit increased transduction or tropism in human pancreatic tissue or human islets as compared to non-variant parent capsid polypeptides.

In some embodiments, the variant AAV capsid polypeptides exhibit increased transduction or tropism in human pancreatic tissue or human islets as compared to non-variant parent capsid polypeptides.

In some embodiments, the variant AAV capsid polypeptides transduced either dissociated or intact human islets.

In some embodiments, the variant AAV capsid polypeptides exhibit increased transduction as compared to non-variant parent capsid polypeptides.

In some embodiments, the variant AAV capsid polypeptides exhibit increased tropism as compared to non-variant parent capsid polypeptides.

In some embodiments, the variant AAV capsid polypeptide further exhibits increased transduction or tropism in one or more types of cells within human islets as compared to a non-variant parent capsid polypeptide.

In some embodiments, the variant AAV capsid polypeptide exhibits increased transduction of human pancreatic tissue or human islets in vivo as compared to a non-variant parent capsid polypeptide.

In some embodiments, the variant AAV capsid polypeptide exhibits increased transduction of human pancreatic tissue or human islets in vitro as compared to a non-variant parent capsid polypeptide.

In some embodiments, the variant AAV capsid polypeptide exhibits increased transduction of a human pancreatic tissue or human islets ex vivo as compared to a non-variant parent capsid polypeptide.

In some embodiments, the variant AAV capsid polypeptide exhibits an enhanced neutralization profile as compared to non-variant parent capsid polypeptides.

In some embodiments, the variant AAV capsid polypeptide exhibits an enhanced neutralization profile against pooled human immunoglobulins as compared to non-variant parent capsid polypeptides.

In some embodiments, the variant AAV capsid polypeptide that exhibits an enhanced neutralization profile is selected from the group consisting of AAV-10A1 (SEQ ID NO:1) and AAV-10A3 (SEQ ID NO:2). In some embodiments, the variant AAV capsid polypeptide that exhibits an enhanced neutralization profile is AAV-10A1 (SEQ ID NO: 1). In some embodiments, the variant AAV capsid polypeptide that exhibits an enhanced neutralization profile is AAV-10A3 (SEQ ID NO:2).

In some embodiments, the variant AAV capsid polypeptide is part of a functional AAV capsid, where said functional AAV capsid packages a nucleic acid sequence selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the nucleic acid sequence is contained within an AAV vector.

In some embodiments, the expression cassette is a CRISPR/CAS expression system.

In some embodiments, the therapeutic expression cassette encodes a therapeutic protein or antibody.

In some embodiments, the variant AAV capsid polypeptide is selected from the group consisting of AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO: 13).

In some embodiments, the variant AAV capsid polypeptide is selected from the group consisting of AAV-10A1 (SEQ ID NO:1), AAV-10A3 (SEQ ID NO:2), and AAV-18A1 (SEQ ID NO:5).

The present invention also provides methods of using the variant AAV capsid polypeptides of the present invention in a therapeutic treatment regimen or vaccine.

In some embodiments, the method is using the variant AAV capsid polypeptide as described above in a therapeutic treatment for an endocrine disorder.

In some embodiments, the method is using the variant AAV capsid polypeptide as described above in a therapeutic treatment for diabetes, including Type I or Type II.

The present invention also provides methods of using the variant AAV capsid polypeptides of the present invention to reduce the amount of total nucleic acid administered to a subject, where the method comprises administering less total nucleic acid amount to the subject when the nucleic acid is transduced using a variant AAV capsid polypeptide as compared to the amount of nucleic acid administered to the subject when the nucleic acid is transduced using a non-variant parent capsid polypeptide in order to obtain a similar therapeutic effect.

The present invention also provides AAV vector comprising a nucleic acid sequence encoding a variant AAV capsid polypeptide, where the variant AAV capsid polypeptide exhibits increased transduction or tropism in human pancreatic tissue or human islets as compared to a non-variant parent capsid polypeptide.

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid polypeptide.

In some embodiments, the variant AAV capsid polypeptide exhibits increased transduction of human pancreatic tissue or human islets in vivo as compared to a non-variant parent capsid polypeptide.

In some embodiments, the variant AAV capsid polypeptide exhibits increased transduction of human pancreatic tissue or human islets in vitro as compared to a non-variant parent capsid polypeptide.

In some embodiments, the variant AAV capsid polypeptide exhibits increased transduction of a human pancreatic tissue or human islets ex vivo as compared to a non-variant parent capsid polypeptide.

In some embodiments, the AAV vector further comprises a nucleic acid sequence selected from the group consisting of a non-coding RNA, a coding sequence, an expression cassette, a multi-expression cassette, a sequence for homologous recombination, a genomic gene targeting cassette, and a therapeutic expression cassette.

In some embodiments, the variant AAV capsid polypeptide allows for nucleic acid expression similarly to a non-variant parent capsid polypeptide.

In some embodiments, the expression cassette is a CRISPR/CAS expression system.

In some embodiments, the therapeutic expression cassette encodes a therapeutic protein or antibody.

In some embodiments, the variant AAV capsid polypeptide sequence is selected from the group consisting of AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13).

In some embodiments, the variant AAV capsid polypeptide sequence is selected from the group consisting of AAV-10A1 (SEQ ID NO:1), AAV-10A3 (SEQ ID NO:2), and AAV-18A1 (SEQ ID NO:5).

The present invention also provides methods of using the AAV vector of the present invention in a therapeutic treatment regimen or vaccine.

In some embodiments, the method is using the AAV vector as described above in a therapeutic treatment for an endocrine disorder.

In some embodiments, the method is using the AAV vector as described above in a therapeutic treatment for diabetes, including Type I or Type II.

The present invention further provides methods of using the variant AAV capsid polypeptides of the present invention to reduce the amount of total AAV vector administered to a subject, where the method comprises administering less total AAV vector amount to the subject when the AAV vector is transduced by a variant AAV capsid polypeptide as compared to the amount of AAV vector administered to the subject when the AAV vector is transduced by a non-variant parent capsid polypeptide in order to obtain a similar therapeutic effect.

In some embodiments, the present invention provides a method for generating a variant AAV capsid polypeptide, wherein said variant AAV capsid polypeptide exhibits increased transduction or tropism in human pancreatic tissue or human islets as compared to a non-variant parent capsid polypeptide, said method comprising:

a) generating a library of variant AAV capsid polypeptide genes, wherein said variant AAV capsid polypeptide genes include a plurality of variant AAV capsid polypeptide genes comprising sequences from more than one non-variant parent capsid polypeptide;
b) generating an AAV vector library by cloning said variant AAV capsid polypeptide gene library into AAV vectors, wherein said AAV vectors are replication competent AAV vectors;
c) screening said AAV vectors library from b) encoding for variant AAV capsid polypeptides for increased transduction or tropism in human pancreatic tissue or human islets as compared to a non-variant parent capsid polypeptide; and
d) selecting said variant AAV capsid polypeptides from c).

In some embodiments, the method further comprises e) determining the sequence of said variant AAV capsid polypeptides from d).

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid polypeptide.

In some embodiments, the variant AAV capsid polypeptide further exhibits an enhanced neutralization profile as compared to a non-variant parent capsid polypeptide. In some embodiments, the variant AAV capsid polypeptide of the invention further exhibits an enhanced neutralization profile against pooled human immunoglobulins as compared to a non-variant parent capsid polypeptide.

In some embodiments, the variant AAV capsid polypeptide that further rexhibits an enhanced neutralization profile is selected from the group consisting of AAV-10A1 (SEQ ID NO:1) and AAV-10A3 (SEQ ID NO:2). In some embodiments, the variant AAV capsid polypeptide that further exhibits an enhanced neutralization profile is AAV-10A1 (SEQ ID NO:1). In some embodiments, the variant AAV capsid polypeptide that further exhibits an enhanced neutralization profile is AAV-10A3 (SEQ ID NO:2).

In some embodiments, the variant AAV capsid polypeptides further exhibit increased transduction or tropism in one or more non-muscle human tissues as compared to non-variant parent capsid polypeptides.

In some embodiments, the variant AAV capsid polypeptide exhibits increased transduction of human pancreatic tissue or human islets in vivo as compared to a non-variant parent capsid polypeptide.

In some embodiments, the variant AAV capsid polypeptides exhibits increased transduction of human pancreatic tissue or human islets in vitro as compared to a non-variant parent capsid polypeptide.

In some embodiments, the variant AAV capsid polypeptides exhibits increased transduction of a human pancreatic tissue or human islets ex vivo as compared to a non-variant parent capsid polypeptide.

Other objects, advantages and embodiments of the invention will be apparent from the detailed description following.

FACS: 2B4/8G12 mAbs.

Figure 24:
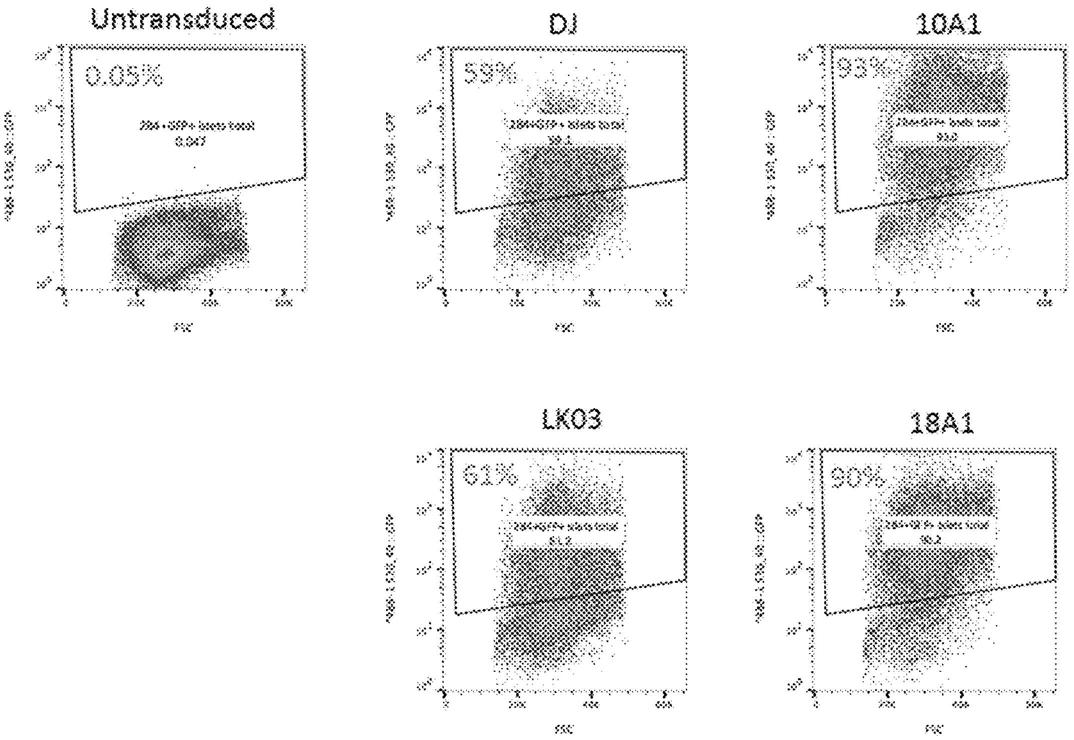

FIG. 24. Quantification of total islets GFP+ (HIC1-2B4+ population).

Figure 25:
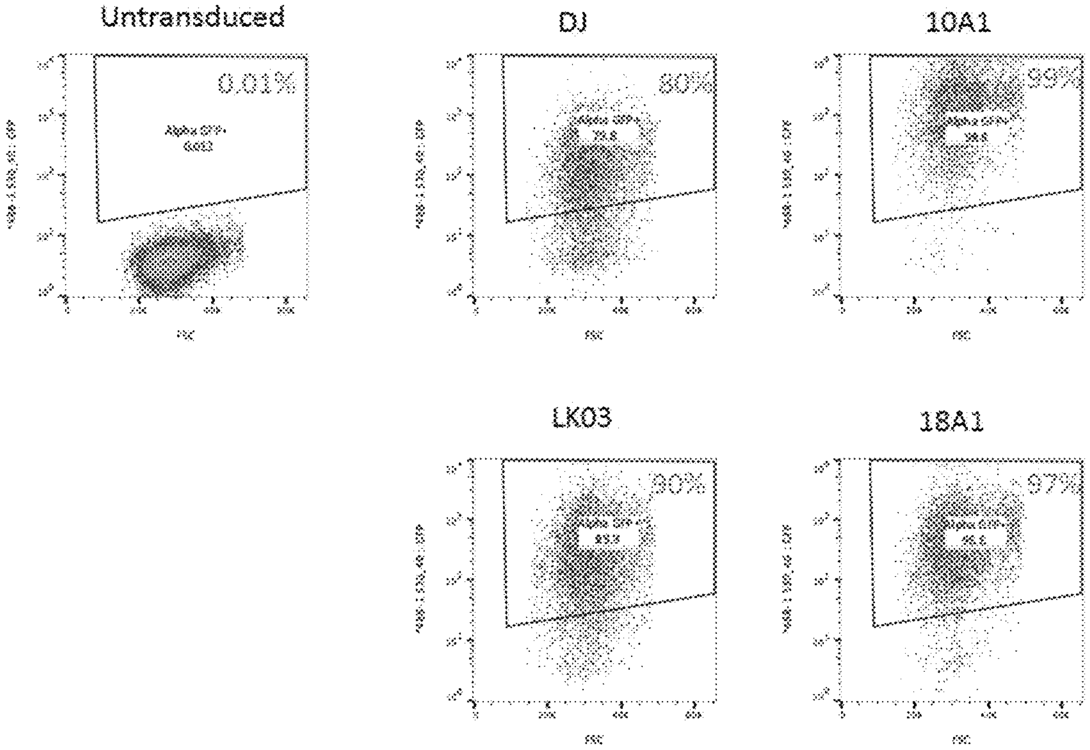

FIG. 25. Quantification of ALPHA GFP+ (2B4+8G12+) cells.

Figure 26:
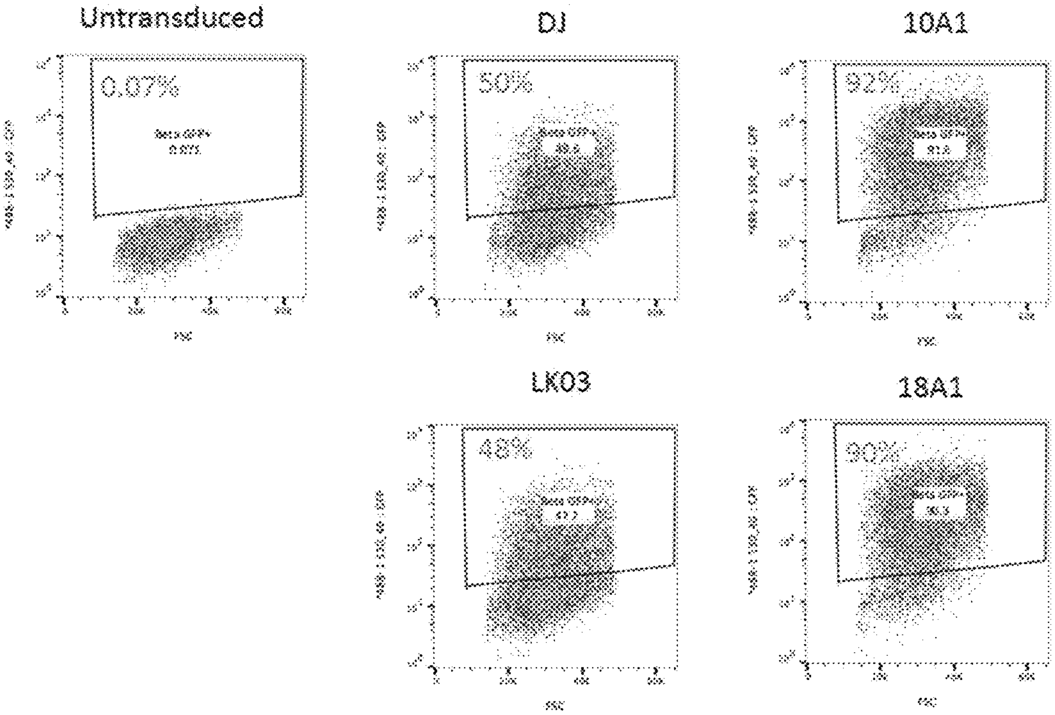

FIG. 26. Quantification of BETA GFP+ (2B4+8G12−/lo) cells. (lo=low expression).

Figure 27:
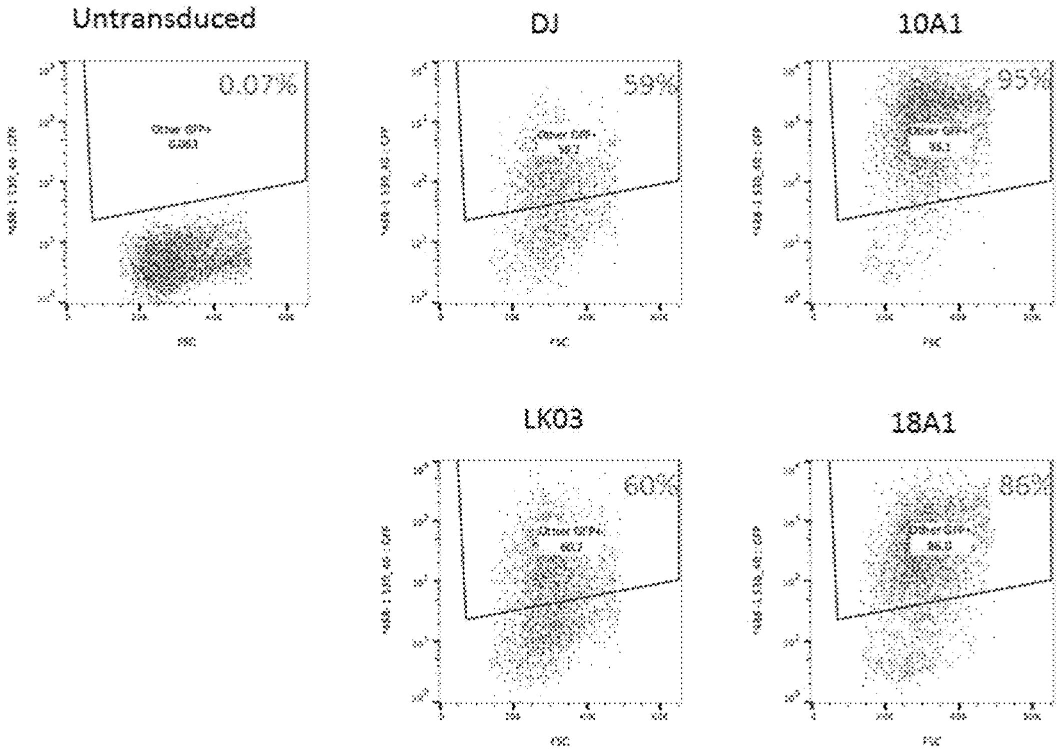

FIG. 27. Quantification of OTHER GFP+ (2B4+8G12int) cells. (int=intermediate expression).

Figure 28:
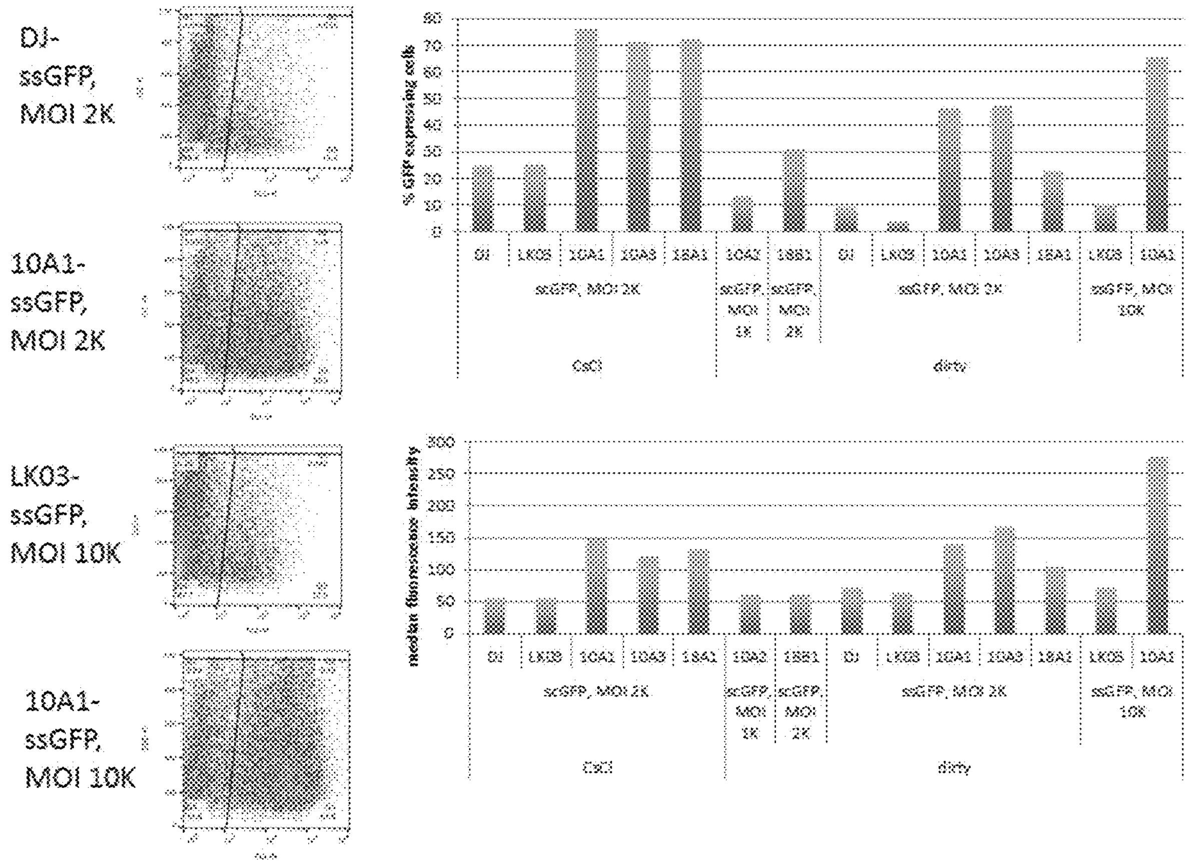

FIG. 28. Quantification of GFP expressing cells and median fluorescence intensity in different groups.

Figure 29:
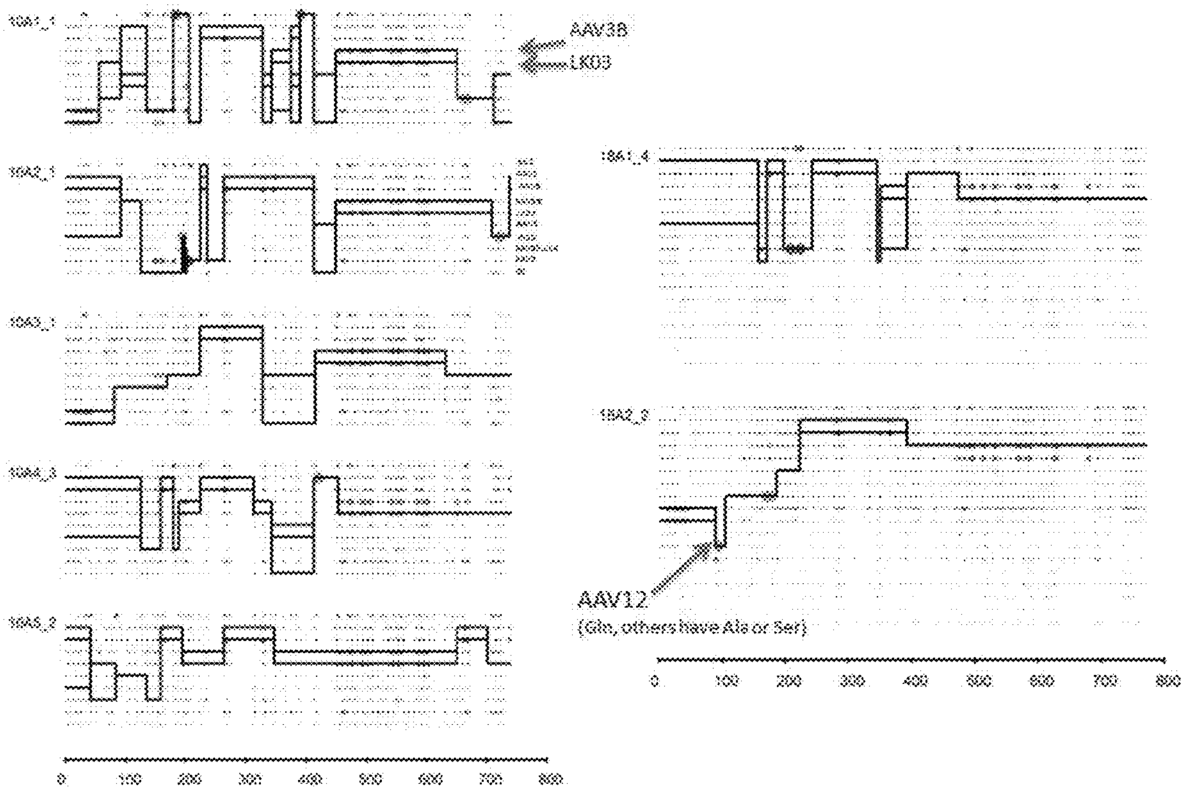

FIG. 29. Vectorized capsid variants from screen A.

Figure 30:
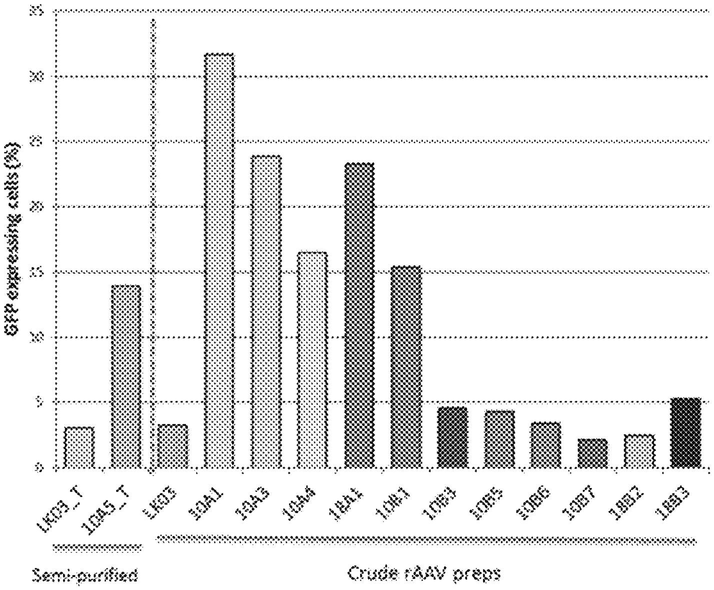

FIG. 30. Transduction efficiency of selected capsid variants on human islet cells. kit 1E+05 dissociated islet cells were transduced with semi-purified or crude rAAV at an MOI of 1K. After 48 hours, transduction efficiency was evaluated by FACS.

Figure 31:
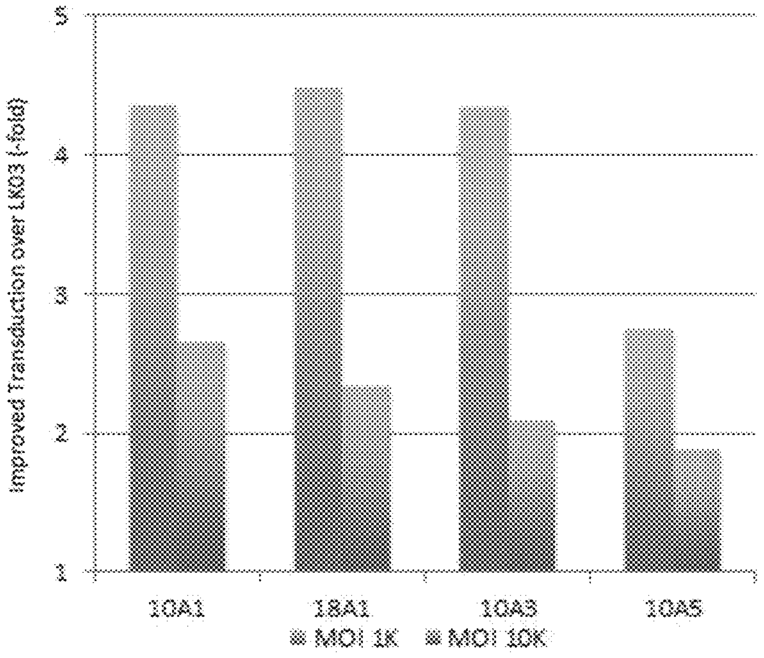

FIG. 31. Transduction efficiency of selected capsid variants on human islet cells. 1E+05 dissociated islet cells were transduced with semi-purified rAAV at an MOI of 1K and 10K. After 48 hrs transduction efficiency was evaluated by FACS. Improvement of transduction over the best parental LK03 is shown.

Figure 32:
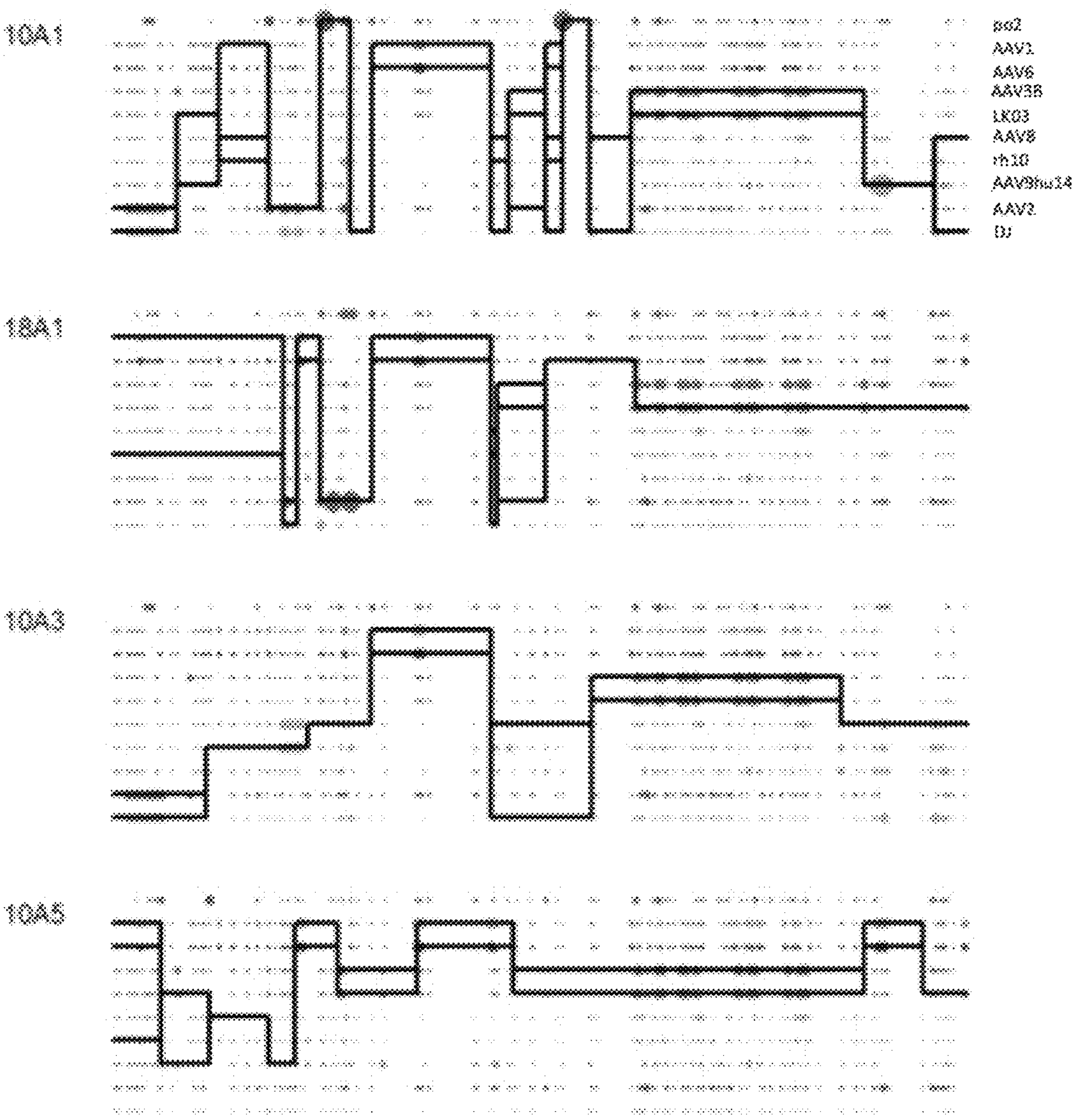

FIG. 32. Crossover analysis of the best capsid variants at the amino acid level.

Figure 33:
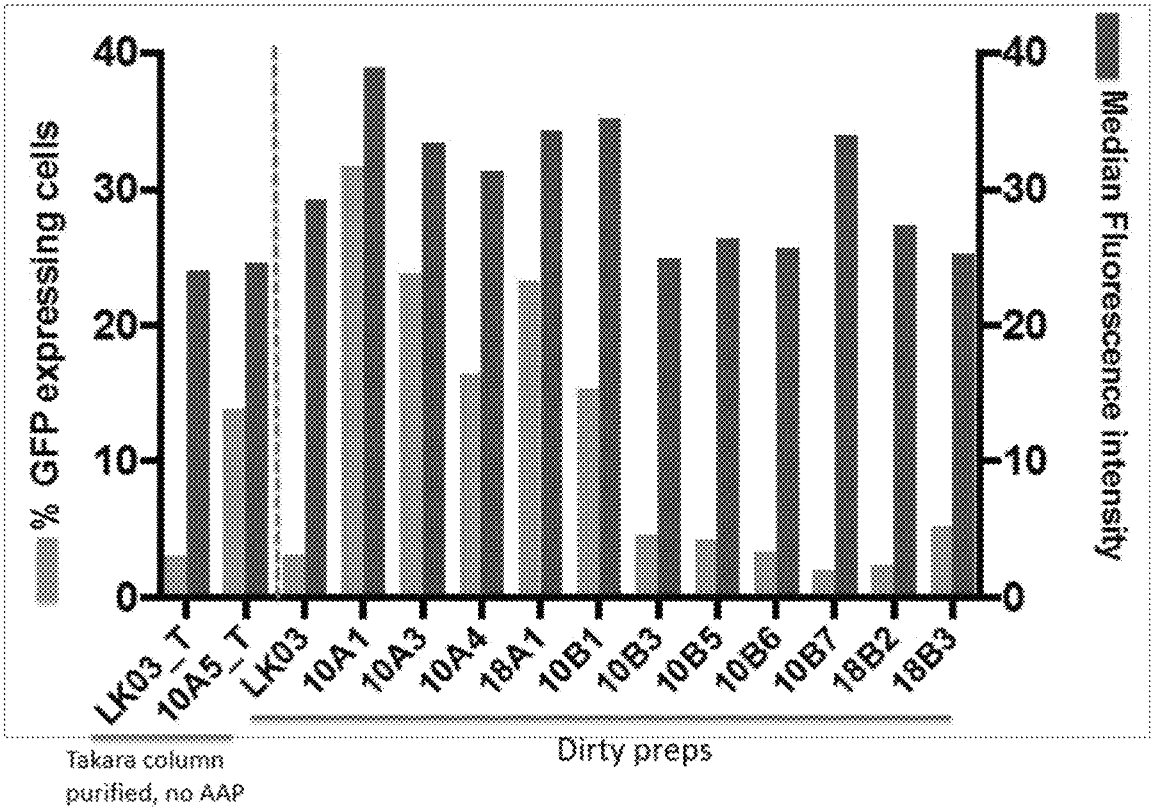

FIG. 33. Quantification of GFP expressing cells after transduction of 1E+05 dissociated islet cells at MOI 1K.

Figure 34:
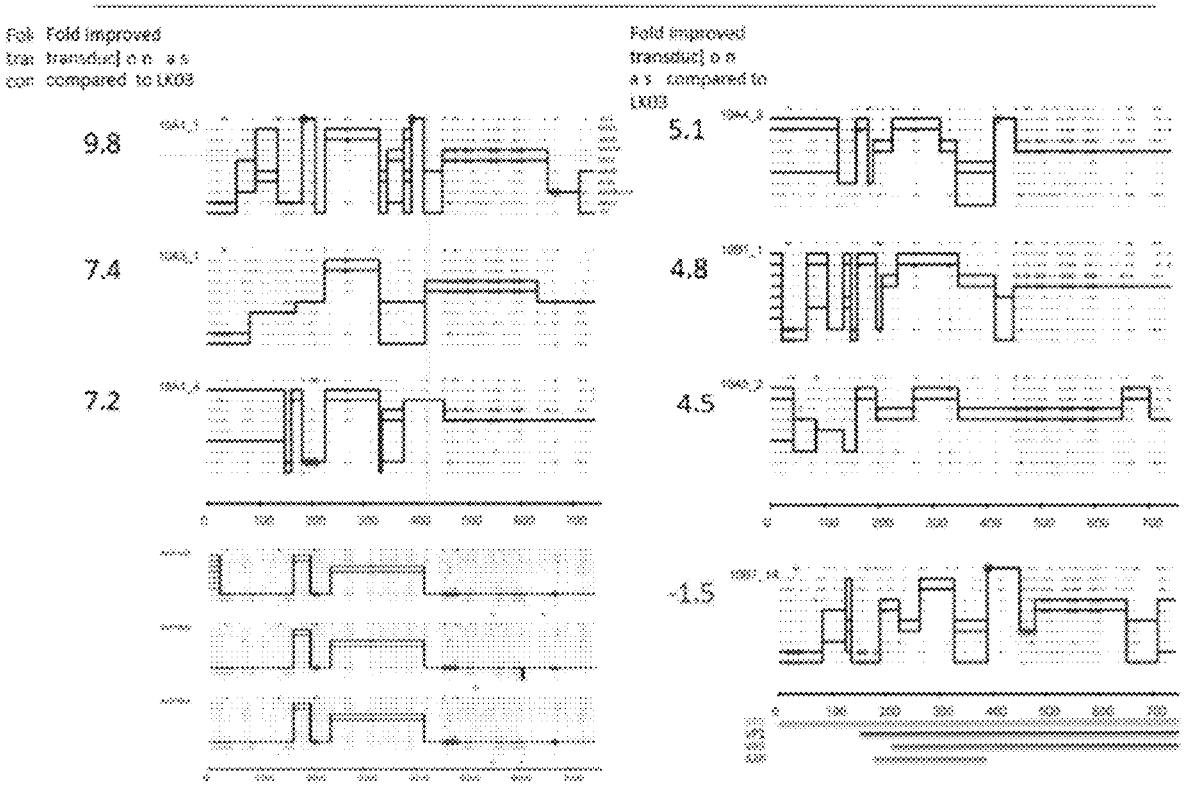

FIG. 34. Capsid variant performance compared to LK03.

FIG. 35A-35D. (A) Vectorization and testing of cap variants for transduction. Validation of enriched variants: (B) Capsid sequences from enriched AAV variants were amplified using a BC specific primer and used to package a sc AAV vector with the GFP transgene. (C) Crude virus preparations of the variants as well as one of the best parents (LK03) were used to transduce dissociated islet cells at an MOI of 1,000. (D) CsCl purified rAAV was prepared for the best variants and transduction of islet cells was analyzed in duplicates using two different MOIs. Validation of enriched variants: (B) Capsid sequences from enriched AAV variants were amplified using a BC specific primer and used to package a sc AAV vector with the GFP transgene. (C) Crude virus preparations of the variants as well as one of the best parents (LK03) were used to transduce dissociated islet cells at an MOI of 1,000. (D) CsCl purified rAAV was prepared for the best variants and transduction of islet cells was analyzed in duplicates using two different MOIs.

Figure 36:
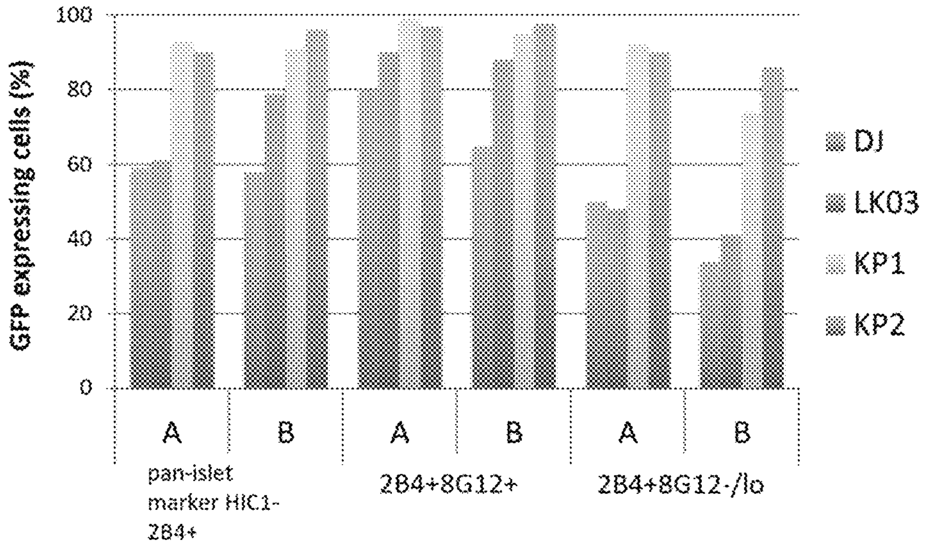
Figure 36:
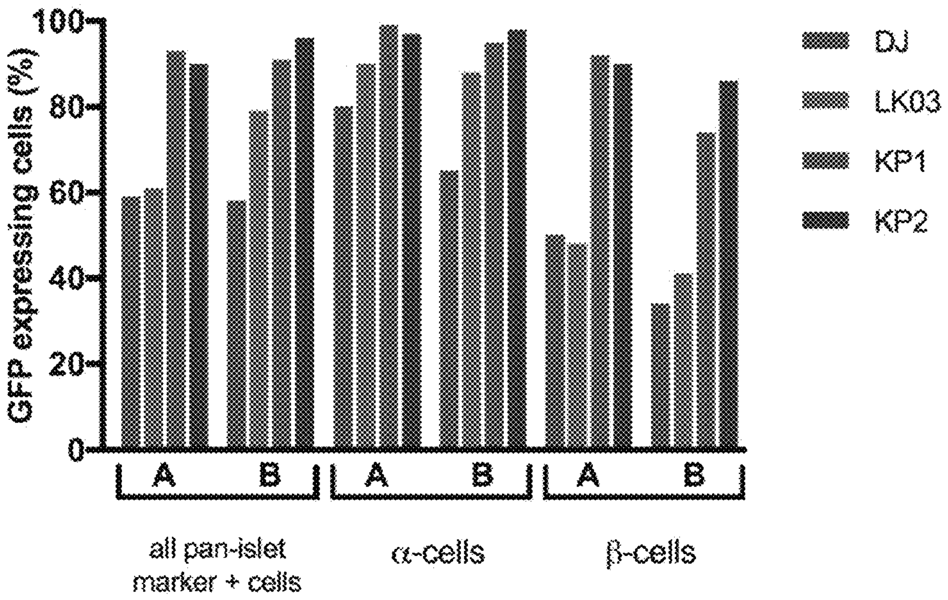

FIG. 36. Transduction of human islets from two different donors (MOI 10,000). Islet subpopulation specific transduction efficiency of AAV DJ, AAV LK03, and two of the new variants. Intact islets from two different donors (A and B) were transduced with GFP expressing rAAV at an MOI of 10,000. After two days islets were dissociated into single cell suspensions and analyzed for α-cell or β-cell specific transduction using staining of surface markers followed by FACS.

Figure 37:
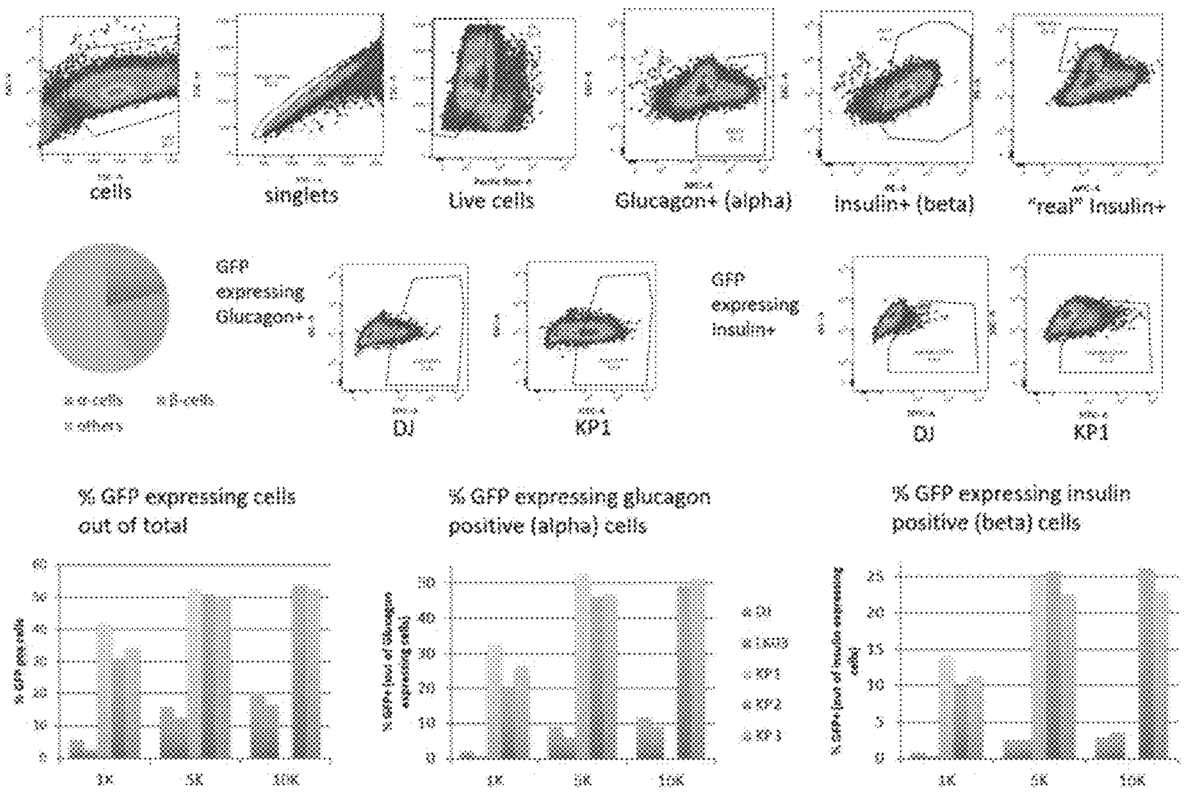

FIG. 37. Islet transduction and intracellular staining.

Figure 38A:
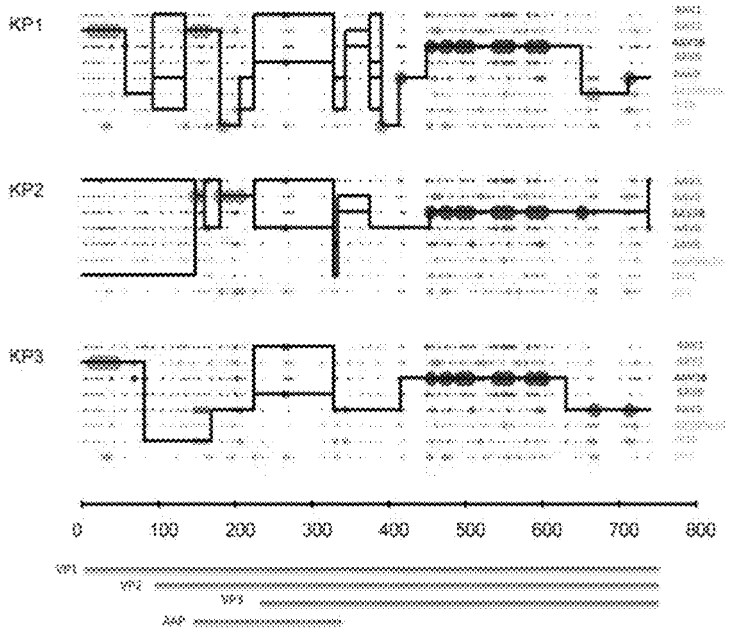
Figure 38B:
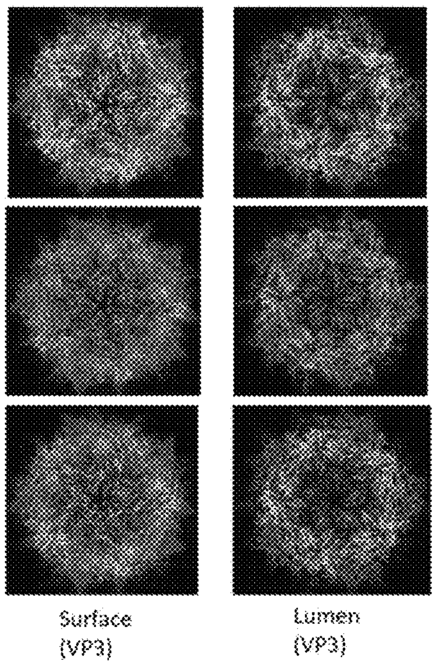

FIG. 38A-38B. Composition of the best capsid variants (X-over, amino acids). Library parents are depicted in different colors in order of entry of the parents. Large dots represent 100% parental match (i.e. the position in question matches only one parent) and small dots represent more than one parental match (i.e. the position matches more than one parent) at each position. The solid line for each chimera represents the library parents identified within the sequence between crossovers. A set of thin horizontal parallel lines between crossovers indicates multiple parents match at an equal probability. (A) Crossover analysis of the capsid amino acid sequences for the three best variants. Sequences for DJ and LK03 are not included as parental sequences since they are chimeras consisting of the parental sequences shown. (B) Shuffled variants were 3D false-color mapped onto the crystal structure of AAV2 VP3 using UCSF CHIMERA. Color-coding indicates amino acid contribution using colors as in (A).

Figure 39:
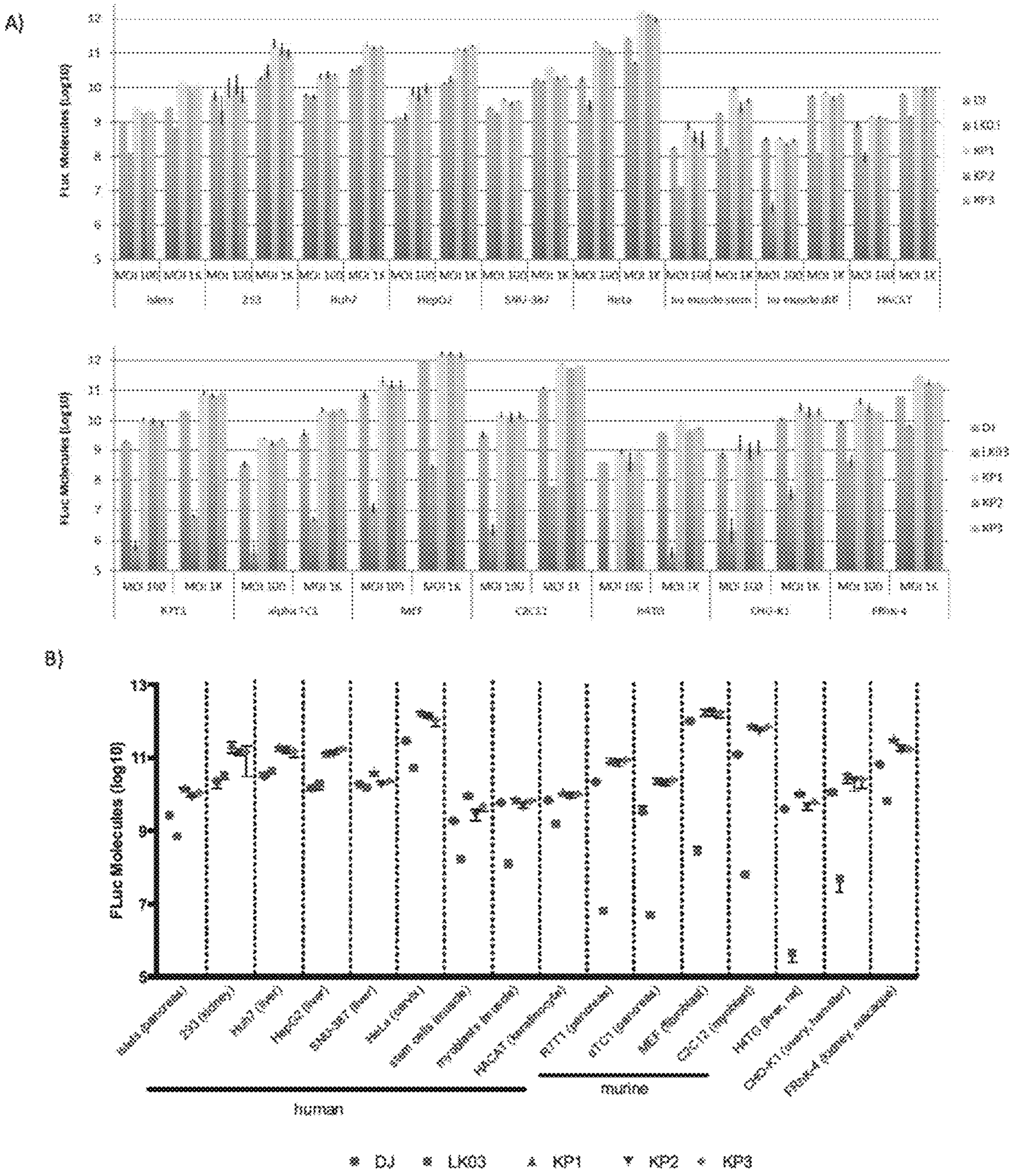

FIG. 39. Transduction efficiency on various human and non-human cell types.

Figure 40:
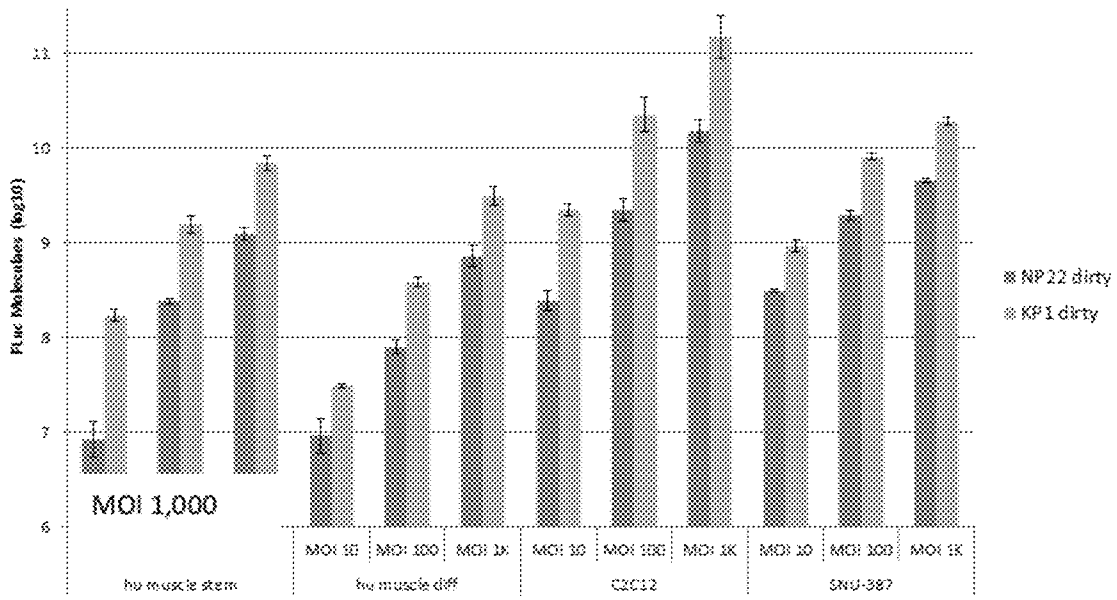

FIG. 40. Islet variant performs better on muscle cells than the best NP22 variant.

Figure 41:
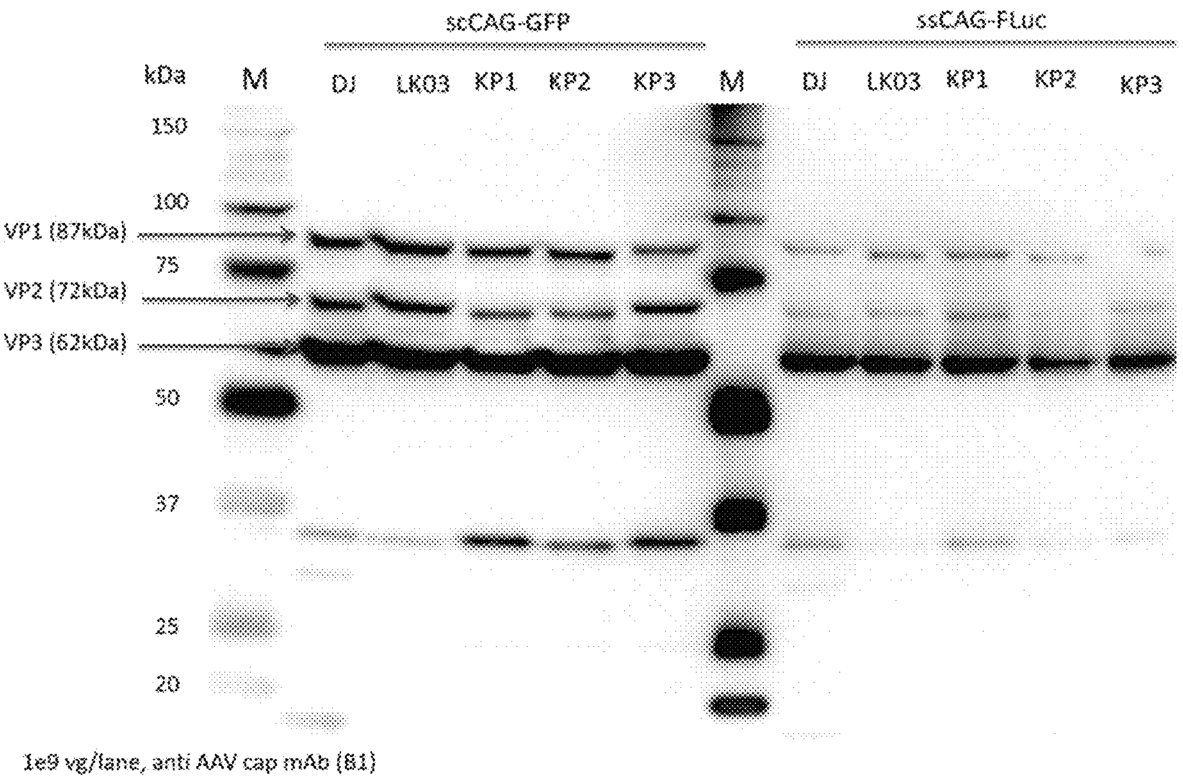

FIG. 41. Western blot results of purified rAAV preparations.

Figure 42:
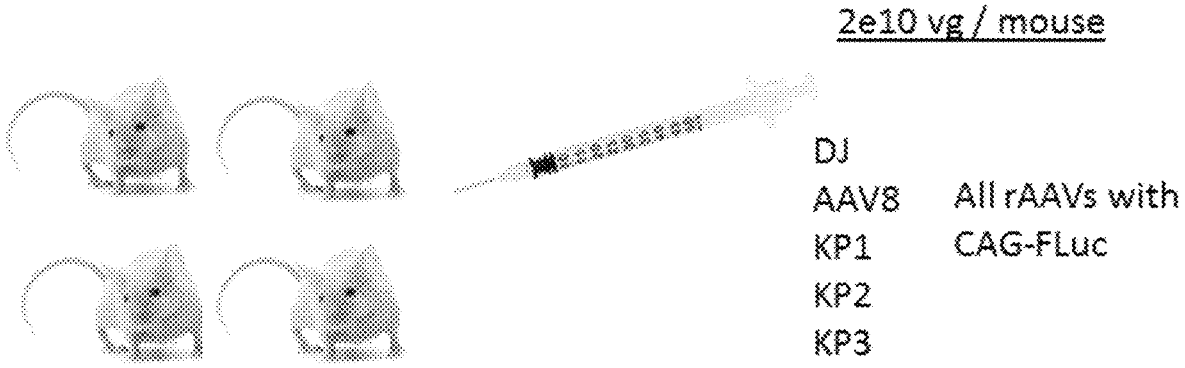

FIG. 42. The new rAAV variants were injected to Balb/SCID mice and transduction efficiency of each variant was tested in vivo.

Figure 43:
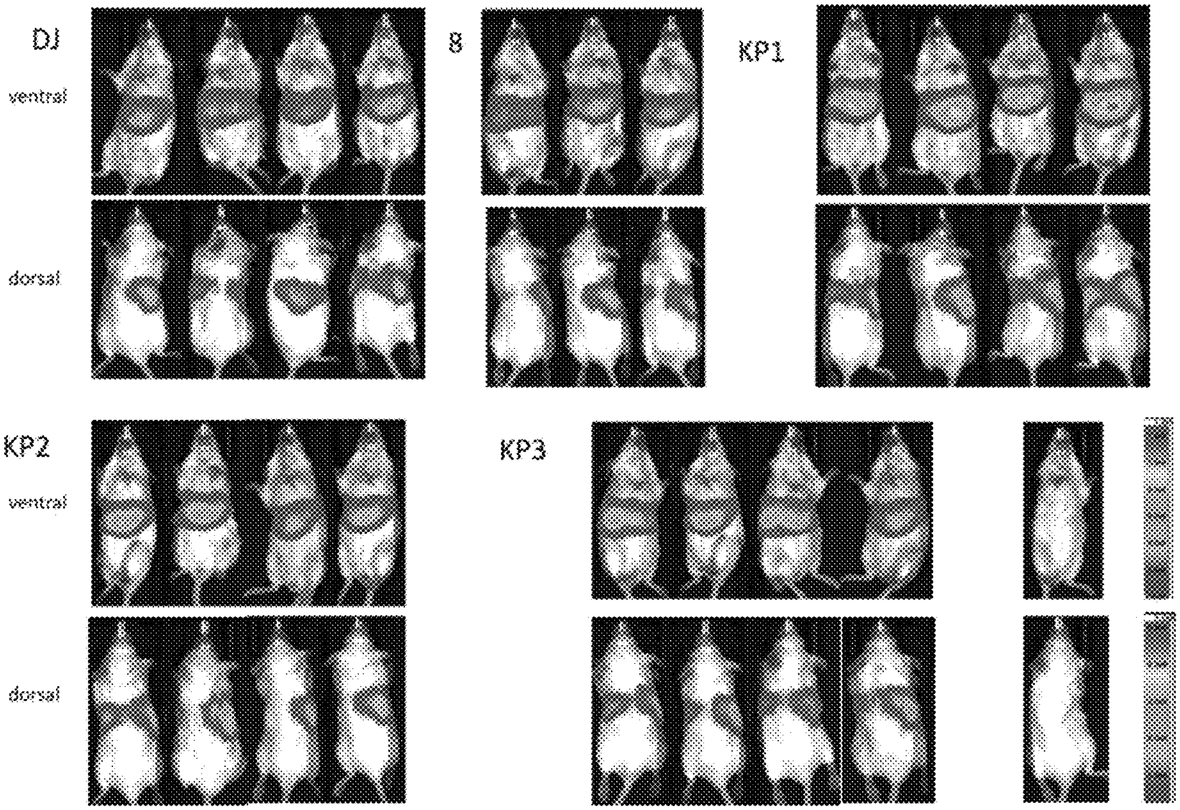

FIG. 43. The in vivo transduction efficiency of new AAV variants was studied via in vivo luciferase imaging.

Figure 44:
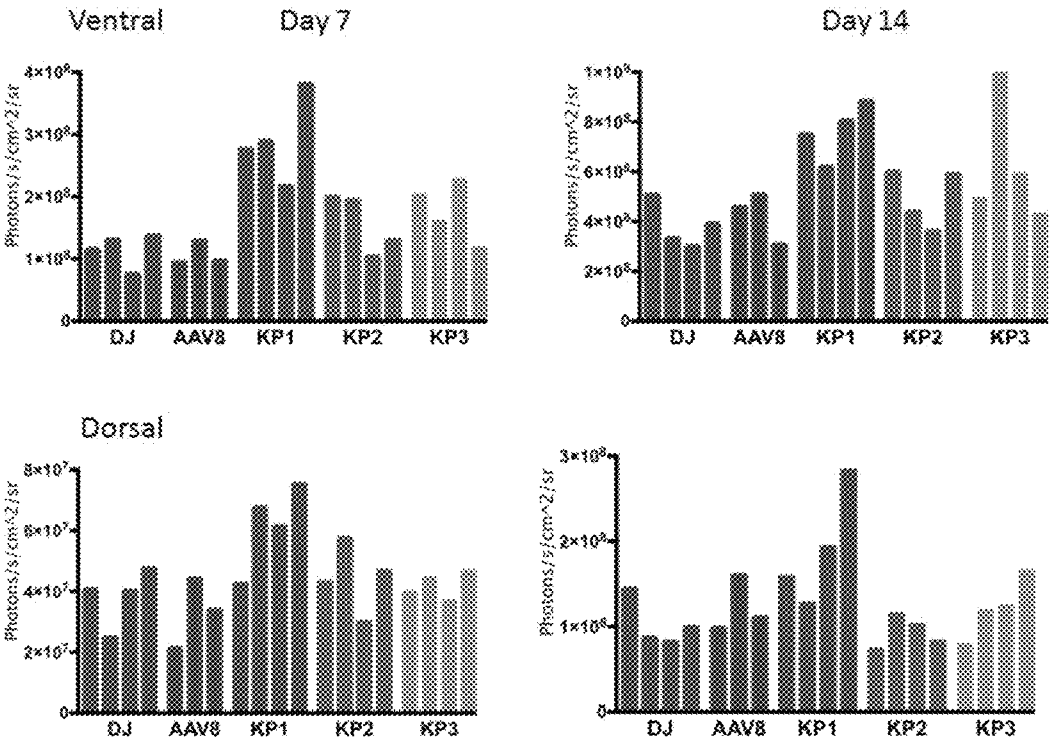

FIG. 44. Quantification of in vivo transduction efficiency of new AAV variants (day 7 and day 14).

Figure 45:
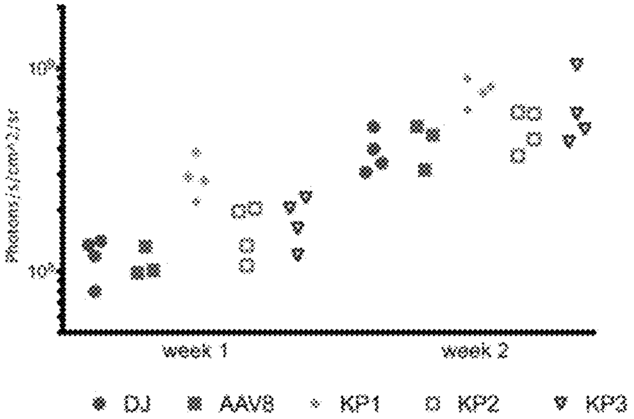
Figure 45:
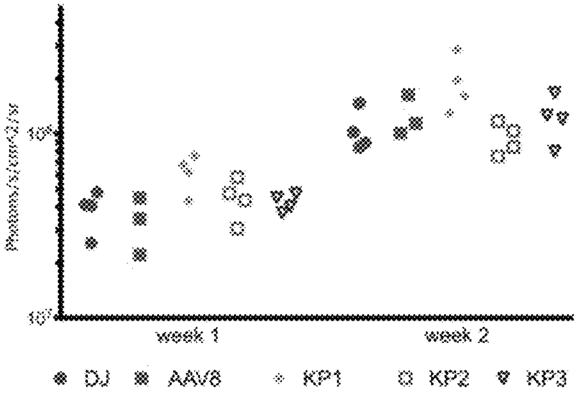

FIG. 45. Results of in vivo transduction efficiency of new AAV variants (week 1 and week 2).

Figure 46:
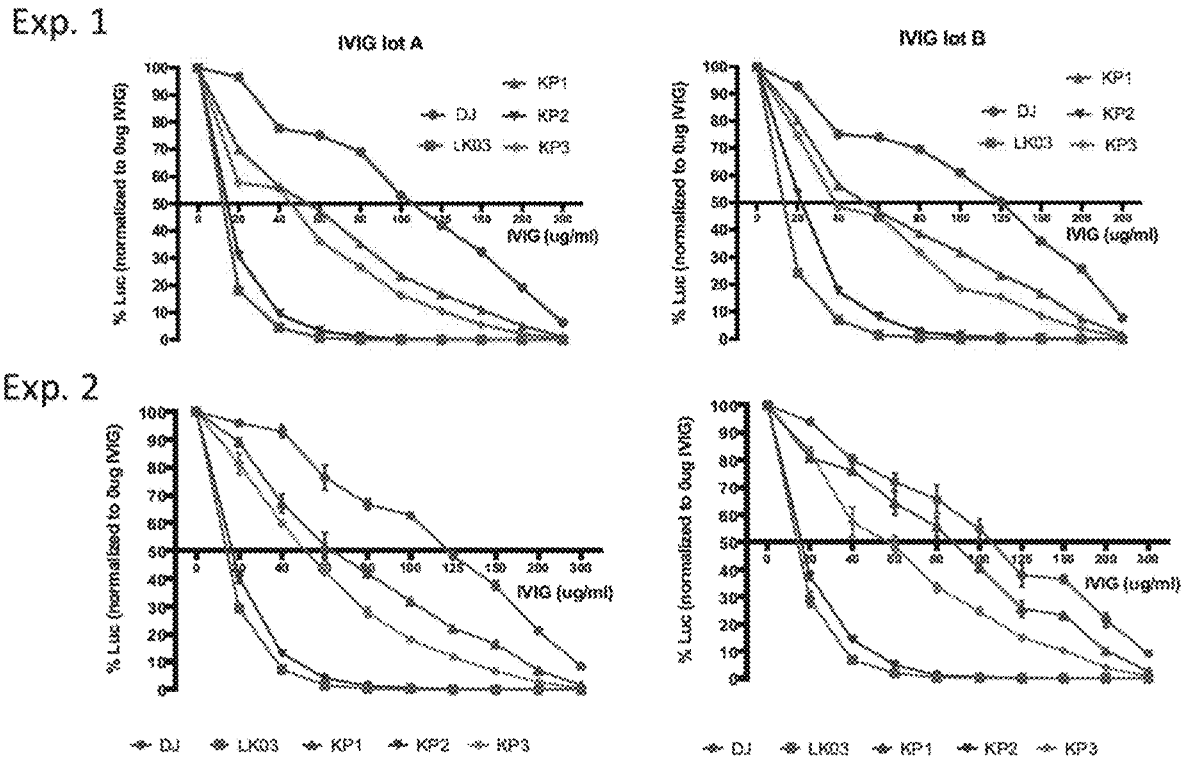

FIG. 46. Neutralization profile of new AAV variants. Sensitivity of the novel capsid variants towards neutralization by pooled human immune globulin (IVIG). The indicated concentrations of IVIG from two different batches were incubated with 2.2E+07 vector copies of rAAV in a volume of 100 ul for 1 hour at 37° C. followed by transduction of permissive Huh7 cells with an MOI of 100 in duplicates. Luciferase activity from cell lysates was determined 24 hours post transduction. Sensitivity of the novel capsid variants towards neutralization by pooled human immune globulin (IVIG). The indicated concentrations of IVIG from two different batches were incubated with 2.2E+07 vector copies of rAAV in a volume of 100 ul for 1 hour at 37° C. followed by transduction of permissive Huh7 cells with an MOI of 100 in duplicates. Luciferase activity from cell lysates was determined 24 hours post transduction.

Figure 47:
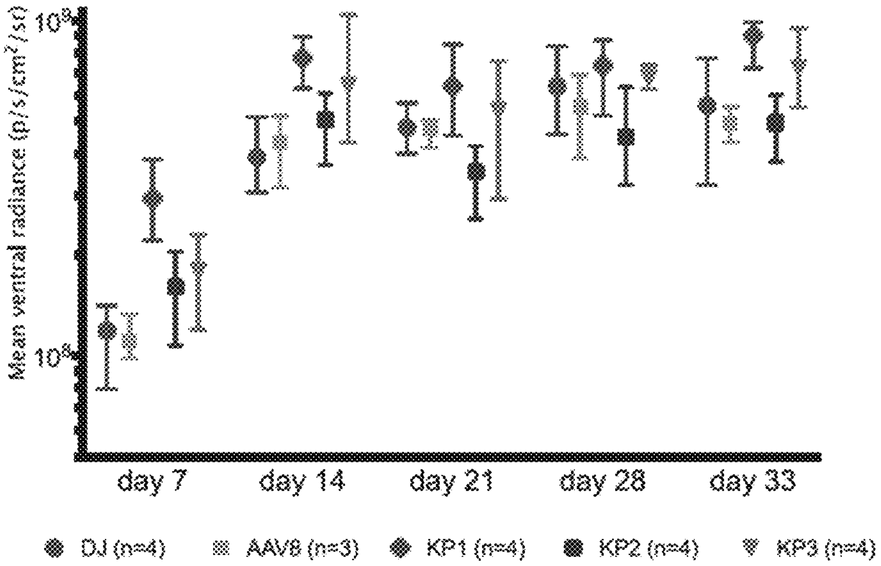

FIG. 47. In vivo liver transduction efficiency of new AAV variants (day 7, 14, 21, and 33). In vivo transduction efficiency of the new capsid variants. Balb/C SCID mice were injected with 2E+10 vg of an AAV luciferase vector packaged with the various capsids and luciferase activity in the liver was monitored over several weeks using an Ami Imaging System. Average values for each group are shown with min and max. In vivo transduction efficiency of the new capsid variants. Balb/C SCID mice were injected with 2E+10 vg of an AAV luciferase vector packaged with the various capsids and luciferase activity in the liver was monitored over several weeks using an Ami Imaging System. Average values for each group are shown with min and max.

Figure 48:
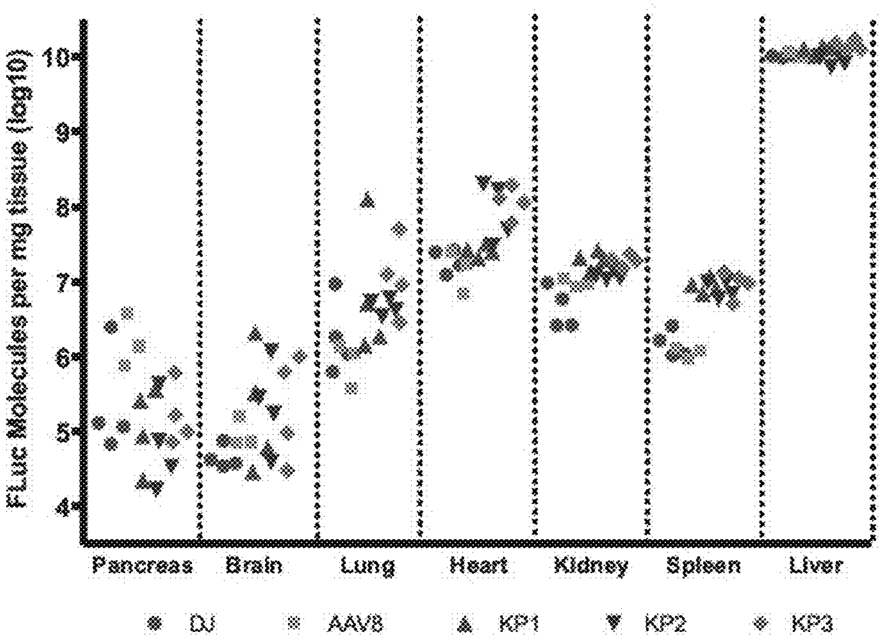

FIG. 48. Luciferase expression in various organs (ex vivo, week 5). Luciferase activity measured in various mouse organs 34 days after injection with rAAV. Organs were homogenized in lysis buffer and assayed for Luciferase activity. Data for each individual mouse are shown and color coded according to group. Luciferase activity measured in various mouse organs 34 days after injection with rAAV. Organs were homogenized in lysis buffer and assayed for Luciferase activity. Data for each individual mouse are shown and color coded according to group.

Figure 13:
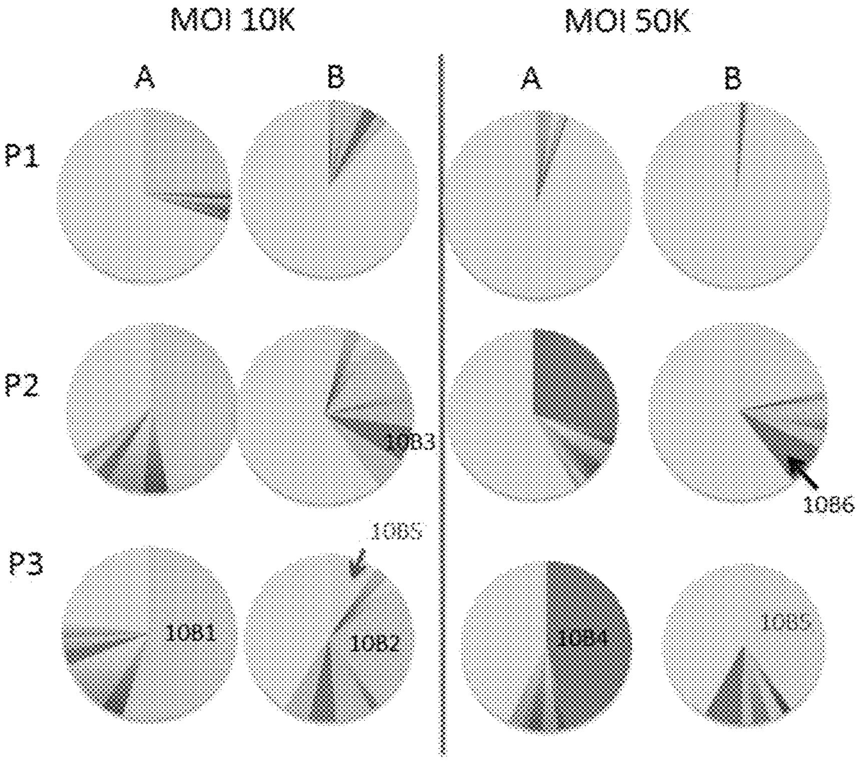
FIG. 13. Enrichment for shuffled AAV cap variants during passaging of the 10 parent library. Only the most enriched AAV variants are shown in different colors, all others are in grey. Variants that were selected for further analysis are indicted by name. The name in red indicate a variant that was enriched in two independent screens.
Figure 49:
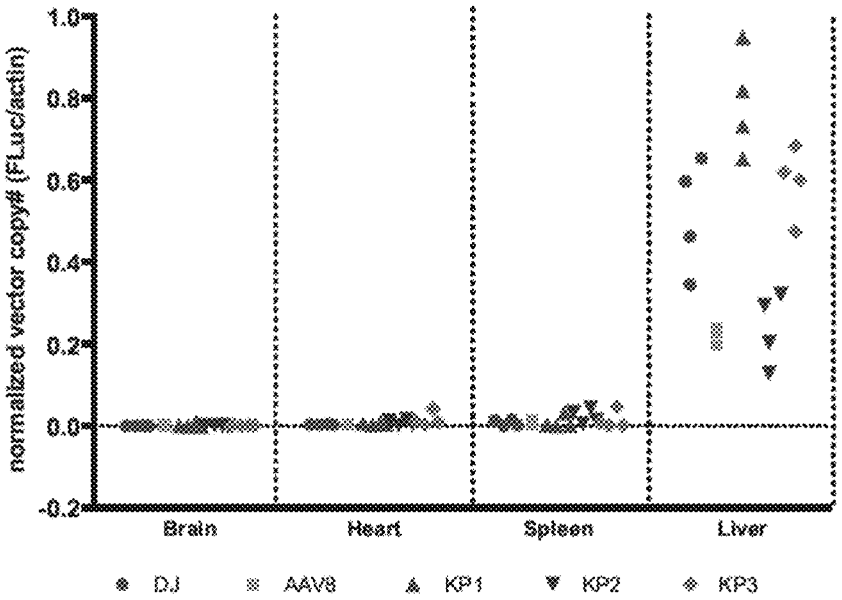

FIG. 49. Vector copy number in various organs (week 5). FIG. 13: Analysis of the new variants for transduction efficiency on various human and nonhuman cell types. Capsid sequences were used to package an AAV luciferase vector and cells were transduced with an MOI of 1,000 in triplicates, except for primary human islets which were transduced in duplicates. Luciferase activity in the cell lysates was determined two days post transduction as a read-out for transduction efficiency. Analysis of the new variants for transduction efficiency on various human and nonhuman cell types. Capsid sequences were used to package an AAV luciferase vector and cells were transduced with an MOI of 1,000 in triplicates, except for primary human islets which were transduced in duplicates. Luciferase activity in the cell lysates was determined two days post transduction as a read-out for transduction efficiency.

FIG. 50A-50D. Parental contributions in the 10 parent library and the 18 parent pool. (A, B) Chimeric capsid sequences obtained from the 10 parent library at the plasmid level (A) or at the AAV level (B) were analysed by PacBio sequencing and parental contribution was assigned for each amino acid position. (C) Parental contribution in the 18 parent pool as analysed using high-throughput sequencing of the barcodes. (D) Parental contribution in the 18 parent pool as analysed using PacBio sequencing of the capsid sequences.

Figure 51:
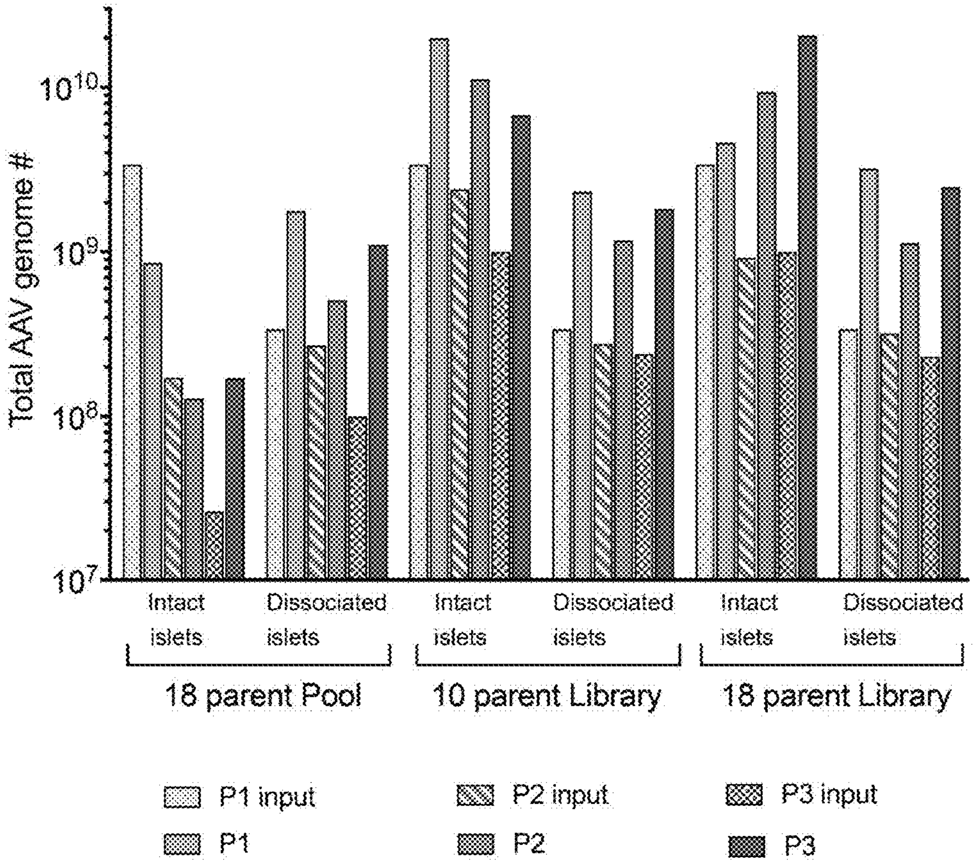

FIG. 51. Replication of the 18 parent mix, the 10 parent library, and the 18 parent library during three rounds of passaging on intact and dissociated islets. Intact islets were infected with the indicated AAV preparations using an MOI of 20,000, dissociated islet cells were infected using an MOI of 2,000. Adenovirus 5 was used to replicate AAV and virus was harvested from the supernatant and cells after 4 days. Replication of viral species was determined by rep qPCR. For each round the total viral genome copies used for infection and the total viral genome copies retrieved are shown.

Figure 52:
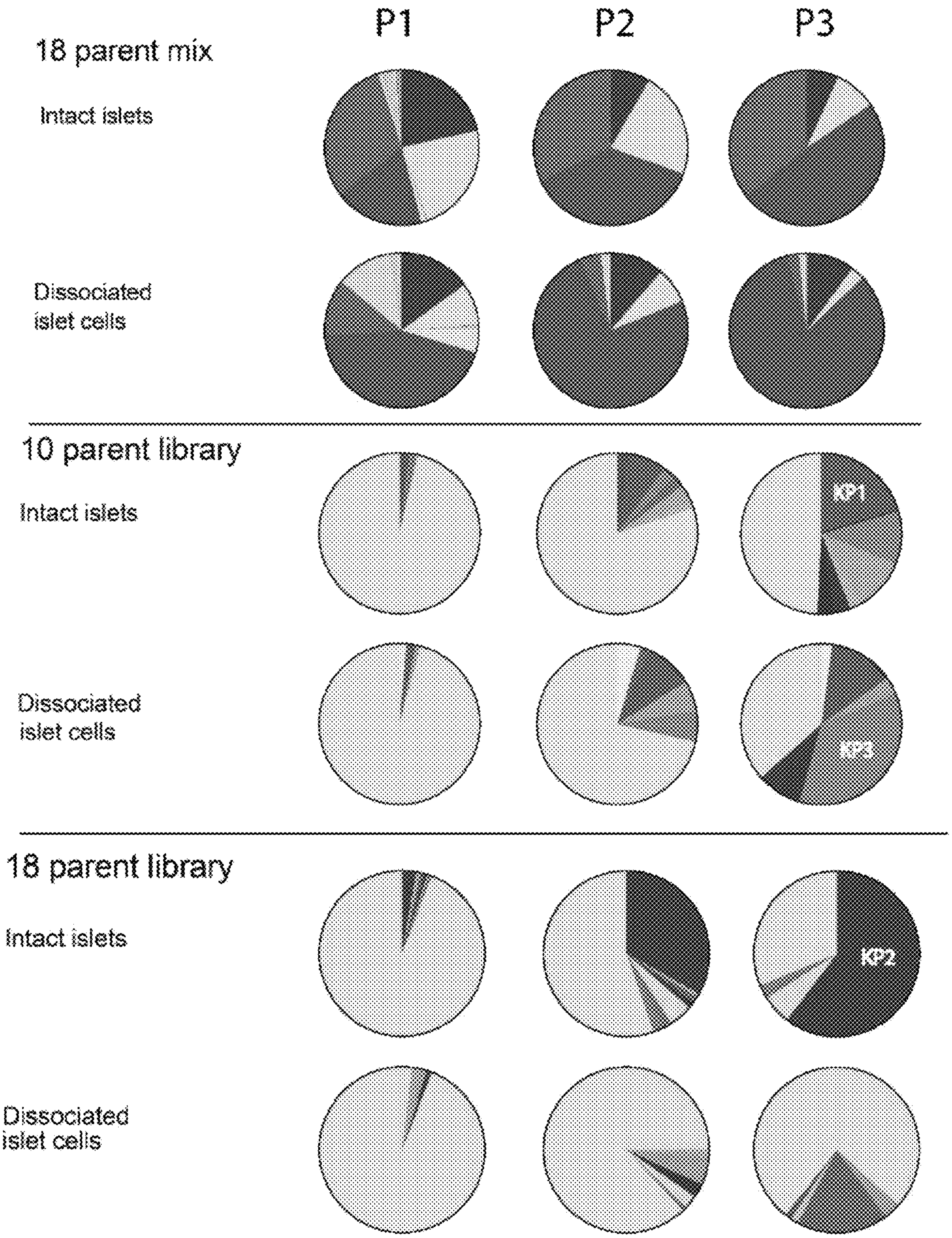

FIG. 52. Enrichment of distinct capsids during three rounds of passaging. Barcode sequences were amplified from viral genomes after each passage and were analysed by high-throughput sequencing. Color coding of enriched parental capsids for passaging of the 18 parent mix is identical to that of the parental pool depicted in FIG. 1*c*. Origin of the most improved capsids (KP1, KP2, KP3) is indicted.

FIG. 53A-53D. Rescue of enriched capsid sequences and evaluation of selected capsids for islet transduction. (A) The forward primer annealed to a sequence in the 3' end of the rep gene, the reverse primer was specific to the sequence of the right barcode of the variant capsid to be amplified. (B) A self-complementary AAV expressing GFP was packaged with LK03 as well as 12 novel capsid sequences and islet cells were transduced using a low MOI of 1,000. Cells were sorted for GFP expression using FACS 48-hrs later. (C) Dissociated islet cells were transduced with CsCl gradient purified scCAG-GFP rAAV preps generated with the two best parental capsids as well as the novel capsids that were the top transducers in the pre-screen. Three different MOIs were used for transduction. Transduction efficiency is depicted both as the percentage of GFP positive cells (left graph) as well as the median fluorescence intensity within the GFP positive cell population (right graph). (D) α- and β-cell specific transduction efficiency of the novel variants. GFP expressing rAAV packaged with two of the novel variant capsids as well as AAV-DJ and AAV-LK03 capsids were used to transduce intact islets at an MOI of 10,000 and α- and β-cell specific transduction was determined by surface staining followed by FACS. Data are shown as the mean with standard deviation from two individual experiments using islets from two different donors and statistically significant differences are indicated. *: $p<0.1$, : $p<0.01$, *: $p<0.001$ FIG. 54A-54E. Amino acid sequence and structural composition of selected shuffled AAV capsid variants. (A) Amino acid sequence mapping analysis of parental capsid fragment crossovers in vectorized shuffled capsids. Library parents are depicted in different colors as indicated on the left. Large dots represent 100% parental match (i.e. the position in question matches only one parent) and small dots represent more than one parental match (i.e. the position matches more than one parent) at each position. The solid line for each chimera represents the library parents identified within the sequence between crossovers. A set of thin horizontal parallel lines between crossovers indicates multiple parents match at an equal probability. A vertical spike indicates a fast single position switch between parents. VP1, VP2, VP3 and AAP ORFs are shown below. (B) Amino acid sequence mapping analysis of parental AAP fragment crossovers in vectorized shuffled capsids. (C) Enrichment scores were calculated for each amino acid position in the sequence of each chimera by comparison of sequences from parental serotypes based on maximum likelihood. Library parents are depicted in different colors as shown. (D) The VP3 sequences of shuffled variants were 3D false-color mapped onto the crystal structure of AAV2 VLP. Color-coding indicates parental amino acid contribution using colors as in (A) and (B). (E) The residues different from AAV3B of shuffled variants were 3D false-color mapped onto the crystal structure of AAV6 VP3. Light gray residues correspond to AAV3B amino acids while colored residues indicate surface exposed amino acids derived from other serotypes. With the exception of AAV3B color coding is as in (A) and (B).

Figure 55A:
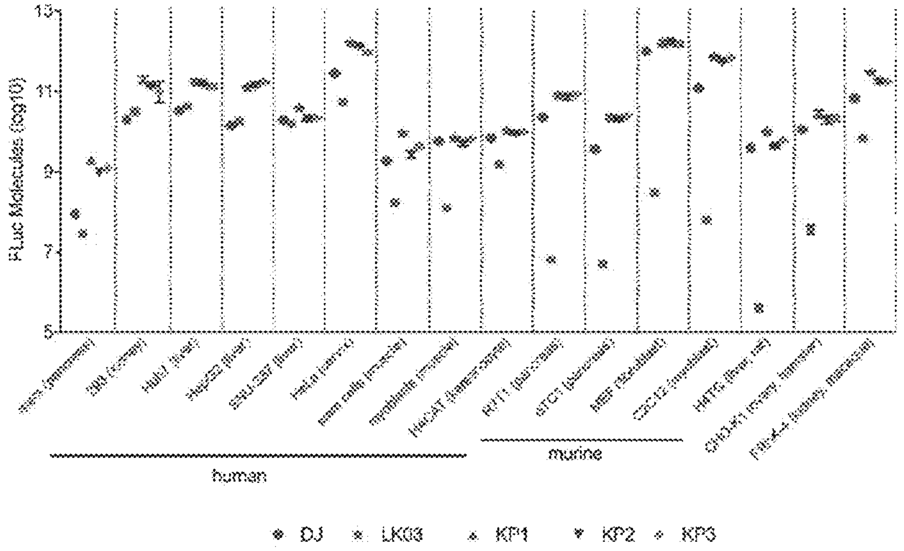
Figure 55B:
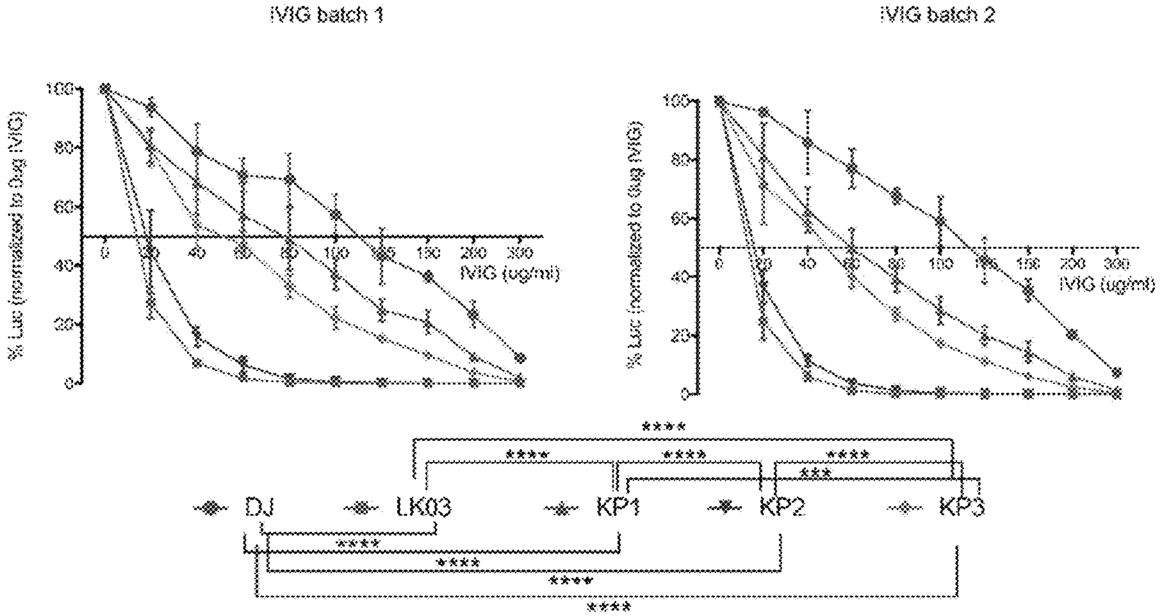

FIG. 55A-55B. In vitro transduction experiments using Firefly Luciferase expressing rAAVs. (A) Transduction efficiency of the novel capsids as well as AAV-DJ and AAV-LK03 capsids on a variety of human and non-human derived cell types. Cells were transduced with the different capsid containing rAAVs packaging a firefly luciferase expression cassette at an MOI of 1,000 in triplicates each (with the exception of islet cells) and cell lysates were analysed 48 hrs post transduction in a luciferase activity assay. Two-fold dilutions of recombinant firefly luciferase enzyme were used to prepare a standard curve and raw luminescence units were calculated into luciferase molecules based on the standard curve. (B) Neutralization assay of rAAVs packaged with different capsids using dilutions of two different batches of pooled human immunoglobulin (IVIG). Huh-7 cells were transduced in biological duplicates at a MOI of 100 with Firefly luciferase expressing rAAVs that had been pre-incubated with different concentrations of IVIG for 1-hr at 37° C. Luciferase activity in cell lysates was measured 24-hrs post transduction. Mean values with standard deviations are shown for each sample. Only statistically significant differences are indicated in the legend below the graph. *: $p<0.001$, **: $p<0.0001$.

Figure 56:
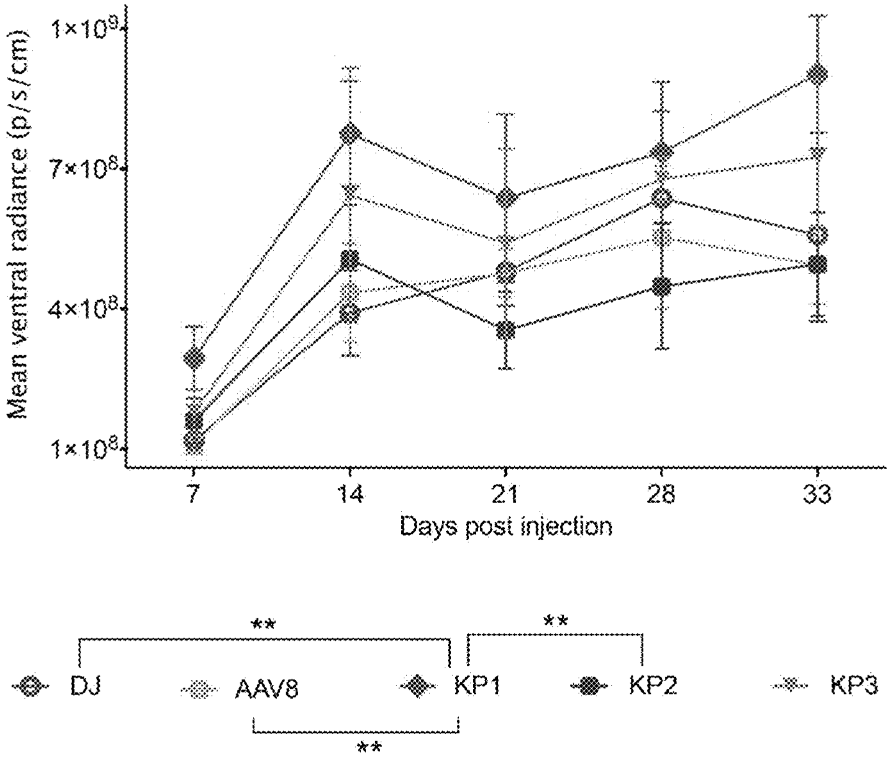
Figure 57A:
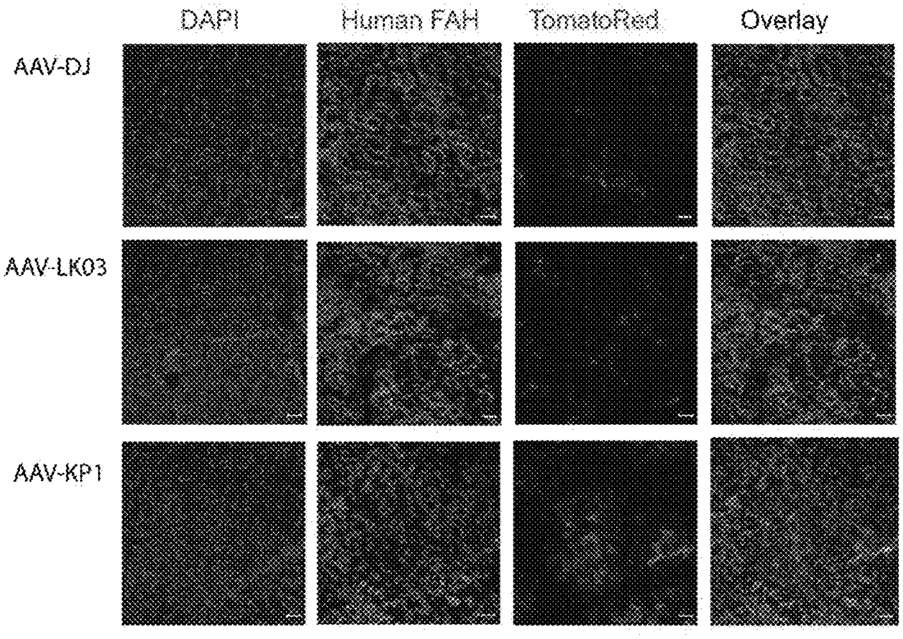
Figure 57B:
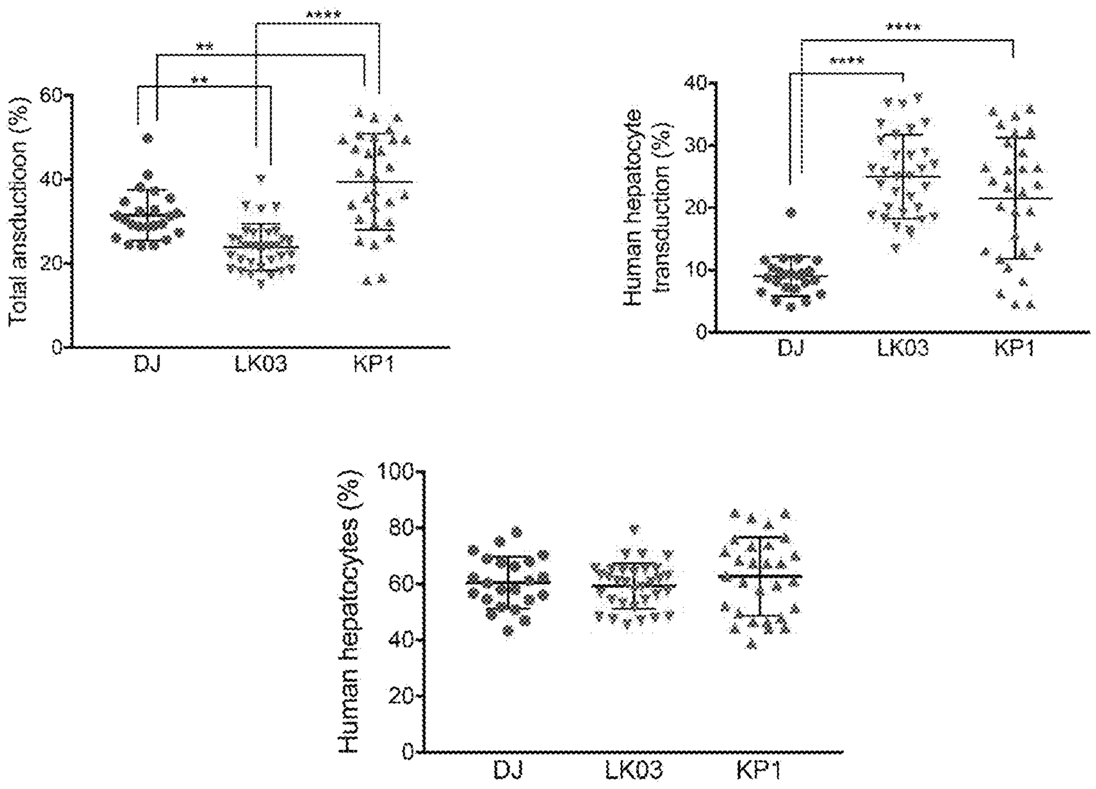

FIG. 56. In vivo transduction efficiency of rAAVs packaged with the novel capsids as well as with AAV8 and DJ capsids. Balb/C SCID mice were injected via tail vein with 2E10 vg each firefly luciferase expressing rAAV and luciferase expression in the livers was monitored over several weeks using live imaging after i.p injection of luciferin substrate. Four animals were injected for each group with the exception of the AAV8 group which contained 3 animals. The mean of each group's mean ventral radiance is shown for each timepoint with standard deviations indicated. One animal from the AAV8 group was omitted from analysis due to a failed substrate injection. Only statistically significant differences are indicated in the legend below the graph. : $p<0.01$ FIG. 57A-57B. Validation and Quantification of Human Hepatocyte Transduction in Mice with Humanized Liver In Vivo. (A) Representative immunofluorescence images from treated mice with humanized liver transduced with ssAAV-RFP at 2E11 vg i.v. with varying capsid serotypes. DAPI (blue), human-specific FAH (green), and viral-RFP (red) on liver sections. Scale bar, 50 μM. (B) Quantification of transduction efficiency for all hepatocytes (left panel) as well as human hepatocytes (right panel), and quantification of human hepatocyte repopulation levels (lower panel). Each data point represents an area of interest for each mouse (individual biological replicate, see "Materials and Methods"). A total of six to nine areas of interests for each mouse were scanned and analyzed. The mean and standard deviation for each group are indicated. Only statistically significant differences are shown in the graphs. : $p<0.01$, ****: $p<0.0001$ FIG. 58A-58C. Parental capsids used for library generation. (A) Phylogenetic relationship of the 18 parental capsids on the amino acid level. The parental capsids used for generation of the 10 parent library are shown in red. The neighbour-joining tree was constructed using Genious 6.0.6. (B) Crossover analysis of chimeric capsids DJ and LK03 with parental contributions indicated. For simple visualization the same parental capsid sequences are shown for both chimeras although they were derived from different libraries with different parental compositions. AAV-DJ was derived from a library that contained AAV2, AAV4, AAV5, AAV8, AAV9hu14, AAV-bovine, AAV-avian, and AAV-goat1 capsid sequences, AAV-LK03 was derived from a library that contained AAV1, AAV2, AAV3B, AAV4, AAV5, AAV6, AAV8, AAV9hu14, AAV-bovine, AAV-avian, and AAV-goatl sequences. (C) Crossover analysis of AAP for AAV-DJ and AAV-LK03 with parental contributions indicated.

Figure 59A:
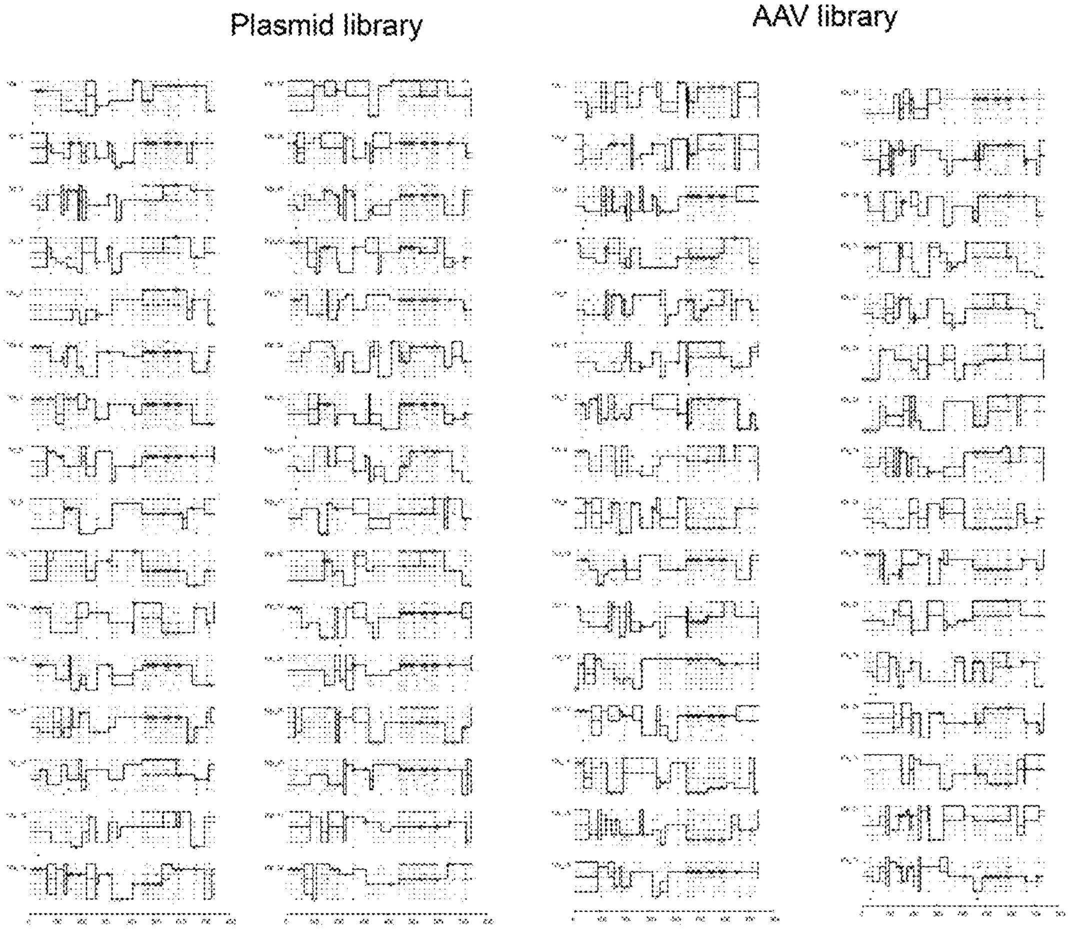
Figure 59B:
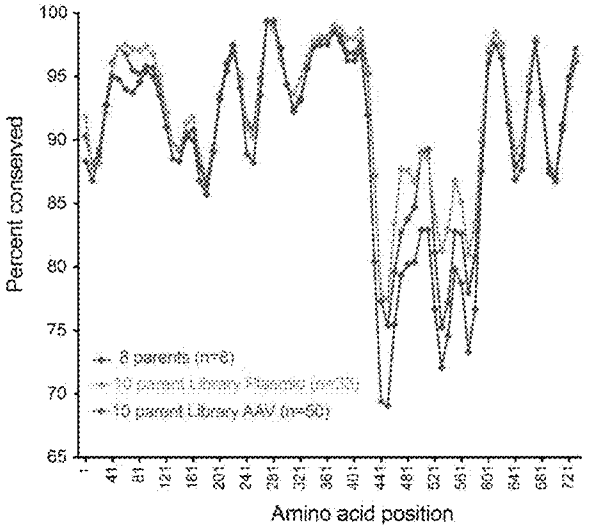

FIG. 59A-59B. Analysis of the 10 parent library by Sanger sequencing of random clones. (A) Crossover analysis of amino acid sequences of several shuffled capsids derived from the plasmid library (left) as well as the AAV library (right). For consistency LK03 and DJ are not shown as individual parents. Positions that are marked with a cross are not de novo mutations, but were derived from AAV-LK03 that contains a short stretch from AAV4. Parental capsids are shown in the following order: AAV1, AAV2, AAV3B, AAV6, AAV8, AAV9hu14, AAV-rhesus10, AAV-porcine2. (B) Conservation analysis along the capsid sequences for the input 8 parental sequences as well as the 10 parent library on the plasmid and on the AAV level (rAAVs).

Figure 60A:
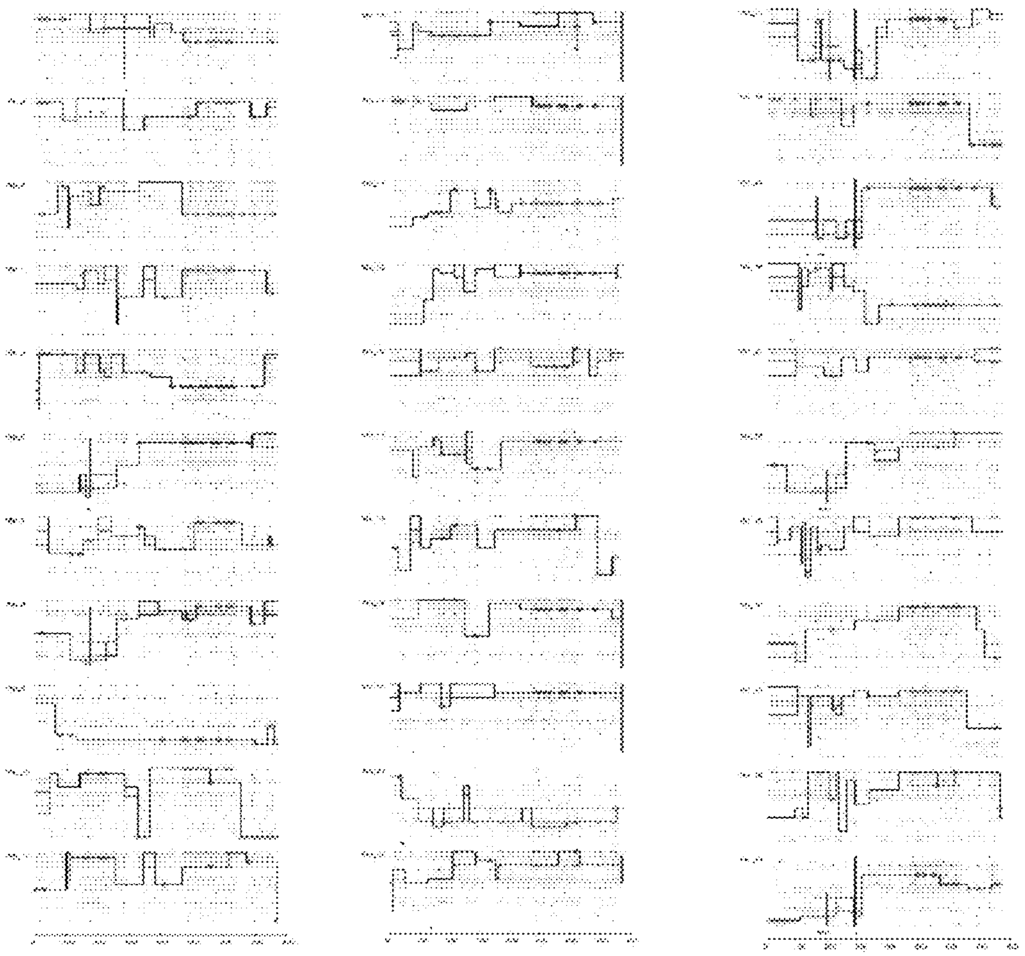
Figure 60B:
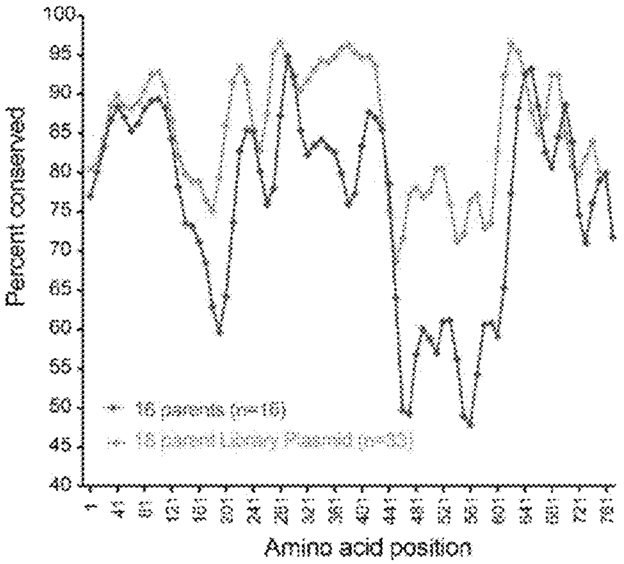

FIG. 60A-60B. Analysis of the 18 parent library by Sanger sequencing of random clones. (A) Crossover analysis of amino acid sequences of several shuffled capsids derived from the plasmid library. Parental capsids are shown in the following order: AAV1, AAV2, AAV3B, AAV6, AAV8, AAV9hu14, AAV-rhesus10, AAV-porcine2, AAV4, AAV5, AAV12, AAV-bovine, AAV-goat1, AAV-porcine1, AAV-mouse1, and AAV-avian. (B) Conservation analysis along the capsid sequences for the input 16 parental sequences as well as the 18 parent library. Capsids D J and LK03 are not listed as parents since they are chimeras consisting of fragments from the parentals used.

Figure 61A:
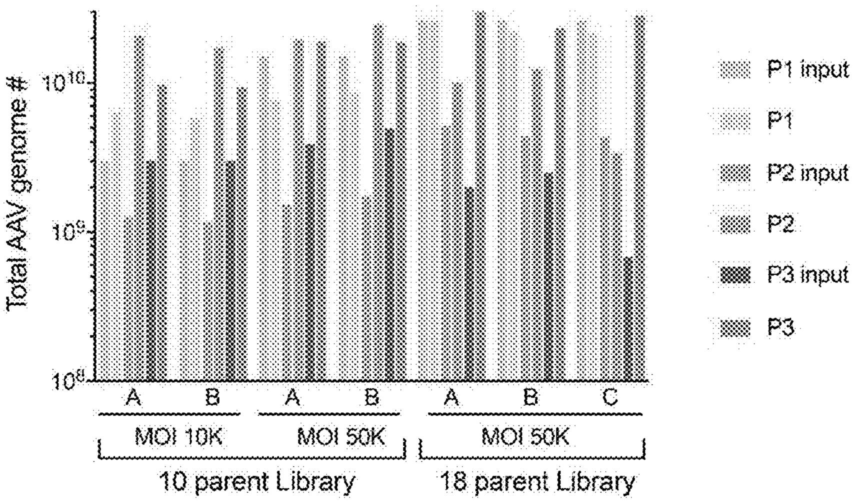
Figure 61B:
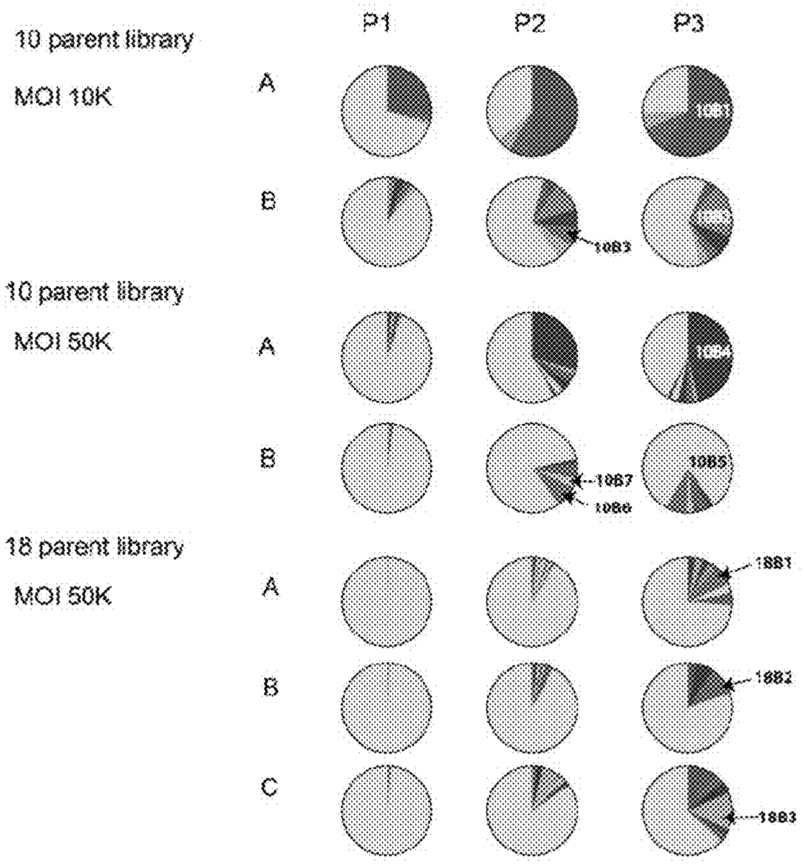

FIG. 61A-61B. Results of the second library screen on human islets. (A) Replication of the 10 parent library and the 18 parent library during three rounds of passaging on intact islets. Islets were infected in biological duplicates with the 10 parent library using an MOI of 10,000 or 50,000. Infection with the 18 parent library was performed in biological triplicates using an MOI of 50,000. Adenovirus 5 was used to replicate AAV and virus was harvested from the supernatant and cells after 4 days. Replication of viral species was determined by rep qPCR. For each round the total viral genome copies used for infection and the total viral genome copies retrieved are shown. (B) Enrichment of distinct capsids during three rounds of passaging. Barcode sequences were amplified from viral genomes after each passage and were analysed by high-throughput sequencing.

Figure 62A:
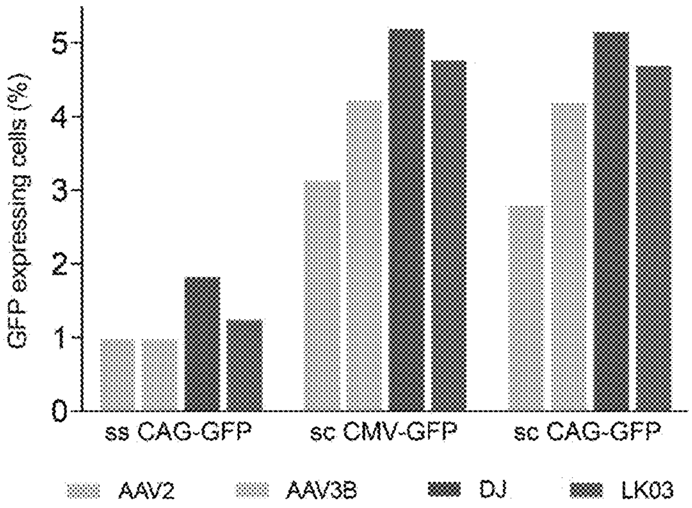
Figure 62B:
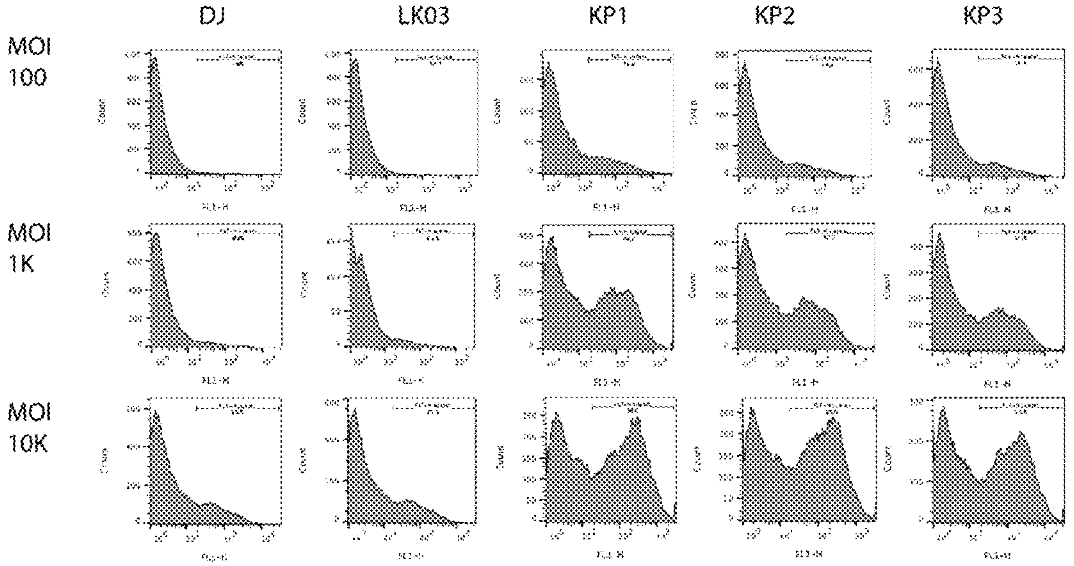

FIG. 62A-62B. Transduction efficiency of different chimeric and wildtype AAV capsids. (A) Dissociated islet cells were transduced with rAAVs (AAV2, AAV3B, DJ, and LK03 capsids) at and MOI of 1,000 and transduction efficiency was determined by flow cytometry 48 hrs post transduction. (B) Dissociated islet cells were transduced with CsCl gradient purified scCAG-GFP rAAV preps generated with the two best parental capsids as well as the novel capsids that were the top transducers in the pre-screen. Three different MOIs were used for transduction. Transduction efficiency is measured as a function of the number of GFP expressing cells in conjunction with fluorescence intensity for each cell.

FIG. 63A-63D. Analysis of the novel capsids for parental contribution on the nucleotide level as well as for packaging of vector genomes and protein composition. (A) Nucleotide sequence mapping analysis of parental capsid fragment crossovers in vectorized shuffled capsids. VP1, VP2, VP3 and AAP coding sequences are indicated below the crossover analysis for KP1, KP2, and KP3 sequences. (B) Alkaline Southern Blot analysis of ssCAG-FLuc vector genomes packaged with DJ, LK03, as well as the novel capsid variants. 1E09 vg were loaded in each lane. Size standards consisted of plasmids digested with different restriction enzymes to obtain fragments of the desired sizes. Vector genomes were probed with a Fluc specific radiolabeled probe (C) Alkaline Southern Blot analysis of scCAG-GFP vector genomes packaged with DJ, LK03, as well as the novel capsid variants. Size standards consisted of plasmids digested with different restriction enzymes to obtain fragments of the desired sizes. Vector genomes were probed with a GFP specific radiolabeled probe. (D) Western Blot analysis of purified scCAG-GFP vector preparations. Purified virus equivalent to 1E09 vg was loaded on a 4-12% Bis-Tris gel, transferred onto a nitrocellulose membrane and probed with B1 antibody that recognizes a highly conserved epitope in the C terminus of all three capsid proteins.

FIG. 64A-64C. In vivo transduction efficiency of rAAVs packaged with the novel capsids as well as with AAV8 and DJ capsids. (A) Balb/C SCID mice were injected via tail vein with 2E10 vg of each Firefly luciferase expressing rAAV and luciferase expression in the livers was monitored over several weeks using live imaging after i.p injection of luciferin substrate. Four animals were injected for each group with the exception of the AAV8 group which contained 3 animals. Maximum radiance was set at 2E09 with a threshold of 5E07. (B) 34 days post injection mice were sacrificed, and several organs were analyzed for luciferase expression ex vivo using the Promega Luciferase assay system. (C) Genomic DNA was isolated from mouse livers and analyzed for vector copy numbers by qPCR. Only statistically significant differences between groups are indicated. *: $p<0.1$, : $p<0.01$, *: $p<0.001$, **: $p<0.0001$ FIG. 65A-65**B. Amino acid alignments of the novel sequences. (A) Capsid sequences of the novel variants as well as the 8 parental serotypes were aligned using MegAlign. Only differences to the consensus sequence are shown. The start sites for VP1, VP2, and VP3 are indicated. (B) Assembly activating protein (AAP) sequences of the novel variants as well as the 8 parental serotypes were aligned.

Figure 66:
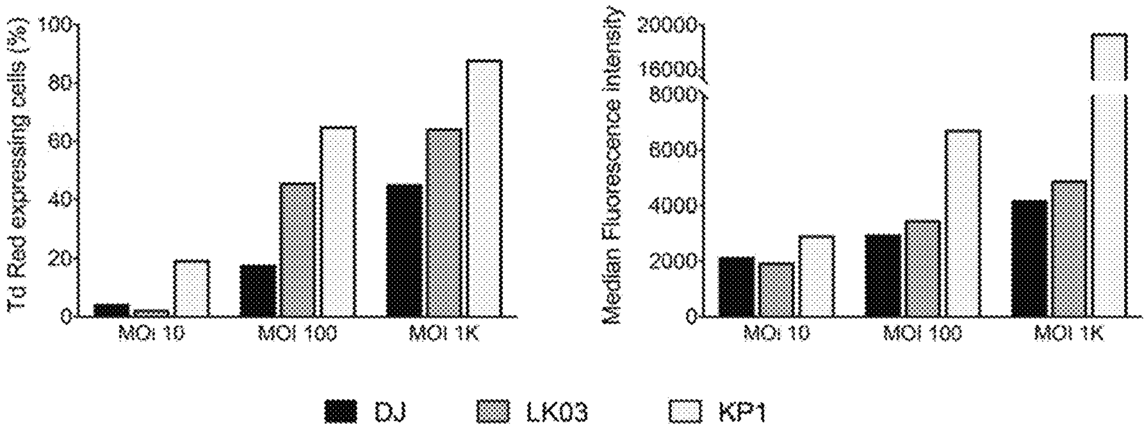

FIG. 66. Transduction efficiency of capsid KP1 for human embryonic stem cell derived β-cells. DJ, LK03 and KP1 capsids were used to package a Tomato Red vector and hESC derived mature β-cells were transduced with the MOIs indicated. Intracellular staining for the β-cell marker C-peptide was performed on day 6 post transduction and cells were analysed by flow cytometry.

Figure 67:
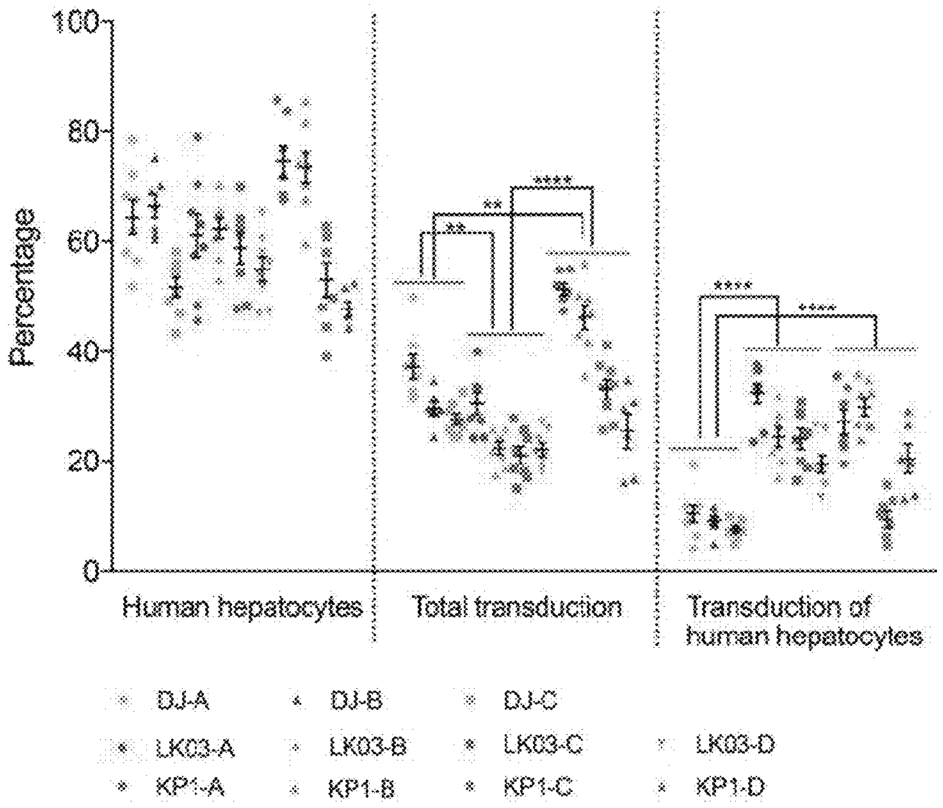

FIG. 67. Quantification of human hepatocyte repopulation levels, transduction efficiency for all hepatocytes as well as human hepatocytes. Each data point represents an area of interest for each mouse. A total of six to nine areas of interest for each mouse were scanned and analyzed. The mean and standard deviation for each mouse are indicated. Only statistically significant differences between the groups are shown in the graphs. :p,0.01, **:p0.0001

Figure 68A:
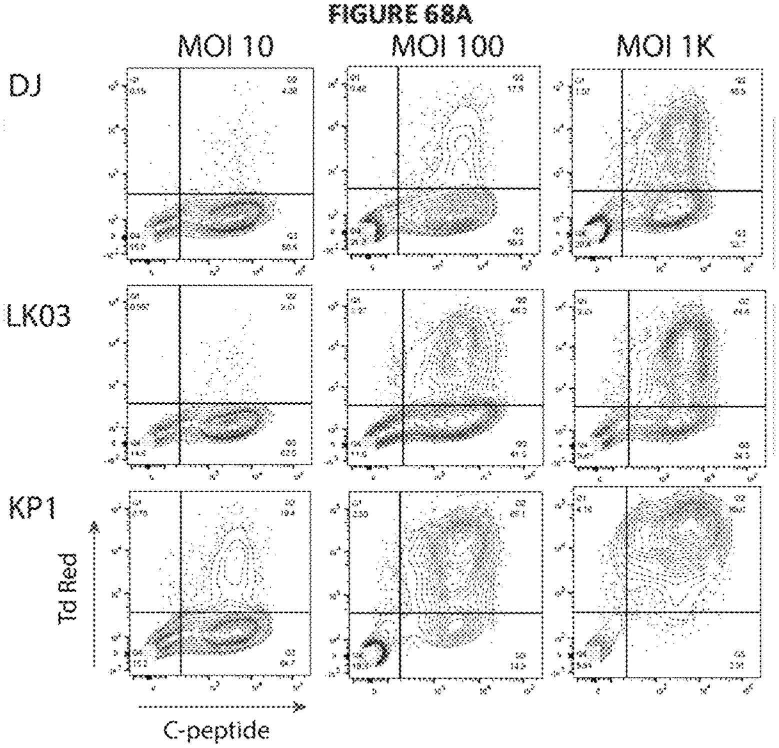
Figure 68B:
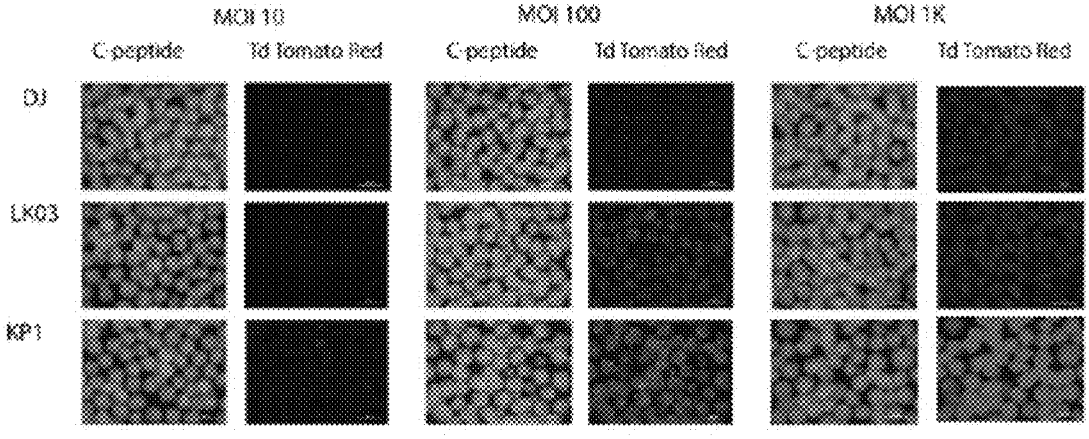

FIG. 68A-68B. Transduction efficiency of novel and parental AAV capsids on human islets and on hESC derived β-cells. (A) DJ, LK03 and KP1 capsids were used to package a Tomato Red vector and hESC derived mature β-cells were transduced with the MOIs indicated. Intracellular staining for the β-cell marker C-peptide was performed on day 6 post transduction and cells were analysed by flow cytometry. (B) The same cells were also analysed by immunofluorescent imaging.

DETAILED DESCRIPTION OF THE INVENTION

Introduction

There remains a need in the art for gene therapy vectors capable of increased transduction in human pancreatic tissue or human islets for gene therapy, so that more therapeutic levels of nucleic acid expression can be achieved. The present invention meets this need and provides variant AAV capsid polypeptides that exhibit increased transduction and/or tropism human pancreatic tissue or human islets as compared to non-variant parent capsid polypeptides.

Detailed Description

In various embodiments, the present invention provides variant adeno-associated virus (AAV) capsid polypeptides, wherein the variant AAV capsid polypeptides exhibit increased transduction or tropism human pancreatic tissue or human islets as compared to non-variant parent capsid polypeptides. In some embodiments the variant AAV capsid polypeptide is referred to as a recombinant variant AAV capsid polypeptide or variant rAAV capsid polypeptide.

In other various embodiments, the present invention provides AAV vectors comprising a nucleic acid sequence coding for a variant AAV capsid polypeptide, wherein the variant AAV capsid polypeptide exhibits increased transduction or tropism human pancreatic tissue or human islets as compared to a vector encoding a non-variant parent capsid polypeptide. In some embodiments the AAV vector is referred to as a recombinant AAV or rAAV vector.

In some embodiments, the present invention provides variant AAV capsid polypeptides, wherein the variant AAV capsid polypeptide comprises at least one amino acid difference (e.g., amino acid substitution, amino acid insertion, amino acid deletion) relative to a substantially identical non-variant parent AAV capsid protein, and where the variant AAV capsid protein exhibits increased transduction or tropism human pancreatic tissue or human islets as compared to a vector encoding a non-variant parent capsid polypeptide. In some embodiments, the variant AAV capsid polypeptide does not comprise an amino acid sequence present in a naturally occurring AAV capsid polypeptide.

In some embodiments, the present invention provides AAV vectors comprising: a) a variant AAV capsid protein, wherein the variant AAV capsid polypeptide comprises at least one amino acid difference (e.g., amino acid substitution, amino acid insertion, amino acid deletion) relative to a substantially identical non-variant parent AAV capsid protein, and where the variant AAV capsid protein exhibits increased transduction or tropism human pancreatic tissue or human islets as compared to a vector encoding a non-variant parent capsid polypeptide. In some embodiments, the AAV capsid polypeptide does not comprise an amino acid sequence present in a naturally occurring AAV capsid polypeptide.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting.

The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

As described in the present invention, the following terms will be employed, and are defined as indicated below.

Abbreviations

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector").

Definitions

The term "AAV" includes AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV 9_hu14, avian AAV, bovine AAV, canine AAV, equine AAV, primate AAV, non-primate AAV, and ovine AAV. "Primate AAV" refers to AAV capable of infecting primates, "non-primate AAV" refers to AAV capable of infecting non-primate mammals, "bovine AAV" refers to AAV capable of infecting bovine mammals, etc.

An "AAV vector" as used herein refers to an AAV vector nucleic acid sequence encoding for various nucleic acid sequences, including in some embodiments a variant capsid polypeptide (i.e., the AAV vector comprises a nucleic acid sequence encoding for a variant capsid polypeptide, also referred to as a variant AAV capsid polypeptide), wherein the variant AAV capsid polypeptides exhibit increased transduction or tropism human pancreatic tissue or human islets as compared to non-variant parent capsid polypeptides. The AAV vectors can also comprise a heterologous nucleic acid sequence not of AAV origin as part of the nucleic acid insert. This heterologous nucleic acid sequence typically comprises a sequence of interest for the genetic transformation of a cell. In general, the heterologous nucleic acid sequence is flanked by at least one, and generally by two AAV inverted terminal repeat sequences (ITRs).

The phrase "non-variant parent capsid polypeptides" includes any naturally occurring AAV capsid polypeptides and/or any AAV wild-type capsid polypeptides. In some embodiments, the non-variant parent capsid polypeptides include AAV1, AAV2, AAV3, AAV4, AAV5, AAV6, AAV7, AAV8, AAV9, bovine AAV and/or avian AAV capsid polypeptides.

The term "substantially identical" in the context of variant AAV capsid polypeptides and non-variant parent capsid polypeptides refers to sequences with 1 or more amino acid changes. In some embodiments, these changes do not affect the packaging function of the capsid polypeptides. In some embodiments, substantially identical include variant AAV capsid polypeptides about 99%, about 98%, about 97%, about 96%, about 95%, about 94%, about 93%, about 92%, about 91%, or about 90% identical to non-variant parent capsid polypeptides. In some embodiments, the variant AAV capsid polypeptides can be substantially identical to non-variant parent capsid polypeptides over a subregion of the variant AAV capsid polypeptide, such as over about 25%., about 50%, about 75%, or about 90% of the total polypeptide sequence length.

An "AAV virion" or "AAV virus" or "AAV viral particle" or "AAV vector particle" refers to a viral particle composed of at least one AAV capsid polypeptide (including both variant AAV capsid polypeptides and non-variant parent capsid polypeptides) and an encapsidated polynucleotide AAV transfer vector. If the particle comprises a heterologous nucleic acid (i.e. a polynucleotide other than a wild-type AAV genome, such as a transgene to be delivered to a mammalian cell), it can be referred to as an "AAV vector particle" or simply an "AAV vector". Thus, production of AAV virion or AAV particle necessarily includes production of AAV vector as such a vector is contained within an AAV virion or AAV particle.

"Packaging" refers to a series of intracellular events resulting in the assembly of AAV virions or AAV particles which encapsidate a nucleic acid sequence and/or other therapeutic molecule. Packaging can refer to encapsidation of nucleic acid sequence and/or other therapeutic molecules into a capsid comprising the variant AAV capsid polypeptides described herein. Generally, AAV have limited packaging capacity of about 5 kb.

The phrase "therapeutic molecule" as used herein can include nucleic acids (including, for example, vectors), polypeptides (including, for example, antibodies), and vaccines, as well as any other therapeutic molecule that could be packaged by the variant AAV capsid polypeptides of the invention.

AAV "rep" and "cap" genes refer to polynucleotide sequences encoding replication and encapsidation proteins of adeno-associated virus (AAV). AAV rep (replication) and cap (capsid) are referred to herein as AAV "packaging genes."

A "helper virus" for AAV refers to a virus allowing AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used as a helper virus. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome allowing AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virion, virus or viral particle is one comprising a polynucleotide component deliverable into a cell tropic for the viral species. The term does not necessarily imply any replication capacity of the virus. As used herein, an "infectious" virus or viral particle is one that upon accessing a target cell, can infect a target cell, and can express a heterologous nucleic acid in a target cell. Thus, "infectivity" refers to the ability of a viral particle to access a target cell, enter a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA) or fluorescence-activated cell sorting (FACS).

A "replication-competent" virion or virus (e.g. a replication-competent AAV) refers to an infectious phenotypically wild-type virus, and is replicable in an infected cell (i.e. in the presence of a helper virus or helper virus functions). In the case of AAV, replication competence generally requires the presence of functional AAV packaging genes. In some embodiments, AAV vectors, as described herein, lack of one or more AAV packaging genes and are replication-incompetent in mammalian cells (especially in human cells). In some embodiments, AAV vectors lack any AAV packaging gene sequences, minimizing the possibility of generating replication competent AAV by recombination between AAV packaging genes and an incoming AAV vector. In many embodiments, AAV vector preparations as described herein are those containing few if any replication competent AAV (rcAAV, also referred to as RCA) (e.g., less than about 1 rcAAV per $10^2$ AAV particles, less than about 1 rcAAV per $10^4$ AAV particles, less than about 1 rcAAV per 108 AAV particles, less than about 1 rcAAV per $10^{12}$ AAV particles, or no rcAAV).

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA, tRNA, lncRNA, RNA antagomirs, and inhibitory DNA or RNA (RNAi, e.g., small or short hairpin (sh)RNA, microRNA (miRNA), aptamers, small or short interfering (si)RNA, trans-splicing RNA, or antisense RNA). Polynucleotides also include non-coding RNA, which include for example, but are not limited to, RNAi, miRNAs, lncRNAs, RNA antagomirs, aptamers, and any other non-coding RNAs known to those of skill in the art. Polynucleotides include naturally occurring, synthetic, and intentionally altered or modified polynucleotides as well as analogues and derivatives. The term "polynucleotide" also refers to a polymeric form of nucleotides of any length, including deoxyribonucleotides or ribonucleotides, or analogs thereof, and is synonymous with nucleic acid sequence. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment as described herein encompassing a polynucleotide encompasses both the double-stranded form and each of two complementary single-stranded forms known or predicted to make up the double-stranded form. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "gene" refers to a polynucleotide containing at least one open reading frame capable of encoding a particular protein or polypeptide after being transcribed and translated.

A "small interfering" or "short interfering RNA" or siRNA is a RNA duplex of nucleotides targeted to a gene interest (a "target gene"). An "RNA duplex" refers to the structure formed by the complementary pairing between two regions of a RNA molecule. siRNA is "targeted" to a gene and the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences forming the duplex. The loop can vary in length. In some embodiments the loop is 5, 6, 7, 8, 9, 10, 11, 12 or 13 nucleotides in length.

The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome capable of modulating the productive utilization of mRNA. An artificial microRNA can be any type of RNA sequence, other than endogenous microRNA, capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA cleaved from a microRNA precursor (a "pre-miRNA"), or synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means the polynucleotide is the product of various combinations of cloning, restriction or ligation steps, and other procedures resulting in a construct distinct and/or different from a polynucleotide found in nature. A recombinant virus is a viral particle encapsidating a recombinant polynucleotide. The terms respectively include replicates of the original polynucleotide construct and progeny of the original virus construct.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters, enhancers and degrons. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

"Heterologous" means derived from a genotypically distinct entity from the rest of the entity to it is being compared too. For example, a polynucleotide introduced by genetic engineering techniques into a plasmid or vector derived from a different species is a heterologous polynucleotide. A promoter removed from its native coding sequence and operatively linked to a coding sequence it is not naturally found linked to a heterologous promoter. For example, an AAV including a heterologous nucleic acid encoding a heterologous gene product is an AAV including a nucleic acid not normally included in a naturally-occurring, wild-type AAV, and the encoded heterologous gene product is a gene product not normally encoded by a naturally-occurring, wild-type AAV. An AAV including a nucleic acid encoding a variant AAV capsid polypeptide includes a heterologous nucleic acid sequence. Once transferred/delivered into a host cell, a heterologous polynucleotide, contained within the virion, can be expressed (e.g., transcribed, and translated if appropriate). Alternatively, a transferred/delivered heterologous polynucleotide into a host cell, contained within the virion, need not be expressed. Although the term "heterologous" is not always used herein in reference to polynucleotides, reference to a polynucleotide even in the absence of the modifier "heterologous" is intended to include heterologous polynucleotides in spite of the omission.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or polynucleotide-liposome complexation. Genetic alteration may also be effected, for example, by transduction or infection with a DNA or RNA virus or viral vector. Generally, the genetic element is introduced into a chromosome or mini-chromosome in the cell; but any alteration changing the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced and inheritable by progeny of the altered cell.

The terms "polypeptide," "peptide," and "protein" are used interchangeably herein to refer to polymers of amino acids of any length. The "polypeptides," "proteins" and "peptides" encoded by the "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of as described herein, such polypeptides, proteins and peptides encoded by the polynucleotide sequences can be but are not required to be identical to the defective endogenous protein, or whose expression is insufficient, or deficient in the treated mammal. The terms also encompass a modified amino acid polymer; for example, disulfide bond formation, glycosylation, lipidation, phosphorylation, methylation, carboxylation, deamidation, acetylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, retaining the desired biochemical function of the intact protein.

As used herein, the abbreviations for the genetically encoded L-enantiomeric amino acids used in the disclosure methods are conventional and are as follows in Table 1.

TABLE 1

Amino acid abbreviations

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydrogen ion. Genetically encoded basic amino acids include His (H), Arg (R) and Lys (K).

"Polar Amino Acid" refers to a hydrophilic amino acid having a side chain uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, *J. Mol. Biol.* 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR and the like where each R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C1-C21)) aryl, substituted (C5-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The term "non-naturally" with regard to amino acids can include any amino acid molecule not included as one of the 20 amino acids listed in Table 1 above as well as any modified or derivatized amino acid known to one of skill in the art. Non-naturally amino acids can include but are not limited to β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-omithine, p-nitro-phenylalanine, hydroxy proline, 1,2,3,4,-tetrahydroisoquinoline-3-carboxylic acid, and thioproline.

The term "variant" or "variants", with regard to polypeptides, such as capsid polypeptides refers to a polypeptide sequence differing by at least one amino acid from a parent polypeptide sequence, also referred to as a non-variant polypeptide sequence. In some embodiments, the polypeptide is a capsid polypeptide and the variant differs by at least one amino acid substitution. Amino acids also include naturally occurring and non-naturally occurring amino acids as well as derivatives thereof. Amino acids also include both D and L forms.

An "isolated" plasmid, nucleic acid, vector, virus, virion, host cell, or other substance refers to a preparation of the substance devoid of at least some of the other components present where the substance or a similar substance naturally occurs or from which it is initially prepared. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

By the term "highly conserved" is meant at least about 80% identity, preferably at least 90% identity, and more preferably, over about 97% identity. Identity is readily determined by one of skill in the art by resort to algorithms and computer programs known by those of skill in the art.

The term "percent sequence identity" or "identical" in the context of nucleic acid sequences refers to the residues in the two sequences that are the same when aligned for maximum correspondence. The length of sequence identity comparison may be over the full-length of the genome, the full-length of a gene coding sequence, or a fragment of at least about 500 to 5000 nucleotides. However, identity among smaller fragments, e.g. of at least about nine nucleotides, usually at least about 20 to about 24 nucleotides, at least about 28 to about 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The terms "pharmaceutically acceptable" and "physiologically acceptable" mean a biologically acceptable formulation, gaseous, liquid or solid, or mixture thereof, suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering an AAV vector or AAV virion as disclosed herein, or transformed cell to a subject.

The phrase a "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, produces a desired effect (e.g., prophylactic or therapeutic effect). In some embodiments, unit dosage forms may be within, for example, ampules and vials, including a liquid composition, or a composition in a freeze-dried or lyophilized state; a sterile liquid carrier, for example, can be added prior to administration or delivery in vivo. Individual unit dosage forms can be included in multi-dose kits or containers. AAV vectors or AAV virions, and pharmaceutical compositions thereof can be packaged in single or multiple unit dosage form for ease of administration and uniformity of dosage.

A "therapeutically effective amount" will fall in a relatively broad range determinable through experimentation and/or clinical trials. For example, for in vivo injection, e.g., injection directly into the tissue of a subject (for example, pancreatic tissue), a therapeutically effective dose will be on the order of from about $10^6$ to about $10^{15}$ of the AAV virions per kilogram bodyweight of the subject. In some embodiments, a therapeutically effective dose will be on the order of from about $10^8$ to $10^{12}$ AAV virions per kilogram bodyweight of the subject. Other effective dosages can be readily established by one of ordinary skill in the art through routine trials establishing dose response curves.

An "effective amount" or "sufficient amount" refers to an amount providing, in single or multiple doses, alone or in combination, with one or more other compositions (therapeutic agents such as a drug), treatments, protocols, or therapeutic regimens agents (including, for example, vaccine regimens), a detectable response of any duration of time (long or short term), an expected or desired outcome in or a benefit to a subject of any measurable or detectable degree or for any duration of time (e.g., for minutes, hours, days, months, years, or cured).

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is also a satisfactory outcome.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for the described methods and uses, but the subject may not manifest the disease. Such subjects therefore include those screened positive for an insufficient amount or a deficiency in a functional gene product (protein), or producing an aberrant, partially functional or non-functional gene product (protein), leading to disease; and subjects screening positive for an aberrant, or defective (mutant) gene product (protein) leading to disease, even though such subjects do not manifest symptoms of the disease.

The phrase "enhanced neutralization profile" refers to the ability of an AAV vector or virion to better evade neutralizing antibody binding in the subject. In some instances, fewer neutralization antibodies allow for the AAV infection to generate higher levels of transduction, making the variant AAV capsid polypeptides, AAV vectors and virions of the present invention better suited for gene therapy purposes.

The phrases "tropism" and "transduction" are interrelated, but there are differences. The term "tropism" as used herein refers to the ability of an AAV vector or virion to infect one or more specified cell types, but can also encompass how the vector functions to transduce the cell in the one or more specified cell types; i.e., tropism refers to preferential entry of the AAV vector or virion into certain cell or tissue type(s) and/or preferential interaction with the cell surface that facilitates entry into certain cell or tissue types, optionally and preferably followed by expression (e.g., transcription and, optionally, translation) of sequences carried by the AAV vector or virion in the cell, e.g., for a recombinant virus, expression of the heterologous nucleotide sequence(s). As used herein, the term "transduction" refers to the ability of an AAV vector or virion to infect one or more particular cell types; i.e., transduction refers to entry of the AAV vector or virion into the cell and the transfer of genetic material contained within the AAV vector or virion into the cell to obtain expression from the vector genome. In some cases, but not all cases, transduction and tropism may correlate.

The term "tropism profile" refers to the pattern of transduction of one or more target cells, tissues and/or organs. For example, some shuffled AAV capsids (variant AAV capsid polypeptides) provide for efficient transduction of human pancreatic tissue or human islets. Conversely, some shuffled AAV capsids have only low level transduction of liver, gonads and/or germ cells. The variant AAV capsid polypeptides disclosed herein provide for efficient and/or enhanced transduction of human pancreatic tissue or human islets.

Unless indicated otherwise, "efficient transduction" or "efficient tropism," or similar terms, can be determined by reference to a suitable control (e.g., at least about 50%, 60%, 70%, 80%, 85%, 90%, 95%, 100%, 110%, 125%, 150%, 175%, or 200% or more of the transduction or tropism, respectively, of the control). Suitable controls will depend on a variety of factors including the desired tropism profile. Similarly, it can be determined if a capsid and/or virus "does not efficiently transduce" or "does not have efficient tropism" for a target tissue, or similar terms, by reference to a suitable control.

As used herein and in the appended claims, the singular forms "a," "an," and "the" include plural referents unless the context clearly dictates otherwise. Thus, for example, reference to "an AAV virion" includes a plurality of such virions and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

AAV Capsid and Vector Features

AAV vectors of the present invention have numerous features. In some embodiments, the vectors comprise nucleic acid sequences encoding for variant AAV capsid polypeptides. Such AAV vectors and their features are described in detail below.

An exemplary AAV vector of the present invention comprises a nucleic acid encoding for a variant AAV capsid protein differing in amino acid sequence by at least one amino acid from a wild-type or non-variant parent capsid protein. The amino acid difference(s) can be located in a solvent accessible site in the capsid, e.g., a solvent-accessible loop, or in the lumen (i.e., the interior space of the AAV capsid). In some embodiments, the lumen includes the interior space of the AAV capsid. For example, the amino acid substitution(s) can be located in a GH loop in the AAV capsid polypeptide. In some embodiments, the variant AAV capsid polypeptide comprises an amino acid substitution in AAV1, AAV2, AAV3, AAV4, AAV5, AAV6, AAV7, AAV8, or AAV9 capsid polypeptides.

In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to non-variant capsid amino acid sequences or to sub-portions of a non-variant parent capsid polypeptide sequence, and exhibits increased transduction or tropism human pancreatic tissue or human islets as compared to a vector encoding a non-variant parent capsid polypeptide. In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV4, AAV5, AAV6, AAV7, AAV8, or AAV9 capsid polypeptides, and where the variant AAV capsid polypeptide exhibits increased transduction or tropism human pancreatic tissue or human islets as compared to a vector encoding a non-variant parent capsid polypeptide. In some embodiments, the variant AAV capsid polypeptide comprises one or more regions or sub-portions from non-variant parent capsid polypeptide sequences from AAV serotypes 1, 3, 6, 8, and 9 (i.e., AAV1, AAV6, AAV8, and AAV9). In some embodiments, the variant AAV capsid polypeptide comprises one or more regions or sub-portions from non-variant parent capsid polypeptide sequences selected from any one of SEQ ID NOs: 27-44

In some embodiments, a subject AAV vector can encode variant capsid polypeptides having an amino acid sequence of at least about 85%, at least about 90%, at least about 95%, at least about 98%, or at least about 99%, or 100%, amino acid sequence identity to non-variant parent capsid polypeptides or to sub-portions of non-variant parent capsid polypeptides. In some embodiments, the variant AAV capsid polypeptide is encoded by other vectors/plasmids known in the art. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides exhibit substantial homology or "substantial similarity," when referring to amino acids or fragments thereof, indicating that, when optimally aligned with appropriate amino acid insertions or deletions with another amino acid (or its complementary strand), there is amino acid sequence identity in at least about 95% to about 99% of the aligned sequences. In some embodiments, the homology is over full-length sequence, or a polypeptide thereof, e.g., a capsid protein, or a fragment thereof of at least 8 amino acids, or more desirably, at least about 15 amino acids in length, including sub-portions of a non-variant parent capsid polypeptide sequence. For example, the variant AAV capsid polypeptide can comprise an amino acid sequence having at least about 85%, at least about 90%, at least about 95%, at least about 98%, at least about 99%, or 100%, amino acid sequence identity to a non-variant parent capsid polypeptide sequence or to sub-portions of a non-variant parent capsid polypeptides. In some embodiments the variant AAV capsid polypeptide sequence comprises any one of SEQ ID NOs: 1-7. In some embodiments, the variant AAV capsid polypeptide sequence is encoded by any one of SEQ ID NOs: 8-14. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

TABLE 2

Variant AAV Capsid Amino Acid Sequences

| Description SEQ ID NO: | Amino Acid Sequence |
|---|---|
| AAV-10A1 SEQ ID NO: 1 | >10A1_KP1<br>MAADGYLPDWLEDTLSEGIRQWWKLKPGPPPPKPAERHKDDSRGLVLPGYKYLGPGNGLD<br>KGEPVNAADAAALEHDKAYDQQLKAGDNPYLRYNHADAEFQERLQEDTSFGGNLGRAVFQ<br>AKKRVLEPLGLVEEPVKTAPGKKRPVEHSPVEPDSSSGTGKAGQQPARKRLNFGQTGDTD<br>SAADPQPLGEPPAAPSGLGTGTMAAGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTQNEGTKTIANNLTSTVQVFTDSEYQLPYVLGSAHQ<br>GCLPPFPADVFMIPQYGYLTLNNGSQAMGRSSFYCLEYFPSQMLRTGNNFQFTYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQILIKNTPVPADPP<br>TAFNKDKLNSFITQYSTGQVSVEIEWELQKENSKRWNPEIQYTSNYYKSTSVDFAVNTEG<br>VYSEPRPIGTRYLTRNL |
| AAV-10A3 SEQ ID NO: 2 | >10A3_KP3<br>MAADGYLPDWLEDTLSEGIRQWWKLKPGPPPPKPAERHKDDSRGLVLPGYKYLGPFNGLD<br>KGEPVNEADAAALEHDKAYDQQLKAGDNPYLRYNHADAEFQERLQEDTSFGGNLGRAVFQ<br>AKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGNASGNWHCDSTWLGDRV<br>ITTSTRTWALPTYNNHLYKQISSASTGASNDNHYFGYSTPWGYFDFNRFHCHFSPRDWQR<br>LINNNWGFRPKRLNFKLFNIQVKEVTQNEGTKTIANNLTSTIQVFTDSEYQLPYVLGSAH<br>QGCLPPFPADVFMIPQYGYLTLNNGSQAVGRSSFYCLEYFPSQMLRTGNNFQFSYTFEDV<br>PFHSSYAHSQSLDRLMNPLIDQYLYYLNRTQGTTSGTTNQSRLLFSQAGPQSMSLQARNW<br>LPGPCYRQQRLSKTANDNNNSNFPWTAASKYHLNGRDSLVNPGPAMASHKDDEEKFFPMH<br>GNLIFGKEGTTASNAELDNVMITDEEEIRTTNPVATEQYGTVANNLQSSNTAPTTRTVND<br>QGALPGMVWQDRDVYLQGPIWAKIPHTDGNFHPSPLMGGFGLKHPPPQILIKNTPVPADP<br>PTTFNQSKLNSFITQYSTGQVSVEIEWELQKENSKRWNPEIQYTSNYYKSTSVDFAVNTE<br>GVYSEPRPIGTRYLTRNL |
| AAV-10A4 SEQ ID NO: 3 | >10A4<br>MAADGYLPDWLEDNLSEGIREWWDLKPGAPKPKANQQKQDDGRGLVLPGYKYLGPFNGLD<br>KGEPVNAADAAALEHDKAYDQQLKAGDNPYLRYNHADAEFQERLQEDTSFGGNLGRAVFQ<br>AKKRLLEPLGLVEEAAKTAPGKKRPVEQSPQEPDSSSGIGKTGQQPAKKRLNFGQTGDTE<br>SVPDPQPLGEPPAAPTSLGSNTMASGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKKLSFKLFNIQVKEVTQNDGTTTIANNLTSTIQVFTDSEYQLPYVLGSAHQ<br>GCLPPFPADVFMIPQYGYLTLNNGSQAVGRSSFYCLEYFPSQMLRTGNNFTFSYTFEEVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10A5 SEQ ID NO: 4 | >10A5<br>MAADGYLPDWLEDNLSEGIREWWDLKPGAPKPKANQQKQDDARGLVLPGYKYLGPGNGLD<br>KGEPVNAADAAALEHDKAYDQQLQAGDNPYLRYNHADAEFQERLQEDTSFGGNLGRAVFQ<br>AKKRVLEPLGLVEEAAKTAPGKKRPVEQSPQEPDSSSGIGKTGQQPAKKRLNFGQTGDSE<br>SVPDPQPLGEPPAAPTSLGSNTMASGGGAPMADNNEGADGVGNSSGNWHCDSQWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQILIKNTPVPANPP<br>AEFSATKFASFITQYSTGQVSVEIEWELQKENSKRWNPEIQYTSNYNKSVNVDFTVDTNG<br>VYSEPRPIGTRYLTRPL |
| AAV-18A1 SEQ ID NO: 5 | >18A1_KP2<br>MAADGYLPDWLEDNLSEGIREWWDLKPGAPKPKANQQKQDDGRGLVLPGYKYLGPFNGLD<br>KGEPVNAADAAALEHDKAYDQQLKAGDNPYLRYNHADAEFQERLQEDTSFGGNLGRAVFQ<br>AKKRVLEPLGLVEEGAKTAPGKKRPVEHSPVEPDSSSGIGKTGQQPAKKRLNFGQTGDAD<br>SVPDPQPLGQPPAAPSGLGTNTMATGSGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTQNEGTTTIANNLTSTVQVFTDSEYQLPYVLGSAHQ |

TABLE 2-continued

Variant AAV Capsid Amino Acid Sequences

| Description SEQ ID NO: | Amino Acid Sequence |
|---|---|
| | GCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10B1<br>SEQ ID<br>NO: 6 | >10B1<br>MAADGYLPDWLEDNLSEGIRQWWKLKPGPPPPKPAERHKDDSRGLVLPGYKYLGPFNGLD<br>KGEPVNAADAAALEHDKAYDQQLKAGDNPYLRYNHADAEFQERLKEDTSFGGNLGRAVFQ<br>AKKRVLEPLGLVEEGAKTAPGKKRPVEHSPVEPDSSSGIGKTGQQPAKKRLNFGQTGDSE<br>SVPDPQPLGEPPAAPSGLGTNTMASGGGAPMADNNEGADGVGNSSGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFTYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10B3<br>SEQ ID<br>NO: 7 | >10B3<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLQEDTSFGGNLGRAVFQ<br>AKKRLLEPLGLVEEAAKTAPGKKRPVEHSPVEPDSSSGTGKAGQQPAKKRLNFGQTGDSE<br>SVPDPQPLGEPPAAPSGVGPNTMAAGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLSFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10B5<br>SEQ ID<br>NO: 8 | >10B5<br>MAADGYLPDWLEDNLSEGIREWWALQPGAPKPKANQQKQDDGRGLVLPGYKYLGPFNGLD<br>KGEPVNAADAAALEHDKAYDQQLKAGDNPYLRYNHADAEFQERLQEDTSFGGNLGRAVFQ<br>AKKRVLEPLGLVEEGAKTAPGKKRPVEQSPQEPDSSSGIGKTGQQPAKKRLNFGQTGDSE<br>SVPDPQPIGEPPAGPSGLGTGTMASGSGAPMADNNEGADGVGNSSGNWHCDSQWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTIQVFTDSEYQLPYVLGSAHQ<br>GCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10B6<br>SEQ ID<br>NO: 9 | >10B6<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLKEDTSFGGNLGRAVFQ<br>AKKRVLEPFGLVEEAAKTAPGKKRPVDQSPQEPDSSSGVGKSGKQPARKRLNFGQTGDSE<br>SVPDPQPLGEPPAAPTSLGSNTMASGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKKLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGMKHPPPQILIKNTPVPADPP<br>TAFNKDKLNSFITQYSTGQVSVEIEWELQKENSKRWNPEIQYTSNYYKSTSVDFAVNTEG<br>VYSEPRPIGTRYLTRNL |
| AAV-10B7<br>SEQ ID<br>NO: 10 | >10B7<br>MAADGYLPDWLEDTLSEGIRQWWKLKPGPPPPKPAERHKDDSRGLVLPGYKYLGPFNGLD<br>KGEPVNEADAAALEHDKAYDQQLKAGDNPYLKYNHADAEFQERLKEDTSFGGNLGRAVFQ<br>AKKRVLEPLGLVEEAAKTAPGKKRPVEHSPVEPDSSSGTGKAGQQPARKRLNFGQTGDAD<br>SVPDPQPLGEPPAAPTSLGSNTMASGGGAPMADNNEGADGVGSSSGNWHCDSTWLGDRVI<br>TTSTRTWALPTYNNHLYKQISSASTGASNDNHYFGYSTPWGYFDFNRFHCHFSPRDWQRL |

TABLE 2-continued

Variant AAV Capsid Amino Acid Sequences

| Description SEQ ID NO: | Amino Acid Sequence |
|---|---|
| | INNNWGFRPKRLNFKLFNIQVKEVTQNEGTKTIANNLTSTIQVFTDSEYQLPYVLGSAHQ<br>GCLPPFPADVFMIPQYGYLTLNNGSQAMGRSSFYCLEYFPSQMLRTGNNFTFSYTFEDVP<br>FHSSYAHSQSLDRLMNPLIDQYLYYLSRTQSTGGTAGTQQLLFSQAGPNNMSAQARNWLP<br>GPCYRQQRLSKTANDNNNSNFPWTAASKYHLNGRDSLVNPGPAMASHKDDEEKFFPMHGN<br>LIFGKEGTTASNAELDNVMITDEEEIRTTNPVATEQYGTVANNLQSSNTAPTTRTVNDQG<br>ALPGMVWQDRDVYLQGPIWAKIPHTDGHFHPSPLMGGFGLKHPPPQILIKNTPVPADPPT<br>TFNQSKLNSFITQYSTGQVSVEIEWELQKENSKRWNPEIQYTSNYNKSVNVDFTVDTNGV<br>YSEPRPIGTRYLTRNL |
| AAV-18B1<br>SEQ ID<br>NO: 11 | >18B1<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLQEDTSFGGNLGRAVFQ<br>AKKRLLEPLGLVEEAAKTAPGKKRPVEHSPVEPDSSSGTGKAGQQPARKRLNFGQTGDAD<br>SVPDPQPLGEPPAAPTSLGSNTMATGSGAPMADNNEGADGVGNSSGNWHCDSQWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQILIKNTPVPANPP<br>TTFNQSKLNSFITQYSTGQVSVEIEWELQKENSKRWNPEIQYTSNYYKSTSVDFAVNTEG<br>VYSEPRPIGTRYLTRNL |
| AAV-18B2<br>SEQ ID<br>NO: 12 | >18B2<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLQEDTSFGGNLGRAVFQ<br>AKKRVLEPFGLVEEGAKTAPGKKRPVEHSPVEPDSSSGTGKAGQQPARKRLNFGQTGDSE<br>SVPDPQPLGEPPAAPSGVGPNTMASGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTQNDGTTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYYKSTSVDFAVNTEG<br>VYSEPRPIGTRYLTRNL |
| AAV-18B3<br>SEQ ID<br>NO: 13 | >18B3<br>MAADGYLPDWLEDNLSEGIREWWDLKPGAPKPKANQQKQDDGRGLVLPGYKYLGPFNGLD<br>KGEPVNAADAAALEHDKAYDQQLQAGDNPYLRYNHADAEFQERLQEDTSFGGNLGRAVFQ<br>AKKRLLEPLGLVEEAAKTAPGKKRPVEHSPVEPDSSSGTGKAGQQPARKRLNFGQTGDAD<br>SVPDPQPIGEPPAAPSGVGSLTMAAGGGAPMADNNEGADGVGNSSGNWHCDSTWMGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |

TABLE 3

Variant AAV Capsid Nucleic Acid Sequences

| Description SEQ ID NO: | Nucleic Acid Sequence |
|---|---|
| AAV-10A1<br>SEQ ID<br>NO: 14 | >10A1_KP1<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCGGGTTACAAATACCTCGGACCCGGCAACGGACTCGACAAGGGGGAGCCCGTCAACGCGGCGGACGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAACCTGTTAAGACGGCTCCG<br>GGAAAAAAGAGGCCGGTAGAGCACTCTCCTGTGGAGCCAGACTCCTCCTCGGGAACCGGAAAGGCGGGCC<br>AGCAGCCTGCGAGGAAGCGACTCAACTTTGGTCAGACTGGAGACACCGACTCCGCCGCTGACCCCCAGCC |

TABLE 3-continued

Variant AAV Capsid Nucleic Acid Sequences

| Description SEQ ID NO: | Nucleic Acid Sequence |
|---|---|
| | TCTCGGAGAACCACCAGCAGCCCCCTCTGGTCTGGGAACTGGTACAATGGCTGCAGGCGGTGGCGCTCCA<br>ATGGCAGACAATAACGAAGGCGCCGACGGAGTGGGTAATGCCTCGGGAAATTGGCATTGCGATTCCACAT<br>GGCTGGGCGACAGAGTCATCACCACCAGCACCCGCACCTGGGCCTTGCCCACCTACAATAACCACCTCTA<br>CAAGCAAATC<br>TCCAGTGCTTCAACGGGGGCCAGCAACGACAACCACTACTTCGGCTACAGCACCCCCTGGGGGTACTTTG<br>ACTTCAACCGCTTCCACTGCCACTTCTCACCACGTGACTGGCAAAGACTCATCAACAACAACTGGGGATT<br>CCGGCCCAAGAGACTCAACTTCAAGCTCTTCAACATCCAGGTCAAGGAGGTCACGCAGAATGAAGGCACC<br>AAGACCATCGCCAATAACCTTACCAGCACGGTTCAGGTGTTTACTGACTCGGAGTACCAGCTGCCGTACG<br>TTCTCGGCTCTGCCCACCAGGGCTGCCTGCCTCCGTTCCCGGCGGACGTGTTCATGATTCCGCAGTACGG<br>CTACCTAACGCTCAACAATGGCAGCCAGGCGATGGGTCGCTCGTCCTTCTACTGCCTGGAGTACTTTCCG<br>TCGCAGATGCTGAGAACCGGCAACAACTTCCAGTTTACTTACACCTTCGAGGACGTGCCTTTCCACAGCA<br>GCTACGCTCACAGCCAGAGTTTGGATCGCTTGATGAATCCTCTTATTGATCAGTATCTGTACTACCTGAA<br>CAGAACGCAAGGAACAACCTCTGGAACAACCAACCAATCACGGCTGCTTTTTAGCCAGGCTGGGCCTCAG<br>TCTATGTCTTTGCAGGCCAGAAATTGGCTACCTGGGCCCTGCTACCGGCAACAGAGACTTTCAAAGACTG<br>CTAACGACAACAACAACAGTAACTTTCCTTGGACAGCGGCCAGCAAATATCATCTCAATGGCCGCGACTC<br>GCTGGTGAAT<br>CCAGGACCAGCTATGGCCAGTCACAAGGACGATGAAGAAAAATTTTTCCCTATGCACGGCAATCTAATAT<br>TTGGCAAAGAAGGGACAACGGCAAGTAACGCAGAATTAGATAATGTAATGATTACGGATGAAGAAGAGAT<br>TCGTACCACCAATCCTGTGGCAACAGAGCAGTATGGAACTGTGGCAAATAACTTGCAGAGCTCAAATACA<br>GCTCCCACGACTAGAACTGTCAATGATCAGGGGGCCTTACCTGGCATGGTGTGGCAAGATCGTGACGTGT<br>ACCTTCAAGGACCTATCTGGGCAAAGATTCCTCACACGGATGGACACTTTCATCCTTCTCCTCTGATGGG<br>CGGCTTTGGCCTGAAACATCCTCCGCCTCAGATCCTGATCAAGAACACGCCTGTACCTGCGGATCCTCCA<br>ACGGCCTTCAACAAGGACAAGCTGAACTCTTTCATCACCCAGTATTCTACTGGCCAAGTCAGCGTGGAGA<br>TCGAGTGGGAGCTGCAGAAGGAAAACAGCAAGCGCTGGAACCCCGAGATCCAGTACACCTCCAACTACTA<br>CAAATCTACAAGTGTGGACTTTGCTGTTAATACAGAAGGCGTGTACTCTGAACCCCGCCCCATTGGCACC<br>CGTTACCTCACCCGTAATCTGTAA |
| AAV-10A3<br>SEQ ID<br>NO: 15 | >10A3_KP3<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAAGGAGAGCCGGTCAACGAGGCGGATGCA<br>GCGGCCCTCGAGCACGACAAGGCCTACGACCAGCAGCTCAAAGCGGGTGACAATCCGTACCTTCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAGAGACCGGTAGAGCCATCACCCCAGCGTTCTCCAGACTCCTCTACGGGCATCGGCAAGAAAG<br>GCCAACAGCCCGCCAGAAAAAGACTCAATTTTGGTCAGACTGGCGACTCAGAGTCAGTTCCAGACCCTCA<br>ACCTCTCGGAGAACCTCCAGCAGCGCCCTCTGGTGTGGGACCTAATACAATGGCTGCAGGCGGTGGCGCA<br>CCAATGGCAGACAATAACGAAGGCGCCGACGGAGTGGGTAATGCCTCAGGAAATTGGCATTGCGATTCCA<br>CATGGCTGGGCGACAGAGTCATCACCACCAGCACCCGCACCTGGGCCTTGCCCACCTACAATAACCACCT<br>CTACAAGCAA<br>ATCTCCAGTGCTTCAACGGGGGCCAGCAACGACAACCACTACTTCGGCTACAGCACCCCTTGGGGGTATT<br>TTGACTTCAACAGATTCCACTGCCACTTTTCACCACGTGACTGGCAAAGACTCATCAACAACAACTGGGG<br>ATTCCGACCCAAGAGACTCAACTTCAAGCTCTTTAACATTCAAGTCAAAGAGGTCACGCAGAATGAAGGC<br>ACCAAGACCATCGCCAATAACCTCACCAGCACCATCCAGGTGTTTACGGACTCGGAGTACCAGCTGCCGT<br>ACGTTCTCGGCTCTGCCCACCAGGGCTGCCTGCCTCCGTTCCCGGCGGACGTGTTCATGATTCCCCAGTA<br>CGGCTACCTAACACTCAACAACGGTAGTCAGGCCGTGGGACGCTCCTCCTTTTACTGCCTGGAGTACTTC<br>CCTTCGCAGATGCTAAGGACTGGAAATAACTTCCAATTCAGCTATACCTTCGAGGATGTACCTTTTCACA<br>GCAGCTACGCTCACAGCCAGAGTTTGGATCGCTTGATGAATCCTCTTATTGATCAGTATCTGTACTACCT<br>GAACAGAACGCAAGGAACAACCTCTGGAACAACCAACCAATCACGGCTGCTTTTTAGCCAGGCTGGGCCT<br>CAGTCTATGTCTTTGCAGGCCAGAAATTGGCTACCTGGGCCCTGCTACCGGCAACAGAGACTTTCAAAGA<br>CTGCTAACGACAACAACAACAGTAACTTTCCTTGGACAGCGGCCAGCAAATATCATCTCAATGGCCGCGA<br>CTCGCTGGTG<br>AATCCAGGACCAGCTATGGCCAGTCACAAGGACGATGAAGAAAAATTTTTCCCTATGCACGGCAATCTAA<br>TATTTGGCAAAGAAGGGACAACGGCAAGTAACGCAGAATTAGATAATGTAATGATTACGGATGAAGAAGA<br>GATTCGTACCACCAATCCTGTGGCAACAGAGCAGTATGGAACTGTGGCAAATAACTTGCAGAGCTCAAAT<br>ACAGCTCCCACGACTAGAACTGTCAATGATCAGGGGGCCTTACCTGGCATGGTGTGGCAAGATAGAGACG<br>TGTACCTGCAGGGTCCTATCTGGGCCAAGATTCCTCACACGGACGGAAACTTTCATCCCTCGCCGCTGAT<br>GGGAGGCTTTGGACTGAAACACCCGCCTCCTCAGATCCTGATCAAGAACACGCCTGTACCTGCGGATCCT<br>CCGACCACCTTCAACCAGTCAAAGCTGAACTCTTTCATCACGCAATACAGCACCGGACAGGTCAGCGTGG<br>AAATTGAATGGGAGCTGCAGAAGGAAAACAGCAAGCGCTGGAACCCCGAGATCCAGTACACCTCCAACTA<br>CTACAAATCTACAAGTGTGGACTTTGCTGTTAATACAGAAGGCGTGTACTCTGAACCCCGCCCCATTGGC<br>ACCCGTTACCTCACCCGTAATCTGTAA |
| AAV-10A4<br>SEQ ID<br>NO: 16 | >10A4<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAACGTCCGGTAGAGCAGTCGCCACAAGAGCCAGACTCCTCCTCGGGCATCGGCAAGACAGGCC<br>AGCAGCCCGCTAAAAAGAGACTCAATTTCGGTCAGACTGGCGACACAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAAGGCGCCGACGGAGTGGGTAATGCCTCAGGAAATTGGCATTGCGATTCCACAT |

TABLE 3-continued

Variant AAV Capsid Nucleic Acid Sequences

| Description SEQ ID NO: | Nucleic Acid Sequence |
|---|---|
| | GGCTGGGCGACAGAGTCATCACCACCAGCACCCGCACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCATTTCTCACCACGTGACTGGCAGCGACTCATCAACAACA<br>ATTGGGGATTCCGGCCCAAGAAACTCAGCTTCAAGCTCTTCAACATCCAAGTTAAAGAGGTCACGCAGAA<br>CGATGGCACGACGACTATTGCCAATAACCTTACCAGCACGATTCAGGTCTTTACGGACTCGGAGTACCAG<br>CTGCCGTACGTTCTCGGCTCTGCCCACCAGGGCTGCCTCCCTCCGTTCCCGGCGGACGTGTTCATGATTC<br>CGCAGTACGGCTACCTAACGCTCAACAATGGCAGCCAAGCCGTGGGACGTTCATCCTTTTACTGCCTGGA<br>GTACTTTCCTTCTCAAATGCTGAGAACGGGCAACAACTTTACCTTCAGCTACACCTTTGAGGAAGTGCCT<br>TTCCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCCAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACGCAGTACAGCAC<br>CGGACAGGTCAGCGTGGAAATTGAATGGGAGCTGCAGAAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTTACCCGTCCCCTGTAA |
| AAV-10A5 SEQ ID NO: 17 | >10A5<br>ATGGCTGCCGATGGTTATCTTCCAGATTGGCTCGAGGACAACCTTTCTGAAGGCATTCGCGAGTGGTGGG<br>ACTTGAAACCTGGAGCCCCGAAACCCAAAGCCAACCAGCAAAAGCAGGACGACGCTCGGGGTCTTGTGCT<br>TCCGGGTTACAAATACCTTGGACCCGGCAACGGACTCGACAAGGGGGAGCCCGTCAACGCGGCGGACGCA<br>GCGGCCCTCGAGCACGACAAAGCCTACGACCAGCAGCTGCAGGCGGGTGACAATCCGTACCTGCGGTACA<br>ACCACGCCGACGCGGAGTTTCAGGAGCGTCTGCAAGAAGATACGTCTTTTGGGGGCAACCTCGGGCGAGC<br>AGTCTTCCAGGCCAAGAAGAGGGTTCTCGAACCTCTCGGTCTGGTTGAGGAAGCGGCTAAGACGGCTCCT<br>GGAAAGAAACGTCCGGTAGAGCAGTCGCCACAAGAGCCAGACTCCTCCTCGGGCATCGGCAAGACAGGCC<br>AGCAGCCCGCTAAAAAGAGACTCAATTTTGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGACGGAGTGGGTAATTCCTCGGGAAATTGGCATTGCGATTCCCAAT<br>GGCTGGGCGACCGAGTCATCACCACCAGCACCCGCACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCACTTTTCACCACGTGACTGGCAAAGACTCATCAACAACA<br>ACTGGGGATTCCGACCCAAGAGACTCAACTTCAAACTCTTCAACATCCAAGTCAAGGAGGTCACGACGAA<br>TGATGGCGTCACGACCATCGCCAATAACCTTACCAGCACGGTTCAAGTGTTTACGGACTCGGAGTATCAG<br>CTCCCGTACGTGCTCGGGTCGGCGCACCAAGGCTGTCTCCCGCCGTTTCCAGCGGACGTCTTCATGGTCC<br>CTCAGTATGGATACCTCACCCTGAACAACGGAAGTCAAGCGGTGGGACGCTCATCCTTTTACTGCCTGGA<br>GTACTTCCCTTCGCAGATGCTAAGGACTGGAAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CACCCGTCTCCTCTCATGGGCGGCTTTGGACTTAAGCACCCGCCTCCTCAGATCCTCATCAAAAACACGC<br>CTGTTCCTGCGAATCCTCCGGCAGAGTTTTCGGCTACAAAGTTTGCTTCATTCATCACCCAGTATTCCAC<br>AGGACAAGTGAGCGTGGAAATTGAATGGGAGCTGCAGAAAGAAAACAGCAAACGCTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTCACCCGTCCCCTGTAA |
| AAV-18A1 SEQ ID NO: 18 | >18A1_KP2<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTTCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGTGCTAAGACGGCTCCT<br>GGAAAGAAACGTCCGGTAGAGCACTCTCCTGTGGAGCCAGACTCCTCCTCGGGCATCGGCAAGACAGGCC<br>AGCAGCCCGCTAAAAAGAGACTCAATTTTGGTCAGACTGGCGACGCAGACTCAGTACCTGACCCCCAGCC<br>TCTCGGACAGCCACCAGCAGCCCCCTCTGGTCTGGGAACTAATACGATGGCTACAGGCAGTGGCGCACCA<br>ATGGCAGACAATAACGAGGGCGCCGACGGAGTGGGTAATGCCTCAGGAAATTGGCATTGCGATTCCACAT<br>GGCTGGGCGACAGAGTCATCACCACCAGCACCCGAACATGGGCCTTGCCCACCTATAACAACCACCTCTA<br>CAAGCAAATCTCCAGTGCTTCAACGGGGGCCAGCAACGACAACCACTACTTCGGCTACAGCACCCCCTGG<br>GGGTACTTTGACTTCAACCGCTTCCACTGCCACTTCTCCCCGCGAGACTGGCAGCGGCTCATCAACAACA<br>ACTGGGGGTTCCGGCCCAAGCGACTCAACTTCAAGCTCTTCAACATCCAGGTCAAGGAGGTCACGCAGAA<br>TGAAGGCACGACGACTATTGCCAATAACCTTACCAGCACGGTTCAAGTGTTTACGGACTCGGAGTATCAG<br>CTCCCGTACGTGCTCGGCTCTGCCCACCAGGGCTGCCTGCCTCCGTTCCCGGCGGACGTGTTCATGATTC |

TABLE 3-continued

Variant AAV Capsid Nucleic Acid Sequences

| Description SEQ ID NO: | Nucleic Acid Sequence |
|---|---|
| | CCCAGTACGGCTACCTAACACTCAACAACGGTAGTCAGGCCGTGGGACGCTCCTCCTTCTACTGCCTGGA<br>ATACTTTCCTTCTCAGATGCTGCGTACCGGAAACAACTTTACCTTCAGCTACACTTTTGAGGACGTTCCT<br>TTCCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AGCCTCGCCCCATTGGCACCCGTTACCTCACCCGTCCCCTGTAA |
| AAV-10B1<br>SEQ ID<br>NO: 19 | >10B1<br>ATGGCTGCCGATGGTTATCTTCCAGATTGGCTCGAGGACAACCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAGAGGCCTGTAGAGCACTCTCCTGTGGAGCCAGACTCCTCCTCGGGCATCGGCAAGACAGGCC<br>AGCAGCCCGCTAAAAAGAGACTCAATTTTGGTCAGACTGGCGACTCAGAGTCAGTCCCCGACCCACAACC<br>TCTCGGAGAACCACCAGCAGCCCCCTCTGGTCTGGGAACTAATACGATGGCTTCAGGCGGTGGCGCACCA<br>ATGGCAGACAATAACGAGGGTGCCGATGGAGTGGGTAATTCCTCAGGAAATTGGCATTGCGATTCCACAT<br>GGCTGGGCGACAGAGTCATCACCACCAGCACCCGAACCTGGGCCCTGCCCACCTACAACAATCACCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCACTTTTCACCACGTGACTGGCAGCGACTCATCAACAACA<br>ATTGGGGATTCCGGCCCAAGAGACTCAACTTCAAGCTCTTCAACATCCAAGTCAAGGAGGTCACGACGAA<br>TGATGGCGTCACGACCATCGCCAATAACCTTACCAGCACGGTTCAAGTGTTTACGGACTCGGAGTACCAG<br>CTCCCGTACGTCCTCGGCTCGGCGCATCAAGGATGCCTCCCGCCGTTCCCAGCAGACGTCTTCATGGTGC<br>CGCAGTACGGGTACCTGACTCTGAACAATGGTAGTCAGGCCGTGGGACGCTCCTCCTTCTACTGCCTGGA<br>ATACTTTCCTTCGCAGATGCTGAGAACCGGCAACAACTTCCAGTTTACTTACACCTTCGAGGACGTGCCT<br>TTCCACAGCAGCTACGCCCACAGCCAGAGCTTGGACCGGCTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>GGGACAGGTCAGCGTGGAAATTGAGTGGGAGCTACAGAAAGAAAACAGCAAACGCTGGAATCCCGAAATT<br>CAGTACACTTCCAACTACAACAAGTCTGTTAATGTGGACTTTACTGTGGACACTAATGGTGTTTATAGTG<br>AACCTCGCCCCATTGGCACCCGTTACCTCACCCGTCCCCTGTAA |
| AAV-10B3<br>SEQ ID<br>NO: 20 | >10B3<br>ATGGCTGCTGACGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCG<br>GGAAAAAAGAGGCCGGTAGAGCACTCTCCTGTGGAGCCAGACTCCTCCTCGGGAACCGGAAAGGCGGGCC<br>AGCAGCCCGCTAAAAAGAGACTCAATTTTGGTCAGACTGGCGACTCAGAGTCAGTTCCAGACCCTCAACC<br>TCTCGGAGAACCTCCAGCAGCGCCCTCTGGTGTGGGACCTAATACAATGGCTGCAGGCGGTGGCGCACCA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGAACCTGGGCCCTGCCCACCTACAACAACCACCTCTA<br>CAAGCAAATCTCCAGTGCTTCAACGGGGGCCAGCAACGACAACCACTACTTTGGCTACAGCACCCCTTGG<br>GGGTATTTTGACTTTAACAGATTCCACTGCCACTTCTCACCACGTGACTGGCAGCGACTCATTAACAACA<br>ACTGGGGATTCCGGCCCAAGAGACTCAGCTTCAAGCTCTTCAACATCCAAGTCAAGGAGGTCACGACGAA<br>TGATGGCGTCACGACCATCGCCAATAACCTTACCAGCACGGTTCAAGTGTTTACGGACTCGGAGTATCAG<br>CTCCCGTACGTCCTCGGATCAGCGCACCAAGGCTGTCTCCCGCCGTTTCCAGCGGACGTCTTCATGGTCC<br>CTCAGTATGGATACCTCACCCTGAACAACGGGAGTCAGGCAGTAGGACGCTCTTCATTTTACTGCCTGGA<br>GTACTTCCCTTCGCAGATGCTAAGGACTGGAAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG |

TABLE 3-continued

Variant AAV Capsid Nucleic Acid Sequences

| Description SEQ ID NO: | Nucleic Acid Sequence |
|---|---|
| | GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAAGAAAACAGCAAACGTTGGAATCCAGAGATT<br>CAGTACACTTCCAACTACAACAAGTCTGTTAATGTGGACTTTACTGTGGACACTAATGGCGTGTATTCAG<br>AGCCTCGCCCCATTGGCACCCGTTACCTCACCCGTCCCCTGTAA |
| AAV-10B5 SEQ ID NO: 21 | >10B5<br>ATGGCTGCTGACGGTTATCTTCCAGATTGGCTCGAGGACAACCTTTCTGAAGGCATTCGAGAGTGGTGGG<br>CGCTGCAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTTCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAACGTCCGGTAGAGCAGTCGCCACAAGAGCCAGACTCCTCCTCGGGCATCGGCAAGACAGGCC<br>AGCAGCCCGCGAAAAAGAGACTCAACTTTGGGCAGACTGGCGACTCAGAGTCAGTGCCCGACCCTCAACC<br>AATCGGAGAACCCCCCGCAGGCCCCTCTGGTCTGGGAACTGGTACGATGGCTTCAGGCAGTGGCGCACCA<br>ATGGCAGACAATAACGAAGGCGCCGATGGAGTGGGTAATTCCTCAGGAAATTGGCATTGCGATTCCCAAT<br>GGCTGGGCGACAGAGTCATCACCACCAGCACCAGAACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGACTTTAACAGATTCCACTGCCACTTCTCACCACGTGACTGGCAGCGACTCATTAACAACA<br>ACTGGGGATTCCGGCCCAAGAGACTCAACTTCAAGCTCTTCAACATCCAAGTCAAGGAGGTCACGACGAA<br>TGATGGCGTCACGACCATTGCCAATAACCTCACCAGCACCATCCAGGTGTTTACGGACTCGGAGTACCAG<br>TTGCCGTACGTCCTCGGCTCTGCGCACCAGGGCTGCCTCCCTCCGTTCCCGGCGGACGTGTTCATGATTC<br>CGCAATACGGCTACCTGACGCTCAACAATGGCAGCCAGGCAGTGGGACGGTCATCCTTTTACTGCCTGGA<br>ATATTTCCCATCGCAGATGCTGAGAACGGGCAATAACTTTACCTTCAGCTACACCTTCGAGGACGTGCCT<br>TTCCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTTACCCGTCCCCTGTAA |
| AAV-10B6 SEQ ID NO: 22 | >10B6<br>ATGGCTGCTGACGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCGGAGTTTCAGGAGCGCCTTAAAGAAGATACGTCTTTTGGGGGCAACCTCGGACGAGC<br>AGTCTTCCAGGCCAAGAAGAGGGTTCTCGAACCTTTTGGTCTGGTTGAGGAAGCGGCTAAGACGGCTCCT<br>GGAAAGAAGAGGCCTGTAGATCAGTCTCCTCAGGAACCGGACTCATCATCTGGTGTTGGCAAATCGGGCA<br>AACAGCCTGCCAGAAAAAGACTAAATTTCGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGACGGAGTGGGTAATGCCTCAGGAAATTGGCATTGCGATTCCACAT<br>GGCTGGGCGACCGAGTCATCACCACCAGCACCCGCACCTGGGCCCTGCCCACCTACAACAACCATCTCTA<br>CAAGCAAATCTCCAGTGCTTCAACGGGGGCCAGCAACGACAACCACTACTTCGGCTACAGCACCCCCTGG<br>GGGTATTTTGACTTTAACAGATTCCACTGCCACTTTTCACCACGTGACTGGCAGCGACTCATCAACAACA<br>ACTGGGGATTCCGGCCCAAGAAACTCAGCTTCAAGCTCTTCAACATCCAGGTCAAGGAGGTCACGCAGAA<br>TGAAGGCACCAAGACCATCGCCAATAACCTCACCAGCACCATCCAGGTGTTTACGGACTCGGAGTACCAG<br>CTGCCGTACGTTCTCGGCTCTGCGCACCAGGGCTGCCTCCCTCCGTTCCCGGCGGACGTGTTCATGATTC<br>CGCAATACGGCTACCTGACGCTCAACAATGGCAGCCAAGCCGTGGGACGTTCATCCTTTTACTGCCTGGA<br>ATATTTCCCATCGCAGATGCTGAGAACCGGCAACAACTTCCAGTTTACTTACACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGGTTTGGAATGAAACACCCGCCTCCTCAGATCCTCATCAAAAACACAC |

TABLE 3-continued

Variant AAV Capsid Nucleic Acid Sequences

| Description SEQ ID NO: | Nucleic Acid Sequence |
|---|---|
| | CTGTACCTGCGGATCCTCCAACGGCCTTCAACAAGGACAAGCTGAACTCTTTCATCACCCAGTATTCTAC<br>TGGCCAAGTCAGCGTGGAAATTGAATGGGAGCTGCAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |
| AAV-10B7 SEQ ID NO: 23 | >10B7<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAGGCCTACGACCAGCAGCTCAAAGCGGGTGACAATCCGTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCGAAAAAGAGGGTTCTTGAACCTCTGGGCCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAAGGCGCCGACGGAGTGGGTAGTTCCTCAGGAAATTGGCATTGCGATTCCACAT<br>GGCTGGGCGACAGAGTCATCACCACCAGCACCCGCACCTGGGCCCTGCCCACTTACAACAACCATCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCATTTCTCACCACGTGACTGGCAGCGACTCATCAACAACA<br>ACTGGGGGTTCCGGCCCAAGCGACTCAACTTCAAGCTCTTCAACATCCAGGTCAAGGAGGTCACGCAGAA<br>TGAAGGCACCAAGACCATCGCCAATAACCTTACCAGCACGATTCAGGTCTTTACGGACTCGGAATACCAG<br>CTCCCGTACGTCCTCGGCTCTGCCCACCAGGGCTGCCTGCCTCCGTTCCCGGCGGACGTGTTCATGATTC<br>CCCAGTACGGCTACCTAACACTCAACAACGGTAGTCAGGCGATGGGTCGCTCGTCCTTCTACTGCCTGGA<br>GTACTTTCCGTCGCAGATGCTGCGGACGGGGAACAACTTCACGTTCAGCTACACCTTCGAGGACGTGCCC<br>TTCCACAGCAGCTACGCGCACAGCCAGAGTCTGGACCGGCTGATGAATCCTCTGATTGACCAGTACCTGT<br>ACTACTTGTCTCGGACTCAGTCCACGGGAGGTACCGCAGGAACTCAGCAGTTGCTATTTTCTCAGGCCGG<br>GCCTAATAACATGTCGGCTCAGGCCAGAAATTGGCTACCTGGGCCCTGCTACCGGCAACAGAGACTTTCA<br>AAGACTGCTAACGACAACAACAACAGTAACTTTCCTTGGACAGCGGCCAGCAAATATCATCTCAATGGCC<br>GCGACTCGCTGGTGAATCCAGGACCAGCTATGGCCAGTCACAAGGACGATGAAGAAAAATTTTTCCCTAT<br>GCACGGCAATCTAATATTTGGCAAAGAAGGGACAACGGCAAGTAACGCAGAATTAGATAATGTAATGATT<br>ACGGATGAAGAAGAGATTCGTACCACCAATCCTGTGGCAACAGAGCAGTATGGAACTGTGGCAAATAACT<br>TGCAGAGCTCAAATACAGCTCCCACGACTAGAACTGTCAATGATCAGGGGGCCTTACCTGGCATGGTGTG<br>GCAAGATCGTGACGTGTACCTTCAAGGACCTATCTGGGCAAAGATTCCTCACACGGATGGACACTTTCAT<br>CCCTCGCCGCTGATGGGAGGCTTTGGACTGAAACACCCGCCTCCTCAGATCCTCATCAAAAACACACCTG<br>TACCTGCGGATCCTCCGACCACCTTCAACCAGTCAAAGCTGAACTCTTTCATCACCCAGTACTCCACTGG<br>ACAGGTCAGCGTGGAGATCGAGTGGGAGCTGCAGAAGGAAAACAGCAAACGCTGGAATCCCGAAATTCAG<br>TACACTTCCAACTACAACAAGTCTGTTAATGTGGACTTTACTGTGGACACTAATGGCGTGTATTCAGAGC<br>CTCGCCCCATTGGCACCCGTTACCTCACCCGTAATCTGTAA |
| AAV-18B1 SEQ ID NO: 24 | >18B1<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>TCTCGGAGAACCACCAGCAGCCCCCACAAGTTTGGGATCTAATACAATGGCTACAGGCAGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCCGAACATGGGCCTTGCCCACCTATAACAACCACCTCTA<br>CAAGCAAATCTCCAGTGCTTCAACGGGGGCCAGCAACGACAACCACTACTTCGGCTACAGCACCCCCTGG<br>GGGTACTTTGACTTCAACCGCTTCCACTGCCACTTCTCCCCGCGAGACTGGCAGCGGCTCATCAACAACA<br>ACTGGGGGTTCCGGCCCAAGCGACTCAACTTCAAGCTCTTCAACATCCAAGTCAAGGAGGTCACGACGAA<br>TGATGGCGTCACGACCATCGCTAATAACCTTACCAGCACGGTTCAAGTGTTTACGGACTCGGAGTATCAG<br>CTCCCGTACGTCCTCGGCTCTGCGCACCAGGGCTGCCTCCCTCCGTTCCCGGCGGACGTCTTCATGGTCC<br>CTCAGTATGGATACCTCACCCTGAACAACGGAAGTCAAGCGGTGGGACGCTCATCCTTTTACTGCCTGGA<br>GTACTTCCCTTCGCAGATGCTAAGGACTGGAAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACACCCTCCTCCACAGATTCTCATCAAGAACACCC<br>CGGTACCTGCGAATCCTCCGACCACCTTCAACCAGTCAAAGCTGAACTCTTTCATCACCCAGTATTCTAC<br>TGGCCAAGTCAGCGTGGAGATCGAGTGGGAGCTGCAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |

TABLE 3-continued

Variant AAV Capsid Nucleic Acid Sequences

| Description SEQ ID NO: | Nucleic Acid Sequence |
|---|---|
| AAV-18B2 SEQ ID NO: 25 | >18B2<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGAGGGTTCTCGAACCTTTTGGTCTGGTTGAGGAAGGTGCTAAGACGGCTCCT<br>GGAAAGAAACGTCCGGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGCGACTCAGAGTCAGTTCCAGACCCTCAACC<br>TCTCGGAGAACCTCCAGCAGCGCCCTCTGGTGTGGGACCTAATACAATGGCTTCAGGCGGTGGCGCACCA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGCACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGACTTCAACAGATTCCACTGCCATTTCTCACCACGTGACTGGCAGCGACTCATCAACAACA<br>ATTGGGGATTCCGGCCCAAGAGACTCAACTTCAAGCTCTTCAACATCCAAGTCAAGGAGGTCACGCAGAA<br>TGACGGTACGACGACGATTGCCAATAACCTTACCAGCACGGTTCAAGTGTTTACGGACTCGGAGTATCAG<br>CTCCCGTACGTGCTCGGGTCGGCGCACCAAGGCTGTCTCCCGCCGTTTCCAGCGGACGTCTTCATGGTCC<br>CGCAGTACGGGTATTTGACGCTGAACAACGGAAGTCAAGCGGTGGGACGCTCATCCTTTTACTGCCTGGA<br>GTACTTCCCTTCGCAGATGCTAAGGACTGGAAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGCGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>GGGACAGGTCAGCGTGGAGATCGAGTGGGAGCTGCAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |
| AAV-18B3 SEQ ID NO: 26 | >18B3<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTGCAGGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>AATCGGAGAACCTCCCGCAGCCCCCTCAGGTGTGGGATCTCTTACAATGGCTGCAGGCGGTGGCGCACCA<br>ATGGCAGACAATAACGAGGGTGCCGACGGAGTGGGTAATTCCTCGGGAAATTGGCATTGCGATTCCACAT<br>GGATGGGCGACAGAGTCATCACCACCAGCACCCGAACCTGGGCCCTGCCCACCTATAACAACCACCTCTA<br>CAAGCAAATCTCCAGTGCTTCAACGGGGGCCAGCAACGACAACCACTACTTCGGCTACAGCACCCCCTGG<br>GGGTATTTTGATTTCAACCGCTTCCACTGCCACTTCTCACCACGTGACTGGCAGCGACTCATCAACAACA<br>ACTGGGGATTCCGGCCCAAGAGACTCAACTTCAAACTCTTCAACATCCAAGTCAAGGAGGTCACGACGAA<br>TGATGGCGTCACGACCATCGCTAATAACCTTACCAGCACGGTTCAAGTCTTCTCGGACTCGGAGTACCAG<br>TTGCCGTACGTCCTCGGCTCTGCGCACCAGGGCTGCCTCCCTCCGTTCCCGGCGGACGTGTTCATGATTC<br>CGCAGTACGGCTACCTAACACTCAACAACGGTAGTCAGGCCGTGGGACGCTCCTCCTTCTACTGCCTGGA<br>ATATTTCCCATCGCAGATGCTGAGAACGGGCAATAACTTTACCTTCAGCTACACCTTCGAGGACGTGCCT<br>TTCCACAGCAGCTACGCGCACAGCCAGAGCCTGGACCGGCTGATGAACCCCCTCATCGACCAGTACCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTTACCCGTCCCCTGTAA |

TABLE 4

Parent AAV Capsid Amino Acid Sequences

| Description SEQ ID NO: | Amino Acid Sequence |
|---|---|
| Avian AAV SEQ ID NO: 27 | >avian<br>MSLISDAIPDWLERLVKKGVNAAADFYHLESGPPRPKANQQTQESLEKDDSRGLVFPGYNYLGPFNGLDK<br>GEPVNEADAAALEHDKAYDLEIKDGHNPYFEYNEADRRFQERLKDDTSFGGNLGKAIFQAKKRVLEPFGL<br>VEDSKTAPTGDKRKGEDEPRLPDTPPQTPKKNKKPRKERPSGGAEDPGEGTSSNAGAAAPASSVGSSIMA<br>EGGGGPVGDAGQGADGVGNSSGNWHCDSQWLENGVVTRTTRTWVLPSYNNHLYKRIQGPSGGDNNNKFFG<br>FSTPWGYFDYNRFHCHFSPRDWQRLINNNWGIRPKAMRFRLFNIQVKEVTVQDSNTTIANNLTSTVQVFA<br>DKDYQLPYVLGSATEGTFPPFPADIYTIPQYGYCTLNYNNEAVDRSAFYCLDYFPSDMLRTGNNFEFTYT<br>FEDVPFHSMFAHNQTLDRLMNPLVDQYLWAFSSVSQAGSSGRALHYSRATKTNMAAQYRNWLPGPFFRDQ<br>QIFTGASNITKNNVFSVWEKGKQWELDNRTNLMQPGPAAATTFSGEPDRQAMQNTLAFSRTVYDQTTATT<br>DRNQILITNEDEIRPTNSVGIDAWGAVPTNNQSIVTPGTRAAVNNQGALPGMVWQNRDIYLQGPIWAKIP<br>DTDNHFHPSPLIGGFGCKHPPPQIFIKNTPVPANPSETFQTAKVASFINQYSTGQCTVEIFWELKKETSK<br>RWNPEIQFTSNFGNAADIQFAVSDTGSYSEPRPIGTRYLTKPL |
| Procine 1 AAV SEQ ID NO: 28 | >porcine_1<br>MSFVDHPPDWLEEIGEGLKEFLGLEPGPPKPKPNQQKQDDARGLVLPGYNYLGPGNGLDRGEPVNRADEV<br>AREHDISYNEQLQAGDNPYLKYNHADAEFQEKLADDTSFGGNLGKAVFQAKKRVLEPFGLVEEPVKTAAK<br>GERIDDHYPKKKKARIEETEAGTSGAQQLQIPAQPASSLGADTMSAGGGSPLGDNNQGADGVGNASGDWH<br>CDSTWMGDRVITKSTRTWVLPSYNNHQYLEIHSGSVDGSNANAYFGYSTPWGYFDENREHSHWSPRDWQR<br>LVNNYWGFRPRSLKVKIFNIQVKEVTTQDGTTTIANNLTSTVQVFTDNDYQLPYVIGNGTEGCLPAFPPQ<br>VETLPQYGYATLNRNNTDDPTERSSFFCLEYFPSKMLRTGNNFEFTYSFEEVPFHCSFAPSQNLFKLANP<br>LVDQYLYRFVSTDTSGNLQFQKNLKARYANTYKNWFPGPMCRTQGWYTSAGTYNNKGVANFDTSNKMELE<br>GASYQVNPQPNGMTNTLQDSNKYALENTMIFNAQNAPPGTTSLYQENNLLITSESETQPVNRLAYNTGGQ<br>VSNNNQNSNTHPTVGVYNHQEVLPGSVWMDRDVYLQGPIWAKIPETGAHFHPSPAMGGFGLKHPPPMMLI<br>KNTPVPSNVAAFSDVPVKSFITQYSTGQVTVEIEWELKKENSKRWNPEIQYTNNYNNPTFVDFAPDTSGE<br>YRTTRAIGTRYLTRPL |
| AAV5 SEQ ID NO: 29 | >AAV5<br>MSFVDHPPDWLEEVGEGLREFLGLEAGPPKPKPNQQHQDQARGLVLPGYNYLGPGNGLDRGEPVNRADEV<br>AREHDISYNEQLEAGDNPYLKYNHADAEFQEKLADDTSFGGNLGKAVFQAKKRVLEPFGLVEEGAKTAPT<br>GKRIDDHFPKRKKARTEEDSKPSTSSDAEAGPSGSQQLQIPAQPASSLGADTMSAGGGGPLGDNNQGADG<br>VGNASGDWHCDSTWMGDRVVTKSTRTWVLPSYNNHQYREIKSGSVDGSNANAYFGYSTPWGYFDENREHS<br>HWSPRDWQRLINNYWGFRPRSLRVKIFNIQVKEVTVQDSTTTIANNLTSTVQVFTDDDYQLPYVVGNGTE<br>GCLPAFPPQVFTLPQYGYATLNRDNTENPTERSSFFCLEYFPSKMLRTGNNFEFTYNFEEVPFHSSFAPS<br>QNLFKLANPLVDQYLYRFVSTNNTGGVQFNKNLAGRYANTYKNWFPGPMGRTQGWNLGSGVNRASVSAFA<br>TTNRMELEGASYQVPPQPNGMTNNLQGSNTYALENTMIFNSQPANPGTTATYLEGNMLITSESETQPVNR<br>VAYNVGGQMATNNQSSTTAPATGTYNLQEIVPGSVWMERDVYLQGPIWAKIPETGAHFHPSPAMGGFGLK<br>HPPPMMLIKNTPVPGNITSFSDVPVSSFITQYSTGQVTVEMEWELKKENSKRWNPEIQYTNNYNDPQFVD<br>FAPDSTGEYRTTRPIGTRYLTRPL |
| Goat 1 AAV SEQ ID NO: 30 | >goat_1<br>MSFVDHPPDWLEEVGEGLREFLGLEAGPPKPKPNQQHQDQARGLVLPGYNYLGPGNGLDRGEPVNRADEV<br>AREHDISYNEQLEAGDNPYLKYNHADAEFQEKLADDTSFGGNLGKAVFQAKKRVLEPFGLVEEGAKTAPT<br>GKRIDDHFPKRKKARTEEDSKPSTSSDAEAGPSGSQQLQIPAQPASSLGADTMSAGGGGPLGDNNQGADG<br>VGNASGDWHCDSTWMGDRVVTKSTRTWVLPSYNNHQYREIKSGSVDGSNANAYFGYSTPWGYFDFNRFHS<br>HWSPRDWQRLINNYWGFRPRSLRVKIFNIQVKEVTVQDSTTTIANNLTSTVQVFTDDDYQLPYVVGNGTE<br>GCLPAFPPQVFTLPQYGYATLNRDNGDNPTERSSFFCLEYFPSKMLRTGNNFEFTYSFEEVPFHCSFAPS<br>QNLFKLANPLVDQYLYRFVSTSATGAIQFQKNLAGRYANTYKNWFPGPMGRTQGWNTSSGSSTNRVSVNN<br>FSVSNRMNLEGASYQVNPQPNGMTNTLQGSNRYALENTMIFNAQNATPGTTSVYPEDNLLLTSESETQPV<br>NRVAYNTGGQMATNAQNATTAPTVGTYNLQEVLPGSVWMERDVYLQGPIWAKIPETGAHFHPSPAMGGFG<br>LKHPPPMMLIKNTPVPGNITSFSDVPVSSFITQYSTGQVTVEMEWELKKENSKRWNPEIQYTNNYNDPQF<br>VDFAPDGSGEYRTTRAIGTRYLTRPL |
| Mouse 1 AAV SEQ ID NO: 31 | >mouse_1<br>MSFFDWLGKQYAQGAAEFWDLKSGPPAPKKARKDGSAGFNFPGHKYLGPGNSLDRGDPVDADDAAAQKHD<br>QSYQEQLEAGDNPYLKYNHADREFQEALKDDTSFEGNLARGLFEAKKLVAEPLGLVEPELAPPSGRKRPV<br>QSSQESGYSSSQDKRPNLDVDEEDREFAAAAAETETGSAPPTGNLGPGTMAGGGSAPIDDGSYGADGVGN<br>ASGDWHCDSTWLDNCVITRTTRTWNLPTYNNHIYKRLNGTTSGDQSYFGFSTPWGYFDFNRFHCHFSPRD<br>WQRLINNNWGLRPKSLRFKIFNIQVKEVTTQDSTKIISNNLTSTVQVFADTEYQLPYVIGSAHEGCLPPF<br>PADVFMLPQYGYCTRQDGNSNNPTPRSAFYCLEYFPSKMLRTGNSFEFTYNFEKVPFHSMWAHNQSLDRL<br>MNPLIDQYLYYLDVTSSTGFTYQKGVHTNLPEQERNWLPGPGIRNQAWFNSATGNNPLTGTWQYSNKYVL<br>ENRASKIAPGPAMGIESTKFDGNGIIFSKEYITNVNTANPNQVNITRETEINSTNPLAGGSLGAHANNSQ<br>NTTTAPTLDHTNVMGVFPGSVWQDRDIYLQGQIWAKIPHTDGHFHPSPLMGGFGLKNPPPQILIKNTPVP<br>ADPPTEFNANKISSFITQYSTGQVTVEMEWELQKETSKRWNPEIQYSDDSSSTSGSILHFAPDDVGNYKE<br>FRSIGTRYLTRPL |
| Procine 2 AAV SEQ ID NO: 32 | >porcine_2<br>MSFVDHPPDWLEEVGEGLHEFLELEAGPPKPKPNQQKQDNARGLVLPGYNYLGPFNGLDKGEPVNRADAV<br>AREHDISYNEQLQAGDNPYLKYNHADAEFQEKLKDDTSFGGNLGKAIFQAKKRVLEPFGLVEAPVKTAPA<br>KKRPIEKSPAEPSSSKGIGKAGQQPARKRLNFGQTGDTDSAADPQPLGEPPAAPSGLGTGTMASGSGAPM<br>ADNNEGADGVGNASGNWHCDSTWLGDRVITTSTRTWALPTYNNHLYKQISSQSGANNDNHYFGYSTPWGY<br>FDFNRFHCHFSPRDWQRLINNNWGFRPKRLNFKLFNIQVKEVTQTDGTKTIANNLTSTVQVFADSEYQLP<br>YVLGSAHQGCFPPFPADVFMVPQYGYLTLNNGSQAMGRSSFYCLEYFPSQMLRTGNNFTFSYTFEDVPFH<br>SSYAHSQSLDRLMNPLIDQYLYYLSKTNGGLGFSQAGPNSMRDQSRNWLPGPCFRQQRISTVPTQNNNGD<br>FSWTGATKYHLNGRNSAMNPGPAMASHKDDEHRFFPQNGVLIFGKQGADKTNAILEKVIVTDEEEIRTTN |

TABLE 4-continued

Parent AAV Capsid Amino Acid Sequences

| Description SEQ ID NO: | Amino Acid Sequence |
|---|---|
| | PVATEEYGFVATNLQSSAETAETERVNAQGILPGMVWQDRDVYLQGPIWAKIPHTDGHFRPSPLMGGFGL<br>KHPPPQILIKNTPVPSNPPETFNPEKLNSFITQYSTGQVSVEIEWELQKENSKRWNPEVQYTSNYNKSVN<br>VEFTVDNNGVYSEPRTIGTRYLTRNL |
| AAV9hu14<br>SEQ ID<br>NO: 33 | >AAV9hu14<br>MAADGYLPDWLEDNLSEGIREWWALKPGAPQPKANQQHQDNARGLVLPGYKYLGPGNGLDKGEPVNAADA<br>AALEHDKAYDQQLKAGDNPYLKYNHADAEFQERLKEDTSFGGNLGRAVFQAKKRLLEPLGLVEEAAKTAP<br>GKKRPVEQSPQEPDSSAGIGKSGAQPAKKRLNFGQTGDTESVPDPQPIGEPPAAPSGVGSLTMASGGGAP<br>VADNNEGADGVGSSSGNWHCDSQWLGDRVITTSTRTWALPTYNNHLYKQISNSTSGGSSNDNAYFGYSTP<br>WGYFDFNRFHCHFSPRDWQRLINNNWGFRPKRLNFKLFNIQVKEVTDNNGVKTIANNLTSTVQVFTDSDY<br>QLPYVLGSAHEGCLPPFPADVFMIPQYGYLTLNDGSQAVGRSSFYCLEYFPSQMLRTGNNFQFSYEFENV<br>PFHSSYAHSQSLDRLMNPLIDQYLYYLSKTINGSGQNQQTLKFSVAGPSNMAVQGRNYIPGPSYRQQRVS<br>TTVTQNNNSEFAWPGASSWALNGRNSLMNPGPAMASHKEGEDRFFPLSGSLIFGKQGTGRDNVDADKVMI<br>TNEEEIKTTNPVATESYGQVATNHQSAQAQAQTGWVQNQGILPGMVWQDRDVYLQGPIWAKIPHTDGNFH<br>PSPLMGGFGMKHPPPQILIKNTPVPADPPTAFNKDKLNSFITQYSTGQVSVEIEWELQKENSKRWNPEIQ<br>YTSNYYKSNNVEFAVNTEGVYSEPRPIGTRYLTRNL |
| AAV1<br>SEQ ID<br>NO: 34 | >AAV1<br>MAADGYLPDWLEDNLSEGIREWWDLKPGAPKPKANQQKQDDGRGLVLPGYKYLGPFNGLDKGEPVNAADA<br>AALEHDKAYDQQLKAGDNPYLRYNHADAEFQERLQEDTSFGGNLGRAVFQAKKRVLEPLGLVEEGAKTAP<br>GKKRPVEQSPQEPDSSSGIGKTGQQPAKKRLNFGQTGDSESVPDPQPLGEPPATPAAVGPTTMASGGGAP<br>MADNNEGADGVGNASGNWHCDSTWLGDRVITTSTRTWALPTYNNHLYKQISSASTGASNDNHYFGYSTPW<br>GYFDENREHCHFSPRDWQRLINNNWGFRPKRLNFKLFNIQVKEVTTNDGVTTIANNLTSTVQVFSDSEYQ<br>LPYVLGSAHQGCLPPFPADVFMIPQYGYLTLNNGSQAVGRSSFYCLEYFPSQMLRTGNNFTFSYTFEEVP<br>FHSSYAHSQSLDRLMNPLIDQYLYYLNRTQNQSGSAQNKDLLFSRGSPAGMSVQPKNWLPGPCYRQQRVS<br>KTKTDNNNSNFTWTGASKYNLNGRESIINPGTAMASHKDDEDKFFPMSGVMIFGKESAGASNTALDNVMI<br>TDEEEIKATNPVATEREGTVAVNFQSSSTDPATGDVHAMGALPGMVWQDRDVYLQGPIWAKIPHTDGHFH<br>PSPLMGGFGLKNPPPQILIKNTPVPANPPAEFSATKFASFITQYSTGQVSVEIEWELQKENSKRWNPEVQ<br>YTSNYAKSANVDFTVDNNGLYTEPRPIGTRYLTRPL |
| AAV6<br>SEQ ID<br>NO: 35 | >AAV6<br>MAADGYLPDWLEDNLSEGIREWWDLKPGAPKPKANQQKQDDGRGLVLPGYKYLGPFNGLDKGEPVNAADA<br>AALEHDKAYDQQLKAGDNPYLRYNHADAEFQERLQEDTSFGGNLGRAVFQAKKRVLEPFGLVEEGAKTAP<br>GKKRPVEQSPQEPDSSSGIGKTGQQPAKKRLNFGQTGDSESVPDPQPLGEPPATPAAVGPTTMASGGGAP<br>MADNNEGADGVGNASGNWHCDSTWLGDRVITTSTRTWALPTYNNHLYKQISSASTGASNDNHYFGYSTPW<br>GYFDENREHCHFSPRDWQRLINNNWGFRPKRLNFKLFNIQVKEVTTNDGVTTIANNLTSTVQVFSDSEYQ<br>LPYVLGSAHQGCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQNQSGSAQNKDLLFSRGSPAGMSVQPKNWLPGPCYRQQRVS<br>KTKTDNNNSNFTWTGASKYNLNGRESIINPGTAMASHKDDKDKFFPMSGVMIFGKESAGASNTALDNVMI<br>TDEEEIKATNPVATERFGTVAVNLQSSSTDPATGDVHVMGALPGMVWQDRDVYLQGPIWAKIPHTDGHFH<br>PSPLMGGFGLKHPPPQILIKNTPVPANPPAEFSATKFASFITQYSTGQVSVEIEWELQKENSKRWNPEVQ<br>YTSNYAKSANVDFTVDNNGLYTEPRPIGTRYLTRPL |
| AAV3B<br>SEQ ID<br>NO: 36 | >A7V3B<br>MAADGYLPDWLEDNLSEGIREWWALKPGVPQPKANQQHQDNRRGLVLPGYKYLGPGNGLDKGEPVNEADA<br>AALEHDKAYDQQLKAGDNPYLKYNHADAEFQERLQEDTSFGGNLGRAVFQAKKRILEPLGLVEEAAKTAP<br>GKKRPVDQSPQEPDSSSGVGKSGKQPARKRLNFGQTGDSESVPDPQPLGEPPAAPTSLGSNTMASGGGAP<br>MADNNEGADGVGNSSGNWHCDSQWLGDRVITTSTRTWALPTYNNHLYKQISSQSGASNDNHYFGYSTPWG<br>YEDENREHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFQFSYTFEDVPF<br>HSSYAHSQSLDRLMNPLIDQYLYYLNRTQGTTSGTTNQSRLLFSQAGPQSMSLQARNWLPGPCYRQQRLS<br>KTANDNNNSNFPWTAASKYHLNGRDSLVNPGPAMASHKDDEEKFFPMHGNLIFGKEGTTASNAELDNVMI<br>TDEEEIRTTNPVATEQYGTVANNLQSSNTAPTTRTVNDQGALPGMVWQDRDVYLQGPIWAKIPHTDGHFH<br>PSPLMGGFGLKHPPPQIMIKNTPVPANPPTTFSPAKFASFITQYSTGQVSVEIEWELQKENSKRWNPEIQ<br>YTSNYNKSVNVDFTVDTNGVYSEPRPIGTRYLTRNL |
| LK03<br>SEQ ID<br>NO: 37 | >LK03<br>MAADGYLPDWLEDNLSEGIREWWALQPGAPKPKANQQHQDNARGLVLPGYKYLGPGNGLDKGEPVNAADA<br>AALEHDKAYDQQLKAGDNPYLKYNHADAEFQERLKEDTSFGGNLGRAVFQAKKRLLEPLGLVEEAAKTAP<br>GKKRPVDQSPQEPDSSSGVGKSGKQPARKRLNFGQTGDSESVPDPQPLGEPPAAPTSLGSNTMASGGGAP<br>MADNNEGADGVGNSSGNWHCDSQWLGDRVITTSTRTWALPTYNNHLYKQISSQSGASNDNHYFGYSTPWG<br>YEDENREHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFQFSYTFEDVPF<br>HSSYAHSQSLDRLMNPLIDQYLYYLNRTQGTTSGTTNQSRLLFSQAGPQSMSLQARNWLPGPCYRQQRLS<br>KTANDNNNSNFPWTAASKYHLNGRDSLVNPGPAMASHKDDEEKFFPMHGNLIFGKEGTTASNAELDNVMI<br>TDEEEIRTTNPVATEQYGTVANNLQSSNTAPTTRTVNDQGALPGMVWQDRDVYLQGPIWAKIPHTDGHFH<br>PSPLMGGFGLKHPPPQIMIKNTPVPANPPTTFSPAKFASFITQYSTGQVSVEIEWELQKENSKRWNPEIQ<br>YTSNYNKSVNVDFTVDTNGVYSEPRPIGTRYLTRPL |
| AAV8<br>SEQ ID<br>NO: 38 | >AAV8<br>MAADGYLPDWLEDNLSEGIREWWALKPGAPKPKANQQKQDDGRGLVLPGYKYLGPFNGLDKGEPVNAADA<br>AALEHDKAYDQQLQAGDNPYLRYNHADAEFQERLQEDTSFGGNLGRAVFQAKKRVLEPLGLVEEGAKTAP<br>GKKRPVEPSPQRSPDSSTGIGKKGQQPARKRLNEGQTGDSESVPDPQPLGEPPAAPSGVGPNTMAAGGGA<br>PMADNNEGADGVGSSSGNWHCDSTWLGDRVITTSTRTWALPTYNNHLYKQISNGTSGGATNDNTYFGYST |

TABLE 4-continued

| Parent AAV Capsid Amino Acid Sequences | |
|---|---|
| Description SEQ ID NO: | Amino Acid Sequence |
| | PWGYFDENREHCHFSPRDWQRLINNNWGFRPKRLSFKLENIQVKEVTQNEGTKTIANNLTSTIQVFTDSE<br>YQLPYVLGSAHQGCLPPEPADVFMIPQYGYLTLNNGSQAVGRSSFYCLEYFPSQMLRTGNNFQFTYTFED<br>VPFHSSYAHSQSLDRLMNPLIDQYLYYLSRTQTTGGTANTQTLGESQGGPNTMANQAKNWLPGPCYRQQR<br>VSTTTGQNNNSNFAWTAGTKYHLNGRNSLANPGIAMATHKDDEERFFPSNGILIFGKQNAARDNADYSDV<br>MLTSEEEIKTTNPVATEEYGIVADNLQQQNTAPQIGTVNSQGALPGMVWQNRDVYLQGPIWAKIPHTDGN<br>FHPSPLMGGEGLKHPPPQILIKNTPVPADPPTTENQSKLNSFITQYSTGQVSVEIEWELQKENSKRWNPE<br>IQYTSNYYKSTSVDFAVNTEGVYSEPRPIGTRYLTRNL |
| Rhesus 10 AAV SEQ ID NO: 39 | >rhesus_10<br>MAADGYLPDWLEDNLSEGIREWWDLKPGAPKPKANQQKQDDGRGLVLPGYKYLGPFNGLDKGEPVNAADA<br>AALEHDKAYDQQLKAGDNPYLRYNHADAEFQERLQEDTSFGGNLGRAVFQAKKRVLEPLGLVEEGAKTAP<br>GKKRPVEPSPQRSPDSSTGIGKKGQQPAKKRLNEGQTGDSESVPDPQPIGEPPAGPSGLGSGTMAAGGA<br>PMADNNEGADGVGSSSGNWHCDSTWLGDRVITTSTRTWALPTYNNHLYKQISNGTSGGSTNDNTYFGYST<br>PWGYFDENREHCHFSPRDWQRLINNNWGFRPKRLNEKLENIQVKEVTQNEGTKTIANNLTSTIQVFTDSE<br>YQLPYVLGSAHQGCLPPEPADVFMIPQYGYLTLNNGSQAVGRSSFYCLEYFPSQMLRTGNNFEFSYQFED<br>VPFHSSYAHSQSLDRLMNPLIDQYLYYLSRTQSTGGTAGTQQLLFSQAGPNNMSAQAKNWLPGPCYRQQR<br>VSTTLSQNNNSNFAWTGATKYHLNGRDSLVNPGVAMATHKDDEERFFPSSGVLMFGKQGAGKDNVDYSSV<br>MLTSEEEIKTTNPVATEQYGVVADNLQQQNAAPIVGAVNSQGALPGMVWQNRDVYLQGPIWAKIPHTDGN<br>FHPSPLMGGEGLKHPPPQILIKNTPVPADPPTTESQAKLASFITQYSTGQVSVEIEWELQKENSKRWNPE<br>IQYTSNYYKSTNVDFAVNTDGTYSEPRPIGTRYLTRNL |
| AAV2 SEQ ID NO: 40 | >AAV2<br>MAADGYLPDWLEDTLSEGIRQWWKLKPGPPPPKPAERHKDDSRGLVLPGYKYLGPFNGLDKGEPVNEADA<br>AALEHDKAYDRQLDSGDNPYLKYNHADAEFQERLKEDTSFGGNLGRAVFQAKKRVLEPLGLVEEPVKTAP<br>GKKRPVEHSPVEPDSSSGTGKAGQQPARKRLNFGQTGDADSVPDPQPLGQPPAAPSGLGTNTMATGSGAP<br>MADNNEGADGVGNSSGNWHCDSTWMGDRVITTSTRTWALPTYNNHLYKQISSQSGASNDNHYFGYSTPWG<br>YFDFNRFHCHFSPRDWQRLINNNWGFRPKRLNFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFTFSYTFEDVPF<br>HSSYAHSQSLDRLMNPLIDQYLYYLSRTNTPSGTTTQSRLQFSQAGASDIRDQSRNWLPGPCYRQQRVSK<br>TSADNNNSEYSWTGATKYHLNGRDSLVNPGPAMASHKDDEEKFFPQSGVLIFGKQGSEKTNVDIEKVMIT<br>DEEEIRTTNPVATEQYGSVSTNLQRGNRQAATADVNTQGVLPGMVWQDRDVYLQGPIWAKIPHTDGHFHP<br>SPLMGGFGLKHPPPQILIKNTPVPANPSTTFSAAKFASFITQYSTGQVSVEIEWELQKENSKRWNPEIQY<br>TSNYNKSVNVDFTVDTNGVYSEPRPIGTRYLTRNL |
| DJ SEQ ID NO: 41 | >DJ<br>MAADGYLPDWLEDTLSEGIRQWWKLKPGPPPPKPAERHKDDSRGLVLPGYKYLGPFNGLDKGEPVNEADA<br>AALEHDKAYDRQLDSGDNPYLKYNHADAEFQERLKEDTSFGGNLGRAVFQAKKRLLEPLGLVEEAAKTAP<br>GKKRPVEHSPVEPDSSSGTGKAGQQPARKRLNFGQTGDADSVPDPQPIGEPPAAPSGVGSLTMAAGGGAP<br>MADNNEGADGVGNSSGNWHCDSTWMGDRVITTSTRTWALPTYNNHLYKQISNSTSGGSSNDNAYFGYSTP<br>WGYFDFNRFHCHFSPRDWQRLINNNWGFRPKRLSFKLFNIQVKEVTQNEGTKTIANNLTSTIQVFTDSEY<br>QLPYVLGSAHQGCLPPFPADVFMIPQYGYLTLNNGSQAVGRSSFYCLEYFPSQMLRTGNNFQFTYTFEDV<br>PFHSSYAHSQSLDRLMNPLIDQYLYYLSRTQTTGGTTNTQTLGFSQGGPNTMANQAKNWLPGPCYRQQRV<br>SKTSADNNNSEYSWTGATKYHLNGRDSLVNPGPAMASHKDDEEKFFPQSGVLIFGKQGSEKTNVDIEKVM<br>ITDEEEIRTTNPVATEQYGSVSTNLQRGNRQAATADVNTQGVLPGMVWQDRDVYLQGPIWAKIPHTDGHF<br>HPSPLMGGFGLKHPPPQILIKNTPVPADPPTTFNQSKLNSFITQYSTGQVSVEIEWELQKENSKRWNPEI<br>QYTSNYYKSTSVDFAVNTEGVYSEPRPIGTRYLTRNL |
| BOVINE AAV SEQ ID NO: 42 | >bovine<br>MSFVDHPPDWLESIGDGFREFLGLEAGPPKPKANQQKQDNARGLVLPGYKYLGPGNGLDKGDPVNFADEV<br>AREHDLSYQKQLEAGDNPYLKYNHADAEFQEKLASDTSEGGNLGKAVFQAKKRILEPLGLVETPDKTAPA<br>AKKRPLEQSPQEPDSSSGVGKKGKQPARKRLNEDDEPGAGDGPPPEGPSSGAMSTETEMRAAAGGNGGDA<br>GQGAEGVGNASGDWHCDSTWSESHVTTTSTRTWVLPTYNNHLYLRLGSSNASDTFNGFSTPWGYFDFNRF<br>HCHFSPRDWQRLINNHWGLRPKSMQVRIFNIQVKEVTTSNGETTVSNNLTSTVQIFADSTYELPYVMDAG<br>QEGSLPPFPNDVFMVPQYGYCGLVTGGSSQNQTDRNAFYCLEYFPSQMLRTGNNFEMVYKFENVPFHSMY<br>AHSQSLDRLMNPLLDQYLWELQSTTSGGTLNQGNSATNFAKLTKTNESGYRKNWLPGPMMKQQRFSKTAS<br>QNYKIPQGRNNSLLHYETRTTLDGRWSNFAPGTAMATAANDATDFSQAQLIFAGPNITGNTTTDANNLMF<br>TSEDELRATNPRDTDLFGHLATNQQNATTVPTVDDVDGVGVYPGMVWQDRDIYYQGPIWAKIPHTDGHFH<br>PSPLIGGFGLKSPPPQIFIKNTPVPANPATTFSPARINSFITQYSTGQVAVKIEWEIQKERSKRWNPEVQ<br>FTSNYGAQDSLLWAPDNAGAYKEPRAIGSRYLTNHL |
| AAV4 SEQ ID NO: 43 | >AAV4<br>MTDGYLPDWLEDNLSEGVREWWALQPGAPKPKANQQHQDNARGLVLPGYKYLGPGNGLDKGEPVNAADAA<br>ALEHDKAYDQQLKAGDNPYLKYNHADAEFQQRLQGDTSFGGNLGRAVFQAKKRVLEPLGLVEQAGETAPG<br>KKRPLIESPQQPDSSTGIGKKGKQPAKKKLVFEDETGAGDGPPEGSTSGAMSDDSEMRAAAGGAAVEGGQ<br>GADGVGNASGDWHCDSTWSEGHVTTTSTRTWVLPTYNNHLYKRLGESLQSNTYNGFSTPWGYFDFNRFHC<br>HFSPRDWQRLINNNWGMRPKAMRVKIFNIQVKEVTTSNGETTVANNLTSTVQIFADSSYELPYVMDAGQE<br>GSLPPFPNDVFMVPQYGYCGLVTGNTSQQQTDRNAFYCLEYFPSQMLRTGNNFEITYSFEKVPFHSMYAH<br>SQSLDRLMNPLIDQYLWGLQSTTTGTTLNAGTATTNFTKLRPTNFSNFKKNWLPGPSIKQQGFSKTANQN<br>YKIPATGSDSLIKYETHSTLDGRWSALTPGPPMATAGPADSKFSNSQLIFAGPKQNGNTATVPGTLIFTS<br>EEELAATNATDTDMWGNLPGGDQSNSNLPTVDRLTALGAVPGMVWQNRDIYYQGPIWAKIPHTDGHFHPS<br>PLIGGFGLKHPPPQIFIKNTPVPANPATTFSSTPVNSFITQYSTGQVSVQIDWEIQKERSKRWNPEVQFT<br>SNYGQQNSLLWAPDAAGKYTEPRAIGTRYLTHHL |

TABLE 4-continued

| Parent AAV Capsid Amino Acid Sequences | |
|---|---|
| Description SEQ ID NO: | Amino Acid Sequence |
| AAV12 SEQ ID NO: 44 | >AAV12<br>MAADGYLPDWLEDNLSEGIREWWALKPGAPQPKANQQHQDNGRGLVLPGYKYLGPFNGLDKGEPVNEADA<br>AALEHDKAYDKQLEQGDNPYLKYNHGDAEFQQRLATDTSFGGNLGRAVFQAKKRILEPLGLVEEGVKTAP<br>GKKRPLEKTPNRPTNPDSGKAPAKKKQKDGEPADSARRTLDFEDSGAGDGPPEGSSSGEMSHDAEMRAAP<br>GGNAVEAGQGADGVGNASGDWHCDSTWSEGRVTTTSTRTWVLPTYNNHLYLRIGTTANSNTYNGFSTPWG<br>YEDENREHCHFSPRDWQRLINNNWGLRPKSMRVKIFNIQVKEVTTSNGETTVANNLTSTVQIFADSTYEL<br>PYVMDAGQEGSFPPFPNDVFMVPQYGYCGVVTGKNQNQTDRNAFYCLEYFPSQMLRTGNNFEVSYQFEKV<br>PFHSMYAHSQSLDRMMNPLLDQYLWHLQSTTTGNSLNQGTATTTYGKITTGDFAYYRKNWLPGACIKQQK<br>FSKNANQNYKIPASGGDALLKYDTHTTLNGRWSNMAPGPPMATAGAGDSDFSNSQLIFAGPNPSGNTTTS<br>SNNLLFTSEEEIATTNPRDTDMFGQIADNNQNATTAPHIANLDAMGIVPGMVWQNRDIYYQGPIWAKVPH<br>TDGHFHPSPLMGGFGLKHPPPQIFIKNTPVPANPNTTFSAARINSFLTQYSTGQVAVQIDWEIQKEHSKR<br>WNPEVQFTSNYGTQNSMLWAPDNAGNYHELRAI GS RFLTHHL |

TABLE 5

| Parent AAV Capsid Nucleic Acid Sequences | |
|---|---|
| Description SEQ ID NO: | Nucleic Acid Sequence |
| Avian AAV SEQ ID NO: 45 | >avian<br>ATGTCTCTCATTTCTGATGCGATTCCAGATTGGTTGGAGCGGTTGGTCAAAAAGGGAGTGAATGCTGCAG<br>CTGATTTCTACCATTTGGAAAGCGGTCCTCCTCGTCCTAAGGCAAATCAGCAAACTCAAGAATCTCTTGA<br>AAAGGACGATTCGAGAGGTCTCGTGTTCCCAGGCTACAATTATCTAGGCCCTTTCAACGGTCTAGATAAA<br>GGAGAACCCGTCAACGAGGCAGACGCTGCCGCCTTAGAACACGACAAGGCTTACGACCTCGAAATCAAGG<br>ACGGGCACAACCCGTACTTTGAGTACAACGAGGCCGACAGACGTTTCCAGGAACGTCTCAAAGACGATAC<br>CTCCTTTGGAGGCAATTTAGGTAAAGCCATCTTCCAGGCCAAAAAGAGGGTTCTCGAACCCTTTGGTCTG<br>GTGGAAGACTCAAAGACGGCTCCGACCGGAGACAAGCGGAAAGGCGAAGACGAACCTCGTCTGCCCGACA<br>CTCCTCCACAGACTCCCAAGAAAAACAAGAAGCCTCGCAAGGAAAGACCTTCCGGCGGGGCAGAAGATCC<br>GGGCGAAGGCACCTCTTCCAACGCTGGAGCAGCAGCACCCGCCTCTAGTGTGGGATCATCTATCATGGCT<br>GAAGGAGGTGGCGGCCCAGTGGGCGATGCAGGCCAGGGTGCCGATGGAGTGGGCAATTCCTCGGGAAATT<br>GGCATTGCGATTCCCAATGGCTGGAAAACGGAGTCGTCACTCGAACCACCCGAACCTGGGTCTTGCCCAG<br>CTACAACAACCACCTGTACAAACGAATCCAAGGACCCAGCGGAGGCGACAACAACAACAAATTCTTTGGA<br>TTCAGCACCCCCTGGGGATACTTTGACTACAATCGATTCCACTGCCACTTTTCCCCGCGAGACTGGCAAC<br>GACTCATCAACAACAACTGGGGCATCCGTCCCAAAGCGATGCGCTTTAGACTCTTTAACATCCAGGTTAA<br>AGAGGTCACGGTCCAAGACTCCAACACCACCATCGCCAACAACCTCACCAGTACGGTCCAGGTCTTTGCG<br>GACAAGGACTACCAACTGCCGTACGTCCTCGGATCGGCTACCGAAGGCACCTTCCCGCCGTTCCCAGCGG<br>ATATCTACACGATCCCGCAGTACGGGTACTGCACGCTAAACTACAACAACGAGGCGGTGGATCGTTCGGC<br>CTTCTACTGTCTGGACTACTTTCCCTCAGACATGCTGCGGACAGGAAATAACTTTGAGTTTACTTACACC<br>TTCGAGGACGTTCCTTTCCATAGCATGTTTGCCCACAACCAGACGCTAGACCGGCTGATGAATCCCCTCG<br>TGGATCAGTACCTCTGGGCTTTCAGCTCCGTCAGCCAAGCAGGCTCATCTGGACGAGCTCTTCATTACTC<br>GCGGGCGACTAAAACCAACATGGC<br>GGCTCAATATAGGAACTGGTTACCTGGGCCTTTCTTCCGTGATCAGCAAATCTTTACGGGCGCTAGCAAC<br>ATCACTAAAAATAACGTCTTTAGCGTTTGGGAAAAAGGCAAGCAATGGGAACTCGACAATCGGACCAACC<br>TAATGCAGCCCGGTCCTGCGGCAGCGACCACCTTTAGCGGAGAACCTGACCGTCAAGCCATGCAAAACAC<br>GCTGGCTTTTAGCAGGACCGTCTACGATCAAACGACCGCCACGACCGATCGTAACCAGATACTCATCACC<br>AACGAAGACGAAATCAGACCCACCAACTCGGTCGGTATCGACGCGTGGGGAGCAGTTCCCACCAACAACC<br>AGTCGATCGTGACCCCCGGCACTCGCGCGGCCGTCAACAATCAAGGGGCGCTTCCCGGGATGGTGTGGCA<br>AAACAGAGACATTTACCTACAGGGACCCATTTGGGCCAAAATTCCCGACACTGACAATCACTTCCATCCG<br>TCCCCGCTTATTGGCGGGTTTGGCTGCAAGCATCCCCCTCCCCAGATTTTCATTAAAAACACACCCGTCC<br>CTGCCAACCCTTCGGAAACGTTCCAGACGGCCAAAGTGGCCTCCTTCATCAACCAGTACTCGACCGGACA<br>GTGCACCGTCGAAATCTTTTGGGAACTCAAGAAGGAAACCTCCAAGCGCTGGAACCCCGAAATCCAGTTC<br>ACCTCCAACTTTGGCAACGCGGCCGACATCCAGTTTGCCGTCTCCGACACGGGATCCTATTCCGAACCTC<br>GTCCCATCGGTACCCGTTACCTTACCAAACCTCTGTAA |
| Procine 1 AAV SEQ ID NO: 46 | >porcine1<br>ATGTCGTTTGTTGATCACCCTCCAGATTGGCTTGAGGAGATTGGTGAGGGTCTAAAGGAGTTTTTGGGAC<br>TCGAACCTGGCCCACCCAAACCGAAGCCCAACCAGCAGAAGCAAGACGACGCCCGTGGTCTTGTACTGCC<br>TGGATATAATTACCTGGGACCCGGAAACGGTCTCGACCGCGGAGAACCTGTCAACCGGGCTGACGAGGTC<br>GCGCGAGAGCACGACATCTCGTACAACGAGCAGCTCCAGGCGGGAGACAACCCCTACCTCAAGTACAACC<br>ACGCGGACGCCGAGTTTCAGGAGAAGCTCGCGGACGACACCTCCTTCGGGGGCAACCTCGGCAAGGCAGT<br>CTTTCAGGCCAAAAAAAGGGTTCTCGAACCTTTTGGCCTGGTTGAGGAGCCTGTTAAGACGGCTGCTAAA<br>GGCGAGCGGATAGACGACCACTATCCCAAAAAGAAGAAGGCTCGGATCGAAGAGACCGAAGCTGGAACCA<br>GCGGAGCCCAGCAGCTGCAGATCCCAGCCCAACCAGCCTCAAGTTTGGGAGCTGATACAATGTCTGCGGG<br>AGGTGGCAGCCCACTGGGCGACAATAACCAAGGCGCCGATGGAGTGGGCAATGCCTCGGGAGATTGGCAT<br>TGCGATTCCACGTGGATGGGGGACCGAGTCATCACCAAGTCCACCCGAACCTGGGTGCTGCCCAGCTACA<br>ACAACCATCAGTACCTTGAGATCCACAGCGGTTCCGTCGACGGAAGCAACGCTAACGCTTATTTTGGATA<br>CAGCACCCCCTGGGGGTACTTTGACTTCAACCGCTTCCACAGCCACTGGAGCCCCCGAGACTGGCAGCGA<br>CTCGTCAACAACTACTGGGGATTCAGACCCCGGTCCCTCAAGGTCAAGATCTTTAACATCCAAGTCAAGG |

TABLE 5-continued

Parent AAV Capsid Nucleic Acid Sequences

| Description SEQ ID NO: | Nucleic Acid Sequence |
|---|---|
| | AAGTCACGACGCAGGACGGCACCACCACCATCGCCAACAACCTCACCTCCACCGTCCAAGTGTTTACGGA<br>CAACGACTACCAGCTACCGTACGTCATCGGCAACGGAACGGAGGGGTGCCTGCCGGCCTTCCCTCCGCAG<br>GTCTTTACGCTGCCGCAGTACGGCTAC<br>GCGACACTGAACCGTAACAACACCGACGATCCCACCGAGCGGAGCAGTTTCTTCTGC<br>CTGGAATACTTTCCCAGCAAGATGCTGCGGACGGGCAACAACTTTGAATTCACCTACAGCTTCGAGGAGG<br>TGCCCTTCCACTGCAGCTTCGCTCCCAGCCAGAACCTCTTCAAGCTGGCCAATCCGCTGGTGGACCAGTA<br>CCTGTACCGCTTTGTGAGCACCGACACTTCCGGTAACCTACAGTTCCAAAAGAACTTGAAGGCCAGATAT<br>GCCAACACTTACAAGAATTGGTTTCCGGGGCCCATGTGCCGGACCCAGGGCTGGTACACAAGCGCGGGCA<br>CATATAACAACAAAGGCGTTGCCAACTTTGATACTTCAAACAAGATGGAACTGGAGGGGGCTAGTTACCA<br>AGTAAACCCTCAACCAAATGGAATGACAAACACGCTTCAGGATAGTAACAAATACGCGCTTGAAAACACC<br>ATGATCTTCAACGCACAGAACGCCCCTCCGGGAACGACCTCTCTGTACCAGGAGAACAATCTTTTGATAA<br>CCAGCGAGAGCGAGACGCAGCCTGTGAACCGATTGGCCTACAACACCGGTGGTCAGGTATCAAACAACAA<br>CCAGAATTCAAATACACATCCTACGGTCGGAGTATACAATCACCAGGAAGTGTTGCCTGGTAGCGTGTGG<br>ATGGACAGAGACGTATACCTTCAGGGCCCCATCTGGGCCAAAATCCCGGAGACAGGGGCACACTTTCATC<br>CTTCTCCGGCTATGGGCGGATTCGGACTCAAACACCCACCGCCCATGATGCTCATCAAGAACACACCGGT<br>ACCTAGCAACGTCGCTGCCTTCTCTGACGTGCCCGTTAAAAGCTTCATCACCCAGTACAGCACCGGACAG<br>GTCACGGTGGAGATTGAATGGGAGCTCAAGAAAGAAAACTCCAAGAGGTGGAATCCCGAGATACAGTACA<br>CCAACAACTACAACAACCCTACATTCGTGGACTTTGCTCCAGACACCTCCGGCGAGTACAGGACTACGAG<br>GGCTATTGGAACCCGTTACCTTACCCGACCCCTGTAA |
| AAV5<br>SEQ ID<br>NO: 47 | >AAV5<br>ATGTCTTTTGTTGATCACCCTCCAGATTGGTTGGAAGAAGTTGGTGAAGGTCTTCGCGAGTTTTTGGGCC<br>TTGAAGCGGGCCCACCGAAACCAAAACCCAATCAGCAGCATCAAGATCAAGCCCGTGGTCTTGTGCTGCC<br>TGGTTATAACTATCTCGGACCCGGAAACGGTCTCGATCGAGGAGAGCCTGTCAACAGGGCAGACGAGGTC<br>GCGCGAGAGCACGACATCTCGTACAACGAGCAGCTTGAGGCGGGAGACAACCCCTACCTCAAGTACAACC<br>ACGCGGACGCCGAGTTTCAGGAGAAGCTCGCCGACGACACATCCTTCGGGGGAAACCTCGGAAAGGCAGT<br>CTTTCAGGCCAAGAAAAGGGTTCTCGAACCTTTTGGCCTGGTTGAAGAGGGTGCTAAGACGGCCCCTACC<br>GGAAAGCGGATAGACGACCACTTTCCAAAAAGAAAGAAGGCTCGGACCGAAGAGGACTCCAAGCCTTCCA<br>CCTCGTCAGACGCCGAAGCTGGACCCAGCGGATCCCAGCAGCTGCAAATCCCAGCCCAACCAGCCTCAAG<br>TTTGGGAGCTGATACAATGTCTGCGGGAGGTGGCGGCCCATTGGGCGACAATAACCAAGGTGCCGATGGA<br>GTGGGCAATGCCTCGGGAGATTGGCATTGCGATTCCACGTGGATGGGGGACAGAGTCGTCACCAAGTCCA<br>CCCGAACCTGGGTGCTGCCCAGCTACAACAACCACCAGTACCGAGAGATCAAAAGCGGCTCCGTCGACGG<br>AAGCAACGCCAACGCCTACTTTGGATACAGCACCCCCTGGGGGTACTTTGACTTTAACCGCTTCCACAGC<br>CACTGGAGCCCCCGAGACTGGCAAAGACTCATCAACAACTACTGGGGCTTCAGACCCCGGTCCCTCAGAG<br>TCAAAATCTTCAACATTCAAGTCAAAGAGGTCACGGTGCAGGACTCCACCACCACCATCGCCAACAACCT<br>CACCTCCACCGTCCAAGTGTTTACGGACGACGACTACCAGCTGCCCTACGTCGTCGGCAACGGGACCGAG<br>GGATGCCTGCCGGCCTTCCCTCCGCAGGTCTTTACGCTGCCGCAGTACGGTTACGCGACGCTGAACCGCG<br>ACAACACAGAAAATCCCACCGAGAGGAGCAGCTTCTTCTGCCTAGAGTACTTTCCCAGCAAGATGCTGAG<br>AACGGGCAACAACTTTGAGTTTACCTACAACTTTGAGGAGGTGCCCTTCCACTCCAGCTTCGCTCCCAGT<br>CAGAACCTCTTCAAGCTGGCCAACCCGCTGGTGGACCAGTACTTGTACCGCTTCGTGAGCACAAATAACA<br>CTGGCGGAGTCCAGTTCAACAAGAACCTGGCCGGGAGATACGCCAACACCTACAAAAACTGGTTCCCGGG<br>GCCCATGGGCCGAACCCAGGGCTGGAACCTGGGCTCCGGGGTCAACCGCGCCAGTGTCAGCGCCTTCGCC<br>ACGACCAATAGGATGGAGCTCGAGGGCGCGAGTTACCAGGTGCCCCCGCAGCCGAACGGCAT<br>GACCAACAACCTCCAGGGCAGCAACACCTATGCCCTGGAGAACACTATGATCTTCAACAGCCAGCCGGCG<br>AACCCGGGCACCACCGCCACGTACCTCGAGGGCAACATGCTCATCACCAGCGAGAGCGAGACGCAGCCGG<br>TGAACCGCGTGGCGTACAACGTCGGCGGGCAGATGGCCACCAACAACCAGAGCTCCACCACTGCCCCCGC<br>GACCGGCACGTACAACCTCCAGGAAATCGTGCCCGGCAGCGTGTGGATGGAGAGGGACGTGTACCTCCAA<br>GGACCCATCTGGGCCAAGATCCCAGAGACGGGGGCGCACTTTCACCCCTCTCCGGCCATGGGCGGATTCG<br>GACTCAAACACCCACCGCCCATGATGCTCATCAAGAACACGCCTGTGCCCGGAAATATCACCAGCTTCTC<br>GGACGTGCCCGTCAGCAGCTTCATCACCCAGTACAGCACCGGGCAGGTCACCGTGGAGATGGAGTGGGAG<br>CTCAAGAAGGAAAACTCCAAGAGGTGGAACCCAGAGATCCAGTACACAAACAACTACAACGACCCCCAGT<br>TTGTGGACTTTGCCCCGGACAGCACCGGGGAATACAGAACCACCAGACCTATCGGAACCCGATACCTTAC<br>CCGACCCCTTTAA |
| Goat 1<br>AAV<br>SEQ ID<br>NO: 48 | >goat1<br>ATGTCTTTTGTTGATCACCCTCCAGATTGGTTGGAAGAAGTTGGTGAAGGTCTTCGCGAGTTTTTGGGCC<br>TTGAAGCGGGCCCACCGAAACCGAAACCCAACCAGCAGCATCAAGATCAAGCCCGTGGTCTTGTGCTGCC<br>TGGTTATAACTATCTCGGACCCGGAAACGGTCTCGATCGAGGAGAGCCTGTCAACAGGGCAGACGAGGTC<br>GCGCGAGAGCACGACATCTCGTACAACGAGCAGCTTGAGGCGGGAGACAACCCCTACCTCAAGTACAACC<br>ACGCGGACGCCGAGTTCCAGGAGAAGCTCGCCGACGACACATCCTTCGGGGGAAACCTCGGAAAGGCAGT<br>CTTTCAGGCCAAGAAAAGGGTTCTCGAACCTTTTGGCCTGGTTGAAGAGGGTGCTAAGACGGCCCCTACC<br>GGAAAGCGGATAGACGACCACTTTCCAAAAAGAAAGAAGGCTCGGACCGAAGAGGACTCCAAGCCTTCCA<br>CCTCGTCAGACGCCGAAGCTGGACCCAGCGGATCCCAGCAGCTGCAAATCCCAGCACAACCAGCCTCAAG<br>TTTGGGAGCTGATACAATGTCTGCGGGAGGTGGCGGCCCATTGGGCGACAATAACCAAGGTGCCGATGGA<br>GTGGGCAATGCCTCGGGAGATTGGCATTGCGATTCCACGTGGATGGGGGACAGAGTCGTCACCAAGTCCA<br>CCCGCACCTGGGTGCTGCCCAGCTACAACAACCACCAGTACCGAGAGATCAAAAGCGGCTCCGTCGACGG<br>AAGCAACGCCAACGCCTACTTTGGATACAGCACCCCCTGGGGGTACTTTGACTTTAACCGCTTCCACAGC<br>CACTGGAGCCCCCGAGACTGGCAAAGACTCATCAACAACTATTGGGGCTTCAGACCCCGGTCTCTCAGAG<br>TCAAAATCTTCAACATCCAAGTCAAAGAGGTCACGGTGCAGGACTCCACCACCACCATCGCCAACAACCT<br>CACCTCCACCGTCCAAGTGTTTACGGACGACGACTACCAACTCCCGTACGTCGTCGGCAACGGGACCGAG<br>GGATGCCTGCCGGCCTTCCCCCCGCAGGTCTTTACGCTGCCGCAGTACGGCTACGCGACGCTGAACCGAG<br>ACAACGGAGACAACCCGACAGAGCGGAGCAGCTTCTTTTGCCTAGAGTACTTTCCCAGCAAGATGCTGAG<br>GACGGGCAACAACTTTGAGTTTACCTACAGCTTTGAAGAGGTGCCCTTCCACTGCAGCTTCGCCCCGAGC<br>CAGAACCTCTTTAAGCTGGCCAACCCGCTGGTGGACCAGTACCTGTACCGCTTCGTGAGCACCTCGGCCA |

TABLE 5-continued

| Parent AAV Capsid Nucleic Acid Sequences | |
|---|---|
| Description SEQ ID NO: | Nucleic Acid Sequence |
| | CGGGCGCCATCCAGTTCCAAAAGAACCTGGCGGGCAGATACGCCAACACCTACAAAAACTGGTTCCCGGG GCCCATGGGCCGAACCCAGGGCTGGAACACGAGCTCTGGCAGCAGCACCAACAGAGTCAGCGTCAACAAC TTTTCCGTCTCAAACCGGATGAACCTGGAGGGGGCCAGCTACCAAGTGAACCCCCAGCCCAACGGGATGA CAAACACGCTCCAAGGCAGCAACCGCTACGCGCTGGAAAACACCATGATCTTCAACGCTCAAAACGCCAC GCCGGGAACTACCTCGGTGTACCCAGAGGACAATCTACTGCTGACCAGCGAGAGCGAGACTCAGCCCGTC AACCGGGTGGCTTACAACACGGGCGGTCAGATGGCCACCAACGCCCAGAACGCCACCACGGCTCCCACGG TCGGGACCTACAACCTCCAGGAAGTGCTTCCTGGCAGCGTATGGATGGAGAGGGACGTGTACCTCCAAGG ACCCATCTGGGCCAAGATCCCAGAGACGGGGGCGCACTTTCACCCCTCTCCGGCCATGGGCGGATTCGGA CTCAAACACCCGCCGCCCATGATGCTCATCAAAAACACGCCGGTGCCCGGCAACATCACCAGCTTCTCGG ACGTGCCCGTCAGCAGCTTCATCACCCAGTACAGCACCGGGCAGGTCACCGTGGAGATGGAATGGGAGCT CAAAAAGGAAAACTCCAAGAGGTGGAACCCAGAGATCCAGTACACCAACAACTACAACGACCCCCAGTTT GTGGACTTTGCTCCAGACGGCTCCGGCGAATACAGAACCACCAGAGCCATCGGAACCCGATACCTCACCC GACCCCTTTAA |
| Mouse 1 AAV SEQ ID NO: 49 | >mouse1 ATGTCTTTCTTTGATTGGTTAGGTAAACAGTACGCTCAAGGAGCTGCTGAATTCTGGGATTTGAAGTCCG GTCCTCCTGCACCAAAAAAGGCGCGAAAGGACGGATCAGCCGGATTCAATTTCCCTGGGCACAAATACCT GGGTCCTGGCAATTCATTGGATCGCGGAGATCCCGTGGACGCTGACGACGCCGCTGCTCAAAAGCACGAC CAGTCGTACCAAGAGCAGCTTGAGGCGGGAGACAATCCCTACCTCAAGTACAACCACGCCGACCGCGAGT TCCAGGAGGCGTTGAAGGACGACACCTCCTTTGAAGGAAATCTCGCGAGAGGACTCTTTGAGGCCAAGAA GCTCGTGGCAGAGCCTCTTGGTCTCGTGGAACCAGAACTGGCGCCACCCAGTGGCCGTAAACGACCGGTG CAATCGAGTCAAGAGTCTGGTTACTCGAGTAGCCAAGACAAGCGGCCCAACCTCGACGTAGACGAGGAGG ACCGTGAGTTCGCTGCCGCTGCAGCGGAGACCGAAACTGGAAGCGCTCCCCCCACCGGCAATTTGGGACC TGGTACGATGGCTGGAGGCGGTAGCGCGCCAATCGACGACGGCTCGTATGGTGCCGATGGAGTGGGCAAT GCCTCGGGAGATTGGCATTGCGATTCCACATGGCTGGACAACTGTGTCATCACCCGAACCACTCGGACCT GGAATCTGCCAACCTACAACAACCACATCTACAAACGACTCAACGGAACGACCTCCGGAGACCAAAGCTA CTTCGGATTCAGCACCCCCTGGGGATACTTTGACTTCAACCGCTTCCACTGTCATTTCTCCCCTCGAGAC TGGCAAAGACTCATCAACAATAACTGGGGACTCCGACCAAAGAGCCTACGGTTCAAAATCTTTAACATTC AAGTTAAAGAAGTCACGACGCAAGACTCAACGAAGATCATCTCCAATAACCTTACCAGCACGGTTCAGGT ATTTGCGGACACGGAGTACCAGCTCCCGTACGTGATTGGATCGGCTCACGAAGGATGTCTGCCTCCTTTC CCGGCTGACGTGTTCATGCTGCCGCAGTATGGATACTGTACTCGACAAGACGGAAACAGCAACAATCCGA CCCCGAGAAGCGCCTTCTATTGTTTGGAGTACTTTCCCAGCAAGATGCTAAGAACTGGGAACAGTTTTGA ATTTACATATAACTTTGAGAAGGTGCCGTTCCACAGCATGTGGGCTCACAACCAGAGTCTGGATCGATTG ATGAATCCATTGATTGATCAGTACCTGTACTACCTTGATGTCACTTCGAG TACCGGGTTTACCTATCAAAAAGGAGTTCACACGAACTTGCCCGAACAAGAGCGCAACTGGCTGCCGGGA CCAGGAATTCGAAATCAAGCTTGGTTTAATTCTGCAACTGGAAACAACCCACTAACTGGTACCTGGCAAT ATTCCAACAAATACGTACTAGAAAACCGTGCTTCGAAGATTGCTCCTGGACCTGCCATGGGAATTGAATC AACAAAATTCGACGGGAACGGAATCATCTTTTCTAAAGAATACATCACCAATGTAAATACAGCCAATCCG AATCAAGTAAACATCACACGCGAGACCGAAATAAACTCAACGAACCCCTTGGCTGGAGGATCTCTCGGAG CCCACGCTAATAATTCACAAAACACAACAACGGCACCGACGCTAGACCACACCAACGTCATGGGTGTGTT TCCGGGTAGTGTCTGGCAAGACAGAGACATTTACCTTCAAGGACAAATCTGGGCCAAGATTCCCCACACA GACGGACATTTCCACCCTTCTCCTCTCATGGGAGGATTTGGACTGAAGAACCCGCCTCCTCAAATTCTGA TCAAAAACACACCTGTTCCGGCTGACCCACCAACTGAATTCAATGCGAACAAAATCTCTTCTTTCATCAC TCAATACTCAACCGGACAAGTTACAGTGGAAATGGAATGGGAACTTCAGAAAGAAACCTCCAAAAGATGG AATCCAGAAATCCAGTACAGCGACGACTCGTCTTCGACGTCTGGCTCCATTCTGCACTTTGCTCCGGATG ATGTTGGAAACTACAAAGAGTTCCGCTCTATCGGAACTCGTTACCTTACCCGTCCTCTGTAA |
| Procine 2 AAV SEQ ID NO: 50 | >porcine2 ATGTCGTTTGTTGATCACCCTCCAGATTGGTTAGAAGAAGTTGGTGAAGGCCTTCACGAGTTTTTGGAGC TCGAAGCTGGCCCACCCAAACCGAAGCCCAACCAGCAGAAGCAGGACAACGCCCGTGGTCTTGTACTGCC TGGATATAATTATCTGGGACCCTTCAACGGACTCGACAAGGGAGAGCCCGTCAACCGAGCGGACGCTGTT GCGCGAGAGCACGACATCTCGTACAACGAGCAGCTCCAGGCGGGAGACAACCCCTACCTCAAGTACAACC ACGCGGACGCCGAGTTTCAGGAGAAGCTCAAGGACGACACCTCCTTTGGGGGCAACCTCGGAAAGGCAAT CTTTCAGGCCAAGAAAAGGGTTCTCGAACCTTTTGGCCTGGTTGAGGCACCTGTTAAGACGGCTCCAGCC AAGAAGCGGCCGATAGAGAAGTCTCCGGCGGAACCGAGCTCTTCGAAGGGCATCGGCAAGGCGGGCCAGC AGCCTGCGAGGAAGCGACTCAACTTTGGTCAGACTGGAGACACCGACTCCGCCGCTGACCCCCAGCCTCT CGGAGAACCACCAGCAGCCCCCTCTGGTCTGGGAACTGGTACGATGGCTTCAGGCAGTGGCGCACCAATG GCAGACAATAACGAAGGCGCCGACGGAGTGGGTAATGCCTCGGGAAATTGGCATTGCGATTCCACATGGC TGGGCGACCGAGTCATCACCACCAGCACCCGCACCTGGGCCCTGCCCACCTACAACAACCATCTCTACAA GCAAATCTCCAGCCAGTCTGGAGCCAACAACGACAACCACTACTTTGGCTACAGCACCCCCTGGGGGTAC TTTGACTTCAACCGCTTCCACTGCCACTTCTCCCCGCGAGACTGGCAGCGGCTCATCAACAACAACTGGG GGTTCCGGCCCAAGCGACTCAACTTCAAGCTCTTCAACATCCAAGTCAAGGAGGTCACTCAGACGGACGG CACGAAGACCATCGCCAATAACCTTACCAGCACGGTTCAGGTCTTTGCGGACTCGGAGTACCAGCTCCCG TACGTCCTCGGATCAGCGCACCAGGGCTGCTTCCCGCCGTTCCCGGCGGACGTCTTCATGGTCCCGCAGT ACGGGTATTTGACGCTGAACAACGGCAGCCAGGCGATGGGTCGCTCGTCCTTCTACTGCCTGGAGTACTT TCCGTCGCAGATGCTGCGGACGGGGAACAACTTCACGTTCAGCTACACCTTCGAGGACGTGCCCTTCCAC AGCAGCTACGCGCACAGCCAGAGTCTGGACCGGCTCATGAACCCACTCATCGACCAGTACCTGTACTACC TAAGCAAGACAAATGGCGGTCTAGGATTTTCCCAAGCGGGACCCAACAGCATGCGCGACCAGTCCAGGAA TTGGCTGCCGGGACCCTGCTTCAGACAACAACGGATTTCAACTGTACCTACACAAAATAACAACGGAGAC TTTTCGTGGACGGGAGCCACAAAGTATCATCTCAATGGAAGAAACTCAGCAATGAATCCCGGCCCGGCCA TGGCCAGCCACAAAGACGACGAACACAGATTCTTCCCTCAGAACGGTGTGCTCATCTTTGGAAAACAGGG CGCAGACAAGACAAATGCGATACTAGAAAAAGTGATCGTTACAGACGAAGAGGAGATTAGGACAACAAAT CCTGTAGCCACGGAGGAGTATGGGTTTGTCGCCACTAATCTACAAAGCTCGGCAGAAACAGCCGAGACCG AAAGAGTCAACGCGCAAGGCATCCTCCCTGGCATGGTGTGGCAAGACCGAGATGTGTATCTGCAGGGGCC |

TABLE 5-continued

| Parent AAV Capsid Nucleic Acid Sequences | |
|---|---|
| Description<br>SEQ ID<br>NO: | Nucleic Acid Sequence |
| | CATCTGGGCCAAGATCCCCCACACCGACGGACACTTCCGCCCCTCACCACTCATGGGAGGATTCGGCCTC<br>AAGCACCCGCCTCCGCAGATCCTCATCAAGAACACGCCTGTGCCTTCGAATCCTCCAGAGACGTTCAACC<br>CGGAAAAGCTCAATTCTTTCATAACTCAATATTCTACGGGCCAGGTCAGCGTGGAGATCGAGTGGGAGCT<br>GCAGAAGGAGAACAGCAAGCGCTGGAACCCCGAGGTCCAGTACACGTCCAACTACAACAAGTCCGTCAAC<br>GTGGAATTTACAGTGGACAACAACGGCGTGTATTCGGAACCGCGCACCATCGGCACCCGCTACCTTACTC<br>GTAATCTGTAA |
| AAV9hu14<br>SEQ ID<br>NO: 51 | >AAV9hu14<br>ATGGCTGCCGATGGTTATCTTCCAGATTGGCTCGAGGACAACCTTAGTGAAGGAATTCGCGAGTGGTGGG<br>CTTTGAAACCTGGAGCCCCTCAACCCAAGGCAAATCAACAACATCAAGACAACGCTCGAGGTCTTGTGCT<br>TCCGGGTTACAAATACCTTGGACCCGGCAACGGACTCGACAAGGGGGAGCCGGTCAACGCAGCAGACGCG<br>GCGGCCCTCGAGCACGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGAGCAGTCTCCTCAGGAACCGGACTCCTCCGCGGGTATTGGCAAATCGGGTG<br>CACAGCCCGCTAAAAAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAGGTGGTGGCGCACCA<br>GTGGCAGACAATAACGAAGGTGCCGATGGAGTGGGTAGTTCCTCGGGAAATTGGCATTGCGATTCCCAAT<br>GGCTGGGGGACAGAGTCATCACCACCAGCACCCGAACCTGGGCCCTGCCCACCTACAACAATCACCTCTA<br>CAAGCAAATCTCCAACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCAGCGACTCATCAACA<br>ACAACTGGGGATTCCGGCCTAAGCGACTCAACTTCAAGCTCTTCAACATTCAGGTCAAAGAGGTTACGGA<br>CAACAATGGAGTCAAGACCATCGCCAATAACCTTACCAGCACGGTCCAGGTCTTCACGGACTCAGACTAT<br>CAGCTCCCGTACGTGCTCGGGTCGGCT<br>CACGAGGGCTGCCTCCCGCCGTTCCCAGCGGACGTTTTCATGATTCCTCAGTACGGGTATCTGACGCTTA<br>ATGATGGAAGCCAGGCCGTGGGTCGTTCGTCCTTTTACTGCCTGGAATATTTCCCGTCGCAAATGCTAAG<br>AACGGGTAACAACTTCCAGTTCAGCTACGAGTTTGAGAACGTACCTTTCCATAGCAGCTACGCTCACAGC<br>CAAAGCCTGGACCGACTAATGAATCCACTCATCGACCAATACTTGTACTATCTCTCAAAGACTATTAACG<br>GTTCTGG<br>ACAGAATCAACAAACGCTAAAATTCAGTGTGGCCGGACCCAGCAACATGGCTGTCCAGGGAAGAAACTAC<br>ATACCTGGACCCAGCTACCGACAACAACGTGTCTCAACCACTGTGACTCAAAACAACAACAGCGAATTTG<br>CTTGGCCTGGAGCTTCTTCTTGGGCTCTCAATGGACGTAATAGCTTGATGAATCCTGGACCTGCTATGGC<br>CAGCCACAAAGAAGGAGAGGACCGTTTCTTTCCTTTGTCTGGATCTTTAATTTTTGGCAAACAAGGAACT<br>GGAAGAGACAACGTGGATGCGGACAAAGTCATGATAACCAACGAAGAAGAAATTAAAACTACTAACCCGG<br>TAGCAACGGAGTCCTATGGACAAGTGGCCACAAACCACCAGAGTGCCCAAGCACAGGCGCAGACCGGCTG<br>GGTTCAAAACCAAGGAATACTTCCGGGTATGGTTTGGCAGGACAGAGATGTGTACCTGCAAGGACCCATT<br>TGGGCCAAAATTCCTCACACGGACGGCAACTTTCACCCTTCTCCGCTGATGGGAGGGTTTGGAATGAAAC<br>ACCCGCCTCCTCAGATCCTCATCAAAAACACACCTGTACCTGCGGATCCTCCAACGGCCTTCAACAAGGA<br>CAAGCTGAACTCTTTCATCACCCAGTATTCTACTGGCCAAGTCAGCGTGGAGATCGAGTGGGAGCTGCAG<br>AAGGAAAACAGCAAGCGCTGGAACCCGGAGATCCAGTACACTTCCAACTATTACAAGTCTAATAATGTTG<br>AATTTGCTGTTAATACTGAAGGTGTATATAGTGAACCCCGCCCCATTGGCACCAGATACCTGACTCGTAA<br>TCTGTAA |
| AAV1<br>SEQ ID<br>NO: 52 | >AAV1<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAGCCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGACGCA<br>GCGGCCCTCGAGCACGACAAGGCCTACGACCAGCAGCTCAAAGCGGGTGACAATCCGTACCTTCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAACGTCCGGTAGAGCAGTCGCCACAAGAGCCAGACTCCTCCTCGGGCATCGGCAAGACAGGCC<br>AGCAGCCCGCTAAAAAGAGACTCAATTTTGGTCAGACTGGCGACTCAGAGTCAGTCCCCGACCCACAACC<br>TCTCGGAGAACCTCCAGCAACCCCCGCTGCTGTGGGACCTACTACAATGGCTTCAGGCGGTGGCGCACCA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGCACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCACTTTTCACCACGTGACTGGCAGCGACTCATCAACAACA<br>ATTGGGGATTCCGGCCCAAGAGACTCAACTTCAAACTCTTCAACATCCAAGTCAAGGAGGTCACGACGAA<br>TGATGGCGTCACAACCATCGCTAATAACCTTACCAGCACGGTTCAAGTCTTCTCGGACTCGGAGTACCAG<br>CTTCCGTACGTCCTCGGCTCTGCGCACCAGGGCTGCCTCCCTCCGTTCCCGGCGGACGTGTTCATGATTC<br>CGCAATACGGCTACCTGACGCTCAACAATGGCAGCCAAGCCGTGGGACGTTCATCCTTTTACTGCCTGGA<br>ATATTTCCCTTCTCAGATGCTGAGAACGGGCAACAACTTTACCTTCAGCTACACCTTTGAGGAAGTGCCT<br>TTCCACAGCAGCTACGCGCACAGCCAGAGCCTGGACCGGCTGATGAATCCTCTCATCGACCAATACCTGT<br>ATTACCTGAACAGAACTCAAAATCAGTCCGGAAGTGCCCAAAACAAGGACTTGCTGTTTAGCCGTGGGTC<br>TCCAGCTGGCATGTCTGTTCAGCCCAAAAACTGGCTACCTGGACCCTGTTATCGGCAGCAGCGCGTTTCT<br>AAAACAAAAACAGACAACAACAACAGCAATTTTACCTGGACTGGTGCTTCAAAATATAACCTCAATGGGC<br>GTGAATCCATCATCAACCCTGGCACTGCTATGGCCTCACACAAAGACGACGAAGACAAGTTCTTTCCCAT<br>GAGCGGTGTCATGATTTTTGGAAAAGAGAGCGCCGGAGCTTCAAACACTGCATTGGACAATGTCATGATT<br>ACAGACGAAGAGGAAATTAAAGCCACTAACCCTGTGGCCACCGAAAGATTTGGGACCGTGGCAGTCAATT<br>TCCAGAGCAGCAGCACAGACCCTGCGACCGGAGATGTGCATGCTATGGGAGCATTACCTGGCATGGTGTG<br>GCAAGATAGAGACGTGTACCTGCAGGGTCCCATTTGGGCCAAAATTCCTCACACAGATGGACACTTTCAC<br>CCGTCTCCTCTTATGGGCGGCTTTGGACTCAAGAACCCGCCTCCTCAGATCCTCATCAAAAACACGCCTG<br>TTCCTGCGAATCCTCCGGCGGAGTTTTCAGCTACAAAGTTTGCTTCATTCATCACCCAATACTCCACAGG<br>ACAAGTGAGTGTGGAAATTGAATGGGAGCTGCAGAAAGAAAACAGCAAGCGCTGGAATCCCGAAGTGCAG |

TABLE 5-continued

| Parent AAV Capsid Nucleic Acid Sequences | |
|---|---|
| Description<br>SEQ ID<br>NO: | Nucleic Acid Sequence |
| | TACACATCCAATTATGCAAAATCTGCCAACGTTGATTTTACTGTGGACAACAATGGACTTTATACTGAGC<br>CTCGCCCCATTGGCACCCGTTACCTCACCCGTCCCCTGTAA |
| AAV6<br>SEQ ID<br>NO: 53 | >AAV6<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGAGGGTTCTCGAACCTTTTGGTCTGGTTGAGGAAGGTGCTAAGACGGCTCCT<br>GGAAAGAAACGTCCGGTAGAGCAGTCGCCACAAGAGCCAGACTCCTCCTCGGGCATTGGCAAGACAGGCC<br>AGCAGCCCGCTAAAAAGAGACTCAATTTTGGTCAGACTGGCGACTCAGAGTCAGTCCCCGACCCACAACC<br>TCTCGGAGAACCTCCAGCAACCCCCGCTGCTGTGGGACCTACTACAATGGCTTCAGGCGGTGGCGCACCA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGAACATGGGCCTTGCCCACCTATAACAACCACCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCATTTCTCACCACGTGACTGGCAGCGACTCATCAACAACA<br>ATTGGGGATTCCGGCCCAAGAGACTCAACTTCAAGCTCTTCAACATCCAAGTCAAGGAGGTCACGACGAA<br>TGATGGCGTCACGACCATCGCTAATAACCTTACCAGCACGGTTCAAGTCTTCTCGGACTCGGAGTACCAG<br>TTGCCGTACGTCCTCGGCTCTGCGCACCAGGGCTGCCTCCCTCCGTTCCCGGCGGACGTGTTCATGATTC<br>CGCAGTACGGCTAC<br>CTAACGCTCAACAATGGCAGCCAGGCAGTGGGACGGTCATCCTTTTACTGCCTGGAATATTTCCCATCGC<br>AGATGCTGAGAACGGGCAATAACTTTACCTTCAGCTACACCTTCGAGGACGTGCCTTTCCACAGCAGCTA<br>CGCGCACAGCCAGAGCCTGGACCGGCTGATG<br>AATCCTCTCATCGACCAGTACCTGTATTACCTGAACAGAACTCAGAATCAGTCCGGAAGTGCCCAAAACA<br>AGGACTTGCTGTTTAGCCGGGGGTCTCCAGCTGGCATGTCTGTTCAGCCCAAAAACTGGCTACCTGGACC<br>CTGTTACCGGCAGCAGCGCGTTTCTAAAAC<br>AAAAACAGACAACAACAACAGCAACTTTACCTGGACTGGTGCTTCAAAATATAACCTTAATGGGCGTGAA<br>TCTATAATCAACCCTGGCACTGCTATGGCCTCACACAAAGACGACAAAGACAAGTTCTTTCCCATGAGCG<br>GTGTCATGATTTTTGGAAAGGAGAGCGCCGGAGCTTCAAACACTGCATTGGACAATGTCATGATCACAGA<br>CGAAGAGGAAATCAAAGCCACTAACCCCGTGGCCACCGAAAGATTTGGGACTGTGGCAGTCAATCTCCAG<br>AGCAGCAGCACAGACCCTGCGACCGGAGATGTGCATGTTATGGGAGCCTTACCTGGAATGGTGTGGCAAG<br>ACAGAGACGTATACCTGCAGGGTCCTATTTGGGCCAAAATTCCTCACACGGATGGACACTTTCACCCGTC<br>TCCTCTCATGGGCGGCTTTGGACTTAAGCACCCGCCTCCTCAGATCCTCATCAAAAACACGCCTGTTCCT<br>GCGAATCCTCCGGCAGAGTTTTCGGCTACAAAGTTTGCTTCATTCATCACCCAGTATTCCACAGGACAAG<br>TGAGCGTGGAGATTGAATGGGAGCTGCAGAAAGAAAACAGCAAACGCTGGAATCCCGAAGTGCAGTATAC<br>ATCTAACTATGCAAAATCTGCCAACGTTGATTTCACTGTGGACAACAATGGACTTTATACTGAGCCTCGC<br>CCCATTGGCACCCGTTACCTCACCCGTCCCCTGTAA |
| AAV3B<br>SEQ ID<br>NO: 54 | >A7V3B<br>ATGGCTGCTGACGGTTATCTTCCAGATTGGCTCGAGGACAACCTTTCTGAAGGCATTCGTGAGTGGTGGG<br>CTCTGAAACCTGGAGTCCCTCAACCCAAAGCGAACCAACAACACCAGGACAACCGTCGGGGTCTTGTGCT<br>TCCGGGTTACAAATACCTCGGACCCGGTAACGGACTCGACAAAGGAGAGCCGGTCAACGAGGCGGACGCG<br>GCAGCCCTCGAACACGACAAAGCCTACGACCAGCAGCTCAAGGCCGGTGACAACCCGTACCTCAAGTACA<br>ACCACGCCGACGCCGAGTTTCAGGAGCGTCTTCAAGAAGATACGTCTTTTGGGGGCAACCTTGGCAGAGC<br>AGTCTTCCAGGCCAAAAAGAGGATCCTTGAGCCTCTTGGTCTGGTTGAGGAAGCAGCTAAAACGGCTCCT<br>GGAAAGAAGAGGCCTGTAGATCAGTCTCCTCAGGAACCGGACTCATCATCTGGTGTTGGCAAATCGGGCA<br>AACAGCCTGCCAGAAAAAGACTAAATTTCGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCCTGCCCACTTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTCAACATCCAAGTTAAAGAGGTCACGCAGAACGA<br>TGGCACGACGACTATTGCCAATAACCTTACCAGCACGGTTCAAGTGTTTACGGACTCGGAGTATCAGCTC<br>CCGTACGTGCTCGGGTCGGCGCACCAAGGCTGTCTCCCGCCGTTTCCAGCGGACGTCTTCATGGTCCCTC<br>AGTATGGATACCTCACCCTGAACAACGGAAGTCAAGCGGTGGGACGCTCATCCTTTTACTGCCTGGAGTA<br>CTTCCCTTCGCAGATGCTAAGGACTGGAAATAACTTCCAATTCAGCTATACCTTCGAGGATGTACCTTTT<br>CACAGCAGCTACGCTCACAGCCAGAGTTTGGATCGCTTGATGAATCCTCTTATTGATCAGTATCTGTACT<br>ACCTGAACAGAACGCAAGGAACAACCTCTGGAACAACCAACCAATCACGGCTGCTTTTTAGCCAGGCTGG<br>GCCTCAGTCTATGTCTTTGCAGGCCAGAAATTGGCTACCTGGGCCCTGCTACCGGCAACAGAGACTTTCA<br>AAGACTGCTAACGACAACAACAACAGTAACTTTCCTTGGACAGCGGCCAGCAAATATCATCTCAATGGCC<br>GCGACTCGCTGGTGAATCCAGGACCAGCTATGGCCAGTCACAAGGACGATGAAGAAAAATTTTTCCCTAT<br>GCACGGCAATCTAATATTTGGCAAAGAAGGGACAACGGCAAGTAACGCAGAATTAGATAATGTAATGATT<br>ACGGATGAAGAAGAGATTCGTACCACCAATCCTGTGGCAACAGAGCAGTATGGAACTGTGGCAAATAACT<br>TGCAGAGCTCAAATACAGCTCCCACGACTAGAACTGTCAATGATCAGGGGGCCTTACCTGGCATGGTGTG<br>GCAAGATCGTGACGTGTACCTTCAAGGACCTATCTGGGCAAAGATTCCTCACACGGATGGACACTTTCAT<br>CCTTCTCCTCTGATGGGAGGCTTTGGACTGAAACATCCGCCTCCTCAAATCATGATCAAAAATACTCCGG<br>TACCGGCAAATCCTCCGACGACTTTCAGCCCGGCCAAGTTTGCTTCATTTATCACTCAGTACTCCACTGG<br>ACAGGTCAGCGTGGAAATTGAGTGGGAGCTACAGAAAGAAAACAGCAAACGTTGGAATCCAGAGATTCAG<br>TACACTTCCAACTACAACAAGTCTGTTAATGTGGACTTTACTGTAGACACTAATGGTGTTTATAGTGAAC<br>CTCGCCCTATTGGAACCCGGTATCTCACACGAAACTTGTAA |

TABLE 5-continued

| Parent AAV Capsid Nucleic Acid Sequences | |
|---|---|
| Description SEQ ID NO: | Nucleic Acid Sequence |
| LK03<br>SEQ ID<br>NO: 55 | >LK03<br>ATGGCTGCTGACGGTTATCTTCCAGATTGGCTCGAGGACAACCTTTCTGAAGGCATTCGAGAGTGGTGGG<br>CGCTGCAACCTGGAGCCCCTAAACCCAAGGCAAATCAACAACATCAGGACAACGCTCGGGGTCTTGTGCT<br>TCCGGGTTACAAATACCTCGGACCCGGCAACGGACTCGACAAGGGGGAACCCGTCAACGCAGCGGACGCG<br>GCAGCCCTCGAGCACGACAAGGCCTACGACCAGCAGCTCAAGGCCGGTGACAACCCCTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGATCAGTCTCCTCAGGAACCGGACTCATCATCTGGTGTTGGCAAATCGGGCA<br>AACAGCCTGCCAGAAAAAGACTAAATTTCGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCCTGCCCACTTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTCAACATCCAAGTTAAAGAGGTCACGCAGAACGA<br>TGGCACGACGACTATTGCCAATAACCTTACCAGCACGGTTCAAGTGTTTACGGACTCGGAGTATCAGCTC<br>CCGTACGTGCTCGGGTCGGCGCACCAAGGCTGTCTCCCGCCGTTTCCAGCGGACGTCTTCATGGTCCCTC<br>AGTATGGATACCTCACCCTGAACAACGGAAGTCAAGCGGTGGGACGCTCATCCTTTTACTGCCTGGAGTA<br>CTTCCCTTCGCAGATGCTAAGGACTGGAAATAACTTCCAATTCAGCTATACCTTCGAGGATGTACCTTTT<br>CACAGCAGCTACGCTCACAGCCAGAGTTTGGATCGCTTGATGAATCCTCTTATTGATCAGTATCTGTACT<br>ACCTGAACAGAACGCAAGGAACAACCTCTGGAACAACCAACCAATCACGGCTGCTTTTTAGCCAGGCTGG<br>GCCTCAGTCTATGTCTTTGCAGGCCAGAAATTGGCTACCTGGGCCCTGCTACCGGCAACAGAGACTTTCA<br>AAGACTGCTAACGACAACAACAACAGTAACTTTCCTTGGACAGCGGCCAGCAAATATCATCTCAATGGCC<br>GCGACTCGCTGGTGAATCCAGGACCAGCTATGGCCAGTCACAAGGACGATGAAGAAAAATTTTTCCCTAT<br>GCACGGCAATCTAATATTTGGCAAAGAAGGGACAACGGCAAGTAACGCAGAATTAGATAATGTAATGATT<br>ACGGATGAAGAAGAGATTCGTACCACCAATCCTGTGGCAACAGAGCAGTATGGAACTGTGGCAAATAACT<br>TGCAGAGCTCAAATACAGCTCCCACGACTAGAACTGTCAATGATCAGGGGGCCTTACCTGGCATGGTGTG<br>GCAAGATCGTGACGTGTACCTTCAAGGACCTATCTGGGCAAAGATTCCTCACACGGATGGACACTTTCAT<br>CCTTCTCCTCTGATGGGAGGCTTTGGACTGAAACATCCGCCTCCTCAAATCATGATCAAAAATACTCCGG<br>TACCGGCAAATCCTCCGACGACTTTCAGCCCGGCCAAGTTTGCTTCATTTATCACTCAGTACTCCACTGG<br>ACAGGTCAGCGTGGAAATTGAGTGGGAGCTACAGAAAGAAAACAGCAAACGTTGGAATCCAGAGATTCAG<br>TACACTTCCAACTACAACAAGTCTGTTAATGTGGACTTTACTGTAGACACTAATGGTGTTTATAGTGAAC<br>CTCGCCCCATTGGCACCCGTTACCTTACCCGTCCCCTGTAA |
| AAV8<br>SEQ ID<br>NO: 56 | >AAV8<br>ATGGCTGCCGATGGTTATCTTCCAGATTGGCTCGAGGACAACCTCTCTGAGGGCATTCGCGAGTGGTGGG<br>CGCTGAAACCTGGAGCCCCGAAGCCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGACGCA<br>GCGGCCCTCGAGCACGACAAGGCCTACGACCAGCAGCTGCAGGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAGAGACCGGTAGAGCCATCACCCCAGCGTTCTCCAGACTCCTCTACGGGCATCGGCAAGAAAG<br>GCCAACAGCCCGCCAGAAAAAGACTCAATTTTGGTCAGACTGGCGACTCAGAGTCAGTTCCAGACCCTCA<br>ACCTCTCGGAGAACCTCCAGCAGCGCCCTCTGGTGTGGGACCTAATACAATGGCTGCAGGCGGTGGCGCA<br>CCAATGGCAGACAATAACGAAGGCGCCGACGGAGTGGGTAGTTCCTCGGGAAATTGGCATTGCGATTCCA<br>CATGGCTGGGCGACAGAGTCATCACCACCAGCACCCGAACCTGGGCCCTGCCCACCTACAACAACCACCT<br>CTACAAGCAAATCTCCAACGGGACATCGGGAGGAGCCACCAACGACAACACCTACTTCGGCTACAGCACC<br>CCCTGGGGGTATTTTGACTTTAACAGATTCCACTGCCACTTTTCACCACGTGACTGGCAGCGACTCATCA<br>ACAACAACTGGGGATTCCGGCCCAAGAGACTCAGCTTCAAGCTCTTCAACA<br>TCCAGGTCAAGGAGGTCACGCAGAATGAAGGCACCAAGACCATCGCCAATAACCTCACCAGCACCATCCA<br>GGTGTTTACGGACTCGGAGTACCAGCTGCCGTACGTTCTCGGCTCTGCCCACCAGGGCTGCCTGCCTCCG<br>TTCCCGGCGGACGTGTTCATGATTCCCCAGTACGGCTACCTAACACTCAACAACGGTAGTCAGGCCGTGG<br>GACGCTCCTCCTTCTACTGCCTGGAATACTTTCCTTCGCAGATGCTGAGAACCGGCAACAACTTCCAGTT<br>TACTTACACCTTCGAGGACGTGCCTTTCCACAGCAGCTACGCCCACAGCCAGAGCTTGGACCGGCTGATG<br>AATCCTCTGATTGACCAGTACCTGTACTACTTGTCTCGGACTCAAACAACAGGAGGCACGGCAAATACGC<br>AGACTCTGGGCTTCAGCCAAGGTGGGCCTAATACAATGGCCAATCAGGCAAAGAACTGGCTGCCAGGACC<br>CTGTTACCGCCAACAACGCGTCTCAACGACAACCGGGCAAAACAACAATAGCAACTTTGCCTGGACTGCT<br>GGGACCAAATACCATCTGAATGGAAGAAATTCATTGGCTAATCCTGGCATCGCTATGGCAACACACAAAG<br>ACGACGAGGAGCGTTTTTTTCCCAGTAACGGGATCCTGATTTTTGGCAAACAAAATGCTGCCAGAGACAA<br>TGCGGATTACAGCGATGTCATGCTCACCAGCGAGGAAGAAATCAAAACCACTAACCCTGTGGCTACAGAG<br>GAATACGGTATCGTGGCAGATAACTTGCAGCAGCAAAACACGGCTCCTCAAATTGGAACTGTCAACAGCC<br>AGGGGGCCTTACCCGGTATGGTCTGGCAGAACCGGGACGTGTACCTGCAGGGTCCCATCTGGGCCAAGAT<br>TCCTCACACGGACGGCAACTTCCACCCGTCTCCGCTGATGGGCGGCTTTGGCCTGAAACATCCTCCGCCT<br>CAGATCCTGATCAAGAACACGCCTGTACCTGCGGATCCTCCGACCACCTTCAACCAGTCAAAGCTGAACT<br>CTTTCATCACGCAATACAGCACCGGACAGGTC<br>AGCGTGGAAATTGAATGGGAGCTGCAGAAGGAAAACAGCAAGCGCTGGAACCCCGAGATCCAGTACACCT<br>CCAACTACTACAAATCTACAAGTGTGGACTTTGCTGTTAATACAGAAGGCGTGTACTCTGAACCCCGCCC<br>CATTGGCACCCGTTACCTCACCCGTAATCTGTAA |

TABLE 5-continued

Parent AAV Capsid Nucleic Acid Sequences

| Description SEQ ID NO: | Nucleic Acid Sequence |
|---|---|
| Rhesus 10 | >rhesus10 |
| AAV | ATGGCTGCCGATGGTTATCTTCCAGATTGGCTCGAGGACAACCTCTCTGAGGGCATTCGCGAGTGGTGGG |
| SEQ ID | ACTTGAAACCTGGAGCCCCGAAACCCAAAGCCAACCAGCAAAAGCAGGACGACGGCCGGGGTCTGGTGCT |
| NO: 57 | TCCTGGCTACAAGTACCTCGGACCCTTCAACGGACTCGACAAGGGGGAGCCCGTCAACGCGGCGGACGCA |
| | GCGGCCCTCGAGCACGACAAGGCCTACGACCAGCAGCTCAAAGCGGGTGACAATCCGTACCTGCGGTATA |
| | ACCACGCCGACGCCGAGTTTCAGGAGCGTCTGCAAGAAGATACGTCTTTTGGGGGCAACCTCGGGCGAGC |
| | AGTCTTCCAGGCCAAGAAGCGGGTTCTCGAACCTCTCGGTCTGGTTGAGGAAGGCGCTAAGACGGCTCCT |
| | GGAAAGAAGAGACCGGTAGAGCCATCACCCCAGCGTTCTCCAGACTCCTCTACGGGCATCGGCAAGAAAG |
| | GCCAGCAGCCCGCGAAAAAGAGACTCAACTTTGGGCAGACTGGCGACTCAGAGTCAGTGCCCGACCCTCA |
| | ACCAATCGGAGAACCCCCCGCAGGCCCCTCTGGTCTGGGATCTGGTACAATGGCTGCAGGCGGTGGCGCT |
| | CCAATGGCAGACAATAACGAAGGCGCCGACGGAGTGGGTAGTTCCTCAGGAAATTGGCATTGCGATTCCA |
| | CATGGCTGGGCGACAGAGTCATCACCACCAGCACCCGAACCTGGGCCCTCCCCACCTACAACAACCACCT |
| | CTACAAGCAAATCTCCAACGGGACTTCGGGAGGAAGCACCAACGACAACACCTACTTCGGCTACAGCACC |
| | CCCTGGGGGTATTTTGACTTTAACAGATTCCACTGCCACTTCTCACCACGTGACTGGCAGCGACTCATCA |
| | ACAACAACTGGGGATTCCGGCCCAAGAGACTCAACTTCAAGCTCTTCAACATCCAGGTCAAGGAGGTCAC |
| | GCAGAATGAAGGCACCAAGACCATCGCCAATAACCTTACCAGCACGATTCAGGTCTTTACGGACTCGGAA |
| | TACCAGCTCCCGTACGTCCTCGGCTCTGCGCACCAGGGCTGCCTGCCTCCGTTCCCGGCGGACGTCTTCA |
| | TGATTCCTCAGTACGGGTACCTGACTCTGAACAATGGCAGTCAGGCCGTGGGCCGTTCCTCCTTCTACTG |
| | CCTGGAGTACTTTCCTTCTCAAATGCTGAGAACGGGCAACAACTTTGAGTTCAGCTACCAGTTTGAGGAC |
| | GTGCCTTTTCACAGCAGCTACGCGCACAGCCAAAGCCTGGACCGGCTGATGAACCCCCTCATCGACCAGT |
| | ACCTGTACTACCTGTCTCGGACTCAGTCCACGGGAGGTACCGCAGGAACTCAGCAGTTGCTATTTTCTCA |
| | GGCCGGGCCTAATAACATGTC |
| | GGCTCAGGCCAAAAACTGGCTACCCGGGCCCTGCTACCGGCAGCAACGCGTCTCCACGACACTGTCGCAA |
| | AATAACAACAGCAACTTTGCCTGGACCGGTGCCACCAAGTATCATCTGAATGGCAGAGACTCTCTGGTAA |
| | ATCCCGGTGTCGCTATGGCAACCCACAAGGACGACGAAGAGCGATTTTTTCCGTCCAGCGGAGTCTTAAT |
| | GTTTGGGAAACAGGGAGCTGGAAAAGACAACGTGGACTATAGCAGCGTTATGCTAACCAGTGAGGAAGAA |
| | ATTAAAACCACCAACCCAGTGGCCACAGAACAGTACGGCGTGGTGGCCGATAACCTGCAACAGCAAAACG |
| | CCGCTCCTATTGTAGGGGCCGTCAACAGTCAAGGAGCCTTACCTGGCATGGTCTGGCAGAACCGGGACGT |
| | GTACCTGCAGGGTCCTATCTGGGCCAAGATTCCTCACACGGACGGAAACTTTCATCCCTCGCCGCTGATG |
| | GGAGGCTTTGGACTGAAACACCCGCCTCCTCAGATCCTGATTAAGAATACACCTGTTCCCGCGGATCCTC |
| | CAACTACCTTCAGTCAAGCTAAGCTGGCGTCGTTCATCACGCAGTACAGCACCGGACAGGTCAGCGTGGA |
| | AATTGAATGGGAGCTGCAGAAAGAAAACAGCAAACGCTGGAACCCAGAGATT |
| | CAATACACTTCCAACTACTACAAATCTACAAATGTGGACTTTGCTGTTAACACAGATGGCACTTATTCTG |
| | AGCCTCGCCCCATCGGCACCCGTTACCTCACCCGTAATCTGTAA |
| AAV2 | >AAV2 |
| SEQ ID | ATGGCTGCCGATGGTTATCTTCCAGATTGGCTCGAGGACACTCTCTCTGAAGGAATAAGACAGTGGTGGA |
| NO: 58 | AGCTCAAACCTGGCCCACCACCACCAAAGCCCGCAGAGCGGCATAAGGACGACAGCAGGGGTCTTGTGCT |
| | TCCTGGGTACAAGTACCTCGGACCCTTCAACGGACTCGACAAGGGAGAGCCGGTCAACGAGGCAGACGCC |
| | GCGGCCCTCGAGCACGACAAAGCCTACGACCGGCAGCTCGACAGCGGAGACAACCCGTACCTCAAGTACA |
| | ACCACGCCGACGCGGAGTTTCAGGAGCGCCTTAAAGAAGATACGTCTTTTGGGGGCAACCTCGGACGAGC |
| | AGTCTTCCAGGCGAAAAAGAGGGTTCTTGAACCTCTGGGCCTGGTTGAGGAACCTGTTAAGACGGCTCCG |
| | GGAAAAAAGAGGCCGGTAGAGCACTCTCCTGTGGAGCCAGACTCCTCCTCGGGAACCGGAAAGGCGGGCC |
| | AGCAGCCTGCAAGAAAAAGATTGAATTTTGGTCAGACTGGAGACGCAGACTCAGTACCTGACCCCCAGCC |
| | TCTCGGACAGCCACCAGCAGCCCCCTCTGGTCTGGGAACTAATACGATGGCTACAGGCAGTGGCGCACCA |
| | ATGGCAGACAATAACGAGGGCGCCGACGGAGTGGGTAATTCCTCGGGAAATTGGCATTGCGATTCCACAT |
| | GGATGGGCGACAGAGTCATCACCACCAGCACCCGAACCTGGGCCCTGCCCACCTACAACAACCACCTCTA |
| | CAAACAAATTTCCAGCCAATCAGGAGCCTCGAACGACAATCACTACTTTGGCTACAGCACCCCTTGGGGG |
| | TATTTTGACTTCAACAGATTCCACTGCCACTTTTCACCACGTGACTGGCAAAGACTCATCAACAACAACT |
| | GGGGATTCCGACCCAAGAGACTCAACTTCAAGCTCTTTAACATTCAAGTCAAAGAGGTCACGCAGAATGA |
| | CGGTACGACGACGATTGCCAATAACCTTACCAGCACGGTTCAGGTGTTTACTGACTCGGAGTACCAGCTC |
| | CCGTACGTCCTCGGCTCGGCGCATCAAGGATGCCTCCCGCCGTTCCCAGCAGACGTCTTCATGGTGCCAC |
| | AGTATGGATACCTCACCCTGAACAACGGGAGTCAGGCAGTAGGACGCTCTTCATTTTACTGCCTGGAGTA |
| | CTTTCCTTCTCAGATGCTGCGTACCGGAAACAACTTTACCTTCAGCTACACTTTTGAGGACGTTCCTTTC |
| | CACAGCAGCTACGCTCACAGCCAGAGTCTGGACCGTCTCATGAATCCTCTCATCGACCAGTACCTGTATT |
| | ACTTGAGCAGAACAAACACTCCAAGTGGAACCACCACGCAGTCAAGGCTTCAGTTTTCTCAGGCCGGAGC |
| | GAGTGACATTCGGGACCAGTCTAGGAACTGGCTTCCTGGACCCTGTTACCGCCAGCAGCGAGTATCAAAG |
| | ACATCTGCGGATAACAACAACAGTGAATACTCGTGGACTGGAGCTACCAAGTACCACCTCAATGGCAGAG |
| | ACTCTCTGGTGAATCCGGGCCCGGCCATGGCAAGCCACAAGGACGATGAAGAAAAGTTTTTTCCTCAGAG |
| | CGGGGTTCTCATCTTTGGGAAGCAAGGCTCAGAGAAAACAAATGTGGACATTGAAAAGGTCATGATTACA |
| | GACGAAGAGGAAATCAGGACAACCAATCCCGTGGCTACGGAGCAGTATGGTTCTGTATCTACCAACCTCC |
| | AGAGAGGCAACAGACAAGCAGCTACCGCAGATGTCAACACACAAGGCGTTCTTCCAGGCATGGTCTGGCA |
| | GGACAGAGATGTGTACCTTCAGGGGCCCATCTGGGCAAAGATTCCACACACGGACGGACATTTTCACCCC |
| | TCTCCCCTCATGGGTGGATTCGGACTTAAACACCCTCCTCCACAGATTCTCATCAAGAACACCCCGGTAC |
| | CTGCGAATCCTTCGACCACCTTCAGTGCGGCAAAGTTTGCTTCCTTCATCACACAGTACTCCACGGGACA |
| | GGTCAGCGTGGAGATCGAGTGGGAGCTGCAGAAGGAAAACAGCAAACGCTGGAATCCCGAAATTCAGTAC |
| | ACTTCCAACTACAACAAGTCTGTTAATGTGGACTTTACTGTGGACACTAATGGCGTGTATTCAGAGCCTC |
| | GCCCCATTGGCACCAGATACCTGACTCGTAATCTGTAA |

TABLE 5-continued

Parent AAV Capsid Nucleic Acid Sequences

| Description SEQ ID NO: | Nucleic Acid Sequence |
|---|---|
| DJ<br>SEQ ID<br>NO: 59 | >DJ<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>AATCGGAGAACCTCCCGCAGCCCCCTCAGGTGTGGGATCTCTTACAATGGCTGCAGGCGGTGGCGCACCA<br>ATGGCAGACAATAACGAGGGCGCCGACGGAGTGGGTAATTCCTCGGGAAATTGGCATTGCGATTCCACAT<br>GGATGGGCGACAGAGTCATCACCACCAGCACCCGAACCTGGGCCCTGCCCACCTACAACAACCACCTCTA<br>CAAGCAAATCTCCAACAGCACATCTGGAGGATCTTCAAATGACAACGCCTACTTCGGCTACAGCACCCCC<br>TGGGGGTATTTTGACTTTAACAGATTCCACTGCCACTTTTCACCACGTGACTGGCAGCGACTCATCAACA<br>ACAACTGGGGATTCCGGCCCAAGAGACTCAGCTTCAAGCTCTTCAACATCCAGGTCAAGGAGGTCACGCA<br>GAATGAAGGCACCAAGACCATCGCCAATAACCTCACCAGCACCATCCAGGTGTTTACGGACTCGGAGTAC<br>CAGCTGCCGTACGTTCTCGGCTCTGCC<br>CACCAGGGCTGCCTGCCTCCGTTCCCGGCGGACGTGTTCATGATTCCCCAGTACGGCTACCTAACACTCA<br>ACAACGGTAGTCAGGCCGTGGGACGCTCCTCCTTCTACTGCCTGGAATACTTTCCTTCGCAGATGCTGAG<br>AACCGGCAACAACTTCCAGTTTACTTACACCTTCGAGGACGTGCCTTTCCACAGCAGCTACGCCCACAGC<br>CAGAGCTTGGACCGGCTGATGAATCCTCTGATTGACCAGTACCTGTACTACTTGTCTCGGACTCAAACAA<br>CAGGAGG<br>CACGACAAATACGCAGACTCTGGGCTTCAGCCAAGGTGGGCCTAATACAATGGCCAATCAGGCAAAGAAC<br>TGGCTGCCAGGACCCTGTTACCGCCAGCAGCGAGTATCAAAGACATCTGCGGATAACAACAACAGTGAAT<br>ACTCGTGGACTGGAGCTACCAAGTACCACCTCAATGGGAGAGACTCTCTGGTGAATCCGGGCCCGGCCAT<br>GGCAAGCCACAAGGACGATGAAGAAAAGTTTTTTCCTCAGAGCGGGGTTCTCATCTTTGGGAAGCAAGGC<br>TCAGAGAAAACAAATGTGGACATTGAAAAGGTCATGATTACAGACGAAGAGGAAATCAGGACAACCAATC<br>CCGTGGCTACGGAGCAGTATGGTTCTGTATCTACCAACCTCCAGAGAGGCAACAGACAAGCAGCTACCGC<br>AGATGTCAACACACAAGGCGTTCTTCCAGGCATGGTCTGGCAGGACAGAGATGTGTACCTTCAGGGGCCC<br>ATCTGGGCAAAGATTCCACACACGGACGGACATTTTCACCCCTCTCCCCTCATGGGTGGATTCGGACTTA<br>AACACCCTCCGCCTCAGATCCTGATCAAGAACACGCCTGTACCTGCGGATCCTCCGACCACCTTCAACCA<br>GTCAAAGCTGAACTCTTTCATCACCCAGTATTCTACTGGCCAAGTCAGCGTGGAGATCGAGTGGGAGCTG<br>CAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |
| BOVINE<br>AAV<br>SEQ ID<br>NO: 60 | >bovine<br>ATGTCTTTTGTTGACCACCCTCCAGATTGGTTGGAATCGATCGGCGACGGCTTTCGTGAATTTCTCGGCC<br>TTGAGGCGGGTCCCCCGAAACCCAAGGCCAATCAACAGAAGCAAGATAACGCTCGAGGTCTTGTGCTTCC<br>TGGGTACAAGTATCTTGGTCCTGGGAACGGCCTTGATAAGGGCGATCCTGTCAATTTTGCTGACGAGGTT<br>GCCCGAGAGCACGACCTCTCCTACCAGAAACAGCTTGAGGCGGGCGATAACCCTTACCTCAAGTACAACC<br>ACGCGGACGCAGAGTTTCAGGAGAAACTCGCTTCTGACACTTCTTTTGGGGGAAACCTTGGGAAGGCTGT<br>TTTCCAGGCTAAAAAGAGGATTCTCGAACCTCTTGGCCTGGTTGAGACGCCGGATAAAACGGCGCCTGCG<br>GCAAAAAAGAGGCCTCTAGAGCAGAGTCCTCAAGAGCCAGACTCCTCGAGCGGAGTTGGCAAGAAAGGCA<br>AACAGCCTGCCAGAAAGAGACTCAACTTTGACGACGAACCTGGAGCCGGAGACGGGCCTCCCCCAGAAGG<br>ACCATCTTCCGGAGCTATGTCTACTGAGACTGAAATGCGTGCAGCAGCTGGCGGAAATGGTGGCGATGCG<br>GGACAAGGTGCCGAGGGAGTGGGTAATGCCTCCGGTGATTGGCATTGCGATTCCACTTGGTCAGAGAGCC<br>ACGTCACCACCACCTCAACCCGCACCTGGGTCCTGCCGACCTACAACAACCACCTGTACCTGCGGCTCGG<br>CTCGAGCAACGCCAGCGACACCTTCAACGGATTCTCCACCCCCTGGGGATACTTTGACTTTAACCGCTTC<br>CACTGCCACTTCTCGCCAAGAGACTGGCAAAGGCTCATCAACAACCACTGGGGACTGCGCCCCAAAAGCA<br>TGCAAGTCCGCATCTTCAACATCCAAGTTAAGGAGGTCACGACGTCTAACGGGGAGACGACCGTATCCAA<br>CAACCTCACCAGCACGGTCCAGATCTTTGCGGACAGCACGTACGAGCTCCCGTACGTGATGGATGCAGGT<br>CAGGAGGGCAGCTTGCCTCCTTTCCCCAACGACGTGTTCATGGTGCCTCAGTACGGGTACTGCGGACTGG<br>TAACCGGAGGCAGCTCTCAAAACCAGACAGACAGAAATGCCTTCTACTGTCTGGAGTACTTTCCCAGCCA<br>GATGCTGAGAACCGGAAACAACTTTGAGATGGTGTACAAGTTTGAAAACGTGCCCTTCCACTCCATGTAC<br>GCTCACAGCCAGAGCCTGGATAGGCTGATGAACCCGCTGCTGGACCAGTACCTGTGGGAGCTCCAGTCTA<br>CCACCTCTGGAGGAACTCTCAACCAGGGCAATTCAGCCACCAACTTTGCCAAGCTGACCAAAACAAACTT<br>TTCTGGCTACCGCAAAAACTGGCTCCCGGGGCCCATGATGAAGCAGCAGAGATTCTCCAAGACTGCCAGT<br>CAAAACTACAAGATTCCCCAGGGAAGAAACAACAGTCTGCTCCATTATGAGACCAGAACTACCCTCGACG<br>GAAGATGGAGCAATTTTGCCCCGGGAACGGCCATGGCAACCGCAGCCAACGACGCCACCGACTTCTCTCA<br>GGCCCAGCTCATCTTTGCGGGGCCCAACATCACCGGCAACACCACCACAGATGCCAATAACCTGATGTTC<br>ACTTCAGAAGATGAACTTAGGGCCACCAACCCCCGGGACACTGACCTGTTTGGCCACCTGGCAACCAACC<br>AGCAAAACGCCACCACCGTTCCTACCGTAGACGACGTGGACGGAGTCGGCGTGTACCCGGGAATGGTGTG<br>GCAGGACAGAGACATTTACTACCAAGGGCCCATTTGGGCCAAAATTCCACACACGGATGGACACTTTCAC<br>CCGTCTCCTCTCATTGGCGGATTTGGACTGAAAAGCCCGCCTCCACAAATATTCATCAAAAACACTCCTG<br>TACCCGCCAATCCCGCAACGACCTTCTCTCCGGCCAGAATCAACAGCTTCATCACCCAGTACAGCACCGG<br>ACAGGTGGCTGTCAAAATAGAATGGGAAATCCAGAAGGAGCGGTCCAAGAGATGGAACCCAGAGGTCCAG<br>TTCACGTCCAACTACGGAGCACAGGACTCGCTTCTCTGGGCTCCCGACAACGCCGGAGCCTACAAAGAGC<br>CCAGGGCCATTGGATCCCGATACCTCACCAACCACCTCTAA |
| AAV4<br>SEQ ID<br>NO: 61 | >AAV4<br>ATGACTGACGGTTACCTTCCAGATTGGCTAGAGGACAACCTCTCTGAAGGCGTTCGAGAGTGGTGGGCGC<br>TGCAACCTGGAGCCCCTAAACCCAAGGCAAATCAACAACATCAGGACAACGCTCGGGGTCTTGTGCTTCC |

TABLE 5-continued

| Parent AAV Capsid Nucleic Acid Sequences | |
|---|---|
| Description SEQ ID NO: | Nucleic Acid Sequence |
| | GGGTTACAAATACCTCGGACCCGGCAACGGACTCGACAAGGGGGAACCCGTCAACGCAGCGGACGCGGCA<br>GCCCTCGAGCACGACAAGGCCTACGACCAGCAGCTCAAGGCCGGTGACAACCCCTACCTCAAGTACAACC<br>ACGCCGACGCGGAGTTCCAGCAGCGGCTTCAGGGCGACACATCGTTTGGGGGCAACCTCGGCAGAGCAGT<br>CTTCCAGGCCAAAAAGAGGGTTCTTGAACCTCTTGGTCTGGTTGAGCAAGCGGGTGAGACGGCTCCTGGA<br>AAGAAGAGACCGTTGATTGAATCCCCCCAGCAGCCCGACTCCTCCACGGGTATCGGCAAAAAAGGCAAGC<br>AGCCGGCTAAAAAGAAGCTCGTTTTCGAAGACGAAACTGGAGCAGGCGACGGACCCCCTGAGGGATCAAC<br>TTCCGGAGCCATGTCTGATGACAGTGAGATGCGTGCAGCAGCTGGCGGAGCTGCAGTCGAGGGCGGACAA<br>GGTGCCGATGGAGTGGGTAATGCCTCGGGTGATTGGCATTGCGATTCCACCTGGTCTGAGGGCCACGTCA<br>CGACCACCAGCACCAGAACCTGGGTCTTGCCCACCTACAACAACCACCTCTACAAGCGACTCGGAGAGAG<br>CCTGCAGTCCAACACCTACAACGGATTCTCCACCCCCTGGGGATACTTTGACTTCAACCGCTTCCACTGC<br>CACTTCTCACCACGTGACTGGCAGCGACTCATCAACAACAACTGGGGCATGCGACCCAAAGCCATGCGGG<br>TCAAAATCTTCAACATCCAGGTCAAGGAGGTCACGACGTCGAACGGCGAGACAACGGTGGCTAATAACCT<br>TACCAGCACGGTTCAGATCTTTGCGGACTCGTCGTACGAACTGCCGTACGTGATGGATGCGGGTCAAGAG<br>GGCAGCCTGCCTCCGTTTCCCAACGACGTCTTTATGGTGCCCCAGTACGGCTACTGTGGACTGGTGACCG<br>GCAACACTTCGCAGCAGCAGACTGACAGAAATGCCTTCTACTGCCTGGAGTACTTTCCTTCGCAGATGCT<br>GCGGACTGGCAACAACTTTGAAATTACGTACAGTTTTGAGAAGGTGCCTTTCCACTCGATGTACGCGCAC<br>AGCCAGAGCCTGGACCGGCTGATGAACCCTCTCATCGACCAGTACCTGTGGGGACTGCAATCGACCACCA<br>CCGGAACCACCCTGAATGCCGGGACTGCCACCACCAACTTTACCAAGCTGCGGCCTACCAACTTTTCCAA<br>CTTTAAAAAGAACTGGCTGCCCGGGCCTTCAATCAAGCAGCAGGGCTTCTCAAAGACTGCCAATCAAAAC<br>TACAAGATCCCTGCCACCGGGTCAGACAGTCTCATCAAATACGAGACGCACAGCACTCTGGACGGAAGAT<br>GGAGTGCCCTGACCCCCGGACCTCCAATGGCCACGGCTGGACCTGCGGACAGCAAGTTCAGCAACAGCCA<br>GCTCATCTTTGCGGGGCCTGAACAGAACGGCAACACGGCCACCGTACCCGGGACTCTGATCTTCACCTCT<br>GAGGAGGAGCTGGCAGCCACCAACGCCACCGATACGGACATGTGGGGCAACCTACCTGGCGGTGACCAGA<br>GCAACAGCAACCTGCCGACCGTGGACAGACTGACAGCCTTGGGAGCCGTGCCTGGAATGGTCTGGCAAAA<br>CAGAGACATTTACTACCAGGGTCCCATTTGGGCCAAGATTCCTCATACCGATGGACACTTTCACCCCTCA<br>CCGCTGATTGGTGGGTTTGGGCTGAAACACCCGCCTCCTCAAATTTTTATCAAGAACACCCCGGTACCTG<br>CGAATCCTGCAACGACCTTCAGCTCTACTCCGGTAAACTCCTTCATTACTCAGTACAGCACTGGCCAGGT<br>GTCGGTGCAGATTGACTGGGAGATCCAGAAGGAGCGGTCCAAACGCTGGAACCCCGAGGTCCAGTTTACC<br>TCCAACTACGGACAGCAAAACTCTCTGTTGTGGGCTCCCGATGCGGCTGGGAAATACACTGAGCCTAGGG<br>CTATCGGTACCCGCTACCTCACCCACCACCTGTAA |
| AAV12<br>SEQ ID<br>NO: 62 | >AAV12<br>ATGGCTGCTGACGGTTATCTTCCAGATTGGCTCGAGGACAACCTCTCTGAAGGCATTCGCGAGTGGTGGG<br>CGCTGAAACCTGGAGCTCCACAACCCAAGGCCAACCAACAGCATCAGGACAACGGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAGGCCTACGACAAGCAGCTCGAGCAGGGGGACAACCCGTATCTCAAGTACA<br>ACCACGGCGACGCCGAGTTCCAGCAGCGCTTGGCGACCGACACCTCTTTTGGGGGCAACCTCGGGCGAGC<br>AGTCTTCCAGGCCAAAAAGAGGATTCTCGAGCCTCTGGGTCTGGTTGAAGAGGGCGTTAAAACGGCTCCT<br>GGAAAGAAACGCCCATTAGAAAAGACTCCAAATCGGCCGACCAACCCGGACTCTGGGAAGGCCCCGGCCA<br>AGAAAAAGCAAAAAGACGGCGAACCAGCCGACTCTGCTAGAAGGACACTCGACTTTGAAGACTCTGGAGC<br>AGGAGACGGACCCCCTGAGGGATCATCTTCCGGAGAAATGTCTCATGATGCTGAGATGCGTGCGGCGCCA<br>GGCGGAAATGCTGTCGAGGCGGGACAAGGTGCCGATGGAGTGGGTAATGCCTCCGGTGATTGGCATTGCG<br>ATTCCACCTGGTCAGAGGGCCGAGTCACCACCACCAGCACCCGAACCTGGGTCCTACCCACGTACAACAA<br>CCACCTGTACCTGCGAATCGGAACAACGGCCAACAGCAACACCTACAACGGATTCTCCACCCCCTGGGGA<br>TACTTTGACTTTAACCGCTTCCACTGCCACTTTTCCCCACGCGACTGGCAGCGACTCATCAACAACAACT<br>GGGGACTCAGGCCGAAATCGATGCGTGTTAAAATCTTCAACATACAGGTCAAGGAGGTCACGACGTCAAA<br>CGGCGAGACTACGGTCGCTAATAACCTTACCAGCACGGTTCAGATCTTTGCGGATTCGACGTATGAACTC<br>CCATACGTGATGGACGCCGGTCAGGAGGGGAGCTTTCCTCCGTTTCCCAACGACGTCTTTATGGTTCCCC<br>AATACGGATACTGCGGAGTTGTCACTGGAAAAAACCAGAACCAGACAGACAGAAATGCCTTTTACTGCCT<br>GGAATACTTTCCATCCCAAATGCTAAGAACTGGCAACAATTTTGAAGTCAGTTACCAATTTGAAAAAGTT<br>CCTTTCCATTCAATGTACGCGCACAGCCAGAGCCTGGACAGAATGATGAATCCTTTACTGGATCAGTACC<br>TGTGGCATCTGCAATCGACCACTACCGGAAATTCCCTTAATCAAGGAACAGCTACCACCACGTACGGGAA<br>AATTACCACTGGAGACTTTGC<br>CTACTACAGGAAAAACTGGTTGCCTGGAGCCTGCATTAAACAACAAAAATTTTCAAAGAATGCCAATCAA<br>AACTACAAGATTCCCGCCAGCGGGGGAGACGCCCTTTTAAAGTATGACACGCATACCACTCTAAATGGGC<br>GATGGAGTAACATGGCTCCTGGACCTCCAATGGCAACCGCAGGTGCCGGGGACTCGGATTTTAGCAACAG<br>CCAGCTGATCTTTGCCGG<br>ACCCAATCCGAGCGGTAACACGACCACATCTTCAAACAATTTGTTGTTTACCTCAGAAGAGGAGATTGCC<br>ACAACAAACCCACGAGACACGGACATGTTTGGACAGATTGCAGATAATAATCAAAATGCCACCACCGCCC<br>CTCACATCGCTAACCTGGACGCTATGGGAATTGTTCCCGGAATGGTCTGGCAAAACAGAGACATCTACTA<br>CCAGGGCCCTATTTGGGCCAAGGTCCCTCACACGGACGGACACTTTCACCCTTCGCCGCTGATGGGAGGA<br>TTTGGACTGAAACACCCGCCTCCACAGATTTTCATCAAAAACACCCCCGTACCCGCCAATCCCAATACTA<br>CCTTTAGCGCTGCAAGGATTAATTCTTTTCTGACGCAGTACAGCACCGGACAAGTTGCCGTTCAGATCGA<br>CTGGGAAATTCAGAAGGAGCATTCCAAACGCTGGAATCCCGAAGTTCAATTTACTTCAAACTACGGCACT<br>CAAAATTCTATGCTGTGGGCTCCCGACAATGCTGGCAACTACCACGAACTCCGGGCTATTGGGTCCCGTT<br>TCCTCACCCACCACTTGTAA |

In some embodiments, the variant AAV capsid polypeptides of the invention exhibit increased transduction human pancreatic tissue or human islets as compared to non-variant parent capsid polypeptides. In some embodiments, transduction is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention exhibit increased tropism human pancreatic tissue or human islets as compared to non-variant parent capsid polypeptides. In some embodiments, tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention further exhibit an enhanced neutralization profile as compared to non-variant parent capsid polypeptides. In some embodiments, the variant AAV capsid polypeptides of the invention further exhibit an enhanced neutralization profile against pooled human immunoglobulins as compared to non-variant parent capsid polypeptides. In some embodiments, the neutralization profile is enhanced by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by a reduction in the generation of neutralizing antibodies in a host. In some embodiments, the reduction in generation of neutralizing antibodies is a reduction of about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptide that exhibits an enhanced neutralization profile is selected from the group consisting of AAV-10A1 (SEQ ID NO:1) and AAV-10A3 (SEQ ID NO:2). In some embodiments, the variant AAV capsid polypeptide that exhibits an enhanced neutralization profile is AAV-10A1 (SEQ ID NO:1). In some embodiments, the variant AAV capsid polypeptide that exhibits an enhanced neutralization profile is AAV-10A3 (SEQ ID NO:2).

In some embodiments, the variant AAV capsid polypeptides of the invention further exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow, progenitor cells, induced pluripotent stem cells, and reprogrammed stem cells. In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention further exhibit increased transduction or tropism in one or more non-pancreas human tissues as compared to non-variant parent capsid polypeptides. In some embodiments, the variant AAV capsid polypeptides further exhibit increased transduction in one or more non-pancreas human tissues as compared to a vector encoding non-variant parent capsid polypeptides. In some embodiments, the variant AAV capsid polypeptides further exhibit increased tropism in one or more non-pancreas human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention further exhibit increased transduction or tropism in one or more non-pancreas human tissues as compared to non-variant parent capsid polypeptides. In some embodiments, the variant AAV capsid polypeptides further exhibit increased transduction in one or more non-pancreas human tissues as compared to a vector encoding non-variant parent capsid polypeptides. In some embodiments, the variant AAV capsid polypeptides further exhibit increased tropism in one or more non-pancreas human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptide sequence is selected from the group consisting of AAV-10A1 (SEQ ID NO: 1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13). In some embodiments, the variant AAV capsid polypeptide sequence is selected from the group consisting of AAV-10A1 (SEQ ID NO:1), AAV-10A3 (SEQ ID NO:2), and AAV-18A1 (SEQ ID NO:5). In some embodiments, the variant AAV capsid polypeptides comprise further de novo mutations. In some embodiments, the variant AAV capsid polypeptides exhibit about 99%, about 98%, about 97%, about 96%, about 95%, about 94%, about 93%, about 92%, about 91%, or about 90% identity to non-variant parent capsid polypeptides. In some embodiments, the variant AAV capsid polypeptides exhibit about 99%, about 98%, about 97%, about 96%, about 95%, about 94%, about 93%, about 92%, about 91%, or about 90% identity to AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13). In some embodiments, the variant AAV capsid polypeptides exhibit about 99%, about 98%, about 97%, about 96%, about 95%, about 94%, about 93%, about 92%, about 91%, or about 90% identity to one or more subregions of AAV-10A1 (SEQ ID NO:1), AAV-10A3 (SEQ ID NO:2), and AAV-18A1 (SEQ ID NO:5). In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

The present invention also provides for generating variant AAV capsid polypeptides, such as AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO: 9), AAV-10B7 (SEQ ID NO:10), AAV-18B2 (SEQ ID NO:12), and AAV-18B3 (SEQ ID NO: 13). In some embodiments, the present invention also provides for generating variant AAV capsid polypeptides, such as AAV-10A1 (SEQ ID NO:1), AAV-10A3 (SEQ ID NO:2), and AAV-18A1 (SEQ ID NO:5). These methods employ known techniques of library generation; however, the methods are novel in that they employ replication competent AAV vectors during the variant AAV capsid polypeptide generation (i.e., selection and evolution of the variant AAV capsid polypeptides). The present invention provides methods for generating variant AAV capsid polypeptides, wherein the variant AAV capsid polypeptides exhibit increased transduction or tropism human pancreatic tissue or human islets as compared to non-variant parent capsid polypeptides, the method comprising:

a) generating a library of variant AAV capsid polypeptide genes, wherein said variant AAV capsid polypeptide genes include a plurality of variant AAV capsid polypeptide genes comprising sequences from more than one non-variant parent capsid polypeptide;
b) generating an AAV vector library by cloning said variant AAV capsid polypeptide gene library into AAV vectors, wherein said AAV vectors are replication competent AAV vectors;
c) screening said AAV vector library from b) encoding for variant AAV capsid polypeptides exhibiting increased transduction or tropism human pancreatic tissue or human islets as compared to a non-variant parent capsid polypeptide; and
d) selecting said variant AAV capsid polypeptides from c).

In some embodiments, the method further comprises e) determining the sequence of said variant AAV capsid polypeptides from d).

In some embodiments, the variant AAV capsid polypeptides generated by screening methods of the invention exhibit increased transduction human pancreatic tissue or human islets as compared to a vector encoding non-variant parent capsid polypeptides. In some embodiments, transduction is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention exhibit increased tropism human pancreatic tissue or human islets as compared to a vector encoding non-variant parent capsid polypeptides. In some embodiments, tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention further exhibit an enhanced neutralization profile as compared to a vector encoding non-variant parent capsid polypeptides. In some embodiments, the neutralization profile is enhanced by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by a reduction in the generation of neutralizing antibodies in a host. In some embodiments, the reduction in generation of neutralizing antibodies is a reduction of about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention further exhibit increased transduction or tropism in one or more non-pancreatic human tissues as compared to a vector encoding non-variant parent capsid polypeptides. In some embodiments, the variant AAV capsid polypeptides further exhibit increased transduction in one or more non-pancreatic human tissues as compared to a vector encoding non-variant parent capsid polypeptides. In some embodiments, the variant AAV capsid polypeptides further exhibit increased tropism in one or more non-pancreatic human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention further exhibit increased transduction or tropism in one or more non-pancreatic human tissues as compared to a vector encoding non-variant parent capsid polypeptides. In some embodiments, the variant AAV capsid polypeptides further exhibit increased transduction in one or more non-pancreatic human tissues as compared to a vector encoding non-variant parent capsid polypeptides. In some embodiments, the variant AAV capsid polypeptides further exhibit increased tropism in one or more non-pancreatic human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

Transduction can be measured by techniques known in the art, including, for example, immunofluorescence and flow-cytometry analysis, including those described in Example 2 below, as well as other methods known in the art. In vitro transduction analysis can be performed in human pancreatic tissue or human islet cells, again as described in the art or as described in Examples 1 and 2 below, including for example by measuring GFP expression (or another marker gene) in order to determine transduction. In vivo or ex vivo transduction analysis can be measured by techniques known in the art, including, for example, Firefly luciferase-based assays, again as described in the art or as described in Examples below, including for example by measuring luciferase expression (or another marker gene) in order to determine transduction. In some embodiments, marker expression from an AAV vector packaged with the variant AAV capsid polypeptides is compared to marker expression from an AAV vector packaged with the non-variant parent capsid polypeptides in order to determine changes in transduction efficiency. In some embodiments, the transduction is compared for different cell types in order to determine tropism, i.e., compare transduction from an AAV vector packaged with the variant AAV capsid polypeptide to transduction from an AAV packaged with the non-variant capsid polypeptide in at least two different cell types in order to determine tropism for a particular cell type, sometimes referred to as a tropism profile. In some embodiments, the at least one cell type is from human pancreatic tissue or human islet cells. In some embodiments, the at least one cell type is human alpha-islet cell or beta-islet cell. In some embodiments, at least a second cell type includes but is not limited to blood cells, blood stem cells, liver cells, gonads, germ cells, joint tissue or cells, pancreas (including $\alpha$-islet cells and/or $\beta$-islet cells), spleen tissue or cells, the gastrointestinal tract, lung tissue or cells and/or kidney tissue or cells.

Figure 1:
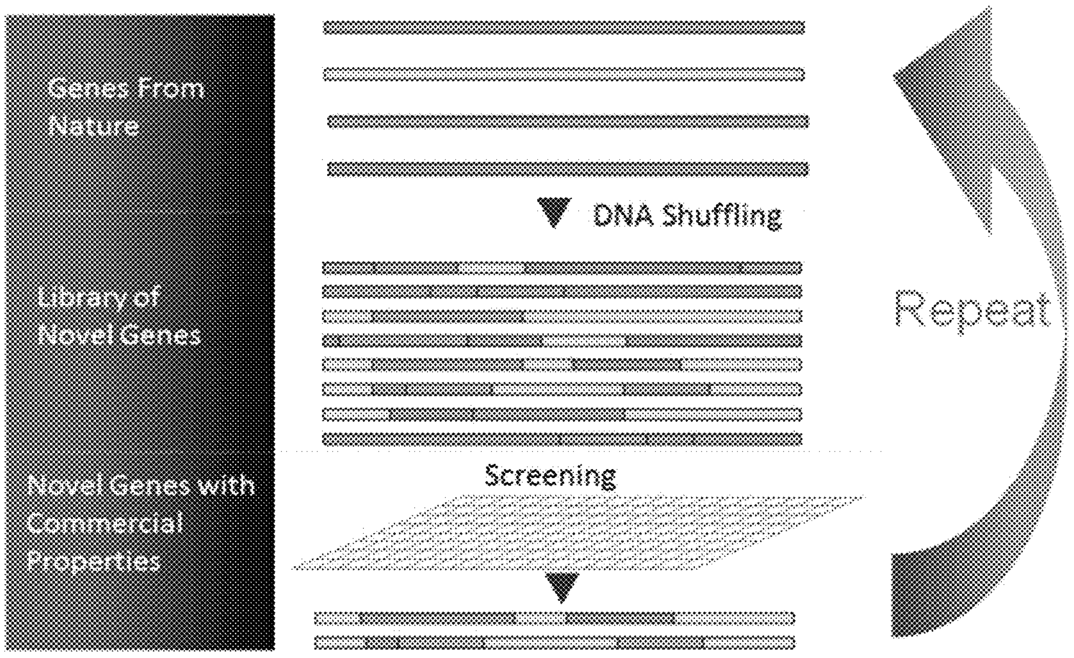
FIG. 1. An illustration for directed molecular evolution.
Figure 3:
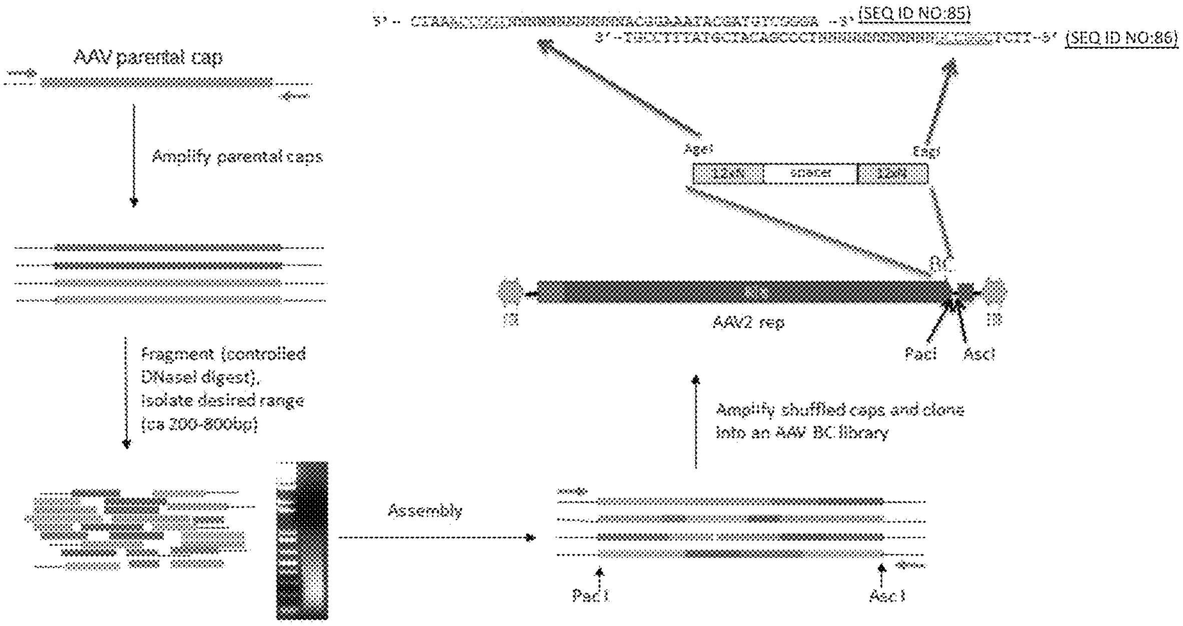
FIG. 3. Generation of barcoded capsid shuffled AAV libraries. Library generation workflow: First, an AAV vector barcode library is generated which was used as backbone for cloning of the shuffled capsid sequences.

Such methods for generating the variant AAV capsid polypeptides include DNA shuffling of capsid proteins, which begins with families of capsid genes from an array or plurality of AAV pseudo-species (for example, AAV1, AAV2, AAV3b, AAV4, AAV5, AAV6, AAV7, AAV8, AAV9, AAV 9_hu14, bovine AAV, avian AAV), that are enzymatically shuffled to create a diverse library of capsid genes that can be cloned back into an AAV shuttle plasmid and utilized to produce live replicating viral libraries (see, for example, FIG. 1 and FIG. 3). To maximize the likelihood that shuffled capsids (i.e., variant AAV capsid polypeptides) could functionally transduce human pancreatic tissue and/or human islets—as compared to non-variant parent capsid polypeptides—the invention contemplates performing two simultaneous screens in primary human intact islets and dissociated human islet cells.

Figure 4:
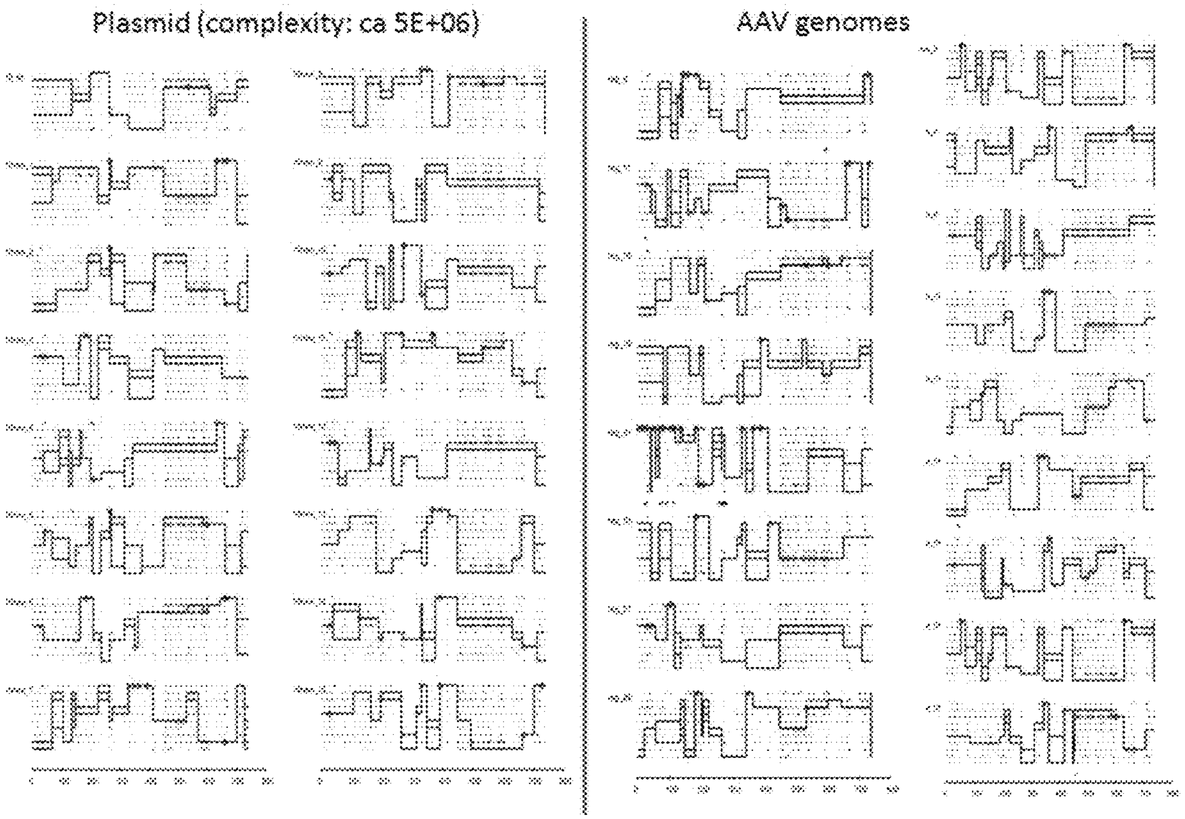
FIG. 4. Crossover analysis of the capsid amino acid sequences in randomly chosen 10 parent library clones on the plasmid and the AAV level. Parental contributions are shown in the following order (top to bottom): po2, AAV1, AAV6, AAV3B, LK03, AAV8, rh10, AAV9hu14, AAV2, DJ.
Figure 10A:
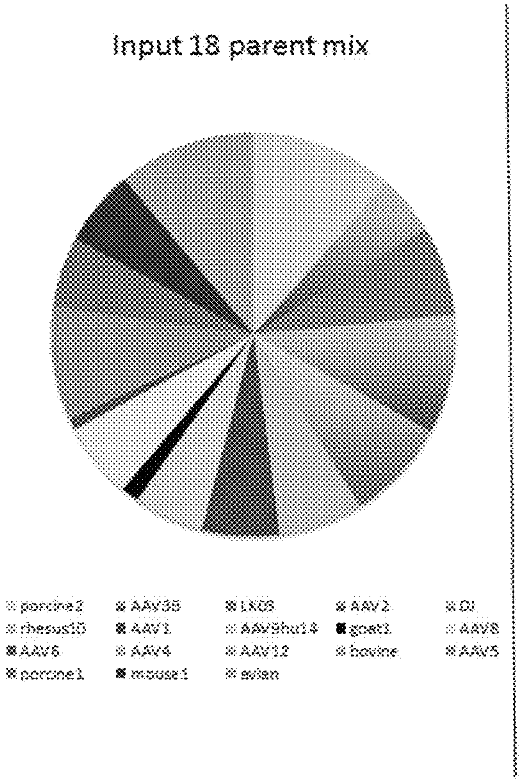
FIG. 10A-10B. Composition of the 18 parent control mix (left) and enrichment for parental cap AAVs during passaging (right). Only the most enriched parental AAVs are shown in the right panel. (A) Composition of the 18 parent pool as determined by NGS BC sequencing. (B) Enrichment of parental AAVs through three consecutive passages of the 18 parent mix on intact islets and on dissociated islet.
Figure 10B:
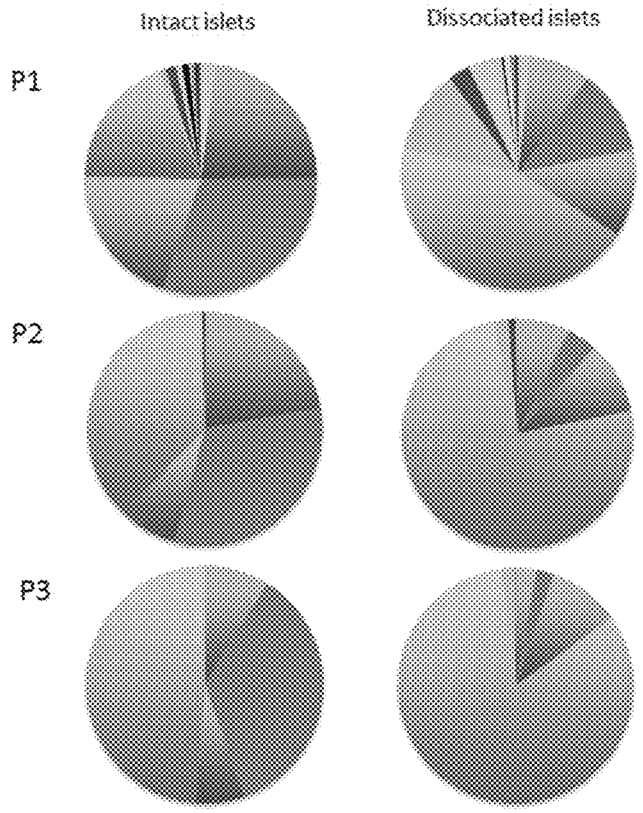
Figure 21:
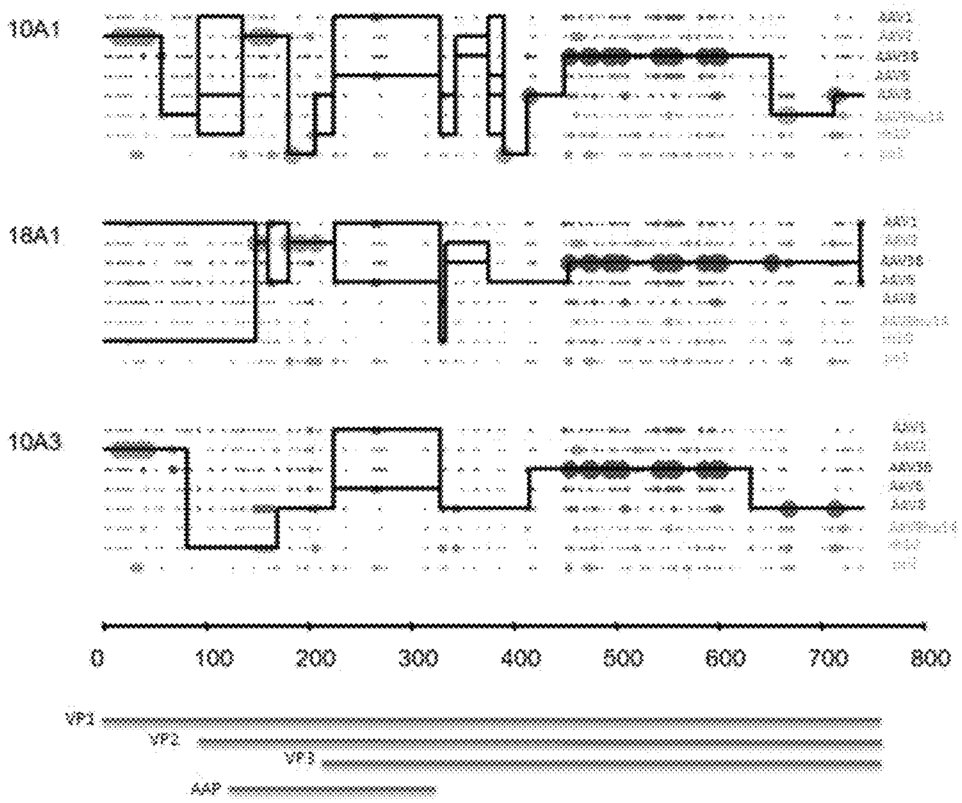
FIG. 21. Composition of the best capsid variants (crossover, amino acids). Library parents are depicted in different colors in order of entry of the parents. Large dots represent 100% parental match (i.e. the position in question matches only one parent) and small dots represent more than one parental match (i.e. the position matches more than one parent) at each position. The solid line for each chimera represents the library parents identified within the sequence between crossovers. A set of thin horizontal parallel lines between crossovers indicates multiple parents match at an equal probability.
Figure 22:
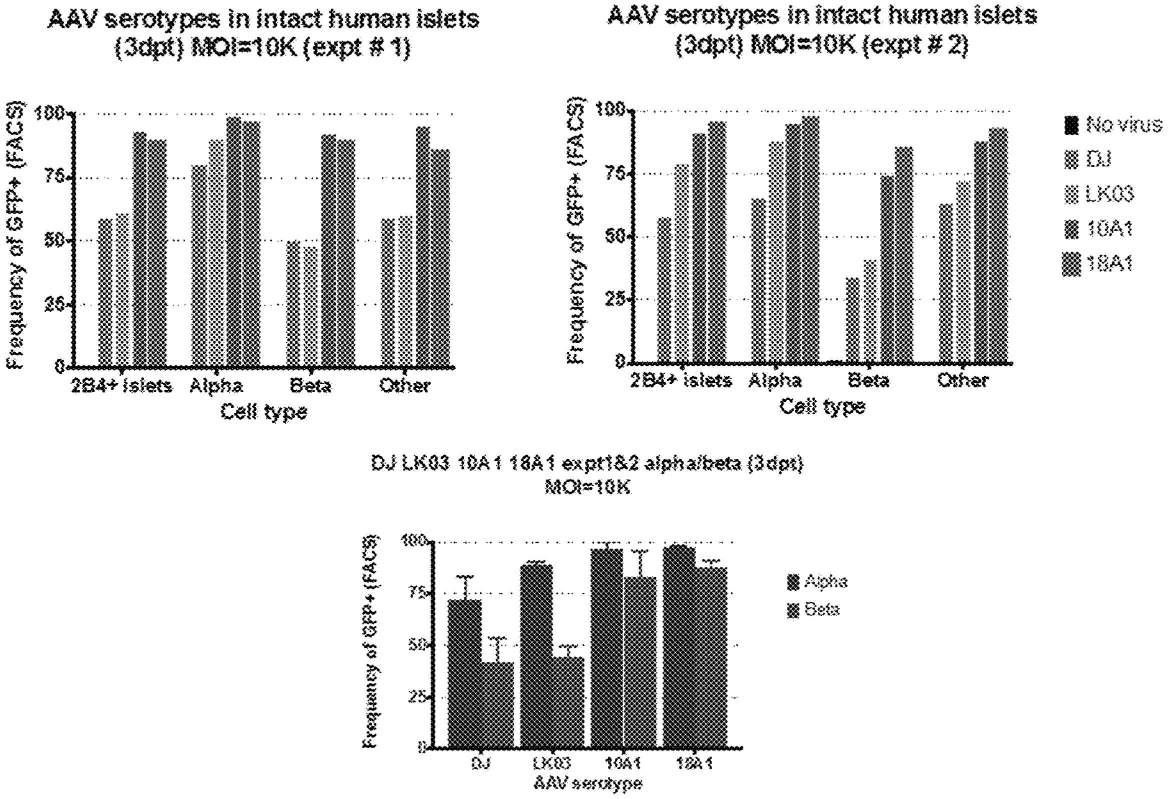
FIG. 22. 10A1 and 18A1 transduce β-cells significantly better than LK03.
Figure 23:
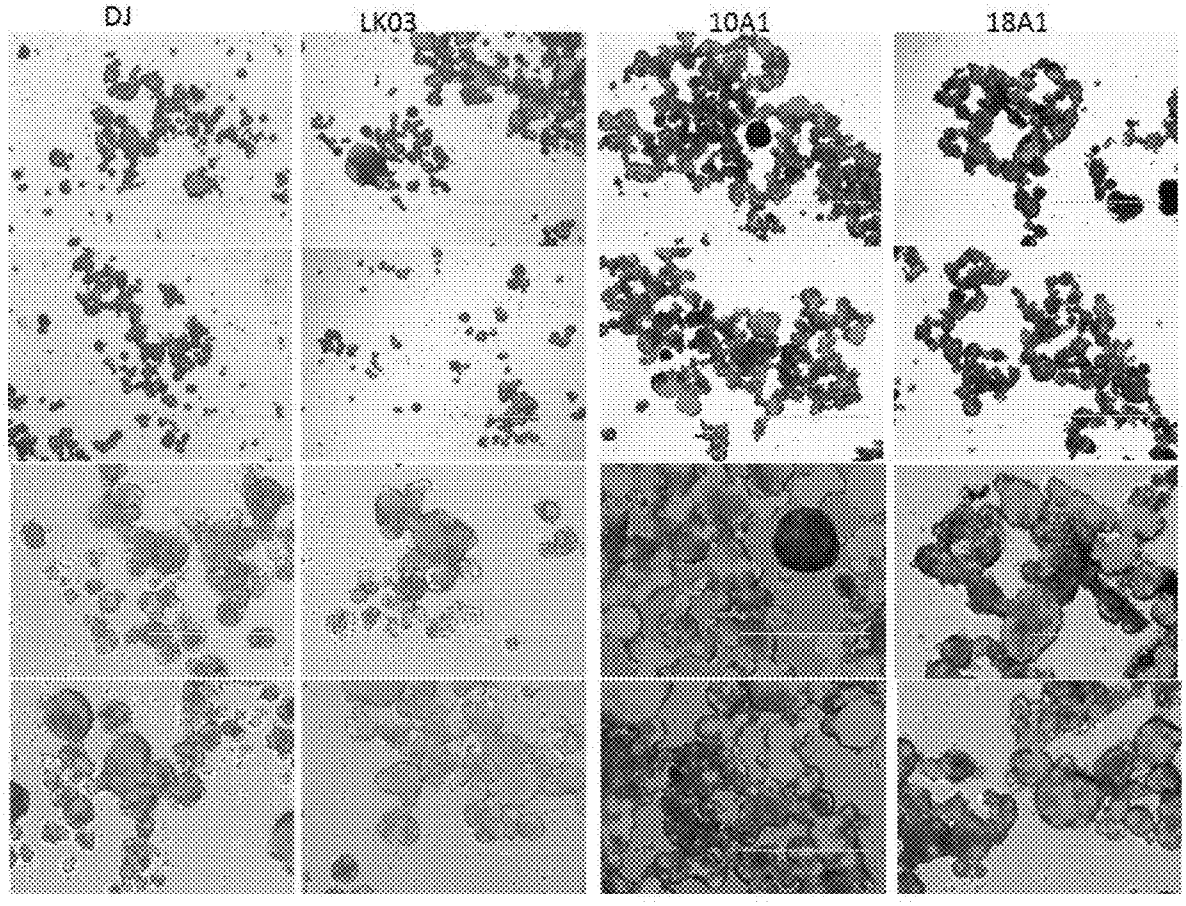
FIG. 23. Grompe Transduction of islets. Intact whole islets were transduced at MOI=10K on ice for 1-2 hours (2% FBS/CMRL) and suspended in culture for 3 days.

At the completion of both screens, variants are chosen from each screen for full Sanger sequencing and phylogenetic comparisons to parental serotypes (i.e., parental non-variant capsid polypeptide sequences). In some embodiments, the parental non-variant capsid polypeptide sequences are those that went into the initial library. The most highly selected variants (for example, those that exhibit the highest increase in transduction and/or tropism) from each screen are isolated and vectorized with expression constructs, in some cases for use in subsequent validation experiments. In some embodiments, in order to assess the genetic contribution of each parental AAV serotype (i.e., non-variant parent capsid polypeptide) to the evolved capsids (i.e., variant AAV capsid polypeptides) selected from each screen, crossover mapping can be performed (see, for example, FIG. 4 and FIG. 21) and bioinformatic prediction analyses (see, for example, FIG. 10 and FIG. 11) to calculate enrichment scores for likelihood of parental (i.e., non-variant parent capsid polypeptide) contribution to each position in the new capsids (i.e., variant AAV capsid polypeptides). Both methodologies demonstrated the highly shuffled nature of the evolved capsid variants and highlighted both unique and shared domains present in selected capsids. In some embodiments, the parental capsids (i.e., non-variant parent capsid polypeptides) that contribute the most to the evolved variants include AAV-10A1 (SEQ ID NO:1), AAV-10A3 (SEQ ID NO:2), and AAV-18A1 (SEQ ID NO:5).

In vitro characterizations are used to demonstrate the significant increase in transduction by variant AAV capsid polypeptides over control serotypes (i.e., non-variant parent capsid polypeptides) in various pancreas-derived cell lines.

For such analyses, large-scale ultrapure productions of AAV vectorized variants (AAV vectors composed of variant AAV capsid polypeptides) can be carried out and those capable of producing high titers sufficient for eventual clinical use (for example, variants AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13), and in particular variants AAV-10A1 (SEQ ID NO:1), AAV-10A3 (SEQ ID NO:2), and AAV-18A1 (SEQ ID NO:5) are considered further for validation.

In order to examine the activity of the AAV vectors encoding the variant AAV capsid polypeptides of the invention, further validation can be performed using ex vivo human pancreatic tissue. Ex vivo human pancreas explant transductions are employed to validate the significantly increased expression in human pancreatic tissue specifically. Samples for use in ex vivo analyses and/or assays can include but are not limited to human pancreas isolation from surgical specimens. Such human pancreas specimens can be obtained from both male and female patients by surgical isolation. Samples for use in ex vivo analyses and/or assays can include but are not limited to non-human pancreas isolation In some embodiments, human pancreas or islets can be used for in vitro analyses and/or assays.

While chimeric humanized pancreas xenografts are powerful tools to model human-like in vivo systems, they are limited in their ability to truly define expected transduction in human patients given the continued presence of mouse cells, as well as the chimeric nature of the fusion products which express both mouse and human protein simultaneously. In some embodiments, islets harvested from deceased organ donors can be treated with rAAV expressing certain transcription factors prior to transplantation into patients. Islet transplantation has been done as treatment for Type 1 diabetes for many years, and is a procedure well-known by those in the art. In some embodiments, islets harvested from deceased organ donors can be treated with the rAAV vectors of the present invention as described herein.

In some embodiments, increased transduction of AAV vectors encoding variant parent capsid polypeptides are exhibited in both dividing and non-dividing human pancreatic cell types. In some embodiments, increased transduction of AAV vectors encoding variant parent capsid polypeptides are exhibited in dividing pancreatic cells. In some embodiments, increased transduction of AAV vectors encoding variant parent capsid polypeptides are exhibited in non-dividing pancreatic cells with long-term transgene expression.

AAV Vector Elements

The nucleic acid insert (also referred to as a heterologous nucleotide sequence) can be operably linked to control elements directing the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, can also be used. Such promoter sequences are commercially available from, e.g., Stratagene (San Diego, Calif.).

In some embodiments, a cell type-specific or a tissue-specific promoter can be operably linked to nucleic acid insert (also referred to as a heterologous nucleotide sequence) encoding the heterologous gene product, and allowing for selectively or preferentially producing a gene product in a particular cell type(s) or tissue(s). In some embodiments, an inducible promoter can be operably linked to the heterologous nucleic acid.

In some embodiments, the nucleic acid is packaged with the variant AAV capsid polypeptides of the invention. In some embodiments, the nucleic acid insert or packaged nucleic acid is at least 50, 100, 200, 300, 400, 500, 600, 700, 800, 900, 1000, 1100, 1200, 1300, 1400, or 1500 nucleic acids in length. In some embodiments, the nucleic acid insert or packaged nucleic acid is at least 50 nucleic acids to at least 1500 nucleic acids. In some embodiments, the nucleic acid insert or packaged nucleic acid is at least 100 nucleic acids to at least 1400 nucleic acids. In some embodiments, the nucleic acid insert or packaged nucleic acid is at least 200 nucleic acids to at least 1100 nucleic acids. In some embodiments, the nucleic acid insert or packaged nucleic acid is at least 300 nucleic acids to at least 1000 nucleic acids. In some embodiments, the nucleic acid insert or packaged nucleic acid is at least 100 nucleic acids to at least 900 nucleic acids. In some embodiments, the nucleic acid insert or packaged nucleic acid is at least 200 nucleic acids to at least 900 nucleic acids. In some embodiments, the nucleic acid insert or packaged nucleic acid is at least 300 nucleic acids to at least 900 nucleic acids. In some embodiments, the nucleic acid insert or packaged nucleic acid is at least 100 nucleic acids to at least 600 nucleic acids.

In some embodiments, the AAV vector packaged by the variant AAV capsid polypeptides is at least about 2000 nucleic acids in total length and up to about 5000 nucleic acids in total length. In some embodiments, the AAV vector packaged by the variant AAV capsid polypeptides is about 2000 nucleic acids, about 2400 nucleic acids, about 2800 nucleic acids, about 3000 nucleic acids, about 3200 nucleic acids, about 3400 nucleic acids, about 3600 nucleic acids, about 3800 nucleic acids, about 4000 nucleic acids, about 4200 nucleic acids, about 4400 nucleic acids, about 4600 nucleic acids, about 4700 nucleic acids, or about 4800 nucleic acids. In some embodiments, the AAV vector packaged by the variant AAV capsid polypeptides is between about 2000 nucleic acids (2 kb) and about 5000 nucleic acids (5 kb). In some embodiments, the AAV vector packaged by the variant AAV capsid polypeptides is between about 2400 nucleic acids (2.4 kb) and about 4800 nucleic acids (4.8 kb). In some embodiments, the AAV vector packaged by the variant AAV capsid polypeptides is between about 3000 nucleic acids (3 kb) and about 5000 nucleic acids (5 kb). In some embodiments, the AAV vector packaged by the variant AAV capsid polypeptides is between about 3000 nucleic acids (3 kb) and about 4000 nucleic acids (4 kb).

The AAV vectors or AAV virions disclosed herein can also include conventional control elements operably linked to the nucleic acid insert (also referred to as a heterologous nucleotide sequence) in a manner permitting transcription, translation and/or expression in a cell transfected with the AAV vector or infected with the AAV virion produced according to the present invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters selected from native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al., Cell, 41:521-530 (1985)), the SV40 promoter, the dihydrofolate reductase promoter, the beta-actin promoter, the phosphoglycerol kinase (PGK) promoter, and the EF1 promoter (Invitrogen). Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clonetech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., (1996) *Proc. Natl. Acad. Sci. USA,* 93:3346-3351), the tetracycline-repressible system (Gossen et al., (1992) *Proc. Natl. Acad. Sci. USA,* 89:5547-5551), the tetracycline-inducible system (Gossen et al., (1995) *Science,* 268:1766-1769, see also Harvey et al., (1998) *Curr. Opin. Chem. Biol.,* 2:512-518), the RU486-inducible system (Wang et al., (1997) *Nat. Biotech.,* 15:239-243 and Wang et al., (1997) *Gene Ther.,* 4:432-441) and the rapamycin-inducible system (Magari et al., (1997) *J Clin. Invest.,* 100:2865-2872). Other types of inducible promoters useful in this context are those regulated by a specific physiological state, e.g., temperature, acute phase, a particular differentiation state of the cell, or in replicating cells only.

In another embodiment, the native promoter for the nucleic acid insert (also referred to as a heterologous nucleotide sequence) will be used. The native promoter may be preferred when it is desired that expression of the nucleic acid insert (also referred to as a heterologous nucleotide sequence) should mimic the native expression. The native promoter may be used when expression of the nucleic acid insert (also referred to as a heterologous nucleotide sequence) must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the nucleic acid insert (also referred to as a heterologous nucleotide sequence) includes a gene operably linked to a tissue-specific promoter. For instance, if expression in pancreas is desired, a promoter active in pancreas should be used. These include the promoters from genes encoding skeletal β-actin, myosin light chain 2A, dystrophin, and muscle creatine kinase with activities higher than naturally-occurring promoters (see Li et al., Nat. Biotech., 17:241-245 (1999)). Examples of promoters that are tissue-specific are known for liver (albumin, Miyatake et al., (1997) *J Virol.,* 71:5124-32; hepatitis B virus core promoter, Sandig et al., (1996) *Gene Ther.,* 3:1002-9; alpha-fetoprotein (AFP), Arbuthnot et al., (1996) *Hum. Gene Ther.,* 7:1503-14), bone osteocalcin (Stein et al., (1997) *Mol. Biol. Rep.,* 24:185-96); bone sialoprotein (Chen et al., (1996) *J. Bone Miner. Res.,* 11:654-64), lymphocytes (CD2, Hansal et al., (1998) *J. Immunol.,* 161:1063-8; immunoglobulin heavy chain; T cell receptor chain), neuronal such as neuron-specific enolase (NSE) promoter (Andersen et al., (1993) *Cell. Mol. Neurobiol.,* 13:503-15), neurofilament light-chain gene (Piccioli et al., (1991) *Proc. Natl. Acad. Sci. USA,* 88:5611-5), and the neuron-specific vgf gene (Piccioli et al., (1995) *Neuron,* 15:373-84), among others.

In various embodiments, AAV vectors or AAV virions carrying one or more therapeutically useful nucleic acid inserts (also referred to as a heterologous nucleotide sequence) also include selectable markers or reporter genes, e.g., sequences encoding geneticin, hygromycin or puromycin resistance, among others. Selectable reporters or marker genes can be used to signal the presence of the plasmids/vectors in bacterial cells, including, for example, examining ampicillin resistance. Other components of the plasmid may include an origin of replication. Selection of these and other promoters and vector elements are conventional and many such sequences are available (see, e.g., Sambrook et al., and references cited therein).

Host Cells and Packaging

Host cells are necessary for generating infectious AAV vectors as well as for generating AAV virions based on the disclosed AAV vectors. Accordingly, the present invention provides host cells for generation and packaging of AAV virions based on the AAV vectors of the present invention.

A variety of host cells are known in the art and find use in the methods of the present invention. Any host cells described herein or known in the art can be employed with the compositions and methods described herein.

The present invention provides host cells, e.g., isolated (genetically modified) host cells, comprising a subject nucleic acid. A subject host cell can be an isolated cell, e.g., a cell in in vitro culture. A subject host cell is useful for producing a subject AAV vector or AAV virion, as described below. Where a subject host cell is used to produce a subject AAV virion, it is referred to as a "packaging cell." In some embodiments, a subject host cell is stably genetically modified with a subject AAV vector. In other embodiments, a subject host cell is transiently genetically modified with a subject AAV vector.

In some embodiments, a subject nucleic acid is introduced stably or transiently into a host cell, using established techniques, including, but not limited to, electroporation, calcium phosphate precipitation, liposome-mediated transfection, baculovirus infection, and the like. For stable transformation, a subject nucleic acid will generally further include a selectable marker, e.g., any of several well-known selectable markers such as neomycin resistance, and the like.

Generally, when delivering the AAV vector according to the present invention by transfection, the AAV vector is delivered in an amount from about 5 μg to about 100 μg DNA, about 10 to about 50 μg DNA to about $1\times10^4$ cells to about $1\times10^{13}$ cells, or about $1\times10^5$ cells. However, the relative amounts of vector DNA to host cells may be adjusted, taking into consideration such factors as the selected vector, the delivery method and the host cells selected and such adjustments are within the level of skill of one in the art.

In some embodiments, the host cell for use in generating infectious virions can be selected from any biological organism, including prokaryotic (e.g., bacterial) cells, and eukaryotic cells, including, insect cells, yeast cells and mammalian cells. A subject host cell is generated by introducing a subject nucleic acid (i.e., AAV vector) into any of a variety of cells, e.g., mammalian cells, including, e.g., murine cells, and primate cells (e.g., human cells). Particularly desirable host cells are selected from among any mammalian species. In some embodiments, cells include without limitation, cells such as A549, WEHI, 10T1/2, BHK, MDCK, COS 1, COS 7, BSC 1, BSC 40, BMT 10, W138, HeLa, CHO, 293, Vero, NIH 3T3, PC12, Huh-7 Saos, C2C12, RAT1, Sf9, L cells, HT1080, human embryonic kidney (HEK), human embryonic stem cells, human adult tissue stem cells, pluripotent stem cells, induced pluripotent stem cells, reprogrammed stem cells, organoid stem cells, bone marrow stem cells, HLHepG2, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirement for the cell used is it is capable of infection or transfection by an AAV vector. In some embodiments, the host cell is one that has Rep and Cap stably transfected in the cell, including in some embodiments a variant AAV capsid polypeptide as described herein. In some embodiments, the host cell expresses a variant AAV capsid polypeptide of the invention or part of an AAV vector as described herein, such as a heterologous nucleic acid sequence contained within the AAV vector.

In some embodiments, the preparation of a host cell according to the invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods providing the desired nucleotide sequence.

In some embodiments, introduction of the AAV vector into the host cell may also be accomplished using techniques known to the skilled artisan and as discussed throughout the specification. In a preferred embodiment, standard transfection techniques are used, e.g., $CaPO_4$ transfection or electroporation, and/or infection by hybrid adenovirus/AAV vectors into cell lines such as the human embryonic kidney cell line HEK293 (a human kidney cell line containing functional adenovirus E1 genes providing trans-acting E1 proteins).

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV Rep proteins. In other embodiments, a subject host cell further comprises an AAV vector. An AAV virion can be generated using a subject host cell. Methods of generating an AAV virion are described in, e.g., U.S. Patent Publication No. 2005/0053922 and U.S. Patent Publication No. 2009/0202490.

In addition to the AAV vector, in exemplary embodiments, the host cell contains the sequences driving expression of the AAV capsid polypeptide (including variant AAV capsid polypeptides and non-variant parent capsid polypeptides) in the host cell and Rep sequences of the same serotype as the serotype of the AAV Inverted Terminal Repeats (ITRs) found in the nucleic acid insert (also referred to as a heterologous nucleotide sequence), or a cross-complementing serotype. The AAV Cap and Rep sequences may be independently obtained from an AAV source and may be introduced into the host cell in any manner known to one of skill in the art or as described herein. Additionally, when pseudotyping an AAV vector in an AAV8 capsid for example, the sequences encoding each of the essential Rep proteins may be supplied by AAV8, or the sequences encoding the Rep proteins may be supplied by different AAV serotypes (e.g., AAV1, AAV2, AAV3, AAV4, AAV5, AAV6, AAV7, and/or AAV9).

In some embodiments, the host cell stably contains the capsid protein under the control of a suitable promoter (including, for example, the variant AAV capsid polypeptides of the invention), such as those described above. In some embodiments, the capsid protein is expressed under the control of an inducible promoter. In some embodiments, the capsid protein is supplied to the host cell in trans. When delivered to the host cell in trans, the capsid protein may be delivered via a plasmid containing the sequences necessary to direct expression of the selected capsid protein in the host cell. In some embodiments, when delivered to the host cell in trans, the vector encoding the capsid protein (including, for example, the variant AAV capsid polypeptides of the invention) also carries other sequences required for packaging the AAV, e.g., the Rep sequences.

In some embodiments, the host cell stably contains the Rep sequences under the control of a suitable promoter, such as those described above. In some embodiments, the essential Rep proteins are expressed under the control of an inducible promoter. In another embodiment, the Rep proteins are supplied to the host cell in trans. When delivered to the host cell in trans, the Rep proteins may be delivered via a plasmid containing the sequences necessary to direct expression of the selected Rep proteins in the host cell. In some embodiments, when delivered to the host cell in trans, the vector encoding the capsid protein (including, for example, the variant AAV capsid polypeptides of the invention) also carries other sequences required for packaging the AAV vector, e.g., the Rep sequences.

In some embodiments, the Rep and Cap sequences may be transfected into the host cell on a single nucleic acid molecule and exist stably in the cell as an unintegrated episome. In another embodiment, the Rep and Cap sequences are stably integrated into the chromosome of the cell. Another embodiment has the Rep and Cap sequences transiently expressed in the host cell. For example, a useful nucleic acid molecule for such transfection comprises, from 5' to 3', a promoter, an optional spacer interposed between the promoter and the start site of the Rep gene sequence, an AAV Rep gene sequence, and an AAV Cap gene sequence.

Although the molecule(s) providing Rep and capsid can exist in the host cell transiently (i.e., through transfection), in some embodiments, one or both of the Rep and capsid proteins and the promoter(s) controlling their expression be stably expressed in the host cell, e.g., as an episome or by integration into the chromosome of the host cell. The methods employed for constructing embodiments of the invention are conventional genetic engineering or recombinant engineering techniques such as those described in the references above.

In some embodiments, the packaging host cell can require helper functions in order to package the AAV vector of the invention into an AAV virion. In some embodiments, these functions may be supplied by a herpesvirus. In some embodiments, the necessary helper functions are each provided from a human or non-human primate adenovirus source, and are available from a variety of sources, including the American Type Culture Collection (ATCC), Manassas, Va. (US). In some embodiments, the host cell is provided with and/or contains an E1a gene product, an E1b gene product, an E2a gene product, and/or an E4 ORF6 gene product. In some embodiments, the host cell may contain other adenoviral genes such as VAI RNA. In some embodiments, no other adenovirus genes or gene functions are present in the host cell.

Heterologous Nucleic Acid, Nucleic Acid Gene Products, and Polypeptide Gene Products In various embodiments, the invention provides variant AAV capsid polypeptides capable of forming capsids capable of packaging a variety of therapeutic molecules, including nucleic acids and polypeptides. In some embodiments, the therapeutic molecule is a vaccine. In various embodiments, the invention provides for AAV vectors capable of containing nucleic acid inserts, including for example, transgene inserts or other nucleic acid inserts. This allows for vectors capable of expressing polypeptides. Such nucleic acids can comprise heterologous nucleic acid, nucleic acid gene products, and polypeptide gene products. Features of the nucleic acid inserts are described below.

In some embodiments, the AAV vectors described herein contain nucleic acid inserts. In some embodiments, the nucleic acid insert includes but is not limited to nucleic acid sequences selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the expression cassette is a CRISPR/CAS expression system.

In some embodiments, a nucleic acid insert comprises a heterologous nucleic acid comprising a nucleotide sequence encoding a heterologous gene product, e.g., a nucleic acid gene product or a polypeptide gene product. In some embodiments, the gene product is an interfering RNA (e.g., shRNA, siRNA, miRNA). In some embodiments, the gene product is an aptamer. The gene product can be a self-complementary nucleic acid. In some embodiments, the gene product is a polypeptide.

Suitable heterologous gene product includes interfering RNA, antisense RNA, ribozymes, and aptamers. Where the gene product is an interfering RNA (RNAi), suitable RNAi include RNAi that decrease the level of a target polypeptide in a cell.

In some embodiments, exemplary polypeptides, nucleic acids, or other therapeutic molecules include those useful in the treatment of pancreatic tissue related diseases. Exemplary pancreatic tissue related diseases include but are not limited to diabetes mellitus (e.g. Type I and Type II), acute pancreatitis, chronic pancreatitis, hereditary pancreatitis, autoimmune pancreatitis, pancreatic cancer (e.g. pancreatic adenocarcinoma, acinar cell carcinoma of the pancreas, cystadenocarcinomas, pancreatoblastoma, pancreatic mucinous cystic neoplasms, etc.), pancreatic benign tumors (e.g. pancreatic serous cystadenoma, solid pseudopapillary tumor of the pancreas, etc.), pancreatic neuroendocrine tumor, cystic fibrosis, exocrine pancreatic insufficiency (EPI), pancreatic pseudocyst, pancreatic cyst, Shwachman-Diamond syndrome, Johanson-Blizzard syndrome, Common Channel syndrome, Zollinger-Ellison syndrome, choledochal cyst, Hemosuccus pancreaticus, and congenital pancreatic abnormalities (e.g. Pancreas divisum, Annular Pancreas, ectopic pancreatic tissue).

In some embodiments, exemplary polypeptides include neuroprotective polypeptides and anti-angiogenic polypeptides. Suitable polypeptides include, but are not limited to, glial derived neurotrophic factor (GDNF), fibroblast growth factor 2 (FGF-2), nurturin, ciliary neurotrophic factor (CNTF), nerve growth factor (NGF; e.g., nerve growth factor-.beta.), brain derived neurotrophic factor (BDNF), neurotrophin-3 (NT-3), neurotrophin-4 (NT-4), neurotrophin-6 (NT-6), epidermal growth factor (EGF), pigment epithelium derived factor (PEDF), a Wnt polypeptide, soluble Flt-1, angiostatin, endostatin, VEGF, an anti-VEGF antibody, a soluble VEGFR, Factor VIII (FVIII), Factor IX (FIX), and a member of the hedgehog family (sonic hedgehog, Indian hedgehog, and desert hedgehog, etc.).

In some embodiments, useful therapeutic products encoded by the heterologous nucleic acid sequence include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor alpha superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

In some embodiments, useful heterologous nucleic acid sequence products include proteins that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors alpha and beta., interferons (alpha, beta, and gamma), stem cell factor, flk-2/flt3 ligand. Gene products produced by the immune system are also useful in the present invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

In some embodiments, useful heterologous nucleic acid sequence products include any one of the receptors for the hormones, growth factors, cytokines, lymphokines, regulatory proteins and immune system proteins. Useful heterologous nucleic acid sequences also include receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses the use of gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP-2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

In some embodiments, useful heterologous nucleic acid sequence products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes useful in enzyme replacement therapy, and which are useful in a variety of conditions resulting from deficient activity of enzyme. For example, enzymes containing mannose-6-phosphate may be utilized in therapies for lysosomal storage diseases (e.g., a suitable gene includes that encoding 0-glucuronidase (GUSB)).

In some embodiments, useful heterologous nucleic acid sequence products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 (Wood et al., (1984) *Nature,* 312:330; Vehar et al., (1984) *Nature* 312:337; and Toole et al., (1984) *Nature,* 342:337). Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, releasing the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, used to reduce overexpression of a target.

In some embodiments, the present invention provides methods for treatment of a stem cell disorder, for example a disorder in either bone marrow stem cells or adult tissue stem cells (i.e., somatic stem cells). In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, the disorder for treatment is a disorder in any one or more organoid stem cells (i.e., stem cells derived from any organ or organ system of interest within the body). In some embodiments, the treatment is in vivo (for example, administration of the variant AAV capsid polypeptides is directly to the subject). In some embodiments, the treatment is ex vivo (for example, administration of the variant AAV capsid polypeptides is to stem cells isolated from the subject and the treated stem cells are then returned to the subject).

Reduction and/or modulation of expression of a heterologous nucleic acid sequence is particularly desirable for treatment of hyperproliferative conditions characterized by hyperproliferating cells, such as cancers and psoriasis. Target polypeptides include those polypeptides produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are used as target antigens for autoimmune disease. Other tumor-associated polypeptides can be used as target polypeptides such as polypeptides found at higher levels in tumor cells including the polypeptide recognized by monoclonal antibody 17-1A and folate binding polypeptides.

In some embodiments, suitable therapeutic polypeptides and proteins include those useful for treating individuals suffering from autoimmune diseases and disorders by conferring a broad based protective immune response against targets that are associated with autoimmunity including cell receptors and cells producing "self"-directed antibodies. T cell mediated autoimmune diseases include Rheumatoid arthritis (RA), multiple sclerosis (MS), Sjogren's syndrome, sarcoidosis, insulin-dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T-cell receptors (TCRs) that bind to endogenous antigens and initiate the inflammatory cascade associated with autoimmune diseases.

In some embodiments, heterologous nucleic acid sequences encode for immunogens useful to immunize (i.e., useful as, for example, a vaccine) a human or non-human animal against other pathogens including bacteria, viruses, fungi, parasitic microorganisms or multicellular parasites infecting human and non-human vertebrates, or from a cancer cell or tumor cell. Examples of bacterial pathogens include pathogenic gram-positive cocci include pneumococci; staphylococci (and the toxins produced thereby, e.g., enterotoxin B); and streptococci. Pathogenic gram-negative cocci include meningococcus; gonococcus. Pathogenic enteric gram-negative bacilli include enterobacteriaceae; *pseudomonas*, acinetobacteria and eikenella; melioidosis; *salmonella; shigella; haemophilus; moraxella; H. ducreyi* (causes chancroid); *brucella* species (brucellosis); *Francisella tularensis* (causes tularemia); *Yersinia pestis* (plague) and other *Yersinia* (*pasteurella*); *Streptobacillus moniliformis* and spirillum; Gram-positive bacilli include *Listeria monocytogenes*; Erysipelothrix rhusiopathiae; *Corynebacterium diphtheria* (causes diphtheria); cholera; *Bacillus. anthracia* (causes anthrax); donovanosis (granuloma inguinale; caused by *Klebsiella granulomatis*); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever; Rocky Mountain spotted fever; Q fever (*Coxiella burnetti*); and Rickettsialpox. Examples of *mycoplasma* and chlamydial infections include: *Mycoplasma pneumoniae*; lymphogranuloma venereum (caused by *Chlamydia trachomatis*); psittacosis; and perinatal chlamydial infections. Pathogenic eukaryotes encompassing pathogenic protozoans and helminths and infections produced thereby include: amebiasis (caused by *Entamoeba hisioltytica*); malaria (caused by *Plasmodium*); Leishmaniasis (caused by *Leishmania*); trypanosomiasis (caused by *Trypanosoma*); toxoplasmosis (caused by *Toxoplasma gondii*); *Pneumocystis carinii*; babesiosis (caused by *Babesia*); giardiasis (caused by *Giardia lamblia*); trichinosis (caused by roundworms of the genus *Trichinella*); filariasis (caused by roundworms of Filarioidea); schistosomiasis (carried by fresh water snails infected with one of the five varieties of the parasite *Schistosoma*); nematodes (Nematoda); trematodes or flukes (Platyhelminthes); and cestode (Cestoidea; tapeworm) infections. Examples of viruses include, but are not limited to, human immunodeficiency virus (HIV; e.g., HIV-1 and HIV-2), influenza (e.g., influenza A, influenza B, and influenza C), parainfluenza hepatitis virus (e.g., hepatitis A, hepatitis B, hepatitis C, hepatitis D, and hepatitis E), herpes viruses (HSV; HHV; e.g., herpes virus types 1, 2, 3, 4, 5, 6A, 6B, 7, and 8, including herpes simplex virus types 1 and 2, aka, HSV-1; HSV-2), varicella-zoster virus (HHV-3), Epstein Barr virus (HHV-4), Roseolovirus (HHV-6A and HHV-6B); Rous sarcoma virus, cytomegalovirus (HHV-5), Kaposi's sarcoma-associated herpesvirus; KSHV; HHV-8), papovirus (e.g., human papilloma virus; HPV; HPV-1, HPV-2, HPV-16, and HPV-18), parvovirus (e.g., Parvovirus B19), orthomyxovirus, paramyxovirus (e.g., morbillivirus, respirovirus, rubulavirus, ferlavirus, pneumovirus, and metapneumovirus), picomavirus (e.g., foot-and-mouth disease virus, aquamavirus A, encephalomyocarditis virus, theilovirus, cosavirus A, cadicivirus A, enterovirus A, enterovirus B, enterovirus C, enterovirus D, enterovirus E, enterovirus F, enterovirus G, enterovirus H, enterovirus J, rhinovirus A, rhinovirus B, rhinovirus C, aichivirus A, aichivirus B, aichivirus C, melegrivirus A, human parechovirus, ljungan virus, and salivirus A), togavirus (e.g., flavivirus, alphavirus, and rubivirus), Cowpox virus, Horsepox virus, Crimean-Congo hemorrhagic fever virus, Dengue virus, Eastern equine encephalitis virus, Ebola virus, Hantaan virus, Human coronavirus, Human enterovirus 68, Human enterovirus 70, non-HIV retroviruses, rhinovirus, respiratory syncytial virus (RSV), SARS coronavirus, Human spumaretrovirus, Human T-lymphotropic virus, Isfahan virus, Japanese encephalitis virus, Lassa virus, Lymphocytic choriomeningitis virus, MERS coronavirus, measles virus, Mengo encephalomyocarditis virus, Monkeypox virus, mumps virus, Norwalk virus, Pichinde virus, Poliovirus, Rabies virus, rotavirus (e.g., rotavirus A, rotavirus B, and rotavirus C), Rubella virus, St. louis encephalitis virus, Toscana virus, Uukuniemi virus, Venezuelan equine encephalitis virus, Western equine encephalitis virus, West Nile virus, Yellow fever virus, and ZIKA virus, as well as any other viruses known to those of skill in the art.

Methods for Generating an AAV Virion

In various embodiments, the invention provides a method for generating an AAV virion of the invention. A variety of methods for generating AAV virions are known in the art and can be used to generate AAV virions comprising the AAV vectors described herein. Generally, the methods involve inserting or transducing an AAV vector of the invention into a host cell capable of packaging the AAV vector into an AAV virion. Exemplary methods are described and referenced below; however, any method known to one of skill in the art can be employed to generate the AAV virions of the invention.

An AAV vector comprising a heterologous nucleic acid and used to generate an AAV virion can be constructed using methods that are well known in the art. See, e.g., Koerber et al. (2009) *Mol. Ther.,* 17:2088; Koerber et al. (2008) *Mol Ther.,* 16: 1703-1709; as well as U.S. Pat. Nos. 7,439,065, 6,951,758, and 6,491,907. For example, the heterologous sequence(s) can be directly inserted into an AAV genome with the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988)*Molec. Cell. Biol.* 8:3988-3996; Vincent et al. (1990) *Vaccines* 90 (Cold Spring Harbor Laboratory Press); Carter, B. J. (1992) *Current Opinion in Biotechnology* 3:533-539; Muzyczka, N. (1992) *Curr. Topics Microbiol. Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

In order to produce AAV virions, an AAV vector is introduced into a suitable host cell using known techniques, such as by transfection. A number of transfection techniques are generally known in the art. See, e.g., Graham et al. (1973) *Virology,* 52:456, Sambrook et al. (1989) *Molecular Cloning, A Laboratory Manual*, Cold Spring Harbor Laboratories, New York, Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome-mediated gene transfer (Mannino et al. (1988) *BioTechniques* 6:682-690), lipid-mediated transduction (Felgner et al. (1987) *Proc. Natl. Acad. Sci. USA* 84:7413-7417), and nucleic acid delivery using high-velocity microprojectiles (Klein et al. (1987) *Nature* 327:70-73).

Suitable host cells for producing AAV virions include any species and/or type of cell that can be, or have been, used as recipients of a heterologous AAV DNA molecule, and can support the expression of required AAV production cofactors from helper viruses. Such host cells can include but are not limited to microorganisms, yeast cells, insect cells, and mammalian cells, that can be, or have been, used as recipients of a heterologous DNA molecule. The term includes the progeny of the original cell transfected. Thus, a "host cell" as used herein generally refers to a cell transfected with an exogenous DNA sequence. Cells from the stable human cell line, HEK293 (readily available through, e.g., the American Type Culture Collection under Accession Number ATCC CRL1573) can be used. The human cell line HEK293 is a human embryonic kidney cell line that has been transformed with adenovirus type-5 DNA fragments (Graham et al. (1977) J. Gen. Virol. 36:59), and expresses the adenoviral Ela and Elb genes (Aiello et al. (1979) Virology 94:460). The HEK293 cell line is readily transfected, and provides a convenient platform in which to produce AAV virions.

Methods of producing an AAV virion in insect cells are known in the art, and can be used to produce a subject AAV virion. See, e.g., U.S. Patent Publication No. 2009/0203071; U.S. Pat. No. 7,271,002; and Chen (2008) *Mol. Ther.* 16:924.

In some embodiments, the AAV virion or AAV vector is packaged into an infectious virion or virus particle, by any of the methods described herein or known in the art.

In some embodiments, the variant AAV capsid polypeptide allows for similar packaging as compared to a non-variant parent capsid polypeptide.

In some embodiments, an AAV vector packaged with the variant AAV capsid polypeptides transduce into cells in vivo better than a vector packaged from non-variant parent capsid polypeptides.

In some embodiments, the AAV vector packaged with the variant AAV capsid polypeptides transduce into cells in vitro better than a vector packaged from non-variant parent capsid polypeptides.

In some embodiments, the variant AAV capsid polypeptides result in nucleic acid expression higher than a nucleic acid packaged from non-variant parent capsid polypeptides.

In some embodiments, the AAV vector packaged with said variant AAV capsid polypeptides result in transgene expression better than a transgene packaged from non-variant parent capsid polypeptides.

Pharmaceutical Compositions & Dosing

The present invention provides pharmaceutical compositions useful in treating subjects according to the methods of the invention as described herein. Further, the present invention provides dosing regimens for administering the described pharmaceutical compositions. The present invention provides pharmaceutical compositions comprising: a) a subject AAV vector or AAV virion, as described herein as well as therapeutic molecules packaged by or within capsids comprising variant polypeptides as described herein; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro, (2000) *Remington: The Science and Practice ofPharmacy,* 20th edition, Lippincott, Williams, & Wilkins; *Pharmaceutical Dosage Forms and Drug Delivery Systems* (1999) H. C. Ansel et al., eds., 7th ed., Lippincott, Williams, & Wilkins; and *Handbook of Pharmaceutical Excipients* (2000) A. H. Kibbe et al., eds., 3rd ed. Amer. Pharmaceutical Assoc.

A subject composition can comprise a liquid comprising a subject variant AAV capsid polypeptide of the invention or AAV virion comprising a variant AAV capsid polypeptide in solution, in suspension, or both. As used herein, liquid compositions include gels. In some cases, the liquid composition is aqueous. In some embodiments, the composition is an in situ gellable aqueous composition, e.g., an in situ gellable aqueous solution. Aqueous compositions have opthalmically compatible pH and osmolality.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound. Preparations are typically sterile and can be isotonic with the blood of the intended recipient. Non-limiting illustrative examples include water, saline, dextrose, fructose, ethanol, animal, vegetable or synthetic oils.

For intraperitoneal or intravenous administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Useful carriers include Vaseline®, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the AAV vector or AAV virion and methods and uses of are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Doses can vary and depend upon whether the treatment is prophylactic or therapeutic, the type, onset, progression, severity, frequency, duration, or probability of the disease treatment is directed to, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within about 1 hour to about 2 hours, about 2 hours to about 4 hours, about 4 hours to about 12 hours, about 12 hours to about 24 hours or about 24 hours to about 72 hours after a subject has been identified as having the disease targeted for treatment, has one or more symptoms of the disease, or has been screened and is identified as positive as set forth herein even though the subject does not have one or more symptoms of the disease. In some embodiments, the invention as disclosed herein can be practiced within about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 36 hours, about 48 hours, or about 72 hours or more. Of course, methods and uses of the invention can be practiced about 1 day to about 7 days, about 7 days to about 14 days, about 14 days to about 21 days, about 21 days to about 48 days or more, months or years after a subject has been identified as having the disease targeted for treatment, has one or more symptoms of the disease, or has been screened and is identified as positive as set forth herein. In some embodiments, the invention as disclosed herein can be practiced within about 1 day, about 2 days, about 3 days, about 4 days, about 5 days, about 6 days, about 7 days, about 8 days, about 9 days, about 10 days, about 11 days, about 12 days, about 14 days, about 21 days, about 36 days, or about 48 days or more.

In some embodiments, the present invention provides kits with packaging material and one or more components therein. A kit typically includes a label or packaging insert including a description of the components or instructions for use in vitro, in vivo, or ex vivo, of the components therein. A kit can contain a collection of such components, e.g., a variant AAV capsid polypeptide, an AAV vector, or AAV virion and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying the manufacturer, lot numbers, manufacturer location and date, expiration dates. Labels or inserts can include information identifying manufacturer information, lot numbers, manufacturer location and date. Labels or inserts can include information on a disease a kit component may be used for. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another incompatible treatment protocol or therapeutic regimen and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Method of Treating a Disease

The present invention also provides methods for treatment of disease in a subject by administering the AAV vectors and/or nucleic acids of the present invention, where AAV vectors and/or nucleic acids described herein packaged within a functional AAV capsid, wherein the functional AAV capsid comprises one or more variant AAV capsid polypeptides of the present invention. In an exemplary embodiment, the invention provides a method of administering a pharmaceutical composition of the invention to a subject in need thereof to treat a disease of a subject. In various embodiments, the subject is not otherwise in need of administration of a composition of the invention. In some embodiments, the invention provides methods for vaccine administration.

In some embodiments, the variant AAV capsid polypeptides package a therapeutic expression cassette comprised of a heterologous nucleic acid comprising a nucleotide sequence encoding a heterologous gene product, such as for example a therapeutic protein or vaccine. In some embodiments, the AAV virion or AAV vector comprises a therapeutic expression cassette comprised of a heterologous nucleic acid comprising a nucleotide sequence encoding a heterologous gene product, such as for example a therapeutic protein or vaccine.

In some embodiments, the variant AAV capsid polypeptides of the invention are employed as part of vaccine delivery. Vaccine delivery can include delivery of any of the therapeutic proteins as well as nucleic acids described herein. In some embodiments, variant AAV capsid polypeptides of the invention are employed as part of a vaccine regimen and dosed according to the methods described herein.

In some embodiments, the variant AAV capsid polypeptides, the AAV virions, or AAV vectors of the invention are used in a therapeutic treatment regimen.

In some embodiments, the variant AAV capsid polypeptides, the AAV virions, or AAV vectors of the invention are used for therapeutic polypeptide production.

In some cases, a subject variant AAV capsid polypeptides or AAV vector, when introduced into the cells of a subject, provides for high level production of the heterologous gene product packaged by the variant AAV capsid polypeptides or encoded by the AAV vector. For example, a heterologous polypeptide packaged by the variant AAV capsid polypeptides or encoded by the AAV can be produced at a level of from about 1 μg to about 50 μg or more.

In some cases, subject variant AAV capsid polypeptides, AAV virion, or AAV vector, when introduced into a subject, provide for production of the heterologous gene product packaged by the variant AAV capsid polypeptides or encoded by the AAV vector in at least about 10%, at least about 15%, at least about 20%, at least about 25%, at least about 30%, at least about 35%, at least about 40%, at least about 50% at least about 60%, at least about 70%, at least about 80%, or more than 80%, of the target cells.

In some embodiments, the present invention provides a method of treating a disease, the method comprising administering to an individual in need thereof an effective amount of a therapeutic molecule packaged by the variant AAV capsid polypeptides or subject AAV vector as described above.

Subject variant AAV capsid polypeptides or subject AAV vectors can be administered systemically, regionally or locally, or by any route, for example, by injection, infusion, orally (e.g., ingestion or inhalation), or topically (e.g., transdermally). Such delivery and administration methods include intravenously, intramuscularly, intraperitoneally, intradermally, subcutaneously, intracavity, intracranially, transdermally (topical), parenterally, e.g. transmucosally or rectally. Exemplary administration and delivery routes include intravenous, intraperitoneal, intrarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, and intralymphatic.

In some cases, a therapeutically effective amount of a therapeutic molecule packaged by the variant AAV capsid polypeptides or a subject AAV vectors is an amount that, when administered to an individual in one or more doses, is effective to slow the progression of the disease or disorder in the individual, or is effective to ameliorate symptoms. For example, a therapeutically effective amount of a therapeutic molecule packaged by the variant AAV capsid polypeptides or a subject AAV vectors can be an amount that, when administered to an individual in one or more doses, is effective to slow the progression of the disease by at least about 15%, at least about 20%, at least about 25%, at least about 30%, at least about 40%, at least about 50%, at least about 60%, at least about 70%, at least about 80%, or more than about 80%, compared to the progression of the disease in the absence of treatment with the therapeutic molecule packaged by the variant AAV capsid polypeptides or AAV vectors.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Improvement of clinical symptoms can also be monitored by one or more methods known to the art, and used as an indication of therapeutic effectiveness. Clinical symptoms may also be monitored by anatomical or physiological means, such as indirect ophthalmoscopy, fundus photography, fluorescein angiopathy, optical coherence tomography, electroretinography (full-field, multifocal, or other), external eye examination, slit lamp biomicroscopy, applanation tonometry, pachymetry, autorefaction, or other measures of functional vision. In some embodiments, a therapeutic molecule (including, for example, a vaccine) packaged by the variant AAV capsid polypeptides, a subject AAV vector, or AAV virus, when introduced into a subject, provides for production of the heterologous gene product for a period of time of from about 2 days to about 6 months, e.g., from about 2 days to about 7 days, from about 1 week to about 4 weeks, from about 1 month to about 2 months, or from about 2 months to about 6 months. In some embodiments, therapeutic molecules (including, for example, a vaccine) packaged by the variant AAV capsid polypeptides, a subject AAV vector or virus, when introduced into a subject provides for production of the heterologous gene product encoded for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years. In some embodiments, the administration regimen is part of a vaccination regimen.

Multiple doses of a subject AAV virion can be administered to an individual in need thereof. Where multiple doses are administered over a period of time, an active agent is administered once a month to about once a year, from about once a year to once every 2 years, from about once every 2 years to once every 5 years, or from about once every 5 years to about once every 10 years, over a period of time. For example, a subject AAV virion is administered over a period of from about 3 months to about 2 years, from about 2 years to about 5 years, from about 5 years to about 10 years, from about 10 years to about 20 years, or more than 20 years. The actual frequency of administration, and the actual duration of treatment, depends on various factors. In some embodiments, the administration regimen is part of a vaccination regimen.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can readily determine a virion dose range to treat a patient having a particular disease or disorder based on the aforementioned factors, as well as other factors. Generally, doses will range from at least about, or more, for example, $1\times10^{9}$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect.

In some embodiments, the variant AAV polypeptides of the present invention can be employed to reduce the amount of total AAV vector or other therapeutic molecule administered to a subject, wherein less total AAV vector or other therapeutic molecule is administered to a subject when said AAV vector or other therapeutic molecule is transduced using variant AAV capsid polypeptides as compared to the amount of AAV vector or other therapeutic molecule administered to a subject when the AAV vector or other therapeutic molecule is transduced using non-variant parent capsid polypeptides in order to obtain a similar therapeutic effect (i.e., both dosages induce similar therapeutic effects or indistinguishable therapeutic effects). In some embodiments, the total vector or other therapeutic molecule administered to a subject is reduced by about 5%, about 10%, about 15%, about 20%, about 25%, about 30%, about 35%, about 40%, about 50%, about 55%, about 60%, about 65%, about 70%, about 75%, about 80% or more when an AAV vector or other therapeutic molecule is transduced using variant AAV capsid polypeptides as compared to when an AAV vector or other therapeutic molecule is transduced using non-variant parent capsid polypeptides in order to obtain a similar therapeutic effect (i.e., both dosages induce similar therapeutic effects or indistinguishable therapeutic effects). In some embodiments, the total AAV vector or other therapeutic molecule administered to a subject is reduced by about 5% to about 80%, about 10% to about 75%, about 15% to about 65%, about 20% to about 60%, or about 10% to about 50% when the AAV vector or other therapeutic molecule is transduced using variant AAV capsid polypeptides as compared to when the AAV vector or other therapeutic molecule is transduced using non-variant parent capsid polypeptides in order to obtain a similar therapeutic effect (i.e., both dosages induce similar therapeutic effects or indistinguishable therapeutic effects).

An effective amount or a sufficient amount can, but need not be, provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, or a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

With regard to a disease or symptom thereof, or an underlying cellular response, a detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal, of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods.

Disclosed methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease.

The compound, agent, drug, treatment or other therapeutic regimen or protocol can be administered as a combination composition, or administered separately, such as concurrently or in series or sequentially (prior to or following) delivery or administration of an AAV vector or AAV virion as described herein. The invention therefore provides combinations where a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of an AAV vector or AAV virion as described herein, to a subject. Specific non-limiting examples of combination embodiments therefore include the foregoing or other compound, agent, drug, therapeutic regimen, treatment protocol, process, remedy or composition.

Methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

The invention is useful in animals including veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases and others known to those of skill in the art.

Non-limiting particular examples of diseases treatable in accordance with the invention include those set forth herein as well as a pancreas disease. A pancreas disease includes but is not limited to diabetes mellitus (e.g. Type I and Type II), acute pancreatitis, chronic pancreatitis, hereditary pancreatitis, autoimmune pancreatitis, pancreatic cancer (e.g. pancreatic adenocarcinoma, acinar cell carcinoma of the pancreas, cystadenocarcinomas, pancreatoblastoma, pancreatic mucinous cystic neoplasms, etc.), pancreatic benign tumors (e.g. pancreatic serous cystadenoma, solid pseudopapillary tumor of the pancreas, etc.), pancreatic neuroendocrine tumor, cystic fibrosis, exocrine pancreatic insufficiency (EPI), pancreatic pseudocyst, pancreatic cyst, Shwachman-Diamond syndrome, Johanson-Blizzard syndrome, Common Channel syndrome, Zollinger-Ellison syndrome, choledochal cyst, Hemosuccus pancreaticus, or congenital pancreatic abnormalities (e.g. Pancreas divisum, Annular Pancreas, ectopic pancreatic tissue).

In one embodiment, a method or use of the invention includes: (a) providing an AAV virion whose capsid comprises the variant AAV capsid polypeptides prepared as described herein, wherein the AAV virion comprises a heterologous nucleic acid sequence, wherein the heterologous nucleic acid sequence is operably linked to an expression control element conferring transcription of said nucleic acid sequence; and (b) administering an amount of the AAV virion to the mammal such that said heterologous nucleic acid is expressed in the mammal.

In one embodiment, a method or use of the invention includes: (a) providing a therapeutic molecule (including, for example, a vaccine) packaged by variant AAV capsid polypeptides prepared as described herein, wherein the therapeutic molecule comprises a heterologous nucleic acid sequence, wherein the heterologous nucleic acid sequence is operably linked to an expression control element conferring transcription of said nucleic acid sequence; and (b) administering an amount of the therapeutic molecule (including, for example, a vaccine) packaged by variant AAV capsid polypeptides to the mammal such that said heterologous nucleic acid is expressed in the mammal.

In another embodiment, a method or use of the invention includes delivering or transferring a heterologous polynucleotide sequence into a mammal or a cell of a mammal, by administering a heterologous polynucleotide packaged by the variant AAV capsid polypeptides, a plurality of heterologous polynucleotides packaged by variant AAV capsid polypeptides, an AAV virion prepared as described herein, or a plurality of AAV virions comprising the heterologous nucleic acid sequence to a mammal or a cell of a mammal, thereby delivering or transferring the heterologous polynucleotide sequence into the mammal or cell of the mammal. In some embodiments, the heterologous nucleic acid sequence encodes a protein expressed in the mammal, or where the heterologous nucleic acid sequence encodes an inhibitory sequence or protein that reduces expression of an endogenous protein in the mammal.

By way of example, respecting hemophilia, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than about 5% of normal is needed. With respect to treating such a hemophilic subject, a typical dose is at least $1\times10^{10}$ AAV vector genomes (vg) per kilogram (vg/kg) of the weight of the subject, or between about $1\times10^{10}$ to about $1\times10^{11}$ vg/kg of the weight of the subject, or between about $1\times10^{11}$ to about $1\times10^{12}$ vg/kg of the weight of the subject, or between about $1\times10^{12}$ to about $1\times10^{13}$ vg/kg of the weight of the subject, to achieve a desired therapeutic effect.

EXAMPLES

Example 1: Directed Evolution of AAV for Human Islet Targeting

Introduction

Adeno-associated viruses (AAV) are of great interest as a potent vehicle for gene transfer into various cell types. While AAV has several features that make it a promising vehicle for human gene therapy, several drawbacks have hampered its use for clinical applications, such as its promiscuity, limited transgene packaging size, and the high prevalence of pre-existing neutralizing antibodies in the general population. For gene therapy purposes, transduction needs to be both efficient and highly cell type specific. AAV cell tropism as well as immunogenicity are determined by sequences of the structural capsid proteins VP1, VP2, and VP3.

DNA shuffling is a powerful method for the in vitro evolution of molecules with specific functions and has applications in areas as diverse as medical, pharmaceutical and agricultural research. Shuffling of the AAV capsid sequences has successfully been used in the past to evolve recombinant AAVs (rAAVs) with improved cell transduction capabilities in vitro and in vivo (D. Grimm. *J. Virol.* 82, 5887-5911 (2008); and L. Lisowski. *Nature,* 506, 382-386 (2013)).

Purpose

The goal of this study is to generate AAV vectors for gene therapy applications in the field of diabetes research. A highly complex AAV library containing shuffled capsid sequences tagged with unique barcodes for high-throughput sequencing has been generated and has been screened for improved islet transduction by performing multiple rounds of passaging in primary human islets.

Results

Figure 2:
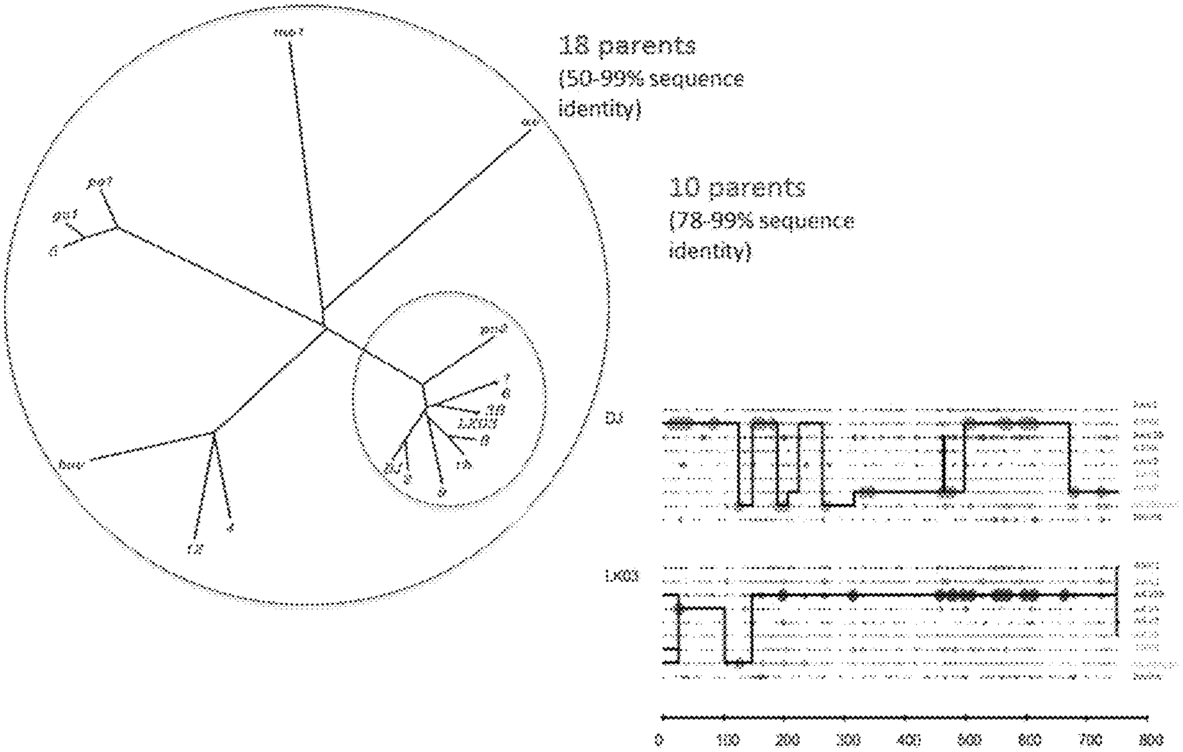
FIG. 2. Phylogenetic relationship of parental capsid amino acid sequences used for shuffling. Phylogenetic distances between the parental capsid sequences used for shuffling. Diversity ranges are shown for amino acid sequences.

Capsid genes from various AAV wild type serotypes and previously described variants (FIG. 2) were shuffled using the DNase shuffling method (W. P. Stemmer. *Proc. Natl. Acad. Sci. USA,* 91, 10747-10751 (1994)) and cloned into an AAV backbone library containing a barcode sequence downstream of the cap polyA (FIG. 3). Tagging each AAV variant with a unique barcode allows for tracking of variant enrichment between rounds of passaging by high-throughput sequencing. The 10 parent library was analyzed in more detail and found to have a good crossover rate by Sanger sequencing (FIG. 4) (W. Huang. *Biotechniques,* 60, 91-94 (2016)). High-throughput capsid+BC sequencing was performed using the PacBio sequencing technology and revealed similar contribution levels of the 10 parental capsid sequences (FIG. 5) as well as good capsid-BC linkage (see, for Example, FIG. 1).

Figure 8:
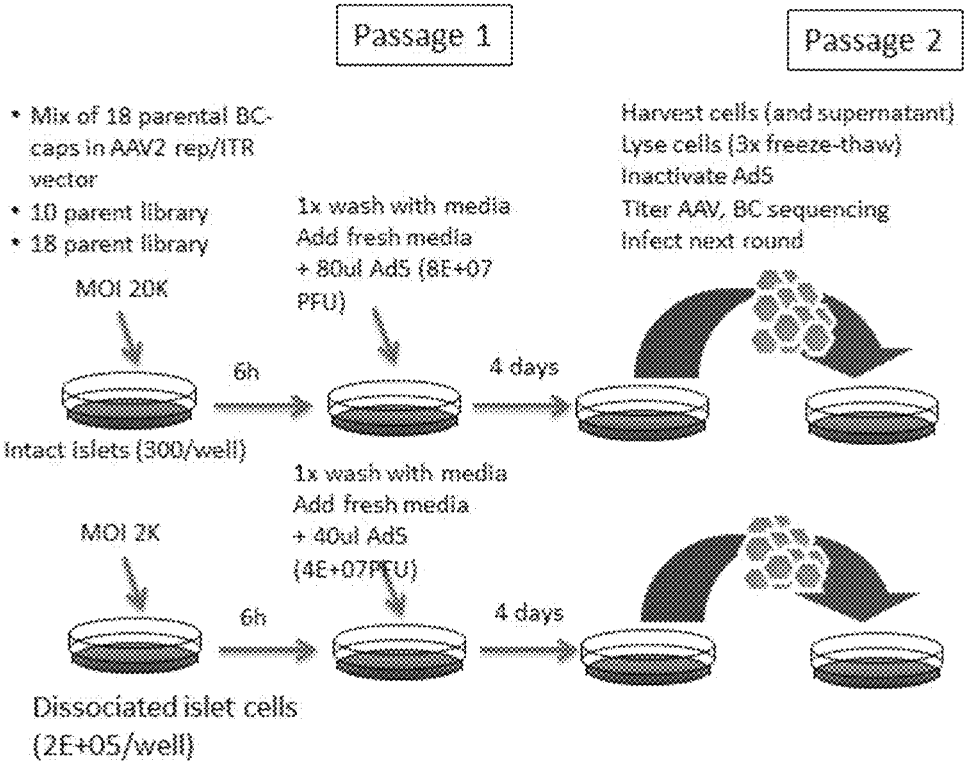
FIG. 8. Passaging regimen of shuffled libraries as well as a parental barcoded AAV mix on intact as well as dissociated islets: Screen A. Passaging regimen of the parental mix as well as the shuffled barcoded AAV libraries on human islets.
Figure 9:
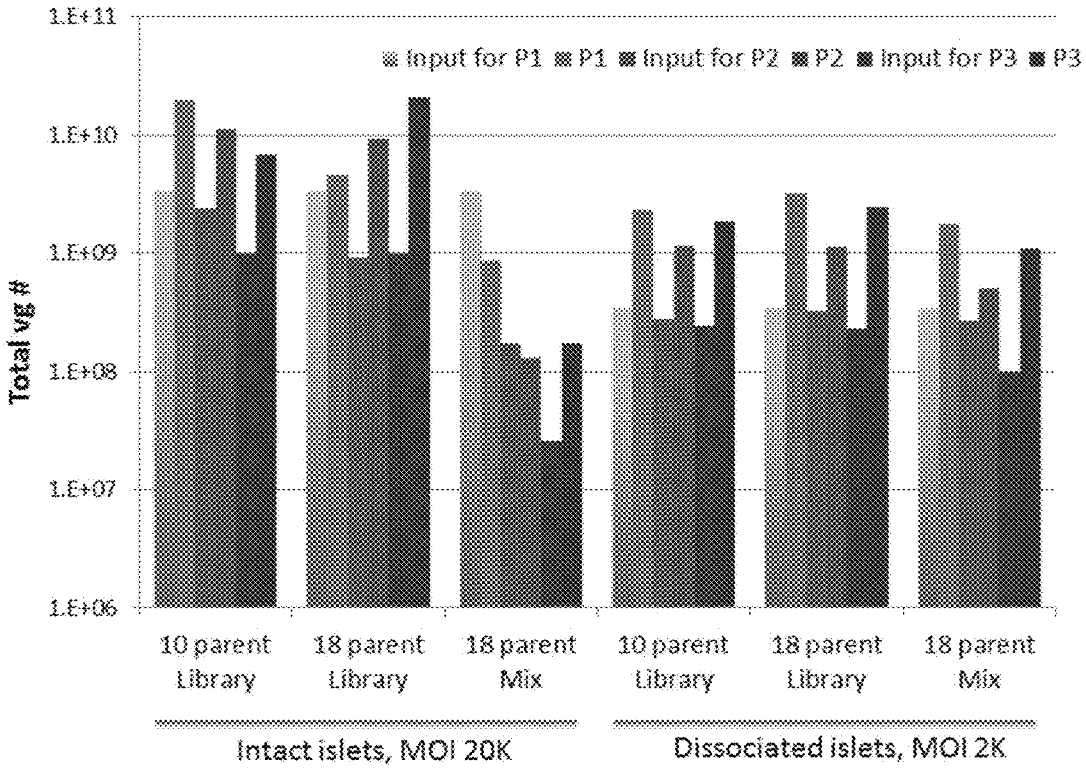
FIG. 9. Replication of AAV libraries and the 18 parent mix.
Figure 12:
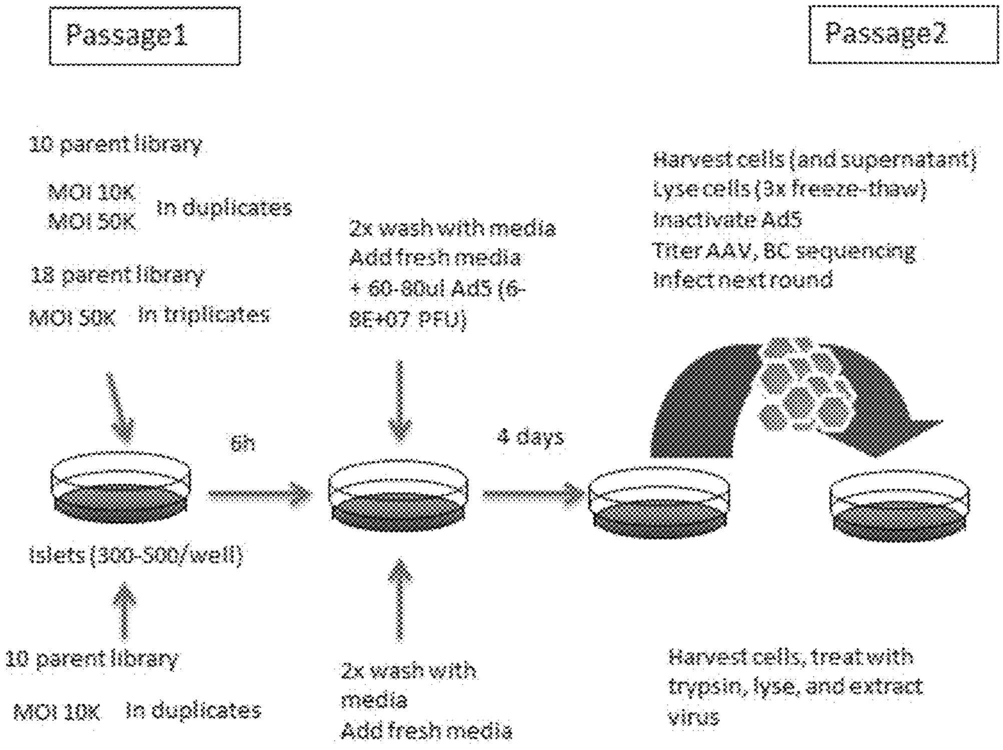
FIG. 12. Passaging regimen of shuffled libraries on intact islets: screen B.

Human islets were infected with high Multiplicity of Infection (MOI) of the cap shuffled barcoded AAV libraries as well as with a control pool of parental cap AAVs each tagged with a unique barcode (FIG. 8 and FIG. 12). Human adenovirus 5 was added as a helper to replicate AAV in most of the screens. Both intact as well as dissociated islets were used in the experiment and three rounds of passaging were performed for each screen. At each round AAV replication was assessed by qPCR and both AAV libraries as well as the 18 parent mix were shown to replicate in the islets (data not shown).

Figure 11:
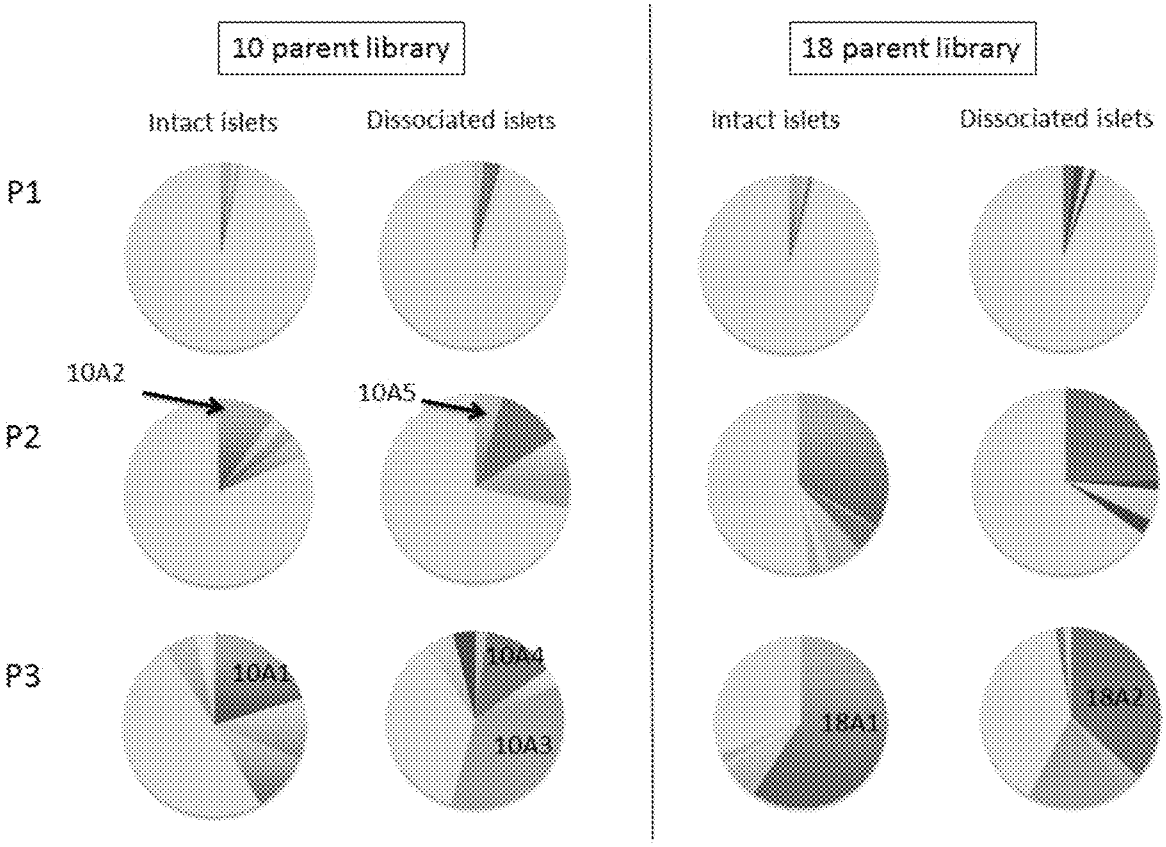
FIG. 11. Enrichment for shuffled AAV cap variants during passaging of the 10 parent (left) and 18 parent (right) libraries. Only the most enriched AAV variants are shown in different colors, all others are in grey. Variants that were selected for further analysis are indicted by name. Enrichment of capsid sequences through three rounds of selection of both libraries on intact islets and dissociated islets. After each passage BC sequences were analyzed by NGS using MiSeq. Colored sections represent enriched AAV populations. Variants with the most improved phenotype are indicated (KP1, KP2, KP3).
Figure 14:
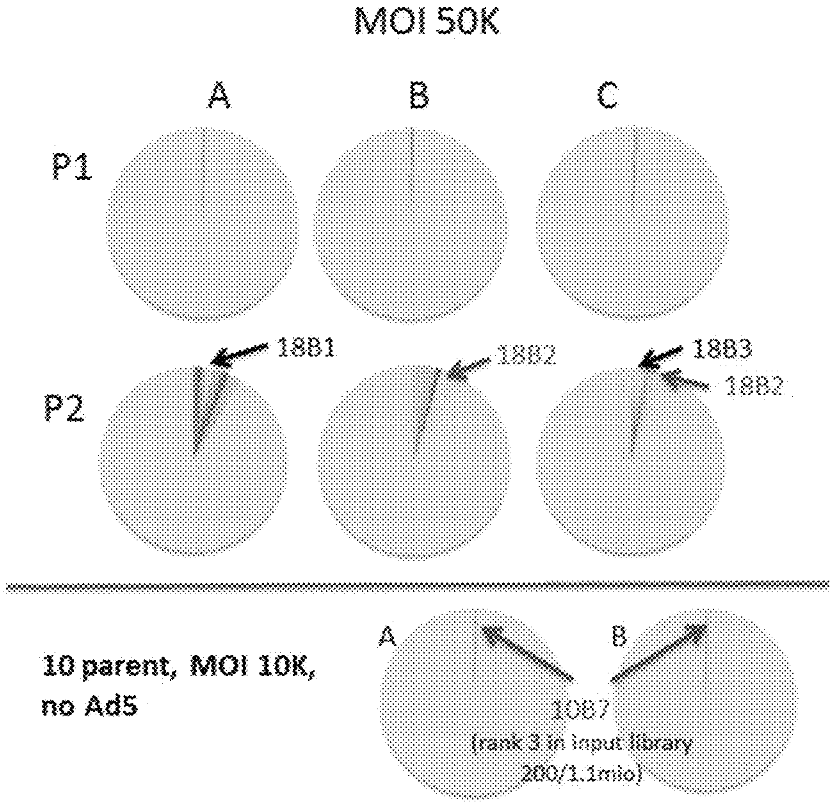
FIG. 14. Enrichment for shuffled AAV cap variants during passaging of the 18 parent library (upper panel), round 1 of the 10 parent library w/o Ad5 (lower panel). Only the most enriched AAV variants are shown in different colors, all others are in grey. Variants that were selected for further analysis are indicted by name. Names in red indicate variants that were enriched in two independent screens.
Figure 15:
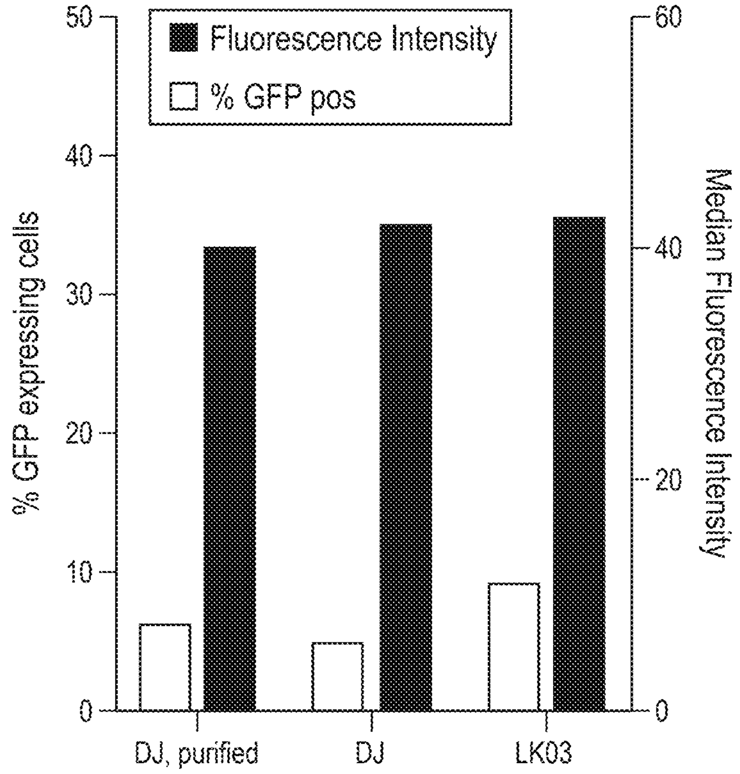
FIG. 15. Transduction of Dissociated Human Islets with AAV-vectors.
Figure 16:
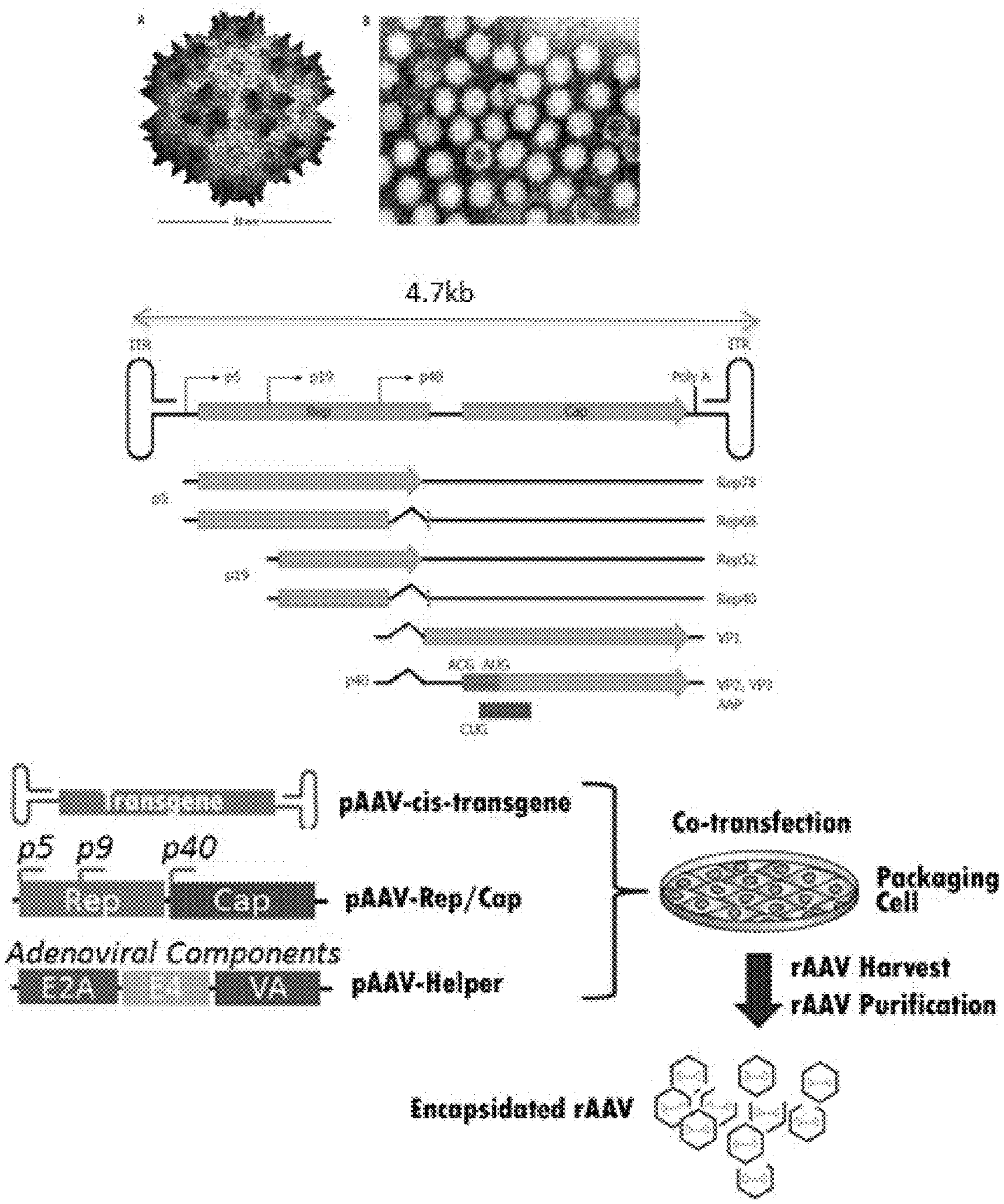
FIG. 16. Recombinant AAV for gene therapy.
Figure 17:
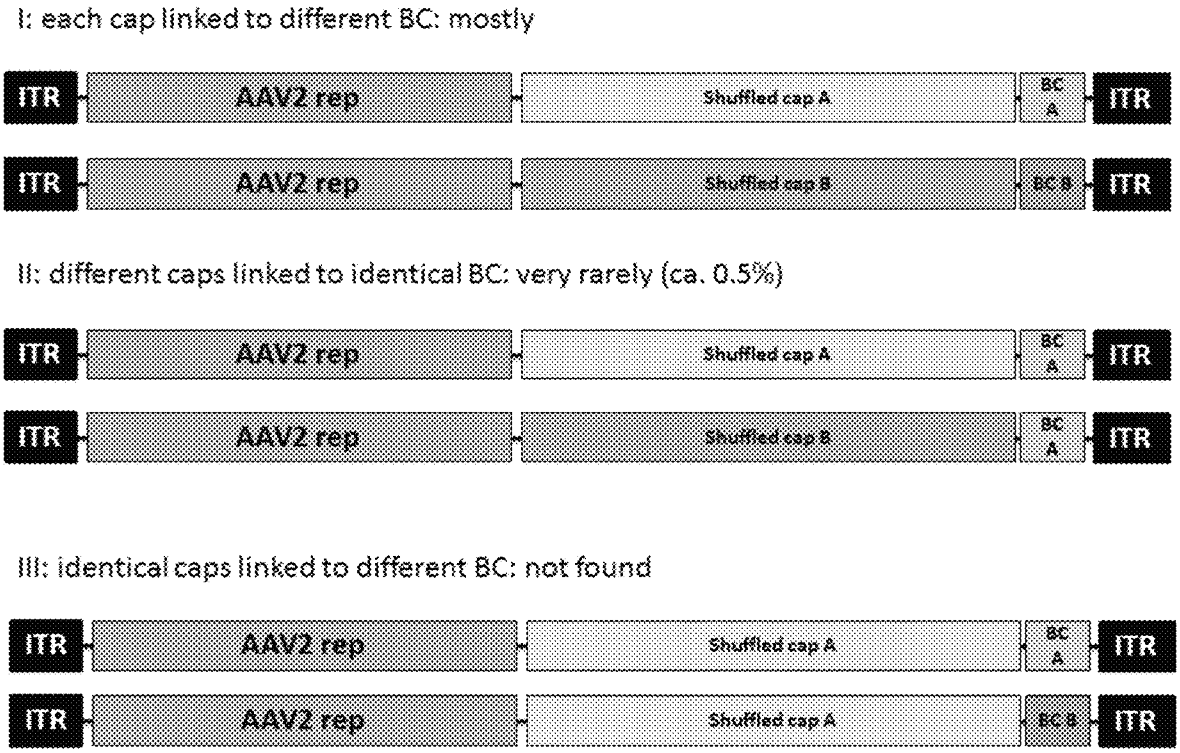
FIG. 17. PacBio Sequencing reveals good cap-BC linkage.

High-throughput sequencing using a MiSeq sequencer (Illumina) of the AAV barcodes amplified from viral genomes was performed after each round of passaging. Infection of intact islets with the 18 parent mix revealed selection pressure towards AAVs containing the DJ capsid sequence (FIG. 10) although LK03 was found to be better at islet transduction than DJ. This suggests that variants with capsid sequences that confer improved transduction may be lost during prolonged passaging while those variants that replicate well may take over the population. For this reason, one screen which did not include superinfection with Ad5 was performed using the 10 parent library. Deep sequencing of barcodes obtained after passaging of both libraries revealed rapid enrichment for several capsid variants (FIGS. 11, 13, 14).

Example 2: Novel Recombinant Adeno-Associated Virus Capsids with Enhanced Human Pancreatic Tissue or Human Islet Cell Tropism Purpose The goal of the invention was to find rAAV vectors with enhanced ability to transduce human islet cells. This is useful for new treatments for endocrine disorders specifically diabetes type 1 and 2.

Technical Description

Figure 18:
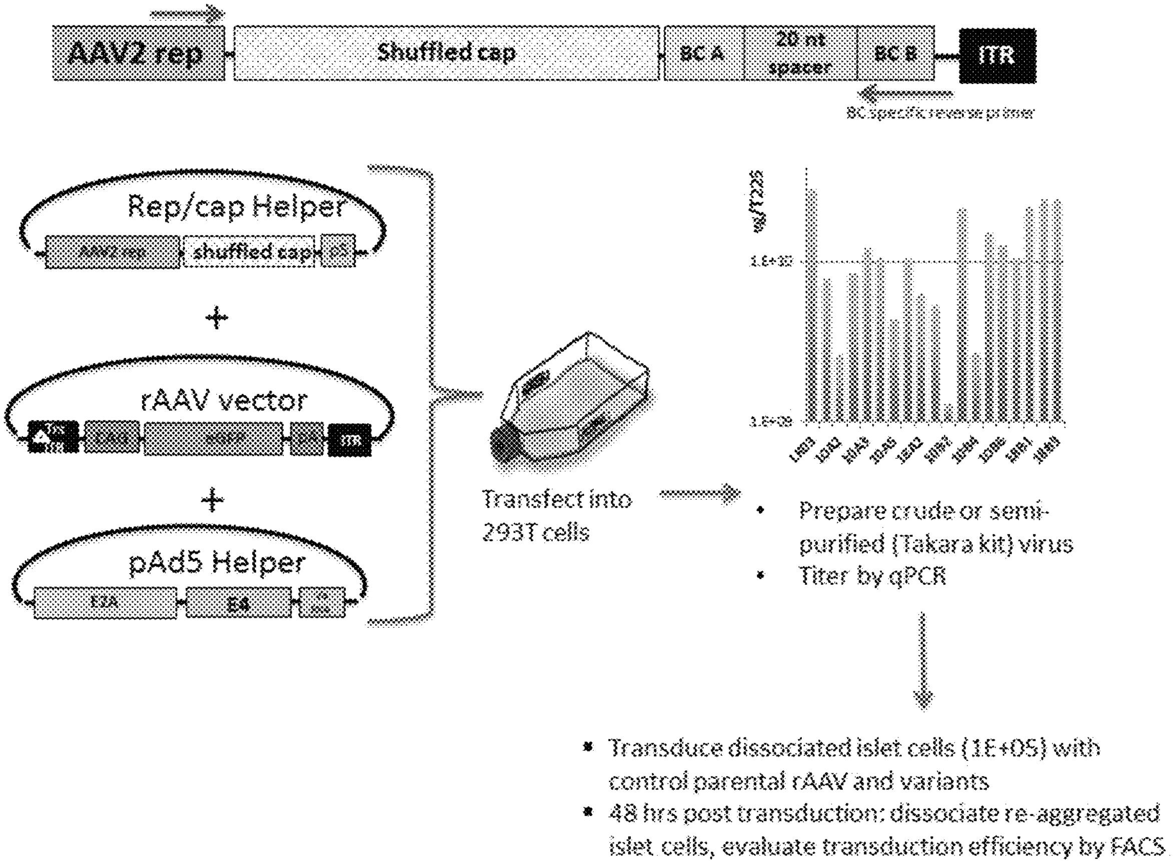
FIG. 18. Generation of rAAV expressing GFP. Capsid sequences from enriched AAV species were amplified using a BC sequence specific reverse primer and rAAV was produced in 293T cells by triple plasmid transfection. Crude or Takara kit purified rAAV preps were then quantified for vector copy numbers by qPCR and used to transduce islet cells.
Figure 19:
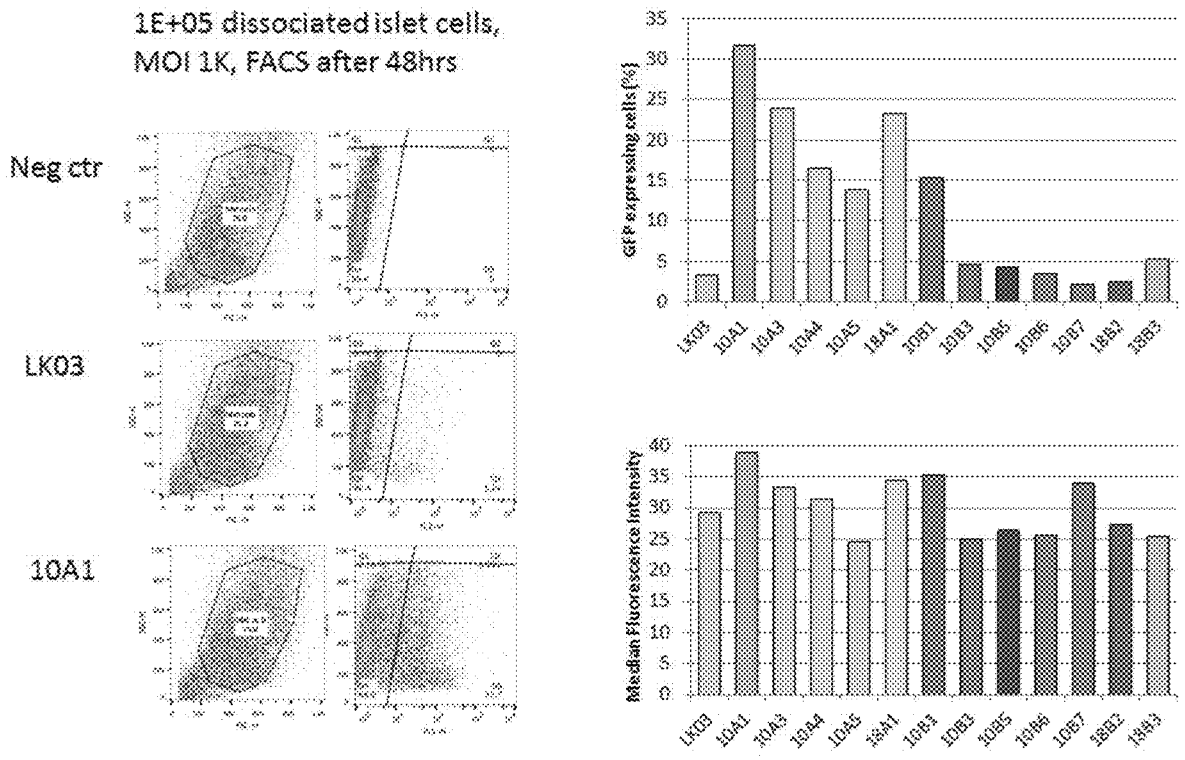
FIG. 19. Transduction efficiency in islet cells.
Figure 20:
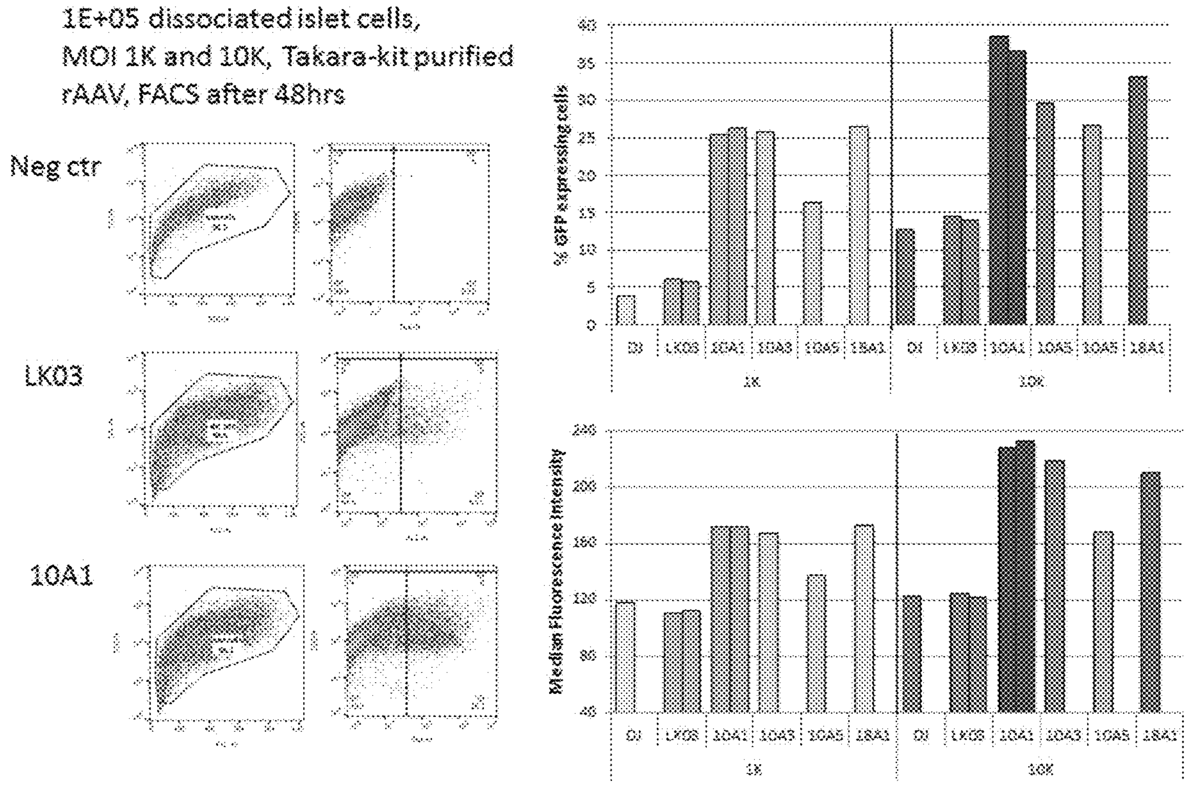
FIG. 20. Transduction repeat: Top variants only, MOI 1K vs 10K.

An AAV capsid library was used to select for AAVs that selectively transduced either dissociated or intact human islets. These capsid sequences were amplified using a barcode specific reverse primer and used to generate rAAV with GFP as a transgene (FIG. 18). Islets were dissociated using Accumax, transduced at MOI=1K or 10K vg/cell at 37° C. for 48 hours (10% FBS/CMRL), plated and analyzed by flow cytometry at 48 hours post transduction. Intact human islets were transduced at MOI=10K vg/cell on ice for 1-2 hours (2% FBS/CMRL) followed by suspension culture for 3 days with media change on day 2 post-transduction, and then were analyzed by flow cytometry. Flow cytometry were done using monoclonal antibodies against 2B4 (an islet surface marker) and 8G12 (an α- cell surface marker). After several rounds of passaging the most prevelant capsids were isolated and sequenced. rAAV vectors expressing a GFP reporter were compared against previously isolated rAAVs that are currently believed to be the most robust at transducing human islets.

Transduction was done on human intact islets from two different donors (MOI 10,000) using the cold transduction protocol. Surface staining was performed using antibodies against pan islet marker and alpha cell specific marker.

Cold transduction protocol. Pelleted whole islets and remove supernatant (in 15 mL Falcon tubes). Added 100 μL of CMRL+2% FBS to the islets. Added AAV, gently flicked tubes several times. Incubated the 15 mL Falcon tube on ice (almost lying flat ~10-15 degree angle) and put ice bucket on top of a horizontal shaker (approximately 100 rpm) in the cold room for 1-2 hours. Pre-warmed islet culture medium (CMRL-1066+10 mM HEPES+0.5% human serum albumin+2% FBS+10 mM nicotinamide+antibiotic/antimycotic+1X glutamax) at 37° C. In 24 well format non-coated/resuspension plate, transfered 350-500 islets (with the AAV) per well. Added 1 mL prewarmed islet culture medium per well. Left in a 37° C., humidified 5% $CO_2$ incubator for 2 days. Changed media on the $2^{nd}$ day. Harvested islets on the $3^{rd}$ day for FACS (Dorrell et al Nature Communications for FACS protocol using surface antibodies to subdivide islets into alpha, beta, non-alpha/non-beta).

The transduction efficiencies of new variants were tested in vivo. Different AAVs in four groups (DJ, AAV8, KP1, KP2 and KP3) with CAG-Fluc were injected at 2elOvg/mouse to Balb/SCID mice (n=4 mice/group) (see FIG. 42). In vivo luciferase imaging were performed weekly for 4-6 weeks. Several organs (e.g. liver, pancreas, lung, heart, brain, spleen, kidneys) were harvested, and analyzed for luciferase activities, Fluc transcript levels and vector copy numbers on day 7 and week 5.

Results

Transduction efficiency of primary human islet cells was assessed by FACS. Several capsid variants showed improved transduction when compared to the best parental LK03 (FIGS. 19, 20, 22-28, 30, 31, 33 and 34). Intracellular staining for insulin and glucagon will reveal if any of the variants exhibit selectivity towards α- or β-cells. Their relative transduction efficiencies were compared and the top candidates were approximately 10 times more robust than previous gold standard.

This study demonstrates that additional genetic modifications to the capsid provides enhanced rAAV transduction for efficient gene transfer into the target cells, e.g. islet cells. It provides a critical solution to targeting specificity for pancreatic alpha- and/or beta-cells.

Figure 35:
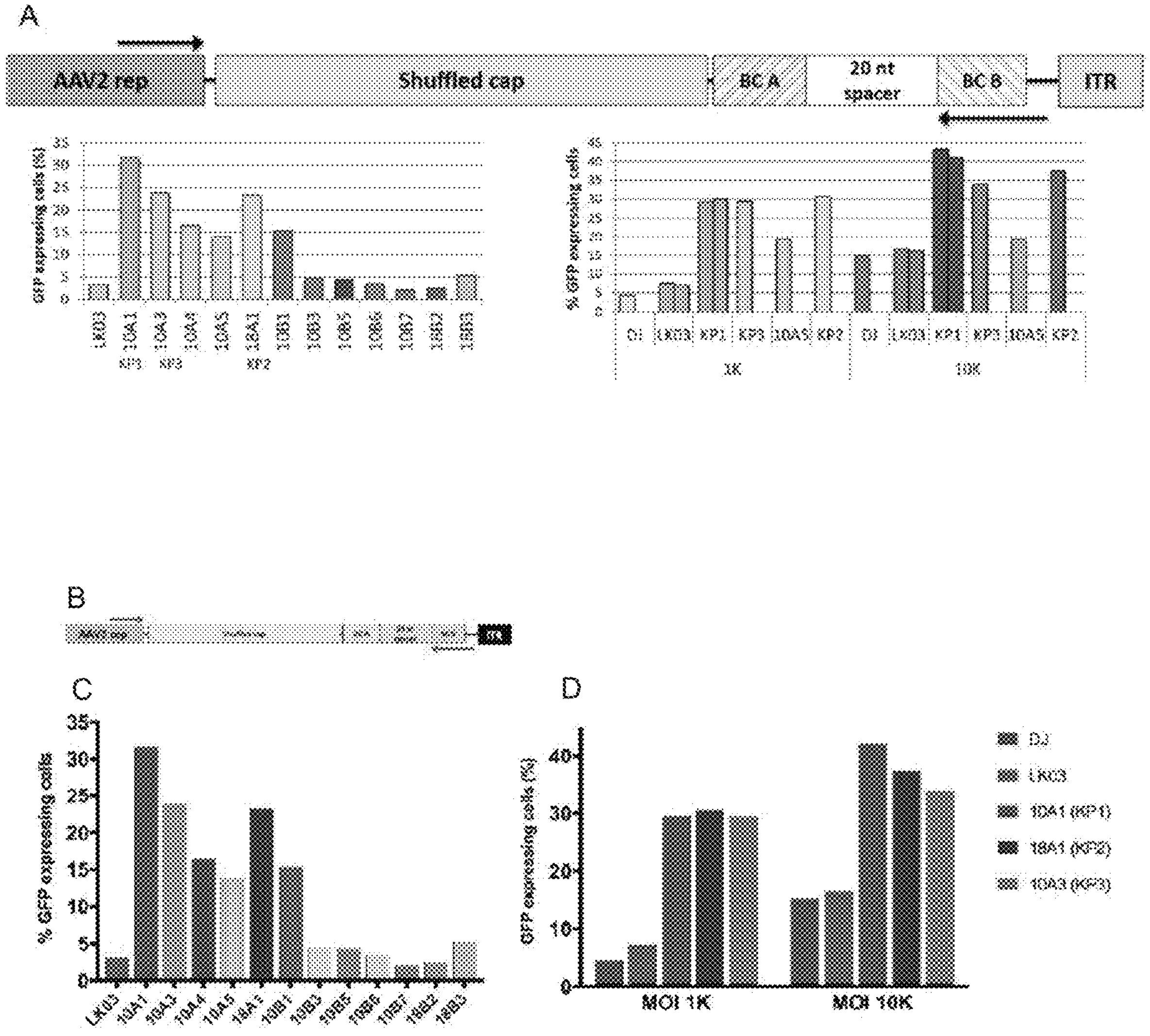

Transduction was done on human intact islets from two different donors (MOI 10,000). Surface staining was performed using antibodies against pan islet marker and alpha cell specific marker, and the results are shown in FIGS. 35-36. Enhanced transduction efficiency of the novel variants was shown on various human and non-human cell lines (FIG. 39). Two of the novel variants, KP1 and KP3, had a better neutralization profile than LK03 (FIG. 46).

The transduction efficiencies of new variants were tested in Balb/SCID mice in vivo. Balb/C SCID mice were tail-ven injected with 2E+10 vg of luciferase vector packaged with the different capsids. Luciferase expression in liver (ventral and dorsal) was monitered for 7 and 14 days. Luciferase expression (ventral) was then monitored weekly through week 5 (day 33). The results of luciferase imaging at day 7 and 14 are shown in FIG. 43 and quantified in FIGS. 44 and 45. The in-vivo liver transduction efficiency of the novel variants was stable from day 14 through day 33 (FIG. 47). Luciferase expression in various organs was tested ex-vivo at week 5 (FIG. 48). Vector copy number in the liver was elevated compared to brain, heart, and spleen (FIG. 49).

Example 3: Generation and Screening of Barcoded Adeno Associated Virus Capsid Shuffled Libraries for Enhanced Transduction of Primary Human Islet Cells Abstract Safe and effective gene transfer into the islets of Langerhans is a promising approach for the treatment of diabetes. Recombinant AAV-mediated gene transfer into islets is hampered by a lack of AAV serotypes that transduce those cells with high efficacy. In order to identify new AAV serotypes with improved tropism for human islets, two highly complex bar-coded replication competent capsid libraries were constructed, diversity was validated by single-molecule DNA sequencing, and serial selection was performed on human islets. The enriched barcodes were tracked by high throughput sequencing and three capsid variants were identified that were capable of transducing dissociated as well as intact islets with 5- to 10-fold higher efficiency when compared to the previously identified best capsids. These novel AAV capsid variants, capable of penetrating intact human islets, represent a powerful gene therapy tool for the treatment of patients with diabetes. One of the capsids was also robust at transducing both mouse and human hepatocytes in a humanized-chimeric mouse model, thus providing a versatile vector eliminating the requirement of using a surrogate capsid for preclinical testing prior for its use in human clinical trials.

Introduction

The development of viral gene transfer vectors remains an active field of investigation[1]. While recombinant AAV vectors have emerged as a safe vehicle for gene transfer into whole organisms in pre-clinical as well as clinical studies there are still important limitations[2]. Major drawbacks of rAAV are the limited packaging size of around 5 kb, rapid virus clearance due to pre-existing neutralizing antibodies, limited host tropism of the naturally occurring serotypes, as well as loss of transgene expressing in dividing cells due to the episomal nature of AAV. The capsid comprised of VP 1, VP2, and VP3 proteins harbors the main determinants for cell tropism based on the recognition of various receptors and co-receptors[3]. In addition, capsid variants may exhibit variable post entry events such as capsid uncoating[4], intracellular trafficking and nuclear entry[5] resulting in differential transduction between tissues and species. Natural and non-natural AAV capsid variants have been isolated using bio-mining, i.e. isolation and characterization of naturally occurring AAVs[6], screening of capsid peptide display libraries[7-9], libraries expressing displaying cell specific Designed Ankyrin Repeat Proteins (DARPins)[10], and screening of capsid libraries obtained by random DNA shuffling[11] have been the paths most thoroughly explored to date. Recently, the creation and screening of libraries consisting of ancestral AAV capsid sequences has been described as a valuable tool to obtain AAVs with very specific cell targeting[12].

Directed evolution is a powerful tool to mimic natural evolution in a vastly accelerated manner. Most importantly, no a priori knowledge about sequence-function relationships is needed, which stands in contrast to rational design strategies. Highly diverse libraries of the desired sequences are created, followed by screening for those variants that exhibit the desired phenotype. Several methods for library generation have been described, such as DNase mediated shuffling[13-14], Staggered Extension Polymerization (STEP)[15], Random Chimeragenesis on Transient Templates[16], restriction enzyme mediated shuffling[17], and others (for detailed protocols see[18]). For this study DNase mediated family shuffling[13, 19] of several full-length AAV capsid sequences was employed to create highly complex and functional libraries. This technology takes advantage of the ability of randomly fragmented DNA derived from a family of related genes to re-assemble into chimeric full-length sequences due to hybridization[13-14]. Crossovers occur when a partially reassembled PCR product primes on the homologous position of a related but not identical template, thus initiating a template switch. Since crossovers based on an identity of less than 15 bases are difficult to obtain[13-14] the degree of library complexity and thus quality tends to negatively correlate with parental sequence diversity. DNA shuffling can be used to create large libraries of genes that can be screened for the desired phenotype. Successful applications of this technology have been described for many areas, such as the improvement of properties of various enzymes, promoters, immune modulating proteins[19-32]. In 2000 Soong et al., were the first to describe the application of DNA shuffling for virus evolution[20]. To take advantage of this highly diverse virus library is subjected to stringent selection pressure throughout several rounds of passaging and enriched variants are recovered. This technology has resulted in the development of Moloney Leukemia virus (MLV) particles with improved envelope stability[26], as well MLV and HIV-1 with novel host cell tropism[25, 28]. In 2008, Grimm, D, et al. were the first to report successful selection of improved AAV variants by capsid shuffling and multiple rounds of selection[8]. A different method for AAV capsid evolution—error-prone PCR combined with STEP—had been described earlier.[33] Soon, others created and screened AAV capsid shuffled libraries[34-40] (for a review see[11]). Some of these screens were performed in presence of human adenovirus 5 to replicate enriched AAV variants between selection rounds, but adenovirus free AAV library screens have also been reported[41-44].

An estimated 30.3 million US Americans are affected by either type 1 or type 2 Diabetes Mellitus[45]. Various strategies to cure diabetes have been evaluated over the years. Transplantation of cadaveric human islets into the hepatic duct has been used to replace β-cells in type 1 diabetic patients, so far with limited success (for a review see[46]). Islets are highly vascularized and require large amounts of oxygen to survive. Because re-vascularization of the transplanted islets takes several weeks those transplants suffer from a large number of cell death due to oxygen deprivation. Ex vivo gene therapy either supplying or repressing certain transcription factors may be used to improve graft survival and function (see[47] for a review). Recently the knockout of PHLDA3 has been shown to lead to increased survival of transplanted islets in mice48. In addition to the approaches described above it is of utmost importance to prevent loss of the transplanted islets due to recurrent autoimmune destruction. Recently a study described the use or AAV to overexpress Igf1 and thus counteract progression to autoimmune diabetes in mice[49].

Another strategy for treatment is the conversion of glucagon producing α-cells or other endocrine or exocrine pancreatic cell types into β-cells by overexpression or repression of certain transcription factors, such as Pdx1, Ngn3, MafA, Pax4, and Arx,[50-58] (for a review, see[59]). Follistatin overexpression in a diabetic mouse model has been shown to preserve β-cell function[60].

To this date only few studies have described the use of AAV as gene therapy vehicle for pancreatic islets and most of the work has been performed with murine islets. AAV8 capsid combined with the β-cell type specific insulin promoter has been described to achieve highly specific transduction of β-cells after intraperitoneal delivery in mice[61]. Another study found AAV6 to transduce mouse islets with high efficiency in vitro as well as via the intraductal route, but AAV8 proved to be the more robust serotype when systemically delivered[62]. Site-directed mutagenesis of surface exposed capsid tyrosine residues to phenylalanine has been described to enhance transduction efficiency of several serotypes due to evasion from intracellular ubiquitination-proteasomal degradation[63-67]. Recently Y—F mutant AAV8 vectors have been reported to achieve up to ten-fold improved gene transfer into mouse islets as compared to wildtype AAV8[68]. Interestingly, studies in rats found that AAV5 was the best capsid for islet transduction in this rodent[69]. AAV2 is the serotype that has been described most frequently for transduction of human islets[70, 71]. More recently capsid variants DJ and LK03 were found to have better transduction efficiency on human islets as compared to AAV2 and AAV3B, however, a strong preference for α-cells was observed for those capsids[72].

This study sought to develop capsid variants with further enhanced human islet cell transduction efficiency. For this purpose, the capsid shuffled barcoded AAV libraries were subject to multiple rounds of selection on human islets and analysed enriched capsid variants for improved transduction efficiency. Barcoding the capsids was performed to follow enrichment of chimeric variants by employing high-throughput sequencing of the barcodes rather than low-throughput Sanger-based sequence analysis of the capsids. This novel technology, termed AAV Barcode Seq has first been described for in vivo tracking of variants derived from small AAV libraries or parental pools[73]. Among all the candidates tested three chimeric variants were found to exhibit considerably improved transduction capacity of human islets—particularly of β-cells as well as other cell types in vitro and in vivo. These novel capsids may be useful for various gene therapy applications besides those targeting pancreatic islets for diabetes treatment.

Results:

Evaluation of Parental Capsids for Human Islet Transduction Efficiency

Figure 50A:
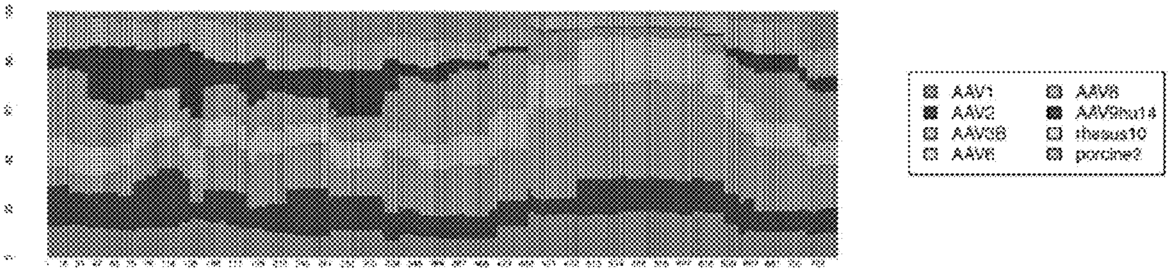
Figure 50B:
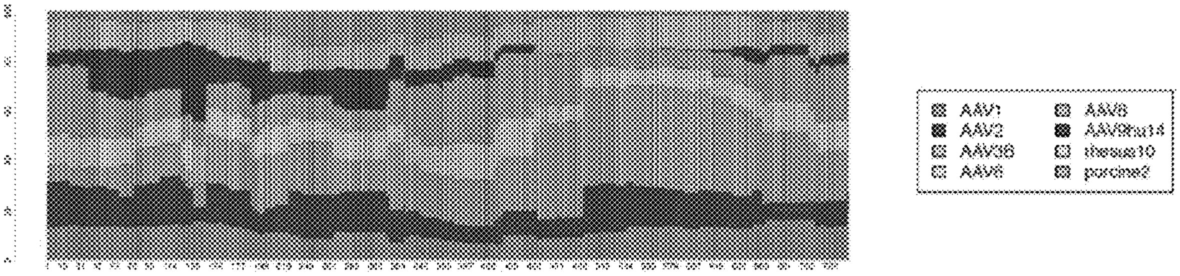
Figure 50C:
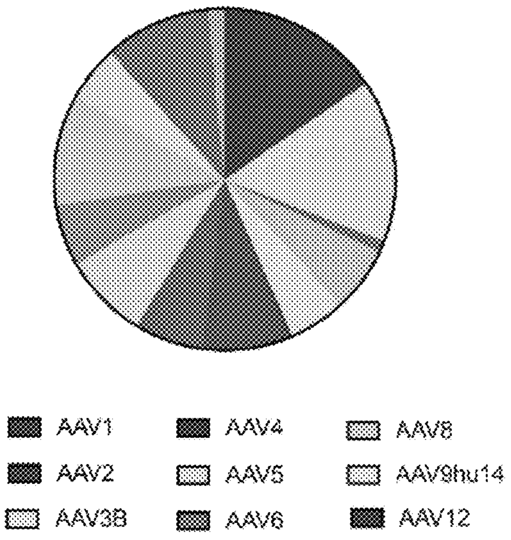

The first step was to confirm previous data showing that AAV-DJ and AAV-LK03 have higher human islet transduction efficiency than the closely related natural serotypes AAV-2 and AAV3B[72]. Human islets were transduced with single stranded (ss) and self-complementary (sc) GFP expressing vectors packaged with the different capsids and measured transduction efficiency using flow cytometry (FIG. 62A). As expected AAV-DJ and AAV-LK03 had higher rates of transduction in human islets than AAV2 and AAV3B. Confirming this result provided the basis of a validation study prior to doing the screening with the shuffled capsid library. For this study a control AAV pool was generated containing parental AAVs that each carried a unique barcode (BC) sequence immediately downstream of the capsid coding sequence. After mixing equal copy numbers of each of the 18 parental AAVs the pool was purified and analysed its composition by high-throughput sequencing of the barcodes (FIG. 50C). Although some of the parental AAVs were under- or over-represented in the pool, the 18 parent pool was found to be useful in a pilot library screen as the first validation for use of barcode sequencing in a capsid selection screen. To evaluate which capsid was best at transducing human islets human intact as well as dissociated islets were infected with the 18 parent pool and and super-infected with human adenovirus 5 to replicate AAVs. A ten-fold higher multiplicity of infection (MOI) for infection of intact than for dissociated islets was used, as it was reasoned that islet cells at the center were harder to infect than those on the periphery. Three consecutive rounds of selection were performed and AAV replication (FIG. 51) as well as composition of the viral pool (FIG. 52) was assessed at each round. For rounds 1 and 2 of selection lower copy numbers of viral genomes were recovered after propagation on intact islets as compared to the input whereas replication picked up at round 3. When a lower MOI of 2K was used to infect dissociated islet cells the amount of virus obtained after islet culture was higher than the input at each round of selection. Next generation sequencing (NGS) of the BC sequences was used to assess the composition of AAVs at each round. Between 400,000 and 1,000,000 sequence reads were obtained for each sample. Certain parental AAVs had a clear advantage over others as the diversity of the pool was already diminished after one round of selection, particularly when intact islets were used (FIG. 52). AAV2, AAV3B, as well as shuffled variants DJ and LK03 were enriched already after the first passage. After the third passage on intact islets as expected AAV-DJ and AAV-LK03 were equally represented while AAV2 and AAV3B were present to a lower extent. Passaging of the 18 parent pool on dissociated islet cells revealed early enrichment of AAV-DJ with lower proportions of AAV2, LK03, AAV3B, and AAV-rhesus10. This experiment validated our selection screen approach as it confirmed previous transduction studies showing that AAV-DJ and AAV-LK03 robustly transduce primary human islets.

Generation of Highly Diverse Barcoded Capsid Shuffled AAV Libraries

Prior to generating the shuffled AAV libraries a highly diverse AAV Barcode (BC) library was created. For this purpose, a fragment consisting of two 12 nucleotide (nt) long random barcode sequences separated by a 20 nucleotide (nt) long linker was cloned into an ITR containing AAV vector containing the AAV2 p5 promoter and rep gene, but no cap sequences. The barcode fragment was cloned immediately 3' of the cap polyA sequence, thus permitting tracking of variant enrichment throughout the selection process by high-throughput sequencing. Insertion of the BC sequence did not negatively impact virus function as shown by replication studies for wild type AAV with and without the BC (data not shown). High-throughput sequencing of the barcode plasmid library showed a sufficiently high degree of diversity with over 93% of all BC reads having a unique sequence (Table 6).

Figure 58A:
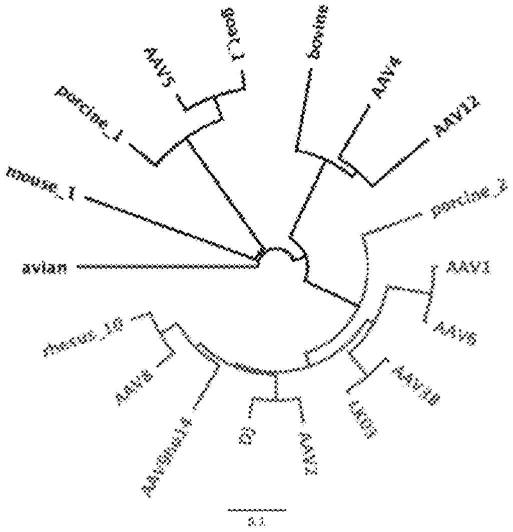
Figure 58B:
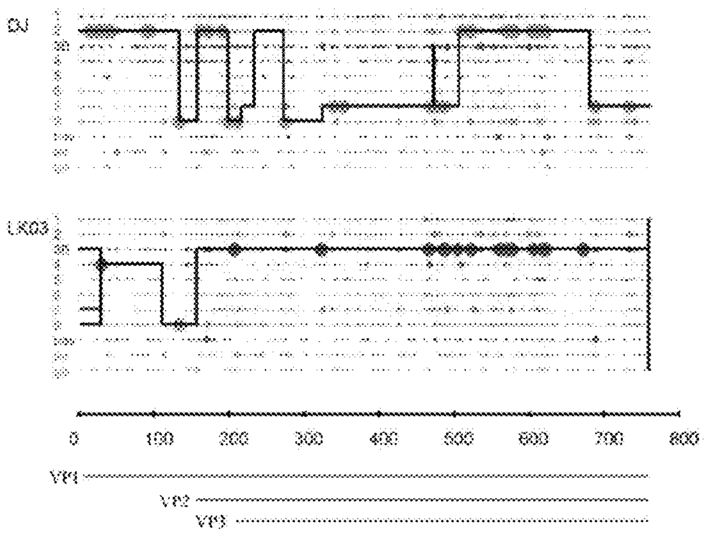
Figure 58C:
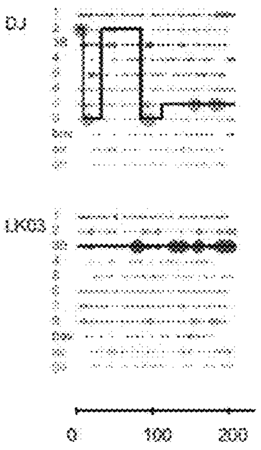

Out of over 1.2 million reads only one single BC sequence was present 6 times, 20 different BC sequences were present in 5 replicates, 342 different BC sequences were found 4 times each, 4844 BC were detected to be present in triplicates each, and 74,433 BC sequences (6%) were found twice. As high-throughput sequencing of the barcodes involved an amplification step it is most likely that the actual number of repetitive barcodes in the BC library was lower than that. The size of the barcode library was estimated to be 1E07 based on the number of colonies obtained from an aliquot of the transformation reaction. Shuffled capsids were then generated using sequences from 10 related AAVs or 18 more diverse AAVs and cloned into the BC library vector. A phylogenetic analysis of the parental sequences used for shuffling is depicted in FIG. 58A. Two of those capsid sequences—DJ and LK03—had been derived from previous screens performed in our laboratory using earlier generation libraries and are hybrids of AAV2, AAV8, and AAV9hu14 for DJ or AAV1, AAV3B, AAV4, AAV8, and AAV9hu14 for LK03 (FIG. 58B). FIG. 58B displays the composition of the DJ and LK03 capsids and FIG. 58C shows the composition of the DJ and LK03 assembly activating protein (AAP). The capsid shuffled barcoded 10 parent library and the 18 parent library each had a size of approximately 5E06 different clones as estimated by the number of colonies that had grown on an agar plate after plating small aliquots of the library transformation reactions. Given the low number of replicates after BC sequencing the complexity was estimated to be at least 1 million for each of the libraries.

TABLE 6

Barcode NGS data of the BC library, and the capsid shuffled libraries at the plasmid as well as the AAV level. The top identical sequences are shown, the number of times each sequence is represented within the sequence reads is shown in paranthesis.

| Sample | BC library | 10 parent plasmid library | 10 parent AAV library | 18 parent plasmid library | 18 parent AAV library |
|---|---|---|---|---|---|
| Total reads (#) | 1,249,614 | 1,256,634 | 1,141,870 | 1,804,277 | 1,000,494 |
| Unique reads (#) | 1,164,408 | 1,110,174 | 866,601 | 1,598,929 | 798,927 |
| Unique reads (%) | 93.18 | 88.35 | 75.89 | 88.62 | 79.85 |
| Identical BC (# of repeats) | 1 (6×) | 7 (7×) | 1 (287×) | 1 (8×) | 1 (232×) |
| Identical BC (# of repeats) | 20 (5×) | 30 (6×) | 1 (195×) | 8 (7×) | 1 (177×) |
| Identical BC (# of repeats) | 342 (4×) | 220 (5×) | 1 (182×) | 63 (6×) | 1 (173×) |
| Identical BC (# of repeats) | 4,844 (3×) | 1,809 (4×) | 1 (177×) | 365 (5×) | 1 (141×) |

The degree of library diversity was assessed using three different methods—high-throughput MiSeq analysis of the barcodes, PacBio sequencing of the capsids including the barcodes, as well as Sanger sequencing of the capsids including the barcodes. Amplification and high-throughput sequencing of the barcodes from the plasmid libraries as well as the AAV libraries revealed a very high degree of complexity with low numbers of replicates. At least 1 million reads were obtained for each sample (Table 6). When the 10 parent library was analysed on the plasmid level, i.e. prior to transfection into 293T cells, it was found that 88.3% of all reads contained unique sequences, with a maximum number of replicates found to be 7 reads out of 1.25 million reads. For the 18 parent plasmid library 88.6% of the reads were unique, the maximum number of reads obtained for one single BC sequence was 8 out of 1.8 million reads. Analysis of the NGS data for the AAV libraries revealed approximately 76% and 80% unique BC sequences for the 10 parent and 18 parent libraries respectively (Table 6). In the 10 parent AAV library one single BC sequence was represented with 287 reads (0.025%), in the 18 parent AAV library the highest number of reads obtained for a single BC was 232 (0.023%). There were also other replicates present in lower numbers, particularly 10 times and less.

As a low-throughput method several capsids from both plasmid libraries as well as from the 10 parent AAV library were analysed by Sanger sequencing and subjected to recombination analysis using the Xover program made available online by the Gillam lab. (FIG. 59A, FIG. 60A). For analysis of diversity on the AAV level the region spanning capsid and barcodes was amplified from extracted viral genomes, cloned and sequenced (FIG. 59A, right panel). In addition to depicting crossover figures of the shuffled capsids, we used the parental contribution data generated by the Xover software to perform conservation analysis throughout the capsid sequences. The conservation values for each amino acid residue were calculated and graphed (FIG. 59B, FIG. 60B). Using this analysis would allow for evaluation to see if sequence diversity within the libraries was drastically diminished when compared to the parental sequences. In case of the 10 parent library on the plasmid as well as the AAV level conservation patterns closely matched those of the parental sequences (FIG. 59B) while the 18 parent plasmid library exhibited higher conservation levels than the parents throughout most of the capsid (FIG. 60B). Crossover analysis of the capsid amino acid sequences showed that the 10 parent library was well shuffled with an average rate of 11 crossover events per capsid. A small number of clones contained a Glutamine at position 24 originating from the AAV4 derived sequence within chimeric parental LK03. For reasons of consistency LK03 and DJ had not been included as parentals in the crossover analysis figures, thus this residue is marked as a de novo mutation. With an average of 8 crossovers, the 18 parent library was less thoroughly shuffled. This observation can be explained with the large proportion of parental capsids that have low homology to each other throughout large stretches. Crossovers based on an identity of less than 15 bases are difficult to obtain.[13] This is likely due to fragments with low homology to each other do not easily recombine when equimolar amounts of each parent are mixed together. The observation that fewer crossovers were found within the 3' half of the library capsids can also be explained by this limitation as this part of the capsid contains several stretches of low sequence homology between the different serotypes. Complexity of the 10 parent library on the AAV level was found to be similar to that on the plasmid level indicating that capsid assembly during AAV production in 293T cells is not a bottleneck that dramatically reduces diversity (FIG. 59). Moreover, the crossover analysis patterns show that the parents appear to be represented roughly equally and randomly within the libraries, although AAV3B sequences seem to be slightly favoured in the 3' part of the shuffled clones. This can be explained in part by the fact that in addition to AAV3B the chimeric capsid LK03 was used as a parental sequence for shuffling. The entire 3' half of LK03 is derived from AAV3B, thus AAV3B sequence containing fragments were overrepresented in the initial fragment pool. In addition to Sanger sequencing of individual capsids, PacBio sequencing of the 10 parent library on the plasmid level prior to transfection into 293T cells (FIG. 50A) was performed, as well as on the AAV level (FIG. 50B). 21,000 full-length reads were obtained for the 10 parent library on the plasmid level while about half of that number of reads was analysed for the 10 parent AAV library. The graph depicts the contribution of each parental amino acid residue throughout the length of the capsid. As already observed by Sanger sequencing, PacBio sequencing revealed that the 5' half of the capsid gene contained a more even distribution of all parental sequences than the 3' half. Particularly residue contribution from AAV porcine2 and AAV9hu14 were starkly diminished in the sequence stretch between amino acid positions 450 and 650 while AAV3B sequences were overrepresented. An overrepresentation of AAV3B sequences is possibly at least in part due to the fact that LK03 which contains large sequence stretches from AAV3B (FIG. 58B) was used as a parental for shuffling.

Another analysis performed was to see if each capsid was linked to a unique barcode sequence and found very high levels of capsid-BC linkage. According to PacBio sequencing only 0.5% of all sequences had different capsids sharing identical barcodes. No cases in which different barcodes shared a common capsid sequence were detected.

Generation and Analysis of a Parental AAV Pool

Figure 50D:
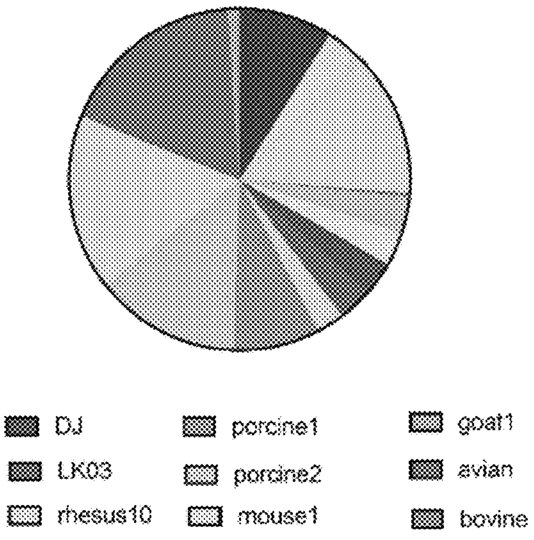

A control AAV pool was generated consisting of equal amounts of each of the 18 barcoded parental AAVs (based on vector genome copy numbers) and then purified this pool by double CsCl centrifugation. The composition of this pool was analysed by high-throughput sequencing of the barcodes (FIG. 50C). Some of the parental AAVs were slightly underrepresented in the pools although equal amounts of each virus were pooled prior to purification. It is possible that those parental AAVs banded at densities outside the collected fractions in the CsCl gradient. Nevertheless, most of the parental sequences were represented fairly equally in the pools. The parental AAV pool was also analysed by PacBio high-throughput sequencing of the amplified capsid plus BC sequence (FIG. 50D). Similar, but not identical data for composition of the pool as compared to the BC NGS data were obtained using PacBio Sequencing. These discrepancies may be due to subtle amplification differences of certain BC sequences or capsid plus BC sequences. Despite its shortcomings the 18 parent pool was found to be useful in a pilot library screen as the first validation for use of barcode sequencing in a capsid selection screen.

Passaging of the 18 Parent Pool on Human Islets

The transduction efficiencies of AAV-2 were first compared with AAV-DJ and AAV-LK03 (FIG. 62A) because of previous unpublished studies showing the latter two vectors as being the most robust in human islets (Song et al., ASGCT abstract). Confirming this result (FIG. 62A), provided the basis of a validation study prior to doing the screening with the shuffled capsid library. The 18 parental pool of AAV capsids were infected onto intact as well as dissociated human islets at MOIs of 20K and 2K, respectively and super-infected with human adenovirus 5 to replicate AAVs. Three consecutive rounds of selection were performed and AAV replication (FIG. 51) as well as composition of the viral pool (FIG. 52) was assessed at each round. For rounds 1 and 2 of selection lower copy numbers of viral genomes were recovered after propagation on intact islets as compared to the input whereas replication picked up at round 3. When a lower MOI of 2K was used to infect dissociated islet cells the amount of virus obtained after islet culture was higher than the input at each round of selection. NGS of the BC sequences was used to assess the composition of AAVs at each round. Between 400,000 and 1,000,000 reads were obtained for each sample. Certain parental AAVs had a clear advantage over others as the diversity of the pool was already diminished after one round of selection, particularly when intact islets were used (FIG. 52). AAV2, AAV3B, as well as shuffled variants DJ and LK03 were enriched already after the first passage. After the third passage on intact islets DJ and LK03 were equally represented while DJ clearly dominated the viral pool after the second passage on dissociated islets further validating our selection screen approach.

Passaging of the Capsid Shuffled Libraries on Human Islets

Both libraries were used to infect intact as well as dissociated islets at MOIs of 20K and 2K respectively and Ad5 was used to replicate AAV. After each round virus replication was assessed by qPCR (FIG. 51) and enrichment of variants was tracked by NGS of the BC sequences (FIG. 52). The NGS sample size was between 400,000 and 800,000 sequence reads. In contrast to the 18 parent pool, replication of the libraries at each round of selection was observed which might indicate that certain capsid sequences confer improved tropism, transduction, and/or replication. Distinct capsid variants were selected for as early as round 1 in case of the 18 parent library. A second set of library screens on intact islets using two different MOIs (10K and 50K) were performed in duplicates for the 10 parent library. Furthermore, another 18 parent library screen was performed in triplicates using an MOI of 50K. Replication data for this library screen are shown in FIG. 61A, the BC NGS data are shown in FIG. 61B. Similar levels of replication and enrichment were observed during this second set of library screens. However, this time one variant was found to be enriched in two independent screens (MOI 10K B and MOI 50K B) of the 10 parent library (variant 10B5, highlighted in yellow), indicating that this particular variant may have a significant selection advantage in islets. A different variant was found to be enriched in two of the triplicate screens of the 18 parent library (18B2, highlighted in magenta).

Evaluation of Selected AAV Capsid Variants for Improved Transduction of Islets

Figure 53A:
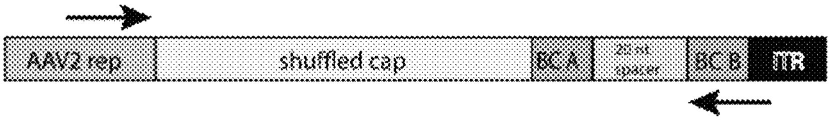
Figure 53B:
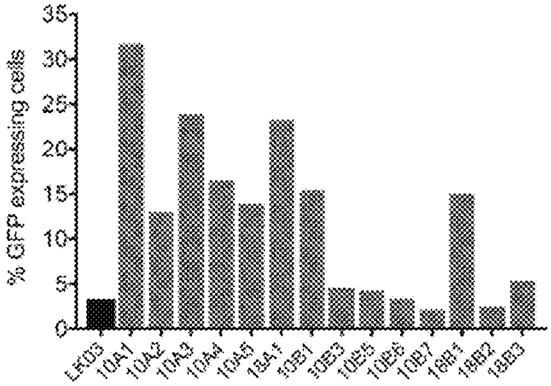
Figure 53C:
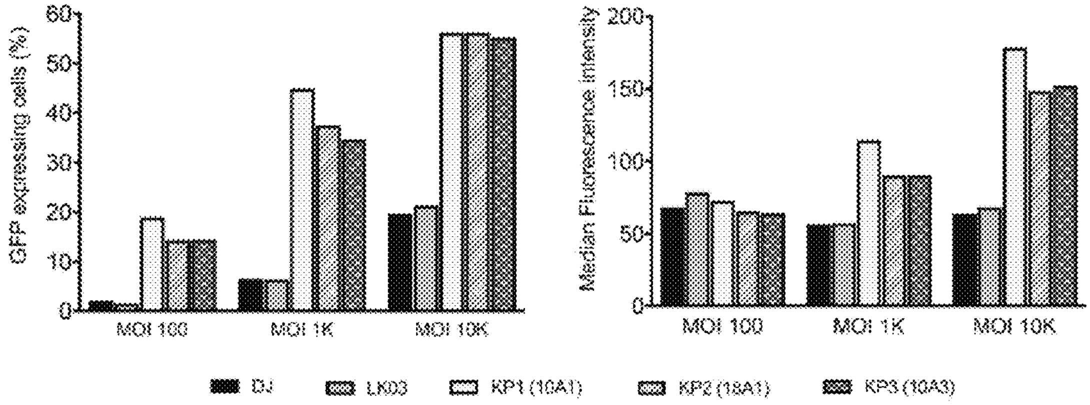
Figure 53D:
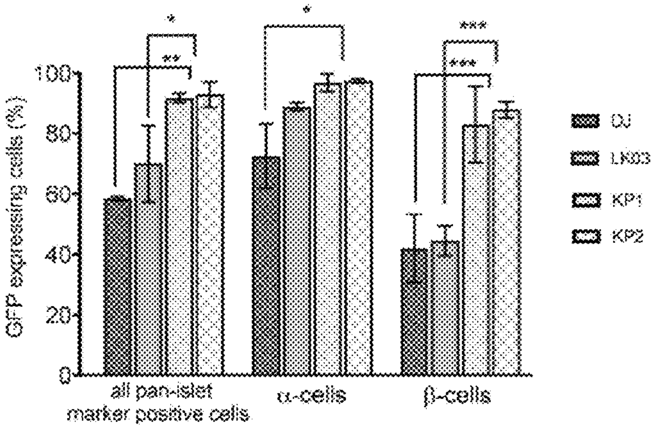

A total of 17 enriched capsid sequences were recovered from the different screens after three rounds of selection (see FIG. 52 and FIG. 61B for enrichment data of those variants) using a BC sequence specific reverse primer (FIG. 53A), TOPO cloned, and sequenced. Several clones for each BC were sequenced to ensure that the left BC sequence matched the sequence obtained by BC NGS. For several of the capsids it was observed that the capsid sequences differed for some of the clones, particularly at the 5' end. This was likely due to template switching after incomplete extension[3-5] and may be alleviated by optimizing PCR conditions and enzymes. It is not believed that it was due to insufficient capsid BC linkage as exhaustive analysis of the input libraries was performed and only found a low level of library clones that contained different capsids linked to identical barcodes. Also, an experiment with two closely related parental sequences revealed that template switching did indeed occur during amplification (data not shown). It was decided to vectorize the capsids that matched the consensus sequence. It was found that all enriched capsids shared large contributions from AAV3B in the 3' half while the 5' half was much more diverse (data not shown). While AAV3B sequence in the 3' half was certainly overrepresented in the input library there was still a fairly good contribution of other parental sequences as shown by Sanger as well as PacBio sequencing. It was established in earlier experiments that DJ and LK03 capsids transduced islets with higher efficiency than AAV2 or AAV3B capsids (FIG. 62A), thus the novel capsids were compared to DJ and LK03 only. All 17 capsid variants as well as one of the previously established best islet capsids (LK03) were used to package a self-complementary AAV vector with GFP as transgene driven by the CAG promoter. Three of the capsids failed to generate high-titer rAAV and were excluded from further evaluation. In an initial pre-screen crude cell lysate derived rAAV was used to transduce dissociated islet cells at a low MOI. Transduction efficiency was determined by flow cytometry of GFP expressing cells two days post transduction. While multiple capsid variants exhibited higher transduction efficiency than AAV-LK03 others were only marginally improved or not improved at all (FIG. 53B). The three most improved capsids (10A1, 18A1, and 10A3) were all derived from the first set of library screening and are referred to as KP1, KP2, and KP3 from now on. Those capsids were used to produce high-titer double CsCl gradient purified rAAV preps. Dissociated islet cells were transduced with those variants as well as with AAV-DJ and AAV-LK03 using three different MOIs and analysed for transduction by FACS. The variants were confirmed to transduce islet cells with considerably higher efficiency than the best parents (FIG. 53C, FIG. 62A). An at least 10-fold higher titer was necessary to transduce the same fraction of islet cells with AAV-DJ or AAV-LK03 as compared to the variant capsid AAVs. The next step was to determine if the novel capsids target α- or β-cells specifically. Subpopulation specific staining of islets that had been transduced with high MOIs of scCAG-GFP vectors packaged with KP1 and KP2 capsids revealed improved β-cell transduction when compared to AAV-DJ and AAV-LK03 while α- cell transduction was marginally improved (FIG. 53D). Moreover, as intact islets were used in this experiment, it was demonstrated that the novel AAVs were capable of penetrating the islets and transduced almost all of the α- and β-cells when a sufficiently high MOI was used.

β-cells were generated from human embryonic stem cells (hESC)s following a recently developed enrichment protocol[75] and tested one of the novel capsids for transduction efficiency as compared to AAV-DJ and AAV-LK03 using three different MOIs. Tomato Red expressing vectors were used in this experiment and cells were stained for the β-cell marker C-peptide (FIG. 66, FIG. 68). Similar to what had been observed in patient derived islet cells a 5- to 10-fold higher titer of AAV-DJ or AAV-LK03 was necessary to achieve similar rates of transduction as with AAV-KP1 in those cells. It should be noted that transduction efficiency is determined both from the percentage of Tomato Red expressing cells and fluorescence intensity of transduced cells AAV-KP1 in those cells.

Figure 5A:
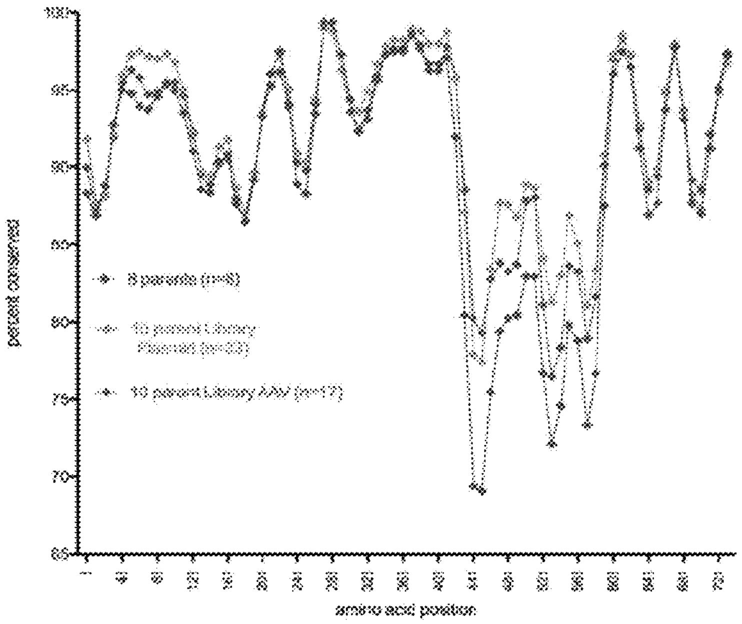
FIG. 5A-5B. Parental contributions in the 10 parent library listed by amino acid position. Capsid sequences were amplified from the plasmid library (upper panel) as well as from the AAV library (lower panel) and analyzed by PacBio high-throughput sequencing. (A) Conservation analysis by amino acid position of random 10 parent library clones at the plasmid level and the AAV level as compared to the 10 parents. (B) PacBio high-throughput sequencing of the 10 parent library capsid at the plasmid level (top) as well as the AAV level (bottom) showing parental contributions throughout the capsid sequence.
Figure 5B:
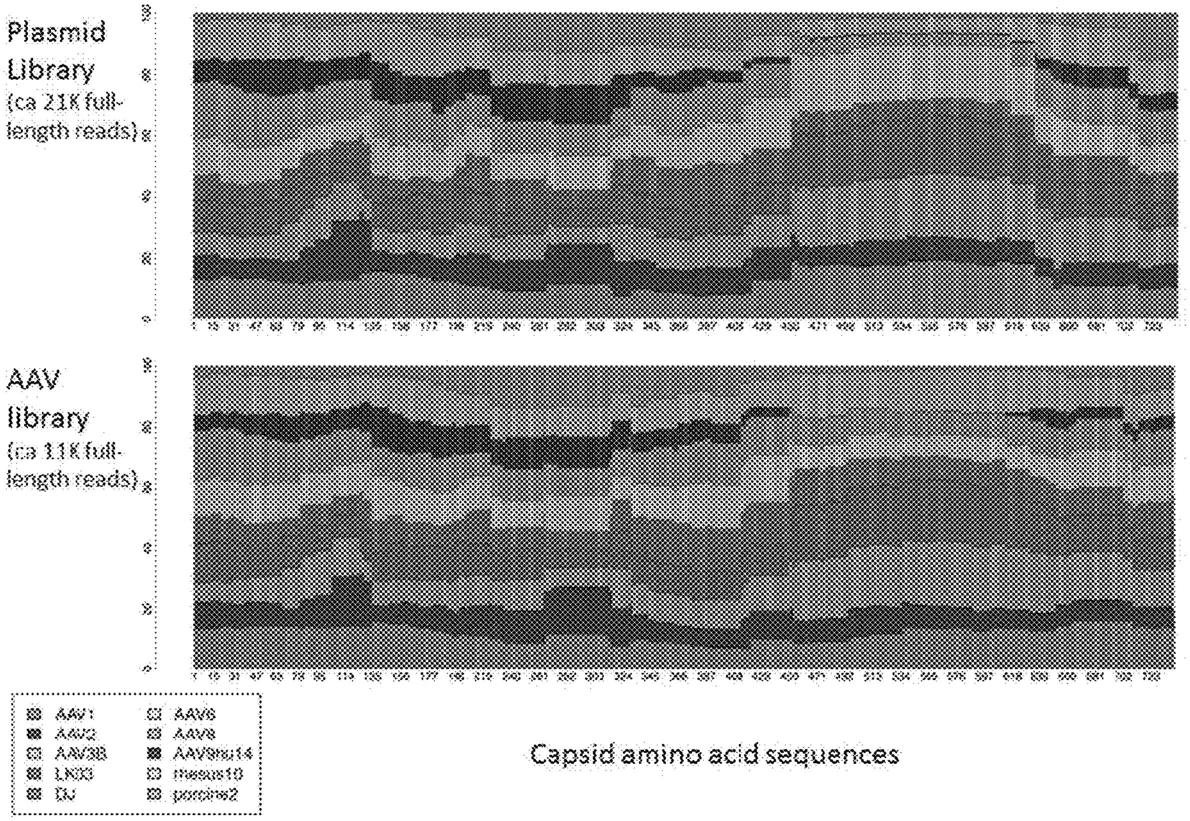
Figure 6:
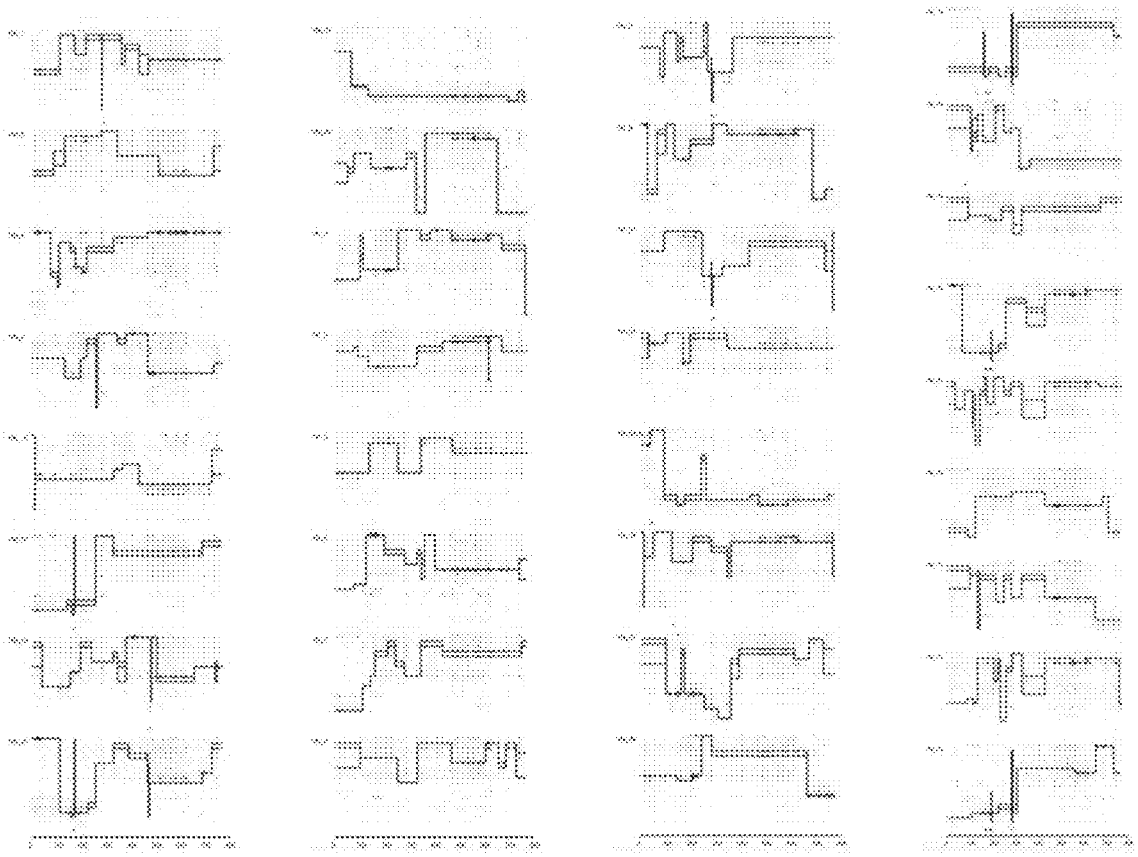
FIG. 6. 18 parent library (plasmid level).
Figure 7:
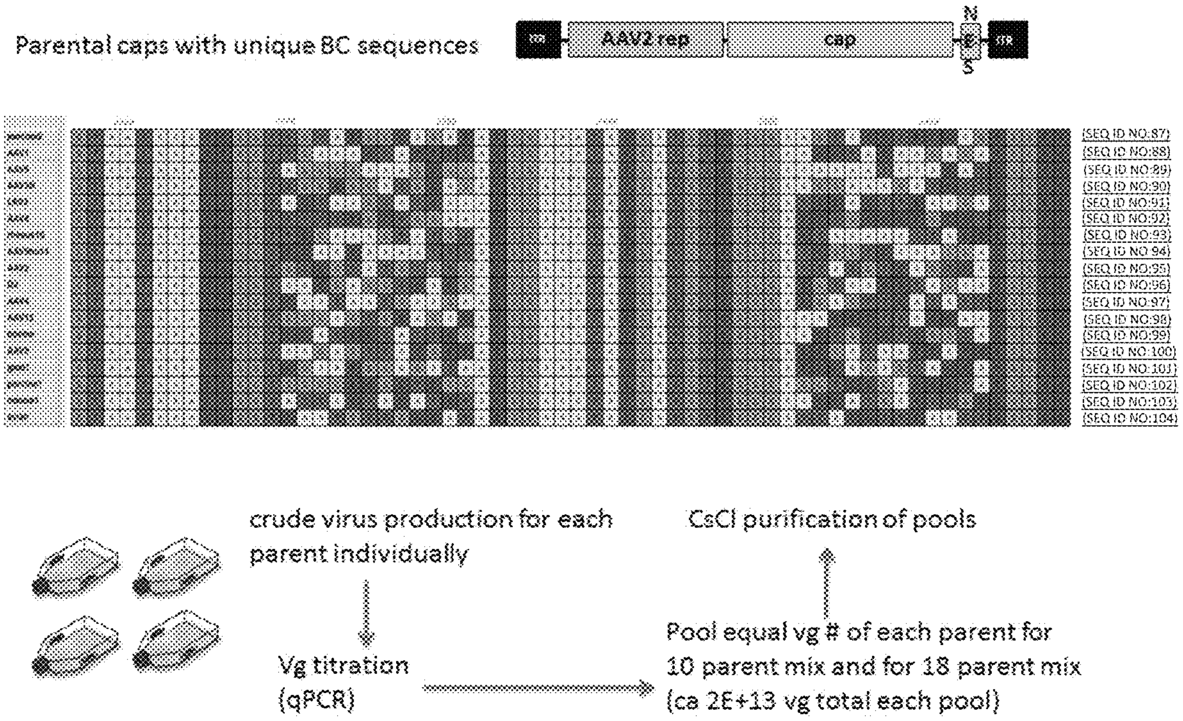
FIG. 7. Production of the 18 parent mix.
Figure 54A:
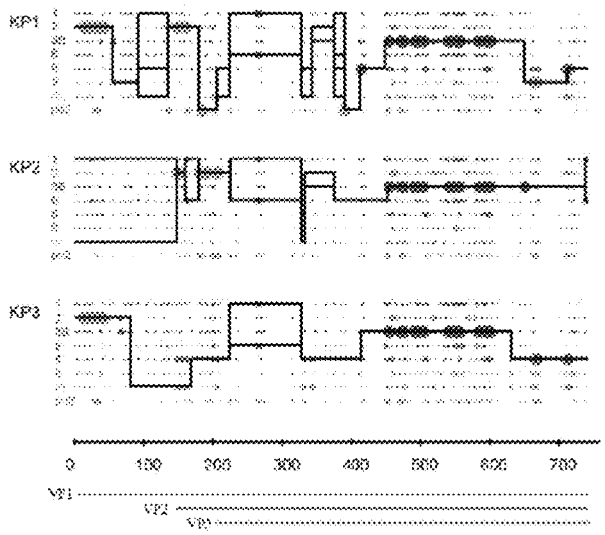
Figure 54B:
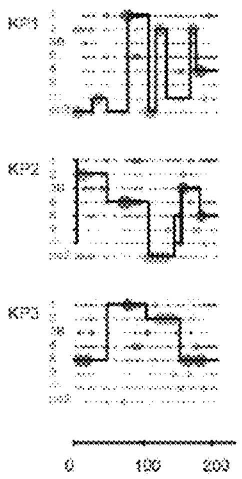
Figure 54C:
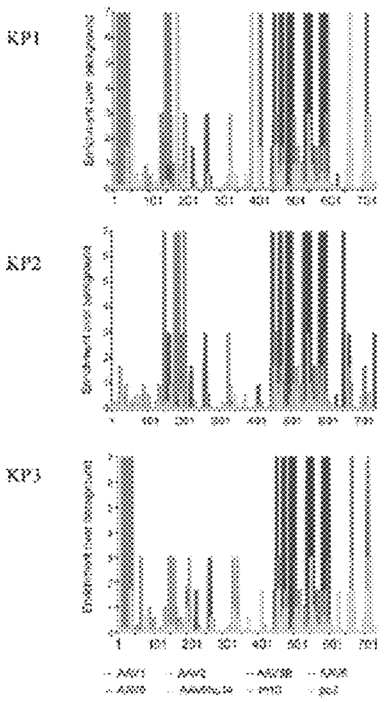
Figure 54D:
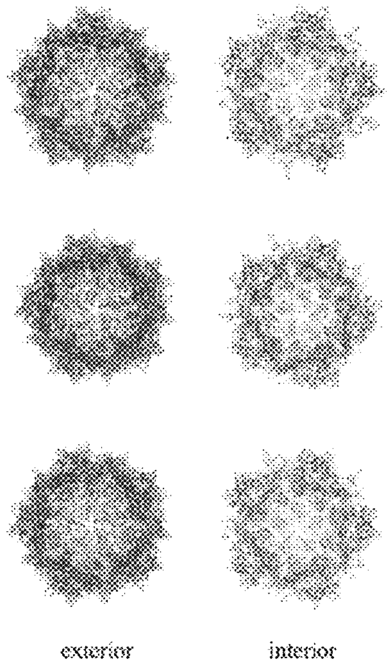
Figure 54E:
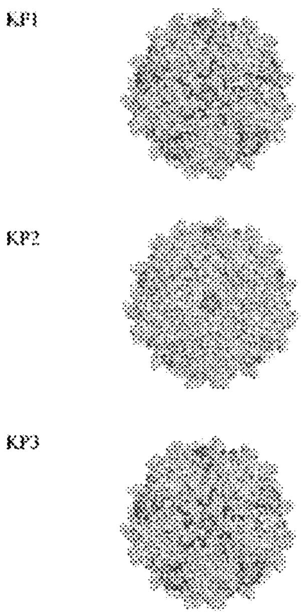
Figure 65A:
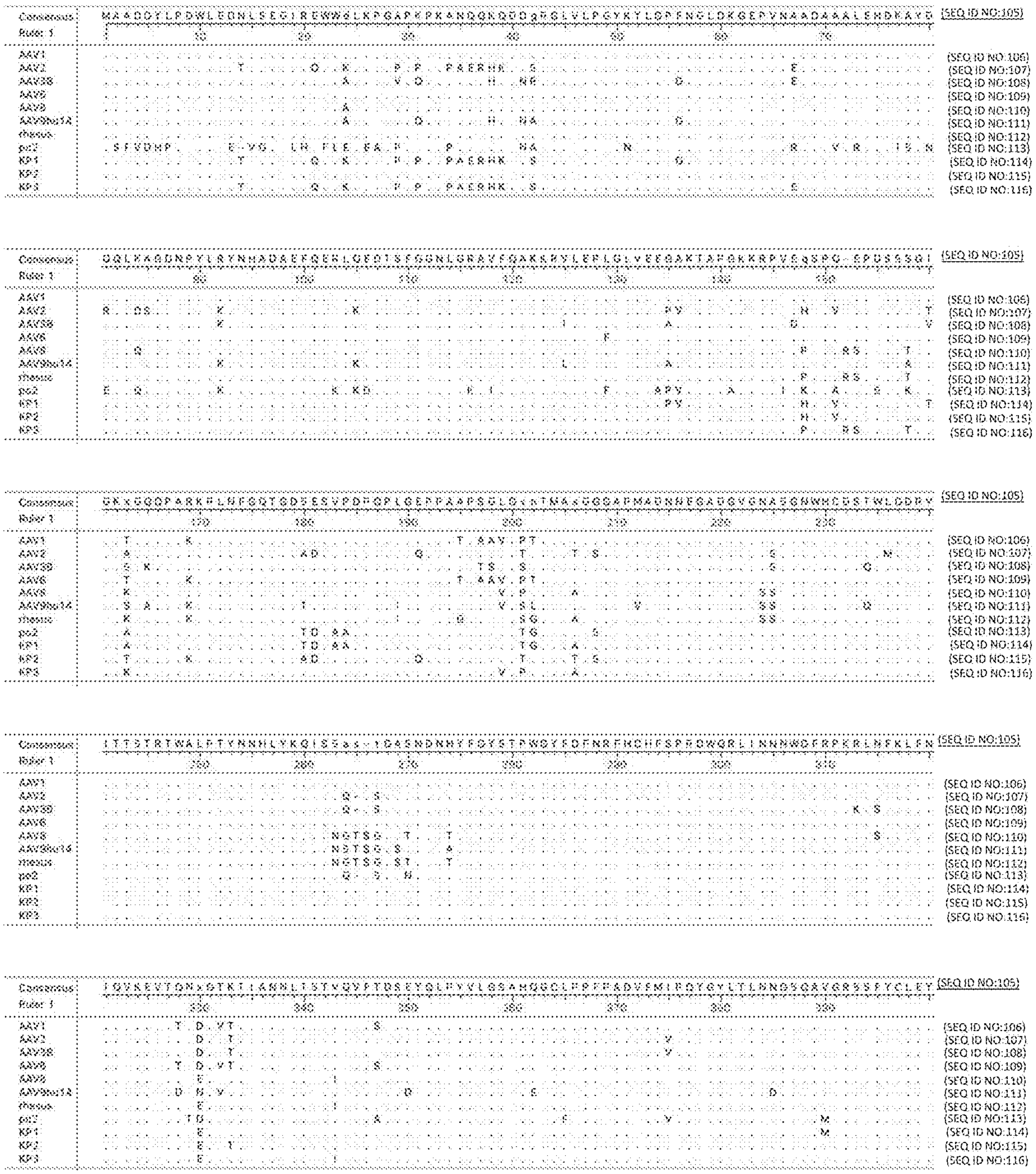
Figure 65A:
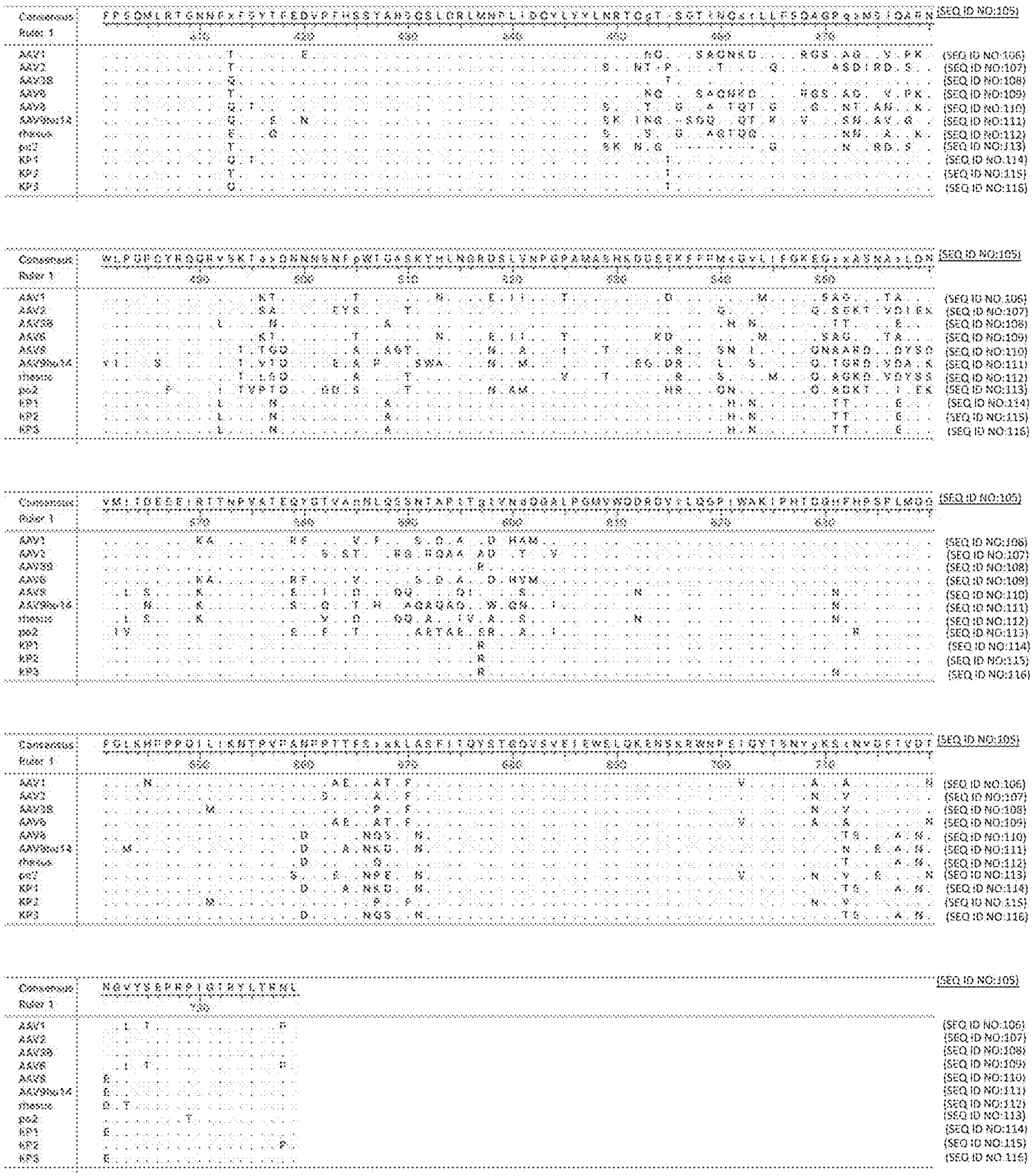
Figure 65B:
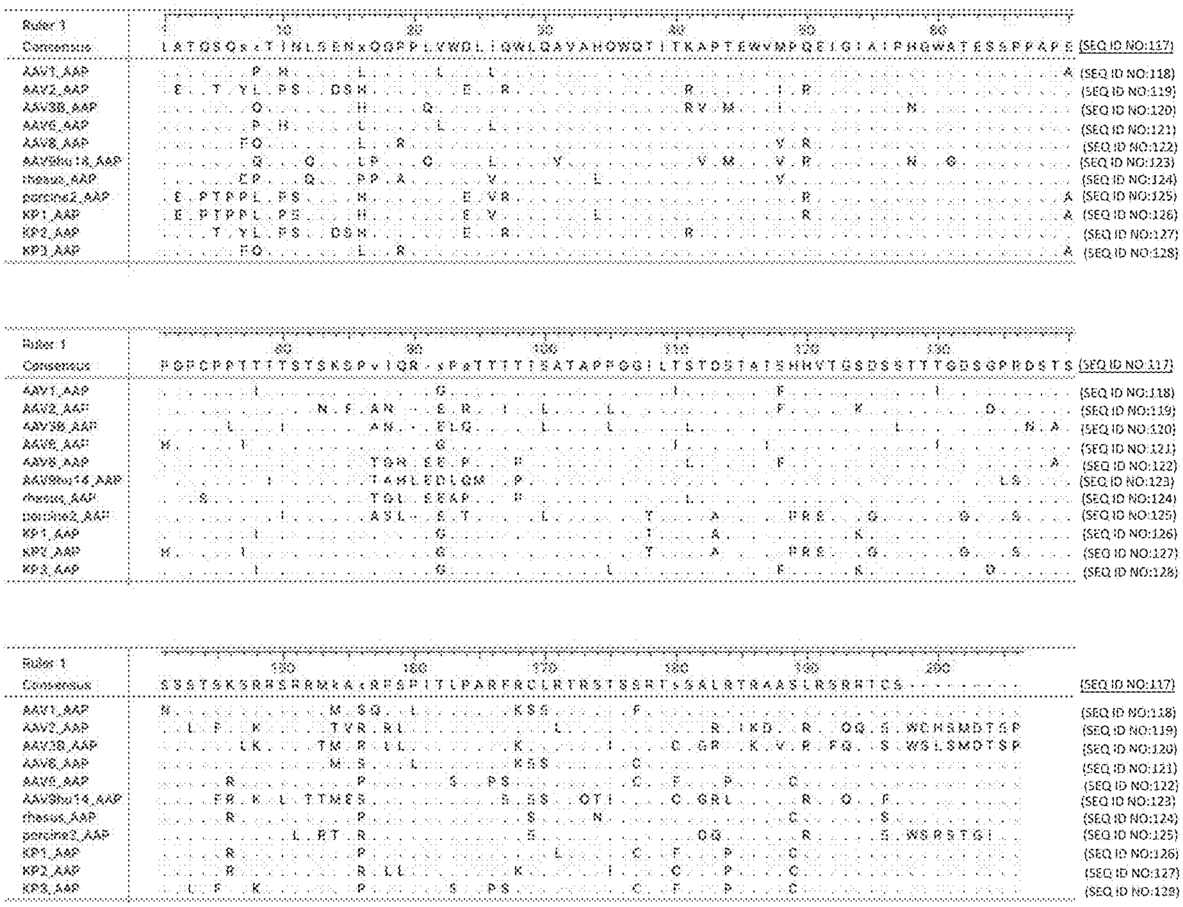

The next step was to try to elucidate common sequence features of the improved capsids. FIG. 54A depicts crossover analyses of the three most improved capsid amino acid capsid sequences with the highest islet cell transduction efficiencies. While the N-terminal part of capsid KP1 contains stretches from many different parental sequences capsids KP2 and KP3 are less diverse in this sequence stretch. However, as seen for all capsids enriched during the islet screen most of the C-terminal half of those capsids was derived from AAV3B, suggesting that this stretch may contain sequence determinants that are crucial for islet cell tropism. AAV3B is the parental capsid that is most closely related to the three novel capsids with 92% sequence identity to KP1 and KP3 and 95% identity to KP2. When performing crossover analysis with the nucleotide sequences (FIG. 63A) the parental contributions were very similar to those found for the amino acid sequences for most part, however some parental contribution patterns differed. As an example in the case of KP2 capsid the region around nucleotide position 900 was derived from AAV-porcine2 capsid rather than AAV1 or AAV6 capsid as the amino acid crossover analysis had suggested. The Xover program will always attempt to minimize the number of crossover events. Since all the parental sequences between amino acid position 275 and 313 share a common amino acid sequence (FIG. 65A), but have different nucleotide sequences, this stretch is shown as being derived from AAV1 or AAV6 when using amino acid sequences, but is shown as being derived from AAV6 and AAV-porcine2 when performing the analysis using the nucleotide sequences. The number of crossovers was also lower for the amino acid sequences as compared to the nucleotide sequences. As an example KP1 capsid has 19 crossovers at the nucleotide level while this was reduced to 15 crossover events on the amino acid level. Since functionality of the capsid is determined by the amino acid sequences focus was put on the amino acid sequence crossover analysis. The fact that all three improved capsids share three residues that are unique to AAV1 and AAV6 in the sequence stretch between aa 225 and 267 may indicate that these residues are important for human islet transduction (FIG. 54A, FIG. 65A). Since AAP uses a different reading frame within the capsid gene crossover analysis for this protein was also performed. It was found that all three novel variants contained chimeric AAP sequences (FIG. 54B, FIG. 65B). As seen for the nucleotide sequence crossover analysis several KP2 AAP residues were derived from AAV-porcine2. Besides the crossover analysis, enrichment analysis was performed that confirmed strong selection pressure for certain amino acid residues in all three capsids (FIG. 54C). In the N-terminus the two most improved variants KP1 and KP3 showed a strong selection of AAV2 residues while they share AAV8 derived residues in the C-terminus. KP2 capsid shows a strong enrichment of several AAV2 residues between positions 150 and 210. All three capsids have an Arginine at the position that has been described to be the key HSPG binding site for AAV3B (position 597 in FIG. S65A)[76]. Predictive three-dimensional structural VP3 capsid mapping of the novel variants was performed to reveal those residues that are displayed on the outside of the capsids (FIG. 5D). All three improved capsids were found to contain Glutamic acid in VP3 hypervariable region (HVR) I (labeling according to[77]) at the 5-fold symmetry pore (position 330 in FIG. S65A) which is derived either from AAV8 or AAV-rhesus10. AAV3B as well as all other parentals except for AAV9hu14 have an Aspartic acid residue at this position. Two other residues shared among all three capsids are the Alanine and the Threonine in HVR I (positions 264 and 266 in FIG. S65A). KP1 and KP3 capsids also contain the surface exposed residue Arginine in HVR II (position 333 in FIG. S65A) which is also shared by parental capsids AAV8, AAV9hu14 and AAV-rhesus10. In addition KP1 and KP3 capsids display residues Aspartic acid, Asparagine, Leucine, and Asparagine within a variable stretch between HVR VIII and IX which was termed HVR 11 by Gao and colleagues[78] (positions 660, 666, 670, and 671 in FIG. S65A). In HVR IX KP1 and KP3 capsids share AAV8 derived surface exposed residues Tyrosine, Threonine, Serine, Alanine, Asparagine, and Glutamic acid (positions 709, 712, 713, 717, 719, and 721 in FIG. S65A). The KP1 capsid displays a suface exposed Methionine which is derived from AAV-porcine2 while KP3 has a AAV3B derived Valin in this position (position 390 in FIG. S65A). Moreover, KP1 contains an Alanine derived from AAV9hu14 at position 664 while KP3 has the same Threonine residue as AAV3B at this position. Surface exposed residues 667 (Lysine) and 668 (Aspartic acid) were derived from AAV9hu14 for KP1 while they originated from AAV8 for KP3 (Glutamine and Serine). In addition to residues displayed on the capsid surface all three novel capsids shared several VP3 residues that are buried inside the capsid (Alanine, Threonine, Arginine, and Asparagine at positions 225, 234, 313, and 315 respectively). Those residues possibly also contribute to the observed strong transduction efficiency as they may be involved in uncoating and other post entry steps.

Figure 63A:
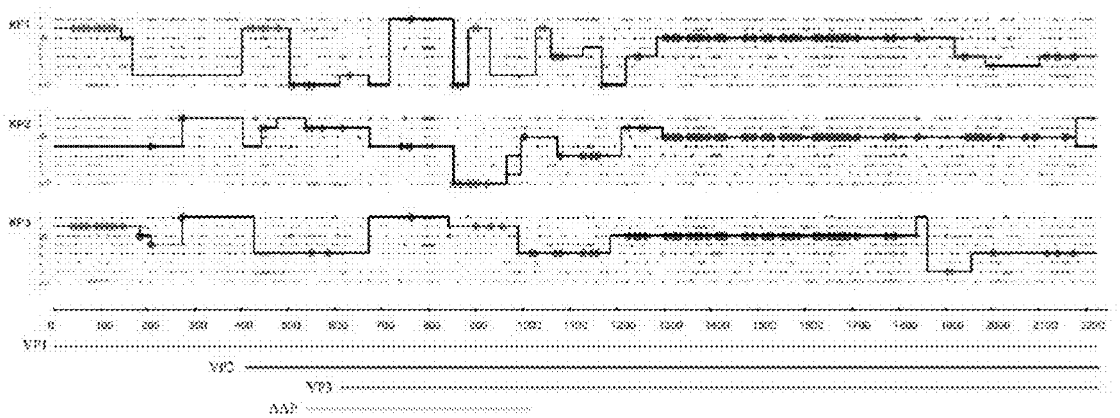
Figure 63B:
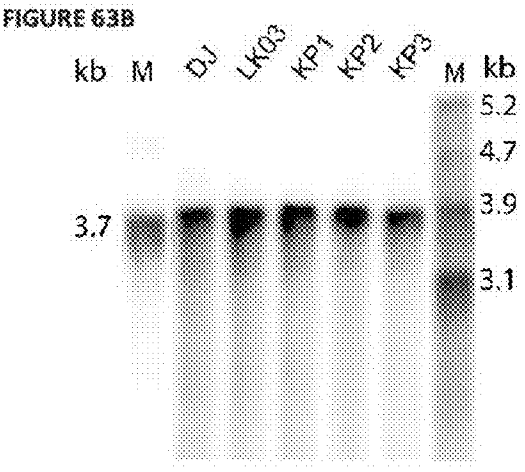
Figure 63C:
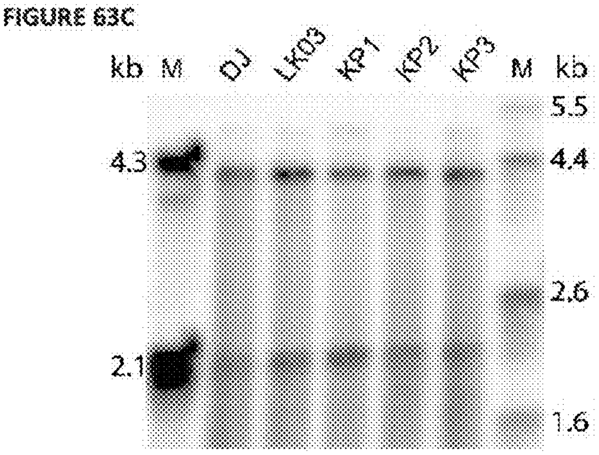
Figure 63D:
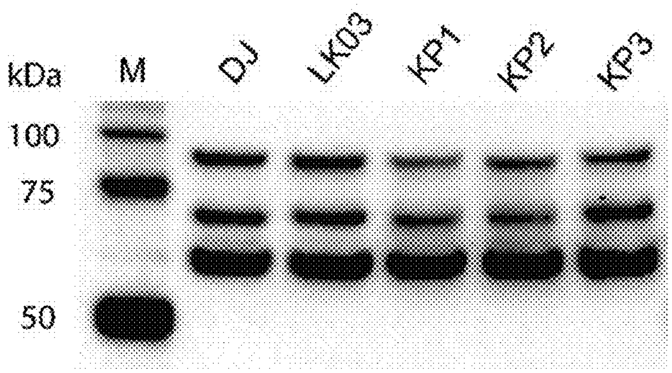

The next step was to evaluate whether the novel capsids would package self-complementary and single stranded vector genomes with similar efficiency as AAV-DJ and AAV-LK03 capsids. Thus Alkaline Southern Blot analysis was performed using isolated vector genomes from CsCl purified rAAV preparations (FIG. 63B) and it was found that a single stranded CAG-Firefly Luciferase genome was packaged at the expected size of 3.7 kb (FIG. 63B). When rAAV preparations packaging self-complementary CAG-GFP genomes were analysed, a band at 4.3 kb was found which represents the self-complementary full-length genome with two expression cassettes joined at the trs deleted ITR. However, in addition to the expected 4.3 kb product, a band of about half the expected size was observed which possibly represents the single stranded vector (FIG. 63C). The reason for this may be the fact that a packaging vector expressing rep with the wild-type ATG start codon was used for virus production as this has been linked to increased levels of ss genome packaging when producing sc vectors. Lower levels of Rep protein expression after mutation of the ATG start codon to the less efficient ACG start codon have been linked to a higher rate of ds genome packaging (Wu et al., 2007).[79] Also incubation times longer than 52 hrs post transfection have been described to increase reversion of double stranded (ds) to single stranded (ss) genomes (Gray et al., 2011).[80] However, for the current study it is of importance to note that the full-length as well as the shorter genome was packaged with equal efficiency for the novel variants as well as AAV-DJ and AAV-LK03. Thus, the improved transduction efficiency of the novel capsids cannot be attributed to increased packaging of full-length functional genomes. Furthermore, the capsid proteins variants consisted of all three capsid proteins VP3, VP1 and VP2 in the expected stoichiometry of 10:1:1 (FIG. 63D).

Evaluation of Transduction Efficiency on a Panel of Diverse Cells Lines

Several primary cells as well as cell lines derived from human as well as animal sources were transduced at an MOI of 1K with a single-stranded firefly luciferase rAAV vector packaged with two parental (DJ, LK03) as well as the three evolved capsids (KP1, KP2, KP3) and analysed for transduction efficiency using a luciferase assay. AAV-LK03 did not transduce murine cells efficiently while AAV-DJ transduced all cell lines with high efficiency. The novel variants showed improved transduction efficiency as compared to AAV-DJ on human islet cells, 293, Hela, HuH7, R7T1, alpha TC1, HepG2, CHO K1, human muscle stem cells, mouse myoblasts, SNU 737, as well as FRhK-4 cells (FIG. 55A, FIG. 64A). AAV-KP1 showed the highest degree of enhancement in general. Transduction of the novel capsid variants as compared to DJ was not or only marginally improved on human keratinocytes, differentiated human myoblasts as well as primary mouse embryonic fibroblasts.

Neutralization Profile of the Novel Capsid Variants

The novel capsid variants as well as AAV-DJ and AAV-LK03 were analysed for sensitivity towards neutralization by two different batches of pooled human immunoglobulin (FIG. 55B). The experiment was performed in seven biological replicates for each sample, split between two independent experiments. While AAV-DJ showed the highest resistance towards neutralization with ~120 ug/ml IVIG needed for 50% inhibition AAV-LK03 was very sensitive with 50% neutralization achieved with only around 15 ug/ml. AAV-KP2 had a neutralization profile similar to that of AAV-LK03 while AAV-KP1 and AAV-KP3 needed more IVIG to be neutralized (45-ug/ml for KP3 and 55-ug/ml for KP1). In summary, when pooled human IVIGs were used for neutralization two of the novel variant capsids performed better than AAV-LK03, but less favourable than AAV-DJ.

In Vivo Biodistribution of the AAV-KP Variants in Mice

Mice were injected intravenously with 2E10 vg per mouse of firefly luciferase vector rAAV packaged with AAV8, AAV-DJ as well as AAV-KP1, KP2, and KP3 capsids and transgene expression was monitored over several weeks by live imaging (FIG. 56, FIG. 64A). The majority of AAV was found to target the liver. AAV-KP1 appeared to transduce mouse liver more rapidly than AAV-DJ, but expression levels were only slightly higher once steady state expression was achieved at later time points. Thirty-five days post injection several organs were harvested from each mouse and analyzed for luciferase expression. With the exception of liver very low levels of expression with a high variation within each group of mice were detected (FIG. 64B). AAV-KP2 as well as AAV-KP3 injected mice had higher luciferase expression in heart tissue than AAV-DJ or AAV8 injected mice and all three variants had transduced spleen with higher efficiency than DJ or AAV8. Kidney tissue from KP variant AAV injected mice also had higher luciferase expression than that from AAV-DJ injected mice, but levels were not significantly higher when compared to AAV-8 injected mice. Vector genomes were quantified in the organs using qPCR. However, vector genome copies clearly above background were detected only for the liver samples (FIG. 64C). Mice injected with AAV-KP1 contained higher vector copy numbers than the mice that had received AAV-DJ or AAV-8 packaged vectors. AAV-KP3 injected mice contained significantly more vector genomes in their livers than AAV8 injected mice. AAV-KP2 injected mice, however, contained similar levels of rAAV genomes as AAV8 injected mice.

Assessing Functional Hepatocyte Transduction in Xenograft Liver Models In Vivo

Humanized FRG xenograft mice were transduced to assess the functional human hepatic transduction capabilities of one of our shuffled capsids in an appropriate in vivo setting. Mice were highly re-populated with human hepatocytes as shown by expression of high levels of human albumin (between 5.6 and 8 mg/ml). Humanized mice were administered Tomato Red expressing rAAV packaged with DJ, LK03, or KP1 capsids at a dose of 1E11vg/mouse via the intravenous injection, and assessed for expression of Tomato Red protein in human and mouse hepatocytes 14-days post-AAV administration (FIG. 57). It was observed that LK03 had high transduction efficiency in human hepatocytes, but not mouse hepatocytes while transduction with DJ was not specific towards human cells. KP1 was also found to transduce both human and mouse hepatocytes, however levels were higher than those found with DJ. In three of the four AAV-KP1 injected mice transduction efficiency for human hepatocytes was similar to that found in AAV-LK03 injected mice. However, total transduction was higher in AAV-KP1 injected mice since unlike AAV-LK03, AAV-KP1 transduced both mouse and human cells.

Discussion

The new capsids identified in the current study were at least 10-fold more efficient at transducing human islet cells, particularly β-cells. When one of the variants was tested for transduction efficiency of hESC derived R-cells similar levels of improvements were achieved. In addition, it was confirmed that prior observations that capsid variants AAV-DJ and AAV-LK03 were capable of transducing primary human islets with equal or better efficiency than AAV2 or AAV3B. However, high MOIs are required to efficiently target cells within the center of the islets, and -cell transduction was less efficient than that of α- cells.

Recently several studies have used retrograde pancreatic intraductal delivery in mice to safely and effectively administer rAAV vectors into the pancreas[49, 81, 82]. Overexpression or inhibition of several transcription factors was found to effectively convert pancreatic islet progenitors and committed islet α-cells into β-cells[50, 52-58]. Endoscopic retrograde cholangio-pancreatography (ERCP) is routinely used in patients to examine the pancreatic and bile ducts and could be used to deliver the novel vectors for diabetes treatment.

The method for generation of barcoded capsid shuffled AAV libraries is described in great detail so that other researchers can easily apply this protocol in their own laboratory, either with genes from AAV or any other virus to generate libraries that can be screened for the desired properties. In addition to the protocol for library generation, also described is the generation of a pool containing parental AAVs that proved to be useful as a parental control during the passaging regimen. This pool can be used in any library selection to optimize the selection parameters to isolate AAV capsids with a desired property. The cost and time can be minimized by predetermining the appropriate MOI and number of selection rounds for a particular screen. In contrast to studies in Applicant's lab that routinely employed five rounds of selection, in the current study it was found that three rounds of selection were sufficient to enrich and amplify variants with improved transduction to a level where they could be isolated reliably.

In addition, combining short DNA barcodes and single molecule DNA sequencing approaches will enable one to optimize other important parameters, such as the best MOI to use during the selection process, and the number of screening rounds necessary for efficient enrichment. When generating the AAV libraries from the plasmid libraries by transfection care was given not to overload the cells with library plasmid DNA by reducing the amount of AAV plasmid DNA almost 20-fold as compared to previous protocols for virus production. It had been reported that a transfected copy number of 5000 AAV genomes per cell is sufficiently low to minimize cross-packaging while still achieving high-titer libraries.[83] While the possibility of cross-packaging, characterized by sequence differences between the packaging capsid and the corresponding viral genome, can not be excluded several of the enriched capsids from our screen were found to exhibit the desired phenotype, suggesting that cross-packaging or mosaicism was not a major problem in our libraries. Moreover, previously generated AAV libraries using high concentrations of AAV plasmid during transfection were successful in generating variants with greatly improved phenotypes[8, 37-39] suggesting that for reasons unknown so far there seems to be a strong capsid genotype linkage in case of AAV packaging[11].

When libraries on human islets were screened several capsid sequences were enriched, three of which have improved transduction efficiency not only for human islets, but also for a variety of other cell types. While it is not clear which amino acid residues in the novel capsids are responsible for the improved islet phenotype, several features were noticed in the improved capsid sequences that may confer enhanced transduction of islet cells as well as other cell types. The C-terminal parts of all three improved capsids are strongly enriched for AAV3B residues suggesting that these amino acids may play an important role for islet tropism. In the N-terminus the two most improved variants KP1 and KP3 showed a strong selection of AAV2 residues and all three capsids contain a Threonine originating from either AAV1 or AAV6 at position 265 (FIG. 65A). All three capsids have an Arginine at position 594 (position 597 in FIG. 65A) that has been described to be the key HSPG binding site for AAV3B[6] (Lerch and Chapman).

It is interesting that KP1—despite its similarity to AAV3B and AAVLK03-transduced mouse hepatocytes as well as human hepatocytes in the humanized liver mouse model. This humanized model was used previously to select for several highly human liver AAV transducing vectors (Lisowski Paulk)[37, 39] one of which has been shown to provide robust hFVIII expression in an early human trial[84, 85]. However, all of the vectors selected in the previous screen showed poor transduction of mouse tissues or cells in vitro and in vivo. In contrast, the KP1 variant showed similar transduction of human hepatocytes in the chimeric mouse model but in contrast to AAVLK03 showed efficient transduction of mouse liver. This is intriguing because some have suggested the transduction of human hepatocytes in this mouse model was exaggerated because of the relatively low transduction of mouse cells. If the human hepatocyte results obtained in the humanized mouse model is influenced by the degree of mouse hepatocyte transduction perhaps the KP1 variant will provide even more robust transduction when tested in human trials. At a minimum because this vector transduces both mouse and human liver, a surrogate capsid for preclinical testing is not required. Ultimately, these capsids are good candidates for future study in human clinical liver based gene therapy trials.

A recent report by the Grimm group laid to rest the concern that functionality of AAV capsid libraries generated for directed evolution studies might be severely compromised by inactivation of the assembly activating protein (AAP) in a large proportion of the chimeric variant pool[86]. AAP had previously been described to play an important role in virus assembly[9, 87-89], but appears to be strikingly tolerant towards recombination. Random capsids from other shuffled libraries were previously tested for packaging efficiency and found that surprisingly the vast majority of the capsids produced normal or only slightly reduced titres of rAAV, indicating that the randomized AAP sequence was not detrimental in most cases. The AAP sequences of all the chimeras selected in the present studies are chimeric and the rAAV titres obtained with two of the capsids were lower than those obtained with LK03. Supplying wildtype AAP during virus production was not evaluated to see if it would enhance titres, but this is a possibility to boost rAAV production.

The use of barcoded libraries for molecular evolution studies was found to be highly beneficial as high-throughput analysis of the barcodes of enriched variants is much more cost-effective and thorough than cloning and sequencing of the entire capsids. The libraries generated for this study are currently evaluated in screens on a number of other target cells and may result in the discovery of other AAV capsid variants that are useful for other clinical gene therapy applications.

Methods:

Generation of an AAV vector containing a library of unique barcode sequences. A wildtype AAV2 vector in which the capsid coding sequences had been replaced by a PacI and AscI containing linker fragment (kindly provided by D. Grimm and S. Grosse, University of Heidelberg, Germany) was used as the starting material for construction of the barcoded AAV library. Two unique restriction sites (AgeI and EagI) were introduced just downstream of the cap polyadenylation signal by mutating two nucleotides in the original sequence (A to T and T to C at positions 6 and 24 when counting the last nucleotide of the cap polyA signal as starting point). Barcodes consisting of two stretches of 12 random nucleotides separated by a 20 nt long spacer sequence were generated as described previously[73]. Briefly, an oligonucleotide with an AgeI restriction site sequence on the 5'-end followed by 12 random nucleotides and the 20nt long spacer sequence (CTA AAC CGG TNN NNN NNN NNN NAC GGA AAT ACG ATG TCG GGA) was annealed to an oligonucleotide containing an Eag I site on the 5' end followed by 12 random nucleotides as well as the antisense spacer sequence (TTC TCG GCC GNN NNN NNN NNN NTC CCG ACA TCG TAT TTC CGT) and extended using Klenow Polymerase devoid of exonuclease activity (NEB). Fragments were purified using a Qiaquick PCR purification kit (Qiagen) and subsequently digested with AgeI and EagI and purified using a Qiaquick PCR purification column. Vector was digested with the same restriction enzymes, dephosphorylated, phenol-chloroform purified and Ethanol precipitated. The optimum vector to insert ratio was evaluated by setting up several ligation reactions initially and testing for possible multiple barcode inserts by performing colony PCR with primers rightF (CGC GCC ACT AGT AAT AAA C) and QSeqRev (TAG AGC AAC TAG AGT TCG). For the scale-up reaction barcodes were ligated with the vector at a molar vector to insert ratio of 1 to 2.5 in a total volume of 30-ul, de-salted using Strataclean resin according to instruction (Agilent Technologies) and electroporated in 2-ul aliquots into DH10B-MegaX cells (Thermo Fisher). Electroporated cells were pooled and used to inoculate 500-ml LB-Amp medium. An aliquot was plated to assess library size and diversity. After 16-hrs in a 37° C. shaker bacteria were harvested and plasmid DNA was isolated using a Megaprep kit (Qiagen). ITR integrity was confirmed by digestion with XmaI as well as with AhdI. Several individual clones from the test plate were sequenced to assess barcode diversity.

Generation of capsid shuffled barcoded AAV libraries. DNAse I mediated family shuffling was essentially performed as described previously[25, 90, 91] Capsid sequences from 16 AAV serotypes (AAV1, AAV2, AAV3B, AAV4, AAV5, AAV6, AAV8, AAV9hu14, AAV12, AAV rhesus10, AAV porcine1, AAV porcine2, AAV bovine, AAV mouse1, AAV avian, AAV goat1) as well as from shuffled variants AAV DJ and AAV LK03 that had been selected in previous screens[8, 37] were used as parental sequences for the shuffling reactions. The capsid sequences had been obtained from various sources (D. Grimm, University of Heidelberg, Germany, Kay lab, Vector Core, Stanford). All sequences contained a PacI site immediately 5' and an AscI site 3' of cap and had been cloned into pBluescript. Prior to shuffling capsid sequences were amplified individually using primers located in the flanking pBluescript sequences (outer F: AAT TAA CCC TCA CTA AAG G, outer R: GTA ATA CGA CTC ACT ATA GGG C). Phusion Hot Start Flex polymerase (NEB) was used for amplification and 25 PCR cycles were employed (30-sec 98° C., 25 cycles of 10-sec 98° C., 15-sec 56° C., 1-min 15-sec 72° C., followed by 10-min 72° C.). PCR products were purified using the Qiaquick PCR purification kit (Qiagen), all 18 capsids (for the 18 parent library) or 10 capsids (for the 10 parent library, AAV1, AAV2, AAV3B, AAV6, AAV8, AAV9hu14, AAV12, AAV rhesus10, DJ, LK03) were pooled in equimolar ratio and fragmented at room temperature (RT) using DNase I (Sigma). At different incubation time points aliquots were analysed on an 1.5% agarose gel while the reaction was temporarily stopped by incubation in a dry ice/ethanol bath.

Incubation time and DNAse concentration was adjusted until the majority of the fragments ranged from 100-bp to 500-bp. The entire reaction was then loaded on an 1.5% agarose gel and fragments in the desired size range were electroeluted from the gel, purified using two rounds of phenol-chloroform purification followed by one round of chloroform purification and ethanol precipitated. DNA fragments were then re-assembled in a primer-less PCR using Phusion Hot Start Flex polymerase and the following cycling conditions: 30-sec 98° C., 40 cycles of 10-sec 98° C., 30-sec 42° C., 45-sec 72° C., followed by 10-min 72° C.

Full-length capsid sequences were amplified from the assembly reactions using primers rescueF (GTC TGA GTG ACT AGC ATT CG) and rescueR (GTC TAC TGA AGC TCA CTG AG) and the following cycling conditions: 30-sec 98° C., 25 cycles of 10-see 98° C., 15-sec 57° C., 1-min 15-sec 72° C., followed by 10-min 72° C. Amplicons were diluted 4-fold with fresh PCR mix and subjected to one additional cycle with a 10-min extension to fill up the ends. After concentrating PCR products using a PCR purification kit (Qiagen) they were digested with PacI and AscI and ligated into the BC library vector that had been treated with PacI, AscI, dephosphorylated and phenol-chloroform purified. Ligation reactions were de-salted using the Strataclean resin, electroporated into MegaX DH10B cells and expanded in liquid culture as described above for generation of the BC library vector. Aliquots of transformed cells were plated to assess library size and diversity of the library using Sanger sequencing. 40 clones of the 10 parent library and 20 clones of the 18 parent library were sequenced using primers capF (TGG ATG ACT GCA TCT TTG AA), capF2 (ATT GGC ATT GCG ATT CC), and QSeqRev (TAG AGC AAC TAG AGT TCG).

AAV libraries were generated in HEK 293T cells using the calcium phosphate transfection method. Compared to the regular protocol the amount of transfected library plasmid DNA was reduced almost 20-fold to approximately 5000 copies per cell to minimize the likelihood of cross-packaging events taking place during AAV production. Briefly, 25 T225 flasks were seeded with 8E06 cells per flask in 40 ml media two days prior to transfection. On the day of transfection cells were between 80% and 90% confluent. 20-ml of media per flask was replaced with fresh media 1.5-hrs prior to transfection and a mixture of 40-ug pAd5 helper plasmid and 2-ug library plasmid in 4-ml 300 mM $CaCl_2$) per T225 was prepared. Equal amounts of $CaCl_2$)/DNA mix and 2×HBS (280 mM NaCl, 50 mM HEPES pH 7.28, 1.5 mM $Na_2HPO_4$, pH 7.12) were mixed and 8-ml of the mixture was added to each flask. After 3 days cells were detached with 0.5-ml 500 mM EDTA each flask and the cell pellet was resuspended in Benzonase digestion buffer (2 mM $MgCl_2$, 50 mM Tris-HCl, pH 8.5). AAVs were released from the cells by submitting them to three freeze-thaw cycles, non-encapsidated DNA was removed by digestion with Benzonase (200-U/ml, 1-hr 37° C.), cell debris was pelleted by centrifugation, followed by another $CaCl_2$) precipitation step (25 mM final concentration, 1-hr on ice) of the supernatant and an AAV precipitation step using a final concentration of 8% PEG-8000 and 625 mM NaCl. Virus was resuspended in HEPES-EDTA buffer (50 mM HEPES pH 7.28, 150 mM NaCl, 25 mM EDTA) and mixed with CsCl to a final refractory index (RI) of 1.371 followed by centrifugation for 23-hrs at 45000 Rpm in a ultracentrifuge. Fractions were collected after piercing the bottom of the centrifuge tube with a 18 gauge needle and fractions ranging in RI from 1.3766 to 1.3711 were pooled and adjusted to an RI of 1.3710 with HEPES-EDTA resuspension buffer. A second CsCl gradient centrifugation step was carried out for at least 8-hrs at 65000 Rpm. Fractions were collected and fractions with an RI of 1.3766 to 1.3711 were dialyzed overnight against PBS, followed by another 4 hr dialysis against fresh PBS and a 2-hr dialysis against 5% sorbitol in PBS. All dialysis steps were carried out at 4° C. Virus was recovered from the dialysis cassette and pluronic F-68 was added to a final concentration of 0.0010%. Virus was sterile-filtered, aliquoted, and stored in aliquots at −80° C. Genomic DNA was extracted from 10-ul of the purified virus using the MinElute Virus Spin Kit (Qiagen Cat #57704), and the viral genome titer was determined by qPCR using an AAV2 rep gene specific primer probe set (repF: TTC GAT CAA CTA CGC AGA CAG, repR: GTC CGT GAG TGA AGC AGA TAT T, rep probe: TCT GAT GCT GTT TCC CTG CAG ACA).

Generation of barcoded parental AAV pools. Capsids from all 18 parental AAVs were cloned into the BC library vector using PacI and AscI restriction sites. Each parental AAV contained a unique barcode sequence as confirmed by sequence analysis and between 2 and 6 T225 with 293T cells were transfected with each parental AAV (37.5-ug AAV plasmid and 37.5-ug pAd5 helper plasmid per T225). Crude lysates of each barcoded parental cap AAV were generated and 2.8E12 vg of the 10 parents or 1.1E12 vg of the 18 parents were pooled to generate the 10 parent and the 18 parent mix respectively. AAV pools were purified by double CsCl gradient centrifugation as described above.

Sequence contribution analysis of evolved AAV capsids. Contigs were assembled using Sequencher 5.3 software and aligned the Muscle multiple sequence alignment software (MacVector, Version 14.5.3). Xover 3.0 DNA/protein shuffling pattern analysis software was used to generate parental fragment crossover maps of shuffled variants. Each parental serotype was color coded as indicated in the figures.

PacBio sequencing of AAV pools and libraries. For the 10 parent library as well as the 18 parent pool a 2.4 kb fragment containing the capsid as well as the BC sequences was amplified using capF and QSeqRev from extracted viral genomes, loaded onto a 1% agarose gel, visualized by staining with SybrSafe, and gel-purified using a gel extraction kit (Qiagen). The 10 parent library was also assessed at the plasmid level prior to generating the AAV library using restriction enzymes (PacI and XbaI) to release the capsid sequences and gel purified as described above for the amplified capsid sequences. Library preparation and Pacific Biosciences (PacBio) sequencing were performed at the University of Washington PacBio Sequencing Service. Briefly, SMRT bell libraries were prepared following the "Procedure and Checklist-2 kb Template Preparation and Sequencing" protocol from PacBio using the SMRTbell Template Prep Kit v1.0 (PacBio Cat #100-259-100). PacBio 'Binding and Annealing' calculator was used to determine appropriate concentrations for annealing and binding of SMRTbell libraries. SMRTbell libraries were annealed and bound to P6 DNA polymerase for sequencing using the DNA/Polymerase Binding Kit P6 v2.0 (PacBio Cat #100-372-700). Bound SMRTbell libraries were loaded onto SMRT cells using standard MagBead protocols and the MagBead Buffer Kit v2.0 (PacBio Cat #100-642-800). The standard MagBead sequencing protocol was followed with the DNA Sequencing Kit 4.0 v2 (PacBio Cat #100-612-400, also known as P6/C4 chemistry). Sequencing data was collected for 6-hour movie times with 'Stage Start' not enabled. Circular consensus sequence (CCS) reads were generated using the PacBio SMRT portal and the RS_ReadsOfinsert.1 protocol, with filtering set at Minimum Full Pass=3 and Minimum Predicted Accuracy=95%.

Bioinformatic assessment of PacBio sequence reads. CCS reads with full capsid sequence lengths from 2,250-2,380 nucleotides were included in downstream bioinformatics analyses. Indels in CCS reads were corrected using an in-house algorithm that first assesses parental fragment identity using Xover 3.0 DNA/protein shuffling pattern analysis software. Once the parental identity of each crossover fragment was determined, this information was used to determine indels for correction. Single nucleotide polymorphisms (SNPs) that did not result in indels were maintained. The SNP error rate with the PacBio platform is 1.3-1.7%. SNP frequencies above this rate range were assumed to have arisen from de novo mutations. Corrected sequences in FASTA format were then aligned with MUSCLE. Phylogenetic analyses were conducted using the maximum-likelihood method in RAxML[12133] (Stamatakis et al. 2005).

False-colored structural capsid mapping. (FIG. 54D) Chimeric capsids (VP3 sequences only) were false-color mapped onto the AAV2 VLP structure 5IPI (Drouin et al., 2016) using UCSF Chimera version 1.12. Mapped colors correspond to parental serotype colors used in the parental fragment crossover maps. Exterior capsid views have all chains represented, while cross-section views have chains surrounding a cylinder at the 5-fold symmetry axis removed exposing the capsid interior lumen.

Alternative False-colored structural capsid mapping. (FIG. 54E) Chimeric capsids (VP3 sequences only) were false-color mapped onto the AAV6 structure 4V86[94] using PyMOL Version 2.3.0. Only surface exposed amino acids that are different from the closest parental AAV3B are shown. With the exception of AAV3B which is shown in gray all mapped amino acid residue colors correspond to parental serotype colors used in the crossover and enrichment figures.

Conservation and enrichment calculations. Amino acid conservation for each position was calculated using the alignment profile obtained with MacVector version 14.5.3. Average conservation values were calculated for stretches of 30 amino acid residues and were used to generate the graphs. Percent parental conservation was determined using an in-house algorithm that identifies the percentage of each parent on each aligned position in the shuffled library. The maximum square size indicates that 100% of variants share that amino acid from that parent at that position. All other square sizes are proportional to the percent of variants from 0-100% that have that amino acid at that position from that parent. Enrichment scores were calculated for each amino acid position in the sequence of each chimera by comparison of sequences from parental serotypes based on maximum likelihood. Xover version 3.0.74 was used to generate a crossover data analysis set for each chimera. Excel version 16.20 was used to convert those data into enrichment scores. Library parents are depicted in different colors as shown.

Statistics. Statistical analyses were conducted with Prism v7.0d. Experimental values were assessed via two-way ANOVA using Tukey's multiple comparisons test. P values <0.05 were considered statistically significant.

High throughput sequencing of AAV barcodes. Barcode sequences were amplified with indexed primers (F: AAT GAT ACG GCG ACC ACC GAG ATC TAC ACT CTT TCC CTA CAC GAC GCT CTT CCG ATC T (I) CGC GCC ACT AGT AAT AAA C and R: CAA GCA GAA GAC GGC ATA CGA GAT CGG TCT CGG CAT TCC TGC TGA ACC GCT CTT CCG ATC T (I) TAG AGC AAC TAG AGT TCG, with the indices (I) containing between 4 and 6 nucleotides), gel-purified from 2% SybrSafe containing agarose gels, pooled (up to 30 samples), and sequenced on a MiSeq instrument. The number of PCR cycles was minimized to avoid amplification bias and was dependent on the concentration of input AAV genomes as determined by rep qPCR. The following cycling conditions were used: 2-min 98° C., 15 to 30 cycles of 15-sec 98° C., 15-sec 50° C., 20-sec 72° C., with a final 15-min extension at 72° C. Phusion Hot Start Flex (NEB) was used for all amplifications.

Cell Culture Conditions

Human islet cultures. Human pancreatic islets from deceased non-diabetic organ donors were provided by the Integrated Islet Distribution Program (IIDP) or the University of Alberta through the Stanford Islet Research Core and cultured in CMRL-1066 with 10% FBS, Pen-Strep, 1% Insulin Transferrin Selenium (Thermo Fisher), 1 mM sodium pyruvate, 2 mM Glutamax, 2.5 mM HEPES. Ultra-low attachment dishes were used for all islet cell culture experiments.

hESC derived β-cells: Mell $INS^{BFP/W}$ human embryonic stem cell (hESC)s were obtained from S. J. Micallef and E. G. Stanley (Monash Immunology and Stem Cell Laboratories, Australia). Cells were maintained and propagated on mouse embryonic fibroblasts (MEFs) in hESC media [DMEM/F12 (Gibco) with 10% KSR (Gibco), 10 ng/ml FGF-2 (R&D Systems)]. A stepwise differentiation of hESC toward β cells was carried out following the protocol described previously[75]. Briefly, confluent hESC were dissociated into single-cell suspensions using TrypLE (Gibco), counted and seeded at $5.5\times10^6$ cells per well in 6-well suspension plates in 5.5 ml hESC media supplemented with 10 ng/ml activin A (R&D Systems) and 10 ng/ml heregulinB (Peprotech). The plates were incubated at 37° C. and 5% $CO_2$ on an orbital shaker at 100 rpm to induce 3D sphere formation. After 24 hours, the spheres were washed with PBS and resuspended in day 1 media. From day 1 to day 20, media was changed every day. Media compositions are as follows: Day 1: RPMI (Gibco) containing 0.2% FBS, 1:5,000 ITS (Gibco), 100 ng/ml activin A and 50 ng/ml WNT3a (R&D Systems). Day 2: RPMI containing 0.2% FBS, 1:2,000 ITS and 100 ng/ml activin A. Day 3: RPMI containing 0.2% FBS, 1:1,000 ITS, 2.5 μM TGFbi IV (CalBioChem) and 25 ng/ml KGF (R&D Systems). Day 4-5: RPMI containing 0.4% FBS, 1:1,000 ITS and 25 ng/ml KGF. Day 6-7: DMEM (Gibco) with 25 mM glucose containing 1:100 B27 (Gibco) and 3 nM TTNPB (Sigma). Day 8: DMEM with 25 mM glucose containing 1:100 B27, 3 nM TTNPB and 50 ng/ml EGF (R&D Systems). Day 9-11: DMEM with 25 mM glucose containing 1:100 B27, 50 ng/ml EGF and 50 ng/ml KGF. Day 12-20: DMEM with 25 mM glucose containing 1:100 B27, 1:100 Glutamax (Gibco), 1:100 NEAA (Gibco), 10 μm ALKi II (Axxora), 500 nM LDN—193189 (Stemgent), 1 μm Xxi (Millipore), 1 μM T3 (Sigma-Aldrich), 0.5 mM vitamin C, 1 mM N-acetyl cysteine (Sigma-Aldrich), 10 μM zinc sulfate (Sigma-Aldrich) and 10 μg/ml of heparin sulfate. At day 20, the spheres were collected, incubated with Accumax (innovative cell technologies) for 10 min at 37° C. and dissociated into single cells. Live GFP-high cells were sorted on Aria II at low flow rates and reaggregated in Aggrewell-400 (StemCell Technologies) at 1,000 cells per cluster in CMRL containing 10% FBS, 1:100 Glutamax (Gibco), 1:100 NEAA (Gibco), 10 μm ALKi II (Axxora), 0.5 mM vitamin C, 1 μM T3 (Sigma-Aldrich), 1 mM N-acetyl Cysteine (Sigma-Aldrich), 10 μM zinc sulfate (Sigma-Aldrich) and 10 μg/ml of heparin sulfate. At day 23, the reaggregated enriched β-clusters (eBCs) were transferred from Aggrewells and placed on orbital shakers at 100 rpm, and further cultured for 6 days. Media was changed every third day following reaggregation.

Human skeletal muscle stem cell and myotube cultures. A pool of primary muscle stem cells isolated from 6 individual donors (kind gift from G. Charville, Stanford) was frozen at an early passage and aliquots were used for experiments. Plates were coated with extracellular matrix protein (Sigma) at 1:500 in DMEM with 1% penicillin/streptomycin. The hMuSC medium was a 1:1 mixture of DMEM:MCDB media supplemented with 20% FBS, 1% insulin-transferrin-selenium, 1% antibiotic/antimycotic, and 10 μM p38i (Cell Signaling Technology Cat #SB203580) to maintain the stem state as described[95]. Media for differentiating primary hMuSCs into myotubes lacked p38i and included a 2% horse serum starve instead of 20% FBS for 7 days. All media was changed every two days.

Mouse skeletal muscle myoblast cultures. Wild-type C2C12 mouse myoblasts (ATCC Cat #CRL-1772) were maintained in DMEM supplemented with 10% FBS and 1% antibiotic/antimycotic.

293 and 293T cell line cultures. HEK 293 cells (ATCC Cat #CRL-1573) and HEK 293T cells (ATCC Cat #CRL-3216) were cultured in DMEM with 10% FBS, 2 mM glutamine, 1% antimycotic-antibiotic, 11 mM HEPES pH 7.28 and 1 mM sodium pyruvate.

HeLa cell cultures. HeLa cells (ATCC Cat #CCL-2) were cultured in DMEM with 10% FBS, 2 mM glutamine, 1% antimycotic-antibiotic.

Mouse pancreatic β-cell cultures. R7T1 cells (kind gift from H. Moeller, Stanford) were cultured in DMEM with 10% FBS, 2 mM glutamine, 1% antimycotic-antibiotic, 1-ug/ml Doxycyclin.

Mouse pancreatic α-cell cultures. Alpha TC1 clone 6 cells (ATCC Cat #CRL-2934) were cultured in DMEM with 10% FBS, 2 mM glutamine, 1% antimycotic-antibiotic, 15 mM HEPES, 0.1 mM NEAA.

Rat hepatoma cell cultures. H4TG cells (ATCC Cat #CRL-1578) were cultured in DMEM with 10% FBS, 4 mM glutamine, 1% antimycotic-antibiotic.

Human hepatocellular carcinoma cell cultures. SNU-387 cells (ATCC Cat #CRL-2237) and HepG2 (ATCC Cat #HB-8065) were cultured in RPMI with 10% FBS, 2 mM glutamine, 1% antimycotic-antibiotic, 1% non-essential amino acids. HuH7 cells were cultured in DMEM with 10% FBS, 2 mM glutamine, 1% antimycotic-antibiotic, 1% non-essential amino acids.

Human keratinocyte cell cultures. HaCaT cells (kind gift from A. Oro, Stanford) were cultured in DMEM with 10% FBS, 2 mM glutamine, 1% penicillin/streptomycin.

Hamster ovary cell cultures. CHO-K1 cells (ATCC Cat #CCL-61) were cultured in Ham's F12 with 10% FBS, 1% penicillin/streptomycin.

Rhesus macaque kidney cell cultures. FRhK-4 cells (ATCC Cat #CRL-1688) were cultured in DMEM with 10% FBS, 2 mM glutamine, 1% penicillin/streptomycin.

Mouse fibroblast cell cultures. Primary mouse embryonic fibroblasts derived at E14 were cultured in DMEM with 10% FBS, 2 mM glutamine, 1% non-essential amino acids, 1% antimycotic-antibiotic, 55 uM β-Mercaptoethanol.

Selection of AAV libraries on human islets. Islets were left in a 10 cm Petri Dish with 1Oml complete media to recover overnight prior to AAV infection. Islets were infected either intact or were dissociated into single cell suspensions using Accumax prior to infection (1 ml Accumax per 1000 islet equivalents [IEQ]). Approximately 300 IEQ or 1.7E05 dispersed islet cells were seeded in several wells of an ultra-low attachment 24-well plate, infected with various MOIs of either the 18 parent AAV mix or the AAV libraries and incubated in a 37° C. incubator for 6 hrs. After two PBS washes to remove left over input virus cells were superinfected with human adenovirus 5 obtained from ATCC (Cat #VR-5). For intact islets 8E07 PFU were used, for dissociated islet cells 4E07 PFU were added into 1 ml media per well. After 4 days at 37° C. the cells and supernatant were harvested, subjected to 3 freeze-thaw cycles and incubated for 30 min at 65° C. to inactivate Ad5. Cell debris was removed by centrifugation (2 min, 10,000×g) and viral genomes were isolated from 100-ul clarified supernatant for titration by qPCR using a rep primer-probe set. For subsequent rounds of passaging similar MOIs as for the initial infections were used if sufficiently high titers were achieved. When titers were low a maximum volume of 200 ul was used for infection.

Vector plasmids. A self-complementary rAAV vector expressing GFP under control of a CAG promoter (pscAAV-CAG-GFP, Addgene, Cat #83279) was generated by replacing the CMV promoter in plasmid pscAAV-GFP (gift from John T Gray, Addgene, Cat #32396) with the CAG promoter derived from pAAV-CAG-GFP (gift from Edward Boyden, Addgene, Cat #37825). A single stranded rAAV vector expressing Firefly luciferase under control of the CAG promoter (pAAV-CAG-FLuc, Addgene, Cat #83281) was generated by replacing the GFP sequences in plasmid pAAV-CAG-GFP with Firefly luciferase sequences obtained from plasmid pAAV-EFlu-FLuc-WPRE-HGHpA (Addgene, Cat #87951). A single stranded rAAV vector expressing codon diversified Tomato Red was a gift from Edward Boyden (pAAV-CAG-tdTomato, Addgene, Cat #59462).

Recovery and evaluation of enriched AAV capsid sequences. Capsid sequences were amplified from viral genomes after the third round of selection using primer capF and a reverse primer containing the respective BC specific sequence on its 3' end. The right BC was chosen to be included in the primer sequences so that the left BC served as a control of specific amplification of the desired variant. The number of PCR cycles was adjusted according to viral titer and frequency of the specific variant in the viral pool. The following amplification parameters were used: 2 min 98° C., 25 to 30 cycles of 15 sec 98° C., 20 sec 61° C., 2 min 72° C., with a final 10 min extension at 72° C. PCR products were gel purified, TOPO cloned and sequenced. Several clones for each BC were sequenced to ensure that the left BC sequence matched the sequence obtained by BC NGS. For several of the capsids it was observed that the capsid sequences differed for some of the clones, particularly at the 5' end. This was likely due to template switching after incomplete extension[96-98] and may be alleviated by optimizing PCR conditions and enzymes. The capsid sequences that matched the consensus sequence were used to package a self-complementary CAG promoter driven GFP expression vector by calcium phosphate triple transfection. For each T225 flask 25 ug sc CAG-GFP transfer vector, 25 ug packaging plasmid, and 25 ug pAd5 helper plasmid was used. Crude cell lysates were generated, rAAV titers determined by qPCR using a GFP specific primer-probe set, and tested for transduction efficiency of dissociated human islet cells using an MOI of 1K. 48-hrs post transduction the re-aggregated pseudo islets were dissociated into single-cell suspensions by incubation with Accumax followed by treatment with Dispase. The number of GFP expressing cells was evaluated using a BD FACS Calibur instrument and FlowJo software Version 10 was used to analyse and graph data.

Selected capsid variants were used to generate CsCl gradient purified vector preparations packaging different expression vectors.

Analysis of packaged vector genomes by Alkaline Southern Blot. Alkaline Southern Blot analysis was performed to analyze the size of the DNA packaged in rAAV capsids using standard methods. Briefly, 1E09 viral genomes in alkaline loading buffer (50 mM NaOH, 1 mM EDTA, 3% Ficoll, 0.025% Bromcresol, 0.042% Xylene) were loaded onto a 1% alkaline agarose gel with 50 mM NaOH, 1 mM as running buffer. The gel was run at 40 mV for 24 hrs at 4° C. with one buffer exchange after 12 hrs. After gel blotting, the membrane was pre-hybridized with 10 μg/ml salmon sperm DNA in PerfectHyb Plus Hybridization buffer (Sigma) for 2 hrs at 65° C. with rotation. A 300 nt long $^{32}$P-labeled probe containing GFP or FLuc sequences was added and left to hybridize o.n. at 65° C. with rotation. The membrane was washed twice under low-stringent condition (2× salt-sodium citrate, 20 min at 65° C.), followed by one wash under high-stringent condition (2× salt-sodium citrate with 0.1% SDS, 30 min at 65° C.). The membrane was exposed onto a phosphoimager screen and visualized using the Personal Molecular Imager (Biorad). Image analysis was performed using QuantityOne software.

Analysis of capsid proteins by Western Blot. Western Blot analysis was performed using standard methods and equipment. Briefly, proteins were resolved on 4-12% NuPAGE Bis-Tris gels (Life Technologies) using MOPS running buffer. For detection of capsid proteins the membrane was probed with monoclonal antibody B1 (ARP, Cat #03-61058) at a 1:200 dilution for 2 hrs at RT. The membrane was then incubated for 1 hr with a horseradish peroxidase (HRP)-labeled secondary antibody directed against mouse IgG, followed by HRP detection using Pierce ECL2 substrate and the Biorad Chemdoc imager.

Evaluation of cell type specific transduction efficiency of capsid variants. The cold transduction method was performed for those studies. Briefly, approximately 300 intact islets were resuspended in 100-ul CMRL with 2% FBS, rAAV was added at an MOI of 10K (assuming 1,000 cells per islet), and the mixture was incubated on ice while gently rocking on a horizontal shaker in the cold room. After 2-hrs 1-ml pre-warmed complete media (CMRL-1066 with 10 mM HEPES, 0.5% human serum albumin, 2% FBS, 10 mM nicotinamide, 1% antimycotic-antibiotic, 1% Glutamax) was added to each sample and islets were incubated on 24-well ultra-low attachment plates. Media was replaced after 2 days and islets were harvested, dissociated, and analyzed by FACS as described previously using surface antibodies to subdivide into α-, β-, and non-α-/non-β-cells[99].

Evaluation of rAAVs for transduction efficiency on hESC derived β-cells. Recombinant AAVs were mixed with 800,000 GFP-high cells sored from 20 spheres at an MOI of 10, 100, 1000 and reaggregated in Aggrewell-400 in CMRL containing 10% FBS, 1:100 Glutamax, 1:100 NEAA, 10 μm ALKi II, 0.5 mM vitamin C, 1 μM T3, 1 mM N-acetyl Cysteine, 10 μM zinc sulfate and 10 μg/ml of heparin sulfate. Media was replaced after 3 days when the reaggregated eBCs were transferred into 6 well suspension plates. They were placed on orbital shakers at 100 rpm, and further cultured for 3 days. Subsequently, the eBCs were dissociated, fixed, permiabilized and stained for anti-human C-peptide abtibody (1: 200), and anti-human RFP antibody (Rockland, 1:500) for analysis on LSRFortessa X20 Dual, as described previously[100]. Data were analyzed with Flowjo software. Anti-human C-peptide antibody was conjugated in-house using the Molecular Probes Antibody Labeling Kits according to manufacturer's instructions. Live images were taken using Leica DMI4000 B.

Evaluation of the variants for transduction efficiency on a variety of cell lines. Capsid sequences of AAV DJ, AAV LK03, as well as the variants AAV KP1, KP2, and KP3 were used to package a single stranded CAG-Firefly Luciferase vector. Recombinant AAV preparations were double CsCl purified and used to transduce a variety of human and mouse primary cells and cell lines at an MOI of 100 and 1000 in triplicates. Except for the differentiated human muscle cells all cells were seeded one day prior to transduction on 48-well plates so that they were about 60-70% confluent at the time of transduction (seeding density of 20,000-80,000 per well, depending on size and proliferation rate). Cells were lysed and assayed for luciferase activity using the Luciferase Assay Kit (Promega) 48-hrs post transduction. Purified recombinant luciferase protein (Promega) was used to generate a standard curve.

Neutralization assay. Two different batches of pooled human immunoglobulin fractions (IVIG, Baxter) were used to evaluate the novel variants for sensitivity to neutralizing antibodies. Neutralization assays were essentially performed as described (Meliani et al., 2015)[101]. Briefly, IVIG preparations were diluted in complement inactivated FBS and incubated for 1-hr at 37° C. with 2E08 vector genomes of each ssCAG-FLuc vector packaged with the different capsids in a total volume of 100 ul. Huh7 cells that had been seeded on 48 well plates the day before (5E04 per well) were transduced with the virus-IVIG mixtures in triplicates (22.5-ul each well, corresponding to MOI of ca 100) and luciferase activity in the cell lysates was determined 24-hrs later.

Mice. Fah/Rag2/Il2rgc (FRG) deficient female mice on a NOD-strain background (FRG/N) were housed and maintained in specific-pathogen-free barrier facilities at Oregon Health & Science University. FRG/N mice were maintained on irradiated high-fat low-protein mouse chow (Lab Diet Cat #Picolab-5LJ5) ad libitum to decrease flux through the tyrosine pathway. Beginning on the day of transplantation, FRG/N mice were maintained for 1 week on acidified water to prevent bacterial growth. The following week, mice were switched to 1 week of 8 mg/L SMX-TMP antibiotic water (supplemented with 0.7-mol/L dextrose for palatability). Thereafter, FRG/N mice were cycled on and off 1 mg/L NTBC water as described. Female Balb/C SCID mice between 6 and 8 weeks of age were purchased from The Jackson Laboratories (Cat #001803) for imaging studies. The Institutional Animal Care & Use Committees of Stanford University, Oregon Health & Science University and the Children's Medical Research Institute approved all mouse procedures.

Hepatocyte transplantation. Donor human hepatocytes for transduction studies were acquired from BioreclarnationIVT (Lot #QIE). Weanling FRG/N mice were pre-conditioned with administration of recombinant human adenovirus expressing urokinase (5E10 PFU retroorbitally) 24 hrs prior to transplant to promote human cell engraftment. Between 5E05 and 1E06 human hepatocytes were injected intrasplenically into anesthetized recipient FRG/N mice and cycled on/off NTBC to promote human hepatocyte engraftment and expansion. Broad-spectrum antibiotic (Ceftiofur 4-mg/kg) was given by intraperitoneal injection immediately prior to surgery and for two days following surgery. Six months post-transplant, circulating human albumin levels as measure of engraftment were determined with the Bethyl Quantitative Human Albumin ELISA kit (Cat #E88-129).

In vivo transduction experiments. For evaluation of wild-type mouse liver transduction efficiency white Balb/C SCID mice were injected with 2E10 vector genomes of each CAG-Firefly Luciferase vector via normodynamic intravenous lateral tail vein injections. AAV8 was used in place of LK03 as this capsid had previously been shown to be highly human specific. Mice were monitored for Luciferase activity in the liver once a week by intraperitoneal injection of 150 ug per g body weight D-Luciferin (Biosynth Cat #L-8220) and ventral luciferase readings using an Ami Imaging System. On day 35 mice were sacrificed and various organs were recovered (liver, pancreas, heart, lung, spleen, brain, and kidney). Organs were homogenized in Passive lysis buffer (Promega) using a Bullet Storm Homogenizer and luciferase activity from 1 mg each tissue sample was measured as described above. Genomic DNA was isolated from 10 mg each tissue sample and vector copy numbers were determined using qPCR. Primers for Luciferase were FLuc F: CAC ATA TCG AGG TGG ACA TTA C and FLuc R: TG TTT GTA TTC AGC CCA TAG. Mouse actin primers (m-actF: CCT GTA TGC CTC TGG TCG TA and m-actR: CCT CGT AGA TGG GCA CAG T) were used for normalization.

For evaluation of human hepatocyte transduction in vivo humanized FRG/N mice (3 mice per group) were injected intravenously with 1E11 ssCAG-Td Tomato Red vector genomes pseudotyped with DJ, LK03, or KP1 capsids and maintained on 1 mg/L NTBC during this 14 day transduction. Livers were harvested under inhalation isoflurane anesthesia. Liver tissue was cut into several 2×5-mm pieces from several lobes and fixed in 10× volume of 4% PFA for 5 hrs at 25° C. protected from light. Fixed tissue was washed 1× in PBS and put through a sucrose cryoprotection and rehydration series (10% w/v sucrose for 2 hrs at 25° C., 20% w/v sucrose overnight at 4° C., 30% w/v sucrose for 4 hrs at 25° C.). Liver pieces were rinsed in PBS, blotted dry and mounted in cryomolds (Tissue-Tek Cat #4557) with OCT (Tissue-Tek Cat #4583) and frozen in a liquid nitrogen-cooled isopentane bath.

Labeled cryomolds were wrapped in aluminum foil and placed at −80° C. until sectioning. Liver immunohistochemistry. Each liver sample with four to five lobes was cut in a microtome at 5 μM per section. Slides were fixed in methanol for 1 min at −20° C. and air dried at room temperature (RT). All following steps were done at RT except for notification. Slides were washed in PBT (PBS+0.1% Tween20) for 3×5 min, permeabilized in 0.3% Triton-X-100 in PBS for 1×10 min, and washed in PBT for 2×5 min. Blocking was performed in PBT+10% normal donkey serum (Cat. no. ab7475; Abcam) for 1 hr in a humidified chamber. A rabbit anti-human FAH antibody (Cat. no. HPA041370; Sigma) was added in PBT at 1:200 and incubated overnight at 4° C. Post-staining wash was conducted in PBT for 3×5 min. A secondary antibody for donkey anti-rabbit Alexa Fluor 488 IgG antibody (Cat. no. A-21206; ThermoFisher) was added in PBT (1:500, with DAPI at 80 ng/mL) and incubated at RT for 1 hr. Slides were washed in PBT for 3×5 min and PBS for 1×5 min, followed by mounting with ProLong Gold Antifade Reagent (Cat. no. 9071S; Cell Signaling). Antibody validity controls included secondary-only staining and demonstration on positive control human liver tissue sections (Cat. no. HF-314; Zyagen) and negative control untreated mouse liver sections (Cat. no. MF-314-C57; Zyagen). Imaging was performed on an inverted Zeiss laser scanning confocal microscope (LSM 880) by a 20× objective with the Zen Pro software. AAV-RFP signals were scanned and captured directly. Quantification of human hepatocyte transduction was done using the Volocity software (v6.3) and confirmed with counts by eye. Briefly, six to nine different areas of interests across different lobes from different sections of each liver sample were scanned, counting ~1,000 cells on average per section. Areas with roughly 30%-80% of FAH-positive staining were chosen for analysis. The percentage of human hepatocytes per scanned area was presented as the number of cells with Alexa Fluor 488 signals (FAH-positive) divided by the number of cells with DAPI signals (total number of cells). Total transduction efficiency was calculated by dividing the number of cells with RFP signals (AAV-positive) by the number of cells with DAPI signals. The overlap of these two numbers represented the transduction efficiency for human hepatocytes for different AAV serotypes.

References for Example 3

1. Kay, M A (2015). Selecting the Best AAV Capsid for Human Studies. Mol Ther 23: 1800-1801.
2. Colella, P, Ronzitti, G, and Mingozzi, F (2018). Emerging Issues in AAV-Mediated In Vivo Gene Therapy. Mol Ther Methods Clin Dev 8: 87-104.
3. Pillay, S, and Carette, J E (2017). Host determinants of adeno-associated viral vector entry. Curr Opin Virol 24: 124-131.
4. Thomas, C E, Storm, T A, Huang, Z, and Kay, M A (2004). Rapid uncoating of vector genomes is the key to efficient liver transduction with pseudotyped adeno-associated virus vectors. J Virol 78: 3110-3122.
5. Keiser, N W, Yan, Z, Zhang, Y, Lei-Butters, D C, and Engelhardt, J F (2011). Unique characteristics of AAV1, 2, and 5 viral entry, intracellular trafficking, and nuclear import define transduction efficiency in HeLa cells. Hum Gene Ther 22: 1433-1444.
6. Grimm, D, and Kay, M A (2003). From virus evolution to vector revolution: use of naturally occurring serotypes of adeno-associated virus (AAV) as novel vectors for human gene therapy. Curr Gene Ther 3: 281-304.
7. Adachi, K, and Nakai, H (2010). A New Recombinant Adeno-Associated Virus (Aav)-Based Random Peptide Display Library System: Infection-Defective Aavl.9-3 as a Novel Detargeted Platform for Vector Evolution. Gene Ther Regul 5: 31-55.
8. Grimm, D, Lee, J S, Wang, L, Desai, T, Akache, B, Storm, T A, et al. (2008). In vitro and in vivo gene therapy vector evolution via multispecies interbreeding and retargeting of adeno-associated viruses. J Virol 82: 5887-5911.
9. Naumer, M, Sonntag, F, Schmidt, K, Nieto, K, Panke, C, Davey, N E, et al. (2012). Properties of the adeno-associated virus assembly-activating protein. J Virol 86: 13038-13048.
10. Munch, R C, Janicki, H, Volker, I, Rasbach, A, Hallek, M, Buning, H, et al. (2013). Displaying high-affinity ligands on adeno-associated viral vectors enables tumor cell-specific and safe gene transfer. Mol Ther 21: 109-118.
11. Grimm, D, and Zolotukhin, S (2015). E Pluribus Unum: 50 Years of Research, Millions of Viruses, and One Goal—Tailored Acceleration of AAV Evolution. Mol Ther 23: 1819-1831.
12. Zinn, E, Pacouret, S, Khaychuk, V, Turunen, H T, Carvalho, L S, Andres-Mateos, E, et al. (2015). In Silico Reconstruction of the Viral Evolutionary Lineage Yields a Potent Gene Therapy Vector. Cell Rep 12: 1056-1068.

13. Stemmer, W P (1994). DNA shuffling by random fragmentation and reassembly: in vitro recombination for molecular evolution. Proc Natl Acad Sci USA 91: 10747-10751.
14. Stemmer, W P (1994). Rapid evolution of a protein in vitro by DNA shuffling. Nature 370: 389-391.
15. Zhao, H, Giver, L, Shao, Z, Affholter, J A, and Arnold, F H (1998). Molecular evolution by staggered extension process (StEP) in vitro recombination. Nat Biotechnol 16: 258-261.
16. Coco, W M, Levinson, W E, Crist, M J, Hektor, H J, Darzins, A, Pienkos, P T, et al. (2001). DNA shuffling method for generating highly recombined genes and evolved enzymes. Nat Biotechnol 19: 354-359.
17. Kikuchi, M, Ohnishi, K, and Harayama, S (1999). Novel family shuffling methods for the in vitro evolution of enzymes. Gene 236: 159-167.
18. Gillam E. M. J., C, J. N., Ackerley, D. F. (2014). Directed Evolution Library Creation, Methods and Protocols, Humana Press.
19. Crameri, A, Raillard, S A, Bermudez, E, and Stemmer, W P (1998). DNA shuffling of a family of genes from diverse species accelerates directed evolution. Nature 391: 288-291.
20. Chang, C C, Chen, T T, Cox, B W, Dawes, G N, Stemmer, W P, Punnonen, J, et al. (1999). Evolution of a cytokine using DNA family shuffling. Nat Biotechnol 17: 793-797.
21. Christians, F C, Scapozza, L, Crameri, A, Folkers, G, and Stemmer, W P (1999).
Directed evolution of thymidine kinase for AZT phosphorylation using DNA family shuffling. Nat Biotechnol 17: 259-264.
22. Crameri, A, Dawes, G, Rodriguez, E, Jr., Silver, S, and Stemmer, W P (1997). Molecular evolution of an arsenate detoxification pathway by DNA shuffling. Nat Biotechnol 15: 436-438.
23. Leong, S R, Chang, J C, Ong, R, Dawes, G, Stemmer, W P, and Punnonen, J (2003). Optimized expression and specific activity of IL-12 by directed molecular evolution. Proc Natl Acad Sci USA 100: 1163-1168.
24. Ness, J E, Welch, M, Giver, L, Bueno, M, Cherry, J R, Borchert, T V, et al. (1999). DNA shuffling of subgenomic sequences of subtilisin. Nat Biotechnol 17: 893-896.
25. Pekrun, K, Shibata, R, Igarashi, T, Reed, M, Sheppard, L, Patten, P A, et al. (2002). Evolution of a human immunodeficiency virus type 1 variant with enhanced replication in pig-tailed macaque cells by DNA shuffling. J Virol 76: 2924-2935.
26. Powell, S K, Kaloss, M A, Pinkstaff, A, McKee, R, Burimski, I, Pensiero, M, et al. (2000). Breeding of retroviruses by DNA shuffling for improved stability and processing yields. Nat Biotechnol 18: 1279-1282.
27. Raillard, S, Krebber, A, Chen, Y, Ness, J E, Bermudez, E, Trinidad, R, et al. (2001). Novel enzyme activities and functional plasticity revealed by recombining highly homologous enzymes. Chem Biol 8: 891-898.
28. Soong, N W, Nomura, L, Pekrun, K, Reed, M, Sheppard, L, Dawes, G, et al. (2000). Molecular breeding of viruses. Nat Genet 25: 436-439.
29. Stutzman-Engwall, K, Conlon, S, Fedechko, R, McArthur, H, Pekrun, K, Chen, Y, et al. (2005). Semi-synthetic DNA shuffling of aveC leads to improved industrial scale production of doramectin by Streptomyces avermitilis. Metab Eng 7: 27-37.
30. Wright, A, Semyonov, A, Dawes, G, Crameri, A, Lyons, R, Stemmer, W P, et al. (2005). Diverse plasmid DNA vectors by directed molecular evolution of cytomegalovirus promoters. Hum Gene Ther 16: 881-892.
31. Zhang, J H, Dawes, G, and Stemmer, W P (1997). Directed evolution of a fucosidase from a galactosidase by DNA shuffling and screening. Proc Natl Acad Sci USA 94: 4504-4509.
32. Apt, D, Raviprakash, K, Brinkman, A, Semyonov, A, Yang, S, Skinner, C, et al. (2006). Tetravalent neutralizing antibody response against four dengue serotypes by a single chimeric dengue envelope antigen. Vaccine 24: 335-344.
33. Maheshri, N, Koerber, J T, Kaspar, B K, and Schaffer, D V (2006). Directed evolution of adeno-associated virus yields enhanced gene delivery vectors. Nat Biotechnol 24: 198-204.
34. Asuri, P, Bartel, M A, Vazin, T, Jang, J H, Wong, T B, and Schaffer, D V (2012). Directed evolution of adeno-associated virus for enhanced gene delivery and gene targeting in human pluripotent stem cells. Mol Ther 20: 329-338.
35. Koerber, J T, Jang, J H, and Schaffer, D V (2008). DNA shuffling of adeno-associated virus yields functionally diverse viral progeny. Mol Ther 16: 1703-1709.
36. Li, W, Asokan, A, Wu, Z, Van Dyke, T, DiPrimio, N, Johnson, J S, et al. (2008). Engineering and Selection of Shuffled AAV Genomes: A New Strategy for Producing Targeted Biological Nanoparticles. Mol Ther 16: 1252-1260.
37. Lisowski, L, Dane, A P, Chu, K, Zhang, Y, Cunningham, S C, Wilson, E M, et al. (2014). Selection and evaluation of clinically relevant AAV variants in a xenograft liver model. Nature 506: 382-386.
38. Paulk, N K, Pekrun, K, Charville, G W, Maguire-Nguyen, K, Wosczyna, M N, Xu, J, et al. (2018). Bioengineered Viral Platform for Intramuscular Passive Vaccine Delivery to Human Skeletal Muscle. Mol Ther Methods Clin Dev 10: 144-155.
39. Paulk, N K, Pekrun, K, Zhu, E, Nygaard, S, Li, B, Xu, J, et al. (2018). Bioengineered AAV Capsids with Combined High Human Liver Transduction In Vivo and Unique Humoral Seroreactivity. Mol Ther 26: 289-303.
40. Ward, P, and Walsh, C E (2009). Chimeric AAV Cap sequences alter gene transduction. Virology 386: 237-248.
41. Choudhury, S R, Fitzpatrick, Z, Harris, A F, Maitland, S A, Ferreira, J S, Zhang, Y, et al. (2016). In Vivo Selection Yields AAV-B1 Capsid for Central Nervous System and Muscle Gene Therapy. Mol Ther 24: 1247-1257.
42. Dalkara, D, Byrne, L C, Klimczak, R R, Visel, M, Yin, L, Merigan, W H, et al. (2013).
In vivo-directed evolution of a new adeno-associated virus for therapeutic outer retinal gene delivery from the vitreous. Sci Transl Med 5: 189ra176.
43. Tervo, D G, Hwang, B Y, Viswanathan, S, Gaj, T, Lavzin, M, Ritola, K D, et al. (2016). A Designer AAV Variant Permits Efficient Retrograde Access to Projection Neurons. Neuron 92: 372-382.
44. Yang, L, Jiang, J, Drouin, L M, Agbandje-McKenna, M, Chen, C, Qiao, C, et al. (2009). A myocardium tropic adeno-associated virus (AAV) evolved by DNA shuffling and in vivo selection. Proc Natl Acad Sci USA 106: 3946-3951.
45. CDC (2017). National Diabetes Statistics Report. U S Department of Health and Human Services.
46. Bruni, A, Gala-Lopez, B, Pepper, A R, Abualhassan, N S, and Shapiro, A J (2014). Islet cell transplantation for the treatment of type 1 diabetes: recent advances and future challenges. Diabetes Metab Syndr Obes 7: 211-223.

47. Wang, X, Meloche, M, Verchere, C B, Ou, D, Mui, A, and Warnock, G L (2011). Improving islet engraftment by gene therapy. J Transplant 2011: 594851.
48. Sakata, N, Yamaguchi, Y, Chen, Y, Shimoda, M, Yoshimatsu, G, Unno, M, et al. (2017). Pleckstrin homology-like domain family A, member 3 (PHLDA3) deficiency improves islets engraftment through the suppression of hypoxic damage. PLoS One 12: e0187927.
49. Mallol, C, Casana, E, Jimenez, V, Casellas, A, Haurigot, V, Jambrina, C, et al. (2017). AAV-mediated pancreatic overexpression of Igf1 counteracts progression to autoimmune diabetes in mice. Mol Metab 6: 664-680.
50. Collombat, P, Xu, X, Ravassard, P, Sosa-Pineda, B, Dussaud, S, Billestrup, N, et al. (2009). The ectopic expression of Pax4 in the mouse pancreas converts progenitor cells into alpha and subsequently beta cells. Cell 138: 449-462.
51. Courtney, M, Gjernes, E, Druelle, N, Ravaud, C, Vieira, A, Ben-Othman, N, et al. (2013). The inactivation of Arx in pancreatic alpha-cells triggers their neogenesis and conversion into functional beta-like cells. PLoS Genet 9: e1003934.
52. Lima, M J, Muir, K R, Docherty, H M, McGowan, N W, Forbes, S, Heremans, Y, et al. (2016). Generation of Functional Beta-Like Cells from Human Exocrine Pancreas. PLoS One 11: e0156204.
53. Wang, Y, Dorrell, C, Naugler, W E, Heskett, M, Spellman, P, Li, B, et al. (2018). Long-Term Correction of Diabetes in Mice by In Vivo Reprogramming of Pancreatic Ducts. Mol Ther 26: 1327-1342.
54. Xiao, X, Guo, P, Shiota, C, Zhang, T, Coudriet, G M, Fischbach, S, et al. (2018). Endogenous Reprogramming of Alpha Cells into Beta Cells, Induced by Viral Gene Therapy, Reverses Autoimmune Diabetes. Cell Stem Cell 22: 78-90 e74.
55. Zhang, Y, Fava, G E, Wang, H, Mauvais-Jarvis, F, Fonseca, V A, and Wu, H (2016). PAX4 Gene Transfer Induces alpha-to-beta Cell Phenotypic Conversion and Confers Therapeutic Benefits for Diabetes Treatment. Mol Ther 24: 251-260.
56. Chakravarthy, H, Gu, X, Enge, M, Dai, X, Wang, Y, Damond, N, et al. (2017). Converting Adult Pancreatic Islet alpha Cells into beta Cells by Targeting Both Dnmtl and Arx. Cell Metab 25: 622-634.
57. Matsuoka, T A, Kawashima, S, Miyatsuka, T, Sasaki, S, Shimo, N, Katakami, N, et al. (2017). Mafa Enables Pdx1 to Effectively Convert Pancreatic Islet Progenitors and Committed Islet alpha-Cells Into beta-Cells In Vivo. Diabetes 66: 1293-1300.
58. Furuyama, K, Chera, S, van Gurp, L, Oropeza, D, Ghila, L, Damond, N, et al. (2019). Diabetes relief in mice by glucose-sensing insulin-secreting human alpha-cells. Nature.
59. Vieira, A, Courtney, M, Druelle, N, Avolio, F, Napolitano, T, Hadzic, B, et al. (2016). beta-Cell replacement as a treatment for type 1 diabetes: an overview of possible cell sources and current axes of research. Diabetes Obes Metab 18 Suppl 1: 137-143.
60. Zhao, C, Qiao, C, Tang, R H, Jiang, J, Li, J, Martin, C B, et al. (2015). Overcoming Insulin Insufficiency by Forced Follistatin Expression in beta-cells of db/db Mice. Mol Ther 23: 866-874.
61. Flores, R R, Zhou, L, and Robbins, P D (2014). Expression of IL-2 in beta cells by AAV8 gene transfer in pre-diabetic NOD mice prevents diabetes through activation of FoxP3-positive regulatory T cells. Gene Ther 21: 715-722.
62. Wang, Z, Zhu, T, Rehman, K K, Bertera, S, Zhang, J, Chen, C, et al. (2006). Widespread and stable pancreatic gene transfer by adeno-associated virus vectors via different routes. Diabetes 55: 875-884.
63. Martini, S V, Silva, A L, Ferreira, D, Rabelo, R, Omellas, F M, Gomes, K, et al. (2016). Tyrosine Mutation in AAV9 Capsid Improves Gene Transfer to the Mouse Lung. Cell Physiol Biochem 39: 544-553.
64. Mowat, F M, Gornik, K R, Dinculescu, A, Boye, S L, Hauswirth, W W, Petersen-Jones, S M, et al. (2014). Tyrosine capsid-mutant AAV vectors for gene delivery to the canine retina from a subretinal or intravitreal approach. Gene Ther 21: 96-105.
65. Zhong, L, Li, B, Mah, C S, Govindasamy, L, Agbandje-McKenna, M, Cooper, M, et al. (2008). Next generation of adeno-associated virus 2 vectors: point mutations in tyrosines lead to high-efficiency transduction at lower doses. Proc Natl Acad Sci USA 105: 7827-7832.
66. Song, L, Kauss, M A, Kopin, E, Chandra, M, Ul-Hasan, T, Miller, E, et al. (2013). Optimizing the transduction efficiency of capsid-modified AAV6 serotype vectors in primary human hematopoietic stem cells in vitro and in a xenograft mouse model in vivo. Cytotherapy 15: 986-998.
67. Song, L, Li, X, Jayandharan, G R, Wang, Y, Aslanidi, G V, Ling, C, et al. (2013). High-efficiency transduction of primary human hematopoietic stem cells and erythroid lineage-restricted expression by optimized AAV6 serotype vectors in vitro and in a murine xenograft model in vivo. PLoS One 8: e58757.
68. Chen, M, Maeng, K, Nawab, A, Francois, R A, Bray, J K, Reinhard, M K, et al. (2017). Efficient Gene Delivery and Expression in Pancreas and Pancreatic Tumors by Capsid-Optimized AAV8 Vectors. Hum Gene Ther Methods 28: 49-59.
69. Craig, A T, Gavrilova, O, Dwyer, N K, Jou, W, Pack, S, Liu, E, et al. (2009). Transduction of rat pancreatic islets with pseudotyped adeno-associated virus vectors. Virol J 6: 61.
70. Flotte, T, Agarwal, A, Wang, J, Song, S, Fenjves, E S, Inverardi, L, et al. (2001).
Efficient ex vivo transduction of pancreatic islet cells with recombinant adeno-associated virus vectors. Diabetes 50: 515-520.
71. Kapturczak, M H, Flotte, T, and Atkinson, M A (2001). Adeno-associated virus (AAV) as a vehicle for therapeutic gene delivery: improvements in vector design and viral production enhance potential to prolong graft survival in pancreatic islet cell transplantation for the reversal of type 1 diabetes. Curr Mol Med 1: 245-258.
72. Song, Z, Galivo, F H, Adachi, K, Grompe, M, Nakai, H (2017). Strong Alpha Cell Preference of the AAV Strains That Best Transduce Human Pancreatic Islets In Vitro. Molecular Therapy 25: 47.
73. Adachi, K, Enoki, T, Kawano, Y, Veraz, M, and Nakai, H (2014). Drawing a high-resolution functional map of adeno-associated virus capsid by massively parallel sequencing. Nat Commun 5: 3075.
74. Huang, W, Johnston, W A, Boden, M, and Gillam, E M (2016). ReX: A suite of computational tools for the design, visualization, and analysis of chimeric protein libraries. Biotechniques 60: 91-94.
75. Nair, G G, Liu, J S, Russ, H A, Tran, S, Saxton, M S, Chen, R, et al. (2019).
Recapitulating endocrine cell clustering in culture promotes maturation of human stem-cell-derived beta cells. Nat Cell Biol 21: 263-274.

76. Lerch, T F, and Chapman, M S (2012). Identification of the heparin binding site on adeno-associated virus serotype 3B (AAV-3B). Virology 423: 6-13.

77. Mays, L E, Wang, L, Tenney, R, Bell, P, Nam, H J, Lin, J, et al. (2013). Mapping the structural determinants responsible for enhanced T cell activation to the immunogenic adeno-associated virus capsid from isolate rhesus 32.33. J Virol 87: 9473-9485.

78. Gao, G, Alvira, M R, Somanathan, S, Lu, Y, Vandenberghe, L H, Rux, J J, et al. (2003). Adeno-associated viruses undergo substantial evolution in primates during natural infections. Proc Natl Acad Sci USA 100: 6081-6086.

79. Wu, J, Zhao, W, Zhong, L, Han, Z, Li, B, Ma, W, et al. (2007). Self-complementary recombinant adeno-associated viral vectors: packaging capacity and the role of rep proteins in vector purity. Hum Gene Ther 18: 171-182.

80. Gray, S J, Choi, V W, Asokan, A, Haberman, R A, McCown, T J, and Samulski, R J (2011). Production of recombinant adeno-associated viral vectors and use in in vitro and in vivo administration. Curr Protoc Neurosci Chapter 4: Unit 4 17.

81. Quirin, K A, Kwon, J J, Alioufi, A, Factora, T, Temm, C J, Jacobsen, M, et al. (2018). Safety and Efficacy of AAV Retrograde Pancreatic Ductal Gene Delivery in Normal and Pancreatic Cancer Mice. Mol Ther Methods Clin Dev 8: 8-20.

82. Jimenez, V, Ayuso, E, Mallol, C, Agudo, J, Casellas, A, Obach, M, et al. (2011). In vivo genetic engineering of murine pancreatic beta cells mediated by single-stranded adeno-associated viral vectors of serotypes 6, 8 and 9. Diabetologia 54: 1075-1086.

83. Nonnenmacher, M, van Bakel, H, Hajjar, R J, and Weber, T (2015). High capsid-genome correlation facilitates creation of AAV libraries for directed evolution. Mol Ther 23: 675-682.

84. Doshi, B S, and Arruda, V R (2018). Gene therapy for hemophilia: what does the future hold? Ther Adv Hematol 9: 273-293.

85. George, L, et al. (2017). Spk-8011: preliminary results from a phase 1/2 dose escalation trial of an investigational AAV-mediated gene therapy for hemophilia A. Blood 130.

86. Herrmann, A K, Grosse, S, Borner, K, Kramer, C, Wiedtke, E, Gunkel, M, et al. (2018). Impact of the assembly-activating protein (AAP) on molecular evolution of synthetic Adeno-associated virus (AAV) capsids. Hum Gene Ther.

87. Sonntag, F, Kother, K, Schmidt, K, Weghofer, M, Raupp, C, Nieto, K, et al. (2011).

The assembly-activating protein promotes capsid assembly of different adeno-associated virus serotypes. J Virol 85: 12686-12697.

88. Sonntag, F, Schmidt, K, and Kleinschmidt, J A (2010). A viral assembly factor promotes AAV2 capsid formation in the nucleolus. Proc Natl Acad Sci USA 107: 10220-10225.

89. Grosse, S, Penaud-Budloo, M, Herrmann, A K, Bomer, K, Fakhiri, J, Laketa, V, et al. (2017). Relevance of Assembly-Activating Protein for Adeno-associated Virus Vector Production and Capsid Protein Stability in Mammalian and Insect Cells. J Virol 91.

90. Herrmann, A K, Bender, C, Kienle, E, Grosse, S, El Andari, J, Botta, J, et al. (2018). A robust and all-inclusive pipeline for shuffling of Adeno-associated viruses (AAV). ACS Synth Biol.

91. Kienle, E, Senis, E, Bomer, K, Niopek, D, Wiedtke, E, Grosse, S, et al. (2012).

Engineering and evolution of synthetic adeno-associated virus (AAV) gene therapy vectors via DNA family shuffling. J Vis Exp.

92. Stamatakis, A (2015). Using RAxML to Infer Phylogenies. Curr Protoc Bioinformatics 51: 6 14 11-14.

93. Stamatakis, A, Ludwig, T, and Meier, H (2005). RAxML-III: a fast program for maximum likelihood-based inference of large phylogenetic trees. Bioinformatics 21: 456-463.

94. Xie, Q, Lerch, T F, Meyer, N L, and Chapman, M S (2011). Structure-function analysis of receptor-binding in adeno-associated virus serotype 6 (AAV-6). Virology 420: 10-19.

95. Charville, G W, Cheung, T H, Yoo, B, Santos, P J, Lee, G K, Shrager, J B, et al. (2015). Ex Vivo Expansion and In Vivo Self-Renewal of Human Muscle Stem Cells. Stem Cell Reports 5: 621-632.

96. Chakravarti, D, and Mailander, P C (2008). Formation of template-switching artifacts by linear amplification. J Biomol Tech 19: 184-188.

97. Odelberg, S J, Weiss, R B, Hata, A, and White, R (1995). Template-switching during DNA synthesis by Thermus aquaticus DNA polymerase I. Nucleic Acids Res 23: 2049-2057.

98. Paabo, S, Irwin, D M, and Wilson, A C (1990). DNA damage promotes jumping between templates during enzymatic amplification. J Biol Chem 265: 4718-4721.

99. Dorrell, C, Abraham, S L, Lanxon-Cookson, K M, Canaday, P S, Streeter, P R, and Grompe, M (2008). Isolation of major pancreatic cell types and long-term culture-initiating cells using novel human surface markers. Stem Cell Res 1: 183-194.

100. Russ, H A, Parent, A V, Ringler, J J, Hennings, T G, Nair, G G, Shveygert, M, et al. (2015). Controlled induction of human pancreatic progenitors produces functional beta-like cells in vitro. EMBO J 34: 1759-1772.

101. Meliani, A, Leborgne, C, Triffault, S, Jeanson-Leh, L, Veron, P, and Mingozzi, F (2015). Determination of anti-adeno-associated virus vector neutralizing antibody titer with an in vitro reporter system. Hum Gene Ther Methods 26: 45-53.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

---

What is claimed is:

1. A method of using an AAV capsid polypeptide to deliver a nucleic acid to a subject, the method comprising the step of administering to the subject an AAV vector whose genome comprises the nucleic acid, wherein the AAV capsid polypeptide is part of a functional AAV capsid, wherein the functional AAV capsid packages a nucleic acid sequence, and wherein the AAV capsid polypeptide sequence has the amino acid sequence selected from the group consisting of AAV-10A1 (SEQ ID NO: 1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13).

2. The method of claim 1, wherein the nucleic acid sequence is selected from the group consisting of a non-coding RNA, a protein coding sequence, an expression cassette, and a sequence for homologous recombination.

* * * * *